US011193154B2

(12) United States Patent
Delisa

(10) Patent No.: US 11,193,154 B2
(45) Date of Patent: Dec. 7, 2021

(54) PROKARYOTE-BASED CELL-FREE SYSTEM FOR THE SYNTHESIS OF GLYCOPROTEINS

(71) Applicant: CORNELL UNIVERSITY, Ithaca, NY (US)

(72) Inventor: Matthew Delisa, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 14/356,258

(22) PCT Filed: Nov. 5, 2012

(86) PCT No.: PCT/US2012/063590

§ 371 (c)(1),
(2) Date: May 5, 2014

(87) PCT Pub. No.: WO2013/067523

PCT Pub. Date: May 10, 2013

(65) Prior Publication Data

US 2014/0255987 A1 Sep. 11, 2014

Related U.S. Application Data

(60) Provisional application No. 61/555,854, filed on Nov. 4, 2011.

(51) Int. Cl.
*C12P 21/00* (2006.01)
*C12N 9/10* (2006.01)

(52) U.S. Cl.
CPC .......... *C12P 21/005* (2013.01); *C12N 9/1081* (2013.01); *C12Y 204/99* (2013.01)

(58) Field of Classification Search
None
See application file for complete search history.

(56) References Cited

U.S. PATENT DOCUMENTS

2002/0123101 A1 9/2002 Inoue
2009/0074798 A1 3/2009 Aebi et al.
2009/0317862 A1* 12/2009 Imataka .................. C12P 21/02 435/69.1
2010/0286067 A1* 11/2010 DeFrees ....................... 514/20.9
2011/0039729 A1 2/2011 Delisa et al.

FOREIGN PATENT DOCUMENTS

CN 101960017 A 1/2011
CN 102037004 A 4/2011
WO 2009089154 A2 7/2009
WO WO 2009089396 A2 * 7/2009 ....... A61K 47/48046

OTHER PUBLICATIONS

Kowarik et al. "N-linked glycosylation of folded proteins by the bacterial oligosaccharyltransferase", Science 314(5802): 1148-1150,2006.*

Chen et al., 'From Peptide to Protein: Comparative Analysis of the Substrate Specificity of N-Linked Glycosylation in C. jejuni,' Biochemistry 46(18):5579-5585 (2007).

Maita et al., 'Comparative Structural Biology of Eubacterial and Archaeal Oligosaccharyltransferases,' J. Biol. Chem. 285(7):4941-4950 (2010).

Fisher et al., 'Production of Secretory and Extracellular N-linked Glyproteins in *Escherichia coli*,' Appl. Environ. Microbiol. 77(3):871-881 (2011).

International Search Report and Written Opinion for corresponding PCT/US2012/063590 filed Nov. 5, 2012 (dated Mar. 14, 2013) (12 pages).

Maita et al., "Comparative Structural Biology and Eubacterial and Archaeal Oligosaccharyltransferases," J. of Biological Chemistry 285(7):4941-4950 (2010).

Chen et al., "From Peptide to Protein: Comparative Analysis of the Substrate Specificity of N-Linked Glycosylation in C. jejuni," Biochemistry 46:5579-5585 (2007).

Fisher et al., "Production of Secretory and Extracellular N-Linked Glycoproteins in *Escherichia coli*," Applied and Environmental Microbiology 77(3):871-881 (2011).

First Office Action and English Translation corresponding to Chinese Patent Application No. 201280066129.1 (dated Oct. 23, 2015).

English Translation and Second Office Action for China Patent Application No. 201280066129.1 (dated Aug. 19, 2016).

International Preliminary Report on Patentability or International Application No. PCT/US2012/063590 (dated May 6, 2014).

English Translation and Third Office Action for Chinese Application No. 201280066129.1 (dated May 8, 2017).

English Translation and Decision of Rejection for China Patent Application No. 201280066129.1 (dated Feb. 12, 2018).

Rothblatt et al., "Secretion in Yeast: Reconstitution of the Translocation and Glycosylation of Alpha-Factor and Invertase in a Homologous Cell-Free System," Cell 44:619-628 (1986).

India Examination Report Application No. 4076/CHENP/2014, dated Feb. 25, 2019.

Lingappa et al., "Coupled Cell-Free Synthesis, Segregation, and Core Glycosylation of a Secretory Protein," Proc. Nat'l. Acad. Sci. U.S.A. 75:2338-2342 (1978).

Rothblatt & Meyer, "Secretion in Yeast: Reconstitution of the Translocation and Glycosylation of Alpha-Factor and Invertase in a Homologous Cell-Free System," Cell 44:619-628 (1986).

(Continued)

*Primary Examiner* — Emily A Cordas
(74) *Attorney, Agent, or Firm* — Troutman Pepper Hamilton Sanders LLP (Rochester)

(57) ABSTRACT

The present invention is directed to a cell-free system for producing a glycosylated protein. This system comprises an isolated oligosaccharyltransferase capable of transferring a glycan from a lipid carrier molecule to a glycoprotein target, one or more isolated glycans, where each glycan is linked to a lipid carrier molecule, and a glycoprotein target comprising one or more glycan acceptor amino acid residues or a nucleic acid molecule encoding said glycoprotein target. The present invention further relates to kits and methods for producing a glycosylated protein in this cell-free system.

18 Claims, 27 Drawing Sheets

Specification includes a Sequence Listing.

(56) References Cited

OTHER PUBLICATIONS

Chinese Patent Application Serial No. 201280066129.1, Notice of Reexamination (dated Mar. 30, 2020).

Decision of Reexamination in China Patent Application No. 201280066129.1 (dated Nov. 11, 2020).

Hearing Notice in India Patent Application No. 4076/CHENP/2014 (dated Jul. 22, 2021).

* cited by examiner

Sequence alignment of PglB homologs from Campylobacter

```
Q9S4V7_CAMJU   ------------------------------------------ISNDGYAF    8  (SEQ ID NO: 2)
H7WYI6_CAMCO   -MLKKEYFKN-PTFILLAFIILAYVFSVLCRFYWIFWASEFNEYFFNNELMIISNDGYAF   58  (SEQ ID NO: 6)
E6LAJ2_CAMUP   --MKNEAVKN-ANLRLVFFILLAFGFSVLCRFYWIYWASDFNEYFFNNQLMISSNDGYTF   57  (SEQ ID NO: 8)
B9KDD4_CAMLR   MKLQQNFTDNNSIKYTCILILIAFAFSVLCRLYWVAWASEFYEFFFNDQLMITTNDGYAF   60  (SEQ ID NO: 4)
                                                     :****.:*
Consensus                                             XXNDGYXF        (SEQ ID NO: 10)

Q9S4V7_CAMJU   AEGARDMIAGFHQPNDLSYYGSSLSTLTYWLYKITPFSFESIILYMSTFLS-LVVIPIIL   67
H7WYI6_CAMCO   AEGARDMIAGFHQPNDLSYYGSSLSTLTYWFYKITPFSLESIFIYISTFLSSLVVIPLIL  118
E6LAJ2_CAMUP   AEGARDKIAGFHQENDLSFINSSLSILTYVLFKITPFSFESIILYMSVFFSSLIVVPLIL  117
B9KDD4_CAMLR   AEGARDMIAGFHQPNDLSYFGSSLSTLTYWLYSILPFSFESIILYMSAFFASLIVVPIIL  120
               ****** ****** ****. ****  *.*.* *:* ** **:*:* *:*:.*::*:**
Consensus      AEGARDXIAGFHQXNDLSXXXSSLSXLTYXXYXILPFSXESIXXYXSXFXXXLXVXPXIL

Q9S4V7_CAMJU   LANEYKRPLMGFVAALLASIANSYNRTMSGYYDTDMLVIVLPMFILFFMV-MILKKDFF   126
H7WYI6_CAMCO   IANEYKRPLMGFVAALLASIANSYNRTMSGYYDTDMLVIVLAMMIVFFMIRLILKKDLL   178
E6LAJ2_CAMUP   IANELKRPLMGLFAAFLASIAKSYNRTMAGYYDTDMLAIVLPMFILYFFIRLILRKDDF   177
B9KDD4_CAMLR   IAREYKLTTYGFIAALLGSIANSYNRTMSGYYDTDMLVLVLPMLILLTFIRLTINKDIF   180
               :*: * . * *:**:* ***:******:********.:*** *:  * *   ::** :
Consensus      XAXEXKXXXXXXGXXAAXLXSIAXSYNRTMXGYYDTDMLXXVLXMXIXXXXXXXXKDXX

Q9S4V7_CAMJU   SLIALPLFIGIYLWWYPSSYTLNVALIGLFLIYTLIFHRKEKIFYIAVIL-SLTLSNIAW  185
H7WYI6_CAMCO   SLITLPLFVGIYLWWYPSSYTLNVALLGLFFIYTLVFHIKEKTLYMAIILASITLSNIAW  238
E6LAJ2_CAMUP   SLLALPFFMGLYLWWYPSSYTLNVAFIALFTLYVLIYHRKERSFYMAALLCAITLSNIAW  237
B9KDD4_CAMLR   TLLLSPVFIMIYLWWYPSSYSLNFAMIGLFGLYTLVFHRKEKIFYLTIALMIIALSMLAW  240
               :*: * .  ::*********:**.* : ** : **::*::* :  **  : ::**: **
Consensus      XLXXXXPXFXXXYLWWYPSSYXLNXAXXXXLFXXYXLXXHXKEXXXYXXXXLXXXLSXXAW

Q9S4V7_CAMJU   FYQSTIIVILFALFALEQKRLNFVIIGILASVTLIFLILSGGVDPILYQLK-YIFRSDES  244
H7WYI6_CAMCO   FYQSAIIVILFSLFVLQNKRFSFALLGILGIATLVFLILSGGIDPILYQLKFYIFRSDES  298
E6LAJ2_CAMUP   FYQSAIIVLLFALFMLKNSFFNFKFIALLALGVLVFLALSGGIDPILYQLKFYLLRSDES  297
B9KDD4_CAMLR   QYKLALIVLLFAIFAFKEEKINFYMIWALIFISILIHLSGGLDPVLYQLKFYVFKASDV   300
               *::.::**:::*:** ::.::* * : .:*   :::** *** ** **** *::::::
Consensus      XYXXXXIVXLFXXFXXXXXXXXFXXXXXLXXXXXLXXXXXXXXLXLSGGXDPXLYQLKXYXXXXXXX
```

Figure 6A

**Sequence alignment of PglB homologs from *Campylobacter* (Cont.)**

```
Q9S4V7_CAMJU   ANLT-QGFMYFNVNQTIQEVENVDLSEFMRRISGGSEIVFLFSLFGFVWLLRK-KSMIMAL     302
H7WYI6_CAMCO   ANLA-QGFMYFNVNQTIQEVESIDLSIFMQRISGGSELVFFVSLIGFIFLVRKHKSMILAL     357
E6LAJ2_CAMUP   ASLA-RGFAYFNVNLTIQEVESIDLSTFMQRISGGSELVFLLSLFGFLWLLKKHKVMLLTL     356
B9KDD4_CAMLR   QNLKDAAFMYFNVNETIMEVNTIDPEVFMQRISSSVLVFILSFIGFILLCKDHKSMLLAL      360
                 . * ****** ** **:.:* . **;:***: * .:*:;.*:;;**: * :. .* *:;;:*
Consensus      XXLXXXXXFXYFNVNXTIXEVXXXXDXXXXFMXRISXSXXXVFXXSXXXGFXXLXXXXXMXXXL

Q9S4V7_CAMJU   PILVLGFLALKGGLRFTIYSVPVMALGFGFLLSEFKAILVKKYS----                  346
H7WYI6_CAMCO   PMLALGFLALKSGLRFTIYAVPVLALGFGFLMSLLQERKQKNNN----                  401
E6LAJ2_CAMUP   PMLLLGFLALRGGLRFTIYAVPIMALGFGFLSVQILSLIQKMRPLKETRKLRIFFYGIFP      416
B9KDD4_CAMLR   PMLALGFMALRAGLRFTIYAVPVMALGFGYFLYAFFNFLEKKQIKLSL----              408
               *:* ****:.*::.********:***::******* :   :
Consensus      PXLXLGFXALXXGLRFTIYXVPXXALGFGXXXXXXXXXXXXXXXX

Q9S4V7_CAMJU   --------------------------------------------QL-TSN               351
H7WYI6_CAMCO   --------------------------------------------TYWWAN               407
E6LAJ2_CAMUP   LFVLVLGAYFYFSQSAIYESMGVEFQKNFVSFFVEDTLLFSLLILAIFTPLIFELLWRKK     476
B9KDD4_CAMLR   ---------------------------------------------RNK                 411

Consensus      ----------------------------------------------XXXXXX

Q9S4V7_CAMJU   ----VCIF----ATILTLAPVFIHIYNYKAPTVFSQNEASLLNQLKNIANREDYVVTWWD     403
H7WYI6_CAMCO   I---GVFI----FTFLSLIPMFYHINNYKAPTVFSQNEATKLDELKKIAQREDYVVTWWD     460
E6LAJ2_CAMUP   DIRFVCSFYIVGVLLFSLWANLSHIYNYRAHTVFSYNEASILDNLKANVSREDYIVAWWD     536
B9KDD4_CAMLR   -----NILLILIAFFSISPALMHIYYYKSSTVFTSYEASILNDLKNKAQREDYVVAWWD      465
                     : :::  .  :  ** :::   *** . ***  . .*****.*;.****:*;***
Consensus      -----XXXX-----XXXXXXXXXXXXHIXXYXXXTVFXXXEAXXLXXLKXXXXREDYXVXWWD

TQ9S4V7_CAMJU  YGYPVRYYSD-KTLVDGGKHLGKDNFFPSFALSKDEQAAANMARLSVEYTEKSFYAPQND    462
H7WYI6_CAMCO   YGYPIRYYSDVKTLADGGKHLGKDNFFPSFVLSKDQVAAANMARLSVEYTEKSFYAPLND    520
E6LAJ2_CAMUP   YGYPIRYYSDVKTLADGGKHLGKDNFFPSFVLSQNPRAAANMARLSVEYTEKGFKTPYND    596
B9KDD4_CAMLR   YGYPIRYYSDVKTLIDGGKHLGKDNFFSSFVLSKEQIPAANMARLSVEYTEKSFKENYPD    525
               **** ****** *** ********** ****   ***********. *
Consensus      YGYPXRYYSDXKTLXDGGKHLGKDNFFXSFXLSXXXXXAANMARLSVEYTEKXFXXXXXD
```

Figure 6B

**Sequence alignment of PglB homologs from *Campylobacter* (Cont.)**

```
Q9S4V7_CAMJU   ILKTDILQA-MKDYNQSNVDLFLASLSKPDFKIDTPKTRDIYLYMPARMSLIFSTVASFS  521
H7WYI6_CAMCO   ILKNDLLQAMMKDYNQNNVDLFLASLSKPDFKINTPKTRDVYIYMPARMSLIFSTVASFS  580
E6LAJ2_CAMUP   -----LLEAMMKDYNYSNVNLFLAALSKEDFTLQTPKTRDIYIYMPSRMAAIFGTVASFS  651
B9KDD4_CAMLR   -----VLKAMVKDYNKTSAKDFLESLNDKDFKFDTNKTRDVYIYMPYRMLRIMPVVAQFA  580
               :*:*  :****  . **   ::  ** :*:  ****:*:**** ** *:  .**.*:.
Consensus      XLXAXXKDYNXXXXXXFLXXLXXXDFXXXTXKTRDXYXYMPXRMXXIXXXVAXFX

Q9S4V7_CAMJU   FINLDTGVL-DPFTFSTAYP--LDVKNGEIYLSNGVVLSDDFRSFKIGDNVVSVNSIVEI  578
H7WYI6_CAMCO   FVDLETGEINKPFTFSAAYP--LDVKNGEIYLSNGIALSDDFRSFKINNSTISVNSIIEI  638
E6LAJ2_CAMUP   YMSLETGELENPFVYSVAYY--LGNEDGKLVLSNNMLLHSDFRSFDLNGKNYAINSLVEF  709
B9KDD4_CAMLR   NTNPDNGEQEKSLFFSQANAIAQDKTTGSVMLDNGVEIINDFRALKVEGASIPLKAFVDI  640
                  : .   :  :**  *      .   * .:::..***  :  .  .:::::
Consensus      XXXXXXXXGXXXXXXXSXAXXXXXXXXGXXXLXNXXXXXXDFRXXXXXXXXXXXXXXXX

Q9S4V7_CAMJU   NSIKQGEYKITPD-DKAQFYIFYLKDSAIPYAQFILMDKTMFNSAYVQMFFLGNYDKNLF  637
H7WYI6_CAMCO   NSIKQGEYKITPIDDMAQFYIFYLKDSTIPYAQFILMDKTMFNSAYVQMFFLGNYDKNLY  698
E6LAJ2_CAMUP   TSVQQKYYSVVEIDKNAKYLFHIKDANIPNVQFILMDKAMYESAFVQMFFFGKYDESLY  769
B9KDD4_CAMLR   ESITNGKFYYNEIDSKAQIYLLFLRE----YKSFVILDESLYNSSYIQMFLLNQYDQDLF  696
                . :: .:  :  :   :: *  :.::  :    ::::::: .*** *:  . ::.::*:
Consensus      XSXXXXXXXXXXXXXXAXXYXXXXXXXYXXXXXXXFXXXXDXXXXSXXXQMFXXXXYDXXLX

Q9S4V7_CAMJU   DLVINSRDAKVFLKI-  652
H7WYI6_CAMCO   DLVINARDAKVFKLKI  714
E6LAJ2_CAMUP   ELIVDSKEAKVYKLKL  785
B9KDD4_CAMLR   EQITNDTRAKIYRLKR  712
                 : :  . **: :*:
Consensus      XXXXXXXXXAKXXXXXX
```

Figure 6C

**Sequence alignment of Stt3 homologs from *Pyrococcus***

```
Q8U4D2_PYRFU ---MVKTQIKEKKKDE------KVTIPLPGKIKTVLAFLVVLAFAAYGFYIRHLT-AGKY 50 (SEQ ID NO: 11)
I3RCF1_9EURY MKSLVKVEVKREKKDRKEKREIGNISRHYGKIKLALTFIVTLIFAWYAFHIRHLT-AGKY 59 (SEQ ID NO: 13)
F4HM23_PYRSN ---MVKRK----KEEK---EIKGEKREFYSKIKRMIIPIIVLGFATYGFYLRHLT-AGRY 49 (SEQ ID NO: 14)
O74088_PYRHO ---MVKSKVKK-VEKG---KEGEEKRSTYVLLKKVLIPILVFGFAIYAFYLRHLT-AGKY 52 (SEQ ID NO: 15)
Q9V250_PYRAB ---MVKTKVKEEKEEK---SEKSEGKSLYPLLKRILIPLAVIGFGIYAYYLRHLT-AGKY 53 (SEQ ID NO: 16)
F8AIG3_PYRYC ---MVKTKVKREKREEKAPE--HRPKTLVVFFKRFGIPLIVLAFATLGFYIRYLPGTGKY 55 (SEQ ID NO: 17)
                 :** :     ..                  :*     : .: *.  .:::*:*  :*:*
Consensus Seq  XVKXXXXXXXXXXXXXXXXXXXXXXXXXXKXXXXXXXXXXXFXXXXXXXXRXLXXXGXY    (SEQ ID NO: 18)

Q8U4D2_PYRFU FSDPDTFYHFEIYKLVLKEGLPRYYPMADAPFGSLIGEPLGLYILPAIFYKIISIFGYNE 110
I3RCF1_9EURY FPDPDTFYHYEIYKLVLKEGLPKYYPMSDAPFGSLIGEPLGLYILPAIFYKILSAFGYNE 119
F4HM23_PYRSN FPDPDTFYHFEIYKLVIKEGLPKYYPLSDAPFGSLIGEPLGLYILPAIFYKVISAFGYNE 109
O74088_PYRHO FPDPDTFYHFEIYKLVLKEGLPRYYPMSDAPFGSLIGEPLGLYLLPAAFYKVVSLFGYNE 112
Q9V250_PYRAB FPDPDTFYHFEIYKLVLKEGLPKYYPMAEAPFGSLIGEPLGLYILPAIFYKVVSVFGYNE 113
F8AIG3_PYRYC FIDPDTYYHYEIYKLVLKEGLPRYYSMAEAPFGSLIGEPLGLYLLPAIFYKLISAFGYTT 115
             * ****:**:******:*****:**  :::*************:*** ***::* ***.
Consensus    FXDPDTXYHXEIYKLVXKEGLPXYYXXXXAPFGSLIGEPLGLYXLPAXFYKXXSXFGYXX

Q8U4D2_PYRFU LEAFLLWPPFVGFLSVIGVYLLGRKVLNEWAGMWGAIILSVLTANFSRTFSGNARGDGPF 170
I3RCF1_9EURY FQAFLLWPPFVGFLSVIGVYLLGRKILNEWAGLWAAAILAVSTANFSRTFSGNARGDGPF 179
F4HM23_PYRSN FQAFLLWPPFVGFLSVVGIYLLGRKVLNEWAGLWAAVILSVSTANFSRTFSGNARGDGPF 169
O74088_PYRHO LQAFLLWPPFVGFLGVIAVYLLGRKVLNEWTGLWGAVVLTVSTANFSRTFSGNARGDGPF 172
Q9V250_PYRAB FQAFLMWPPFVGFLGVIAVYLLGRKVLNEWAGLWAAVILSVSTANFSRTFSGNARGDGPF 173
F8AIG3_PYRYC LQAFKLWPPTVGFLSIIATYLLARKIHGEWAGLWSAAIMSFLLAHFTRTFSGNARGDGPF 175
             ::** :*** ****.::. ***.**:  **:*:*.* :::.  *.*:*************
Consensus    XXAFXXWPPXVGFLXXXXXYLLXRKXXXEWXGXWXAXXXXXXXXAXFXRTFSGNARGDGPF

Q8U4D2_PYRFU MMLFTFSAVLMLYYLTEENKNKKIIWGTLFVLLAGISTAAWNGSPFGLMVLLGFASFQTI 230
I3RCF1_9EURY MMLFVFSMVALLYYLEEARIKRKAVWGALFVILAGLSTMAWNGSPFGLMVLLGFASLQTI 239
F4HM23_PYRSN MMLFVFSAILMFHYLRETSKTKKVLYGTLFVILASISLGAWNGSPFGLMVLLGFASFQTI 229
O74088_PYRHO MALFIFASVAMLYYLKESNKTRKIIYGTLFVLLTVISLGAWNGSPFGLMVLLGFASLQTI 232
Q9V250_PYRAB MTLFLFSLVAMLYYLKENDIKKKSLWGAVFVLLASISLGAWNGSPFGLMVLIGFASFQTI 233
F8AIG3_PYRYC LMLFLFASVAMLYYLEAKDVKRKMVYGTLFVALSVIALSAWNGSPFSLMVFLGFGALQAI 235
             : ** *: : :::**      .:* ::*::** *: ::  *******.***::**.::*:*
Consensus    XXLFXFXXXXXXXYLXXXXXXXKXXXGXXFVXLXXXXXXAWNGSPFXLMVXXGFXXXQXI
```

Figure 7A

**Sequence alignment of Stt3 homologs from *Pyrococcus* (Cont.)**

```
Q8U4D2_PYRFU ILFIFGKINELREFIKEYYPAYLGILAISYLLTIPGIGKIGGFVRFAFEVFLGLVFLAIV 290
I3RCF1_9EURY ALFIFGKIDELKKFIKEFYPAYVSVLILSYLLTIPGLAKIQSFIRFAFEVFLGLVFLAIV 299
F4HM23_PYRSN ALFIFGKISELKKFATEFYPAYLGILALGYLLTIPGIVKIGSFIKFAFEVFLGLVVLLTI 289
O74088_PYRHO ILFIFGKLEELKKFVKEFYPAYLAILAFGYALTFPGIVKIGGFIRFAFEVFLGLIFLLVI 292
Q9V250_PYRAB ALFIFGKIKELKKFVKEFYPAYLAILAIGYGLTIPGIAKIGGFIKFAFEVFLGLVLLVTI 293
F8AIG3_PYRYC VLFVFGRIEELREFIKLYYPTYLTVLLLGYLLTFPRIVAVKGHILFALKVFLGLAGLTVL 295
              **:**::.**::* . :**:*: :* :.* **:* :  : ..: **::*****  *  :
Consensus    XLFXFGXXXELXXFXXXXYPXYXXXLXXXYXLTXPXXXXXXXXXXFAXXVFLGLXXLXXX

Q8U4D2_PYRFU MLYGGKYLNYSDKKHRFAVVAVIVIAGFAGAYIYVGPKLFTLMGGAYQSTQVYETVQELA 350
I3RCF1_9EURY MLYGEKFLNYSDKKHRFLVVAIIVLIGFAGAYAYVGPKLFRLMGGAYQSTQVYQTVQELA 359
F4HM23_PYRSN MLYGGRYLNYSDKKHRFLVVAVVVLIGFAGAYAYVGPKLFRLMGGAYQSTQVYETVQELA 349
O74088_PYRHO MLYGGRYLNYSDKKHRFLVVTIIVLLGFGGAYAYVGPKLFRLMGGAYQSTQVYETVQELA 352
Q9V250_PYRAB MLYGGKFLNYSDKKHRFAVVAVIVLLGFAGAYAYVGPKLFRLMGGAYQSTQVYQTVQELA 353
F8AIG3_PYRYC MLYGGKWLNYSDRRHRFAVVAVVTLLGFVGAYIYVGPKLFSLMAGAYQSTQVYETVQELA 355
             **** ::*****::*** **::::: ** *** ******* **.*********:******
Consensus    MLYGXXXLNYSDXXHRFXVVXXXXXXGFXGAYXYVGPKLFXLMXGAYQSTQVYXTVQELA

Q8U4D2_PYRFU KTDWGDVKVYYGVEKPNGIVFFLGLVGAMIVTARYLYKLFKDGRRPHEELFAITFYVMSI 410
I3RCF1_9EURY KTSMQDIKLYYGVEKANGLIFFLSIPGFLIMLSLYLIGLWSKSESPNKELLGITFYVMSI 419
F4HM23_PYRSN KTTMRDIKVYYGVENPNGLIFFLSIPGIIIILVKYLVDLFRKSESSNETLFAAVFYIMSI 409
O74088_PYRHO KTTIGDVKAYYGVESGNGLIFFLSIPGLLILLTKYLYDLFKKAKSDNETLFALVFYTMSL 412
Q9V250_PYRAB KTTLSDIKLYYGVEGNNGLVFFLSIPGFLIILGLYLNALLKKSESSNEYMLSLVFYIMSL 413
F8AIG3_PYRYC KTTLGDIKAYYGIKGTDGIVFFMSLAGVLVLLYRYLTTLLREGRSSHEYLFALTLYGMSL 415
             **   *:* ***::  :*::**:.: * :::   **  *   ...  .: ::. .:* **:
Consensus    KKXXXDXKXYYGXXXXXGXXFFXXXXGXXXXXXXYLXXLXXXXXXXXXXXXXXXXYXMSX

Q8U4D2_PYRFU YLLWTAARFLFLASYAIALMSGVFAGYVLETVEKMKESIPIKAALGGVIAIMLLLIPLTH 470
I3RCF1_9EURY YLMSLAVRFLFLASYAIALFAGILVGYGLEVIEKMKENVGIKAALAIVISIMILLIPITH 479
F4HM23_PYRSN YLLSLAVRFLFLASYAIALFAGIFAGFVIEIVEKMKESIGIKAALGIVISIMILMIPITH 469
O74088_PYRHO YLLYLAVRFLFLASYAVALFFGIFIGFSMDVIEKMKENIGIKAALGIVLSLMILVIPFVH 472
Q9V250_PYRAB YLLSLAVRFLFLASYAIALFSGIFAGFTMEVIEKMKENVGIKAALGIAIAVMILMVPITH 473
F8AIG3_PYRYC YLVWSAVRFLFLASGAVILMAGVFAGELFRIIEDMKEKATTKITLGLALTVMLLLMPVTG 475
             **:  *.******* *: *: *:: *  :  :*.***.   * :*. .:::*:*::*..
Consensus    YLXXXAXRFLFLASXAXXLXXGXXXGXXXXXXEXMKEXXXXKXXLXXXXXXMXLXXPXXX
```

Figure7B

**Sequence alignment of Stt3 homologs from *Pyrococcus* (Cont.)**

```
Q8U4D2_PYRFU GPLLAQSAKSMRTTEIETSGWEDALKWLRENTPEYSTATSWWDYGYWIESSLLGQRRASA 530
I3RCF1_9EURY GPVLARSAKAMSKTEVETSGWEQALKWLRNNTPKYATATSWWDYGYWIESSLLGNRRASA 539
F4HM23_PYRSN APVLARSARSLSRTEVETTGWEQVLKWLRSNTSQYATATSWWDYGYWIESSLLGNRRASA 529
O74088_PYRHO APVLARSARALKNTEIEVTGWEQALKWLRSNTSKYATATSWWDYGYWIESSLLGNRRASA 532
Q9V250_PYRAB GPVIARNAKALKVSEIETTGWEQVLKWLNENTSKYATATSWWDYGYWIESSLLGHRRASA 533
F8AIG3_PYRYC VPLMINTAKAMKTSEVERSGWEDALMWLRENTSEYATATSWWDYGYWIESSLLGNRRASA 535
              *:: ..*:::  :*:* :***:.* **..** :*:*****************.*****

Consensus    XPXXXXXAXXXXXXEXEXXGWEXXLXWLXXNTXXYXTATSWWDYGYWIESSLLGXRRASA

Q8U4D2_PYRFU DGGHARDRDHILALFLARDGNISEVDFESWELNYFLVYLNDWAKFNAISYLGGAITRREY 590
I3RCF1_9EURY DGGHARDRDHILALFLARDGNVSEVDFESWELNYFIVYLNDWAKFNAISYLGGAITKREY 599
F4HM23_PYRSN DGGHARDRDHILALFLARDGNVSEVDFESWELNYFIVYLNDWAKFNAISYLGGALTRREY 589
O74088_PYRHO DGGHARDRDHILALFLARDGNISEVDFESWELNYFIIYLNDWAKFNAISYLGGAITRKEY 592
Q9V250_PYRAB DGGHARDRDHILALFLARDGNVSEVDFESWELNYFIIYLNDWAKFNAISYLGGAITRREY 593
F8AIG3_PYRYC DGGHARDRDHILALFLARDGNVSEVDFESWELNYFIAYMQDWRKFNAISYLGGAITRREY 595
             *********************:*************: *::** **********:*::**

Consensus    DGGHARDRDHILALFLARDGNXSEVDFESWELNYFXXYXXDWXKFNAISYLGGAXTXXEY

Q8U4D2_PYRFU NGDESGRGAVTTLLPLPRYGEKYVNLYAKVIVDVSNSS----VKVTV-GDRECDPLMVTF 645
I3RCF1_9EURY SGDEKGRGSIPTIILAPRFGEQYINPYNGVSIKVLNNSQ---VTVTI-GSTTCSPLMTVF 655
F4HM23_PYRSN KGDETGRGSVTSILITQGAGNVYVNPYAGITIKVVEENKTRKVVVNI-GRLECSPMTTVV 648
O74088_PYRHO NGDENGRGRVTTILLTQAAGNVYVNPYARIVIKVIQQNKTRRIAVNI-GQLECSPILSVA 651
Q9V250_PYRAB NGDETGRGQVTTILPLQGSGGIYVNPYAGISVRVVQSNTTSKVTVNVRGRAECSPIYTLL 653
F8AIG3_PYRYC KGDESGRGGVTTIVLLPGANGVYSNPYMGLTLRVENRT--------VKVNGYCEPMESVI 647
             .***.*** : :::         * * *  : : * : .         :     *.*:

Consensus    XGDEXGRGXXXXXXXXXXXXXXYXNXYXXXXXXVXXXXXXXXXXXXXXXXXXCXPXXXXX

Q8U4D2_PYRFU TPSGKTIKGTGTCSDGNAFPYVLHLTPTIGVLAYYKVATANFIKLAFGVPASTIPGFSDK 705
I3RCF1_9EURY IPGNKKVKGQGSCTNGGSFPFVVYLTPTLGVISYYKVATSNFLKLAYGIPASKEPGFTDK 715
F4HM23_PYRSN FPGNIHIKGTGSCNNGSSFPYVVYLTPSLGIIAYYKVATSNFIKLAFGIPVSNYKGFTEK 708
O74088_PYRHO FPGNIKIKGSGRCSDGSPFPYVVYLTPSLGVLAYYKVATSNFVKLAFGIPTSSYSEFAEK 711
Q9V250_PYRAB IPGNKKIPGNGRCSDGSPFPYVLYLAPNFGLITYYKVATSNFIKLAFNIPISKYSGFTEK 713
F8AIG3_PYRYC LPSNTHIKGSGQCETGSYFPYVAYVTPTFAVLAYYKVATSNFLKLAFGIPASKEANFTEK 707
              *.   : * * *  *  **:* :::*.:.:::******:**:***: :* *.   *::*

Consensus    XPXXXXXXGXGXCXXGXXFPXVXXXXPXXXXXXYYKVATXNFXKLAXXXPXSXXXXFXXK
```

Figure 7C

**Sequence alignment of Stt3 homologs from *Pyrococcus* (Cont.)**

```
Q8U4D2_PYRFU   LFSNFEPVYESGNVIVYRFTPFGIYKIEENINGTWKQVYNLTPGKHELKLKLYISAFGRDIE   765
I3RCF1_9EURY   LFSNFKMVYQEGNVVIYEFRPFAIYKLQEFTNGTWKTITTLSPGKHTLKLYISAFGRDIK    775
F4HM23_PYRSN   LFSNFVPVYQAGNVIVYEFRPFAIYGMEELVNGSWRYIGYLTPGKHTLRLYISAFGRDIK    768
O74088_PYRHO   LFSNFIPVYQYGSVIVYEFRPFAIYKIEDFINGTWREVGKLSPGKHTLRLYISAFGRDIK    771
Q9V250_PYRAB   LYSNFVPVYGYGNVIVYEFRPFAIYRIEELINGTWKAVNSLTPGKHELKLYISAFGRDIR    773
F8AIG3_PYRYC   LYANFELVFQSGDVIVYEFKPFAVYKAEELVNGTWRAVETLTPGEHTLKLYISAFGRDVK    767
               *::**  *:  *.*:::*.* **..:*        ::   *.:**:* *:***********
Consensus      LXXNFXXXVXXXGXVXXYXFXPFXXYXXXXXNGXWXXXXXLXPGXHXLXLYISAFGRDXX

Q8U4D2_PYRFU   NATLYIYAINNEKIIEKIKIAEISHMDYLNEYPIAVNVTLPNATSYRFVLVQKGPIGVLL    825
I3RCF1_9EURY   NATLYIDAIKDNRTIQRIKIGEIKYMSHLNETPITVNVTLPDADKYKFVLVQKGPVGVLT    835
F4HM23_PYRSN   NATLYVYAINGTEITAKIRLTKIDYMNHLNEYPITVNVTLPPAQKYRFVLVQKGPVGVLT    828
O74088_PYRHO   NATLYVYALNGTKIIKRIKVGEIKYMNHLEEYPIIVNVTLPTAQKYRFILAQKGPVGVLT    831
Q9V250_PYRAB   NATLYVYAIGNK--TEKIKIGEIEYMNHLNEKPIIVNVTLPKAEKYRLVLVQKGPVGVLT    831
F8AIG3_PYRYC   NATLYVEALKDGKVVERIKVAEGLYIDHLNEKPIEVKVNLPEADEYRFVLVQKGPXGVLX    827
               ******.*:      ::*:  :  :::.:** * *::***  . :.*:: .**** **
Consensus      NATLYXXAXXXXXXIXXXXXXXXXXLXEXPIXVXVXLPXAXXYXXXLXQKGPXGVLX

Q8U4D2_PYRFU   DAPKVNGEIRSPTNILREGESGEIELKVGVDKDYTADLYLRATFIYLVRKSGKDNEDYDA    885
I3RCF1_9EURY   APPKVNGKIANPVRVLNDGESGRLELKVGVDKDYKADLYLRATFIYLVRKSGTSNDDYNA    895
F4HM23_PYRSN   GPPKLNGKIVNPISVLKEGEEGELELKVGVDKNYTADLYLRATFIYLVRKGGTSNEDYNA    888
O74088_PYRHO   GPVRVNGKITNPAYIMREGESGRLELKVGVDKEYTADLYLRATFIYLVRKGGKSNEDYDA    891
Q9V250_PYRAB   GPPKLNGEIANPIRIAREGEKGTLSLKVGVDKDYTADLYLRATFIYLVRKEGKSNDDYNA    891
F8AIG3_PYRYC   SAPRVNGSIANPIKVLGEGQSGTLELKAAFDRDYTADLYLRVTFIYLRXTFIYLVRKSGRSNDDIDA    887
               .  ::**.*    :  ..*: *  :** .::*:************   .* * .: : *
Consensus      XXXXXNGXIXXPXXXXXXGXXGXXXXLKXXXXDXXYXADLYLRXTFIYLVRKXGXXNXDXXA

Q8U4D2_PYRFU   AFEPQMDVFFITKIGENIQLKEGENTVKVRAELPEGVISSYKDELQRKYGDKLIIRGIRV    945
I3RCF1_9EURY   AFEPHMDVFFITKLKSGISLHKGENEVTVEAKMPENVISDYKKKLEAEYGDKLIIRGIRV    955
F4HM23_PYRSN   AFEPHMDVFFISRVKEGIKLHPGDNYVKAHVEMPKGVISSYKEELEKKYGDRLIIRGIRV    948
O74088_PYRHO   SFEPHMDTFFITKLKEGIKLRPGENEIVVNAEMPKNAISSYKEKLEKEHGDKLIIRGIRV    951
Q9V250_PYRAB   AFEPHMDTFFITKLKGGIKLHKGDNVVTAELNMPNGVISSYKEKLEKEYGDKLIIRGIRV    951
F8AIG3_PYRYC   AFEPHMDTFFAAKLAEGLKLKKGEDTITVNAGLPAGVISYYEEKLALYGDRLIIRGIRV    947
               :***.:*:**       .:*   :  : .     .:* ** :* : *.::*********
Consensus      XFEPXMDXFFXXXXXXXXLXXGXXXXXXXXXXPXXXISXYXXXLXXXXGDXLIIRGIRV
```

Figure 7D

**Sequence alignment of Stt3 homologs from *Pyrococcus* (Cont.)**

```
Q8U4D2_PYRFU EPVFIAEKEYLMLEVSASAPHH--- 967
I3RCF1_9EURY EPVFIAEKEYVMLEVRASAPHHSSE 980
F4HM23_PYRSN EPVFIAEKEYTMLEVSASAPHHSSE 973
O74088_PYRHO EPVFIVEKEYTMIEVSASAPHHSSE 976
Q9V250_PYRAB EPVFIAEKEYVMAEVRASAPHHGSE 976
F8AIG3_PYRYC EPVFIADKAYTIWEVRASAPHHGSE 972
             *****.:* * : ** ******
Consensus    EPVFIXXKXYXXXEVXASAPHHXXX
```

Figure 7E

**Sequence alignment of Stt3 homologs from *Leishmania***

```
Q9U5N8_LEIMA MAAASNVNAPESNVMTTRSAVAPPSTAAPKEASSETLLIGLYKMPSQTRSLIYSSCFAVA 60 (SEQ ID NO: 19)
E9BRZ2_LEIDB -------------------------------------------MSSQTRSIIYSSCFAVA 17 (SEQ ID NO: 21)
A4IB10_LEIIN -------------------------------------------MSSQTRSIIYSSCFAVA 17 (SEQ ID NO: 22)
E9B5Z4_LEIMU -------------------------------------------MSSQTRSLIYSSCFAVV 17 (SEQ ID NO: 23)
A4HMD6_LEIBR --------------MVTERGAATPSTAASGEAPSETLLLGEYKVSLHARSTIYTACFAVP 46 (SEQ ID NO: 24)
                                                        :  ::** **::****

Consensus                                                  XXXXXXSTXYTXXFAVP    (SEQ ID NO: 25)

Q9U5N8_LEIMA MAIALPIAYDMRVRSIGVYGYLFHSSDPWFNYRAAEYMSTHGWSAFFSWFDYMSWYPLGR 120
E9BRZ2_LEIDB MAIALPIAYDMRVRSIGVYGYLFHRSDPWFNYRAAEYMSTHGWSAFFSWFDYMSWYPLGR 77
A4IB10_LEIIN MAIALPIAYDMRVRSIGVYGYLFHRSDPWFNYRAAEYMSTHGWSAFFSWFDYMSWYPLGR 77
E9B5Z4_LEIMU MAIGLSIAYDMRVRSIGVYGYLFHSSDPWFNYRAAEYMSTHGWSAFFSWFDYMSWYPLGR 77
A4HMD6_LEIBR MAILFPIAYKMRVRSIDVYGYLFHRNDPWFNYRAAEYMSAHGWSAFFSWFDYMSWYPLGR 106
             *** : ***.****** ******* .*************:********************

Consensus    MAIXXXIAYXMRVRSIXVYGYLFHXXDPWFNYRAAEYMSXHGWSAFFSWFDYMSWYPLGR

Q9U5N8_LEIMA PVGSTTYPGLQLTAVAIHRALAAAGMPMSLNNVCVLMPAWFSLVSSAMAALLAHEMSGNM 180
E9BRZ2_LEIDB PVGSTTYPGLQLTAVAIHRALAAAGMPMSLNNVCVLMPAWFSLVSSAMVALLAHELSGNM 137
A4IB10_LEIIN PVGSTTYPGLQLTAVAIHRALAAAGMPMSLNNVCVLMPAWFSLVSSAMVALLAHELSGNM 137
E9B5Z4_LEIMU PVGSTTYPGLQFTAVAIHRALAAAGMPMSLNDVCVLIPAWFSLLSSAMVALLAHEISGNM 137
A4HMD6_LEIBR PVGTTTYPGLQLTAVAIHRALAAAGVPMSLNNVCVLIPAWFSLVSSAMVALLAHEMTGNM 166
             ***:*******:*************:*****:****:******:****.******::***

Consensus    PVGXTTYPGLQXTAVAIHRALAAAGXPMSLNXVCVLXPAWFSLXSSAMXALLAHEXXGNM

Q9U5N8_LEIMA AVASISSILFSVVPAHLMRSMAGEFDNECIAVAAMLLTFYCWVRSLRTRSSWPIGVLTGV 240
E9BRZ2_LEIDB AVASISSILFSVVPAHLMRSMAGEFDNECIAVAAMLLTFYCWVRSLRTRSSWPIGVLTGV 197
A4IB10_LEIIN AVASISSILFSVIPAHLMRSMAGEFDNECIAVAAMLLTFYCWVRSLRTRSSWPIGVLTGV 197
E9B5Z4_LEIMU AVASVSSILFSVVPAHLMRSMAGEFDNECIAVTAMLLTFYCWVRSLRTRSSWPIGVLTGV 197
A4HMD6_LEIBR ATSSISSILFSVVPAHLMRSMAGEFDNECIAVAAMLLTFYLWVRSLRTRCSWPIGILTGI 226
             *.:*:*******:*******************:******* ********.*****:***:

Consensus    AXXSXSSILFSVXPAHLMRSMAGEFDNECIAVXAMLLTFYXWVRSLRTRXSWPIGXLTGX
```

Figure 8A

**Sequence alignment of Stt3 homologs from *Leishmania* (Cont.)**

```
Q9U5N8_LEIMA AYGYMAAAWGGYIFVLNMVAMHAGISSMVDWARNTYNPSLLRAYTLFYVVGTAIAVCVPP 300
E9BRZ2_LEIDB AYGYMVAAWGGYIFVLNMVAMHAGISSMVDWARNTYNPSLLRAYTLFYVVGTAIAVCVPP 257
A4IB10_LEIIN AYGYMVAAWGGYIFVLNMVAMHAGISSMVDWARNTYNPSLLRAYTLFYVVGTAIAVCVPP 257
E9B5Z4_LEIMU AYGYMVAAWGGYIFVLNMVAMHAGISSMVDWARNTYNPSLLRAYTLFYVVGTAIAVCVPP 257
A4HMD6_LEIBR AYGYMVAAWGGYIFVLNMVAMHAGISSMVDWARNTYNPSLLRAYALFYVVGTAIATRVPP 286
             *****.*********************************:**********. ***

Consensus    AYGYMXAAWGGYIFVLNMVAMHAGISSMVDWARNTYNPSLLRAYXLFYVVGTAIAXXVPP

Q9U5N8_LEIMA VGMSPFKSLEQLGALLVLVFIFGQSVCEAQRRRLGIARLSKEGVALLIRIDAAFFVGIVA 360
E9BRZ2_LEIDB VGMSPFKSLEQLGALLVLLFIFGQSVCEAQRRRLEIARFSKEGVALLIRIYAAFFVGIVA 317
A4IB10_LEIIN VGMSPFKSLEQLGALLVLLFIFGQSVCEAQRRRLEIARFSKEGVALLIRIYAAFFVGIVA 317
E9B5Z4_LEIMU VGMSPFKSLEQLGALLVLLFIFGQALCEAQRSRLGIERFSKEGVALLIRIYAAFFVGIVA 317
A4HMD6_LEIBR VGMSPFRSLEQLGALVVLLFLCGLQACETQRSRLGVERFSTEGVSLLVRIYAAFFVGIVA 346
             ******:*******:**:*: *    **:** ** : *:*.***:**:** *********

Consensus    VGMSPFXRSLEQLGAXVVXLXXCXXXACXTQXSRXXXEXFXTEGXSLXRIXAAFFVGIVA

Q9U5N8_LEIMA VATIAPAGFFKPLSLQANAIITGVSRTGNTLVDILLAQDASNLLMVWQLFLFPFLGWVAG 420
E9BRZ2_LEIDB VATIAPAGFFKPLSLQASAIITGVSRTGNTLVDTLIAQDASNLLIVWQLFLFPVFGWVAG 377
A4IB10_LEIIN VATIAPAGFFKPLSLQASAIITGVSRTGNTLVDTLIAQDASNLLIVWQLFLFPVFGWVAG 377
E9B5Z4_LEIMU VAAVAPAGFFKPLSLQATAIIAGVSRTGNTLVDILIAQDASNLLIVWQLFLFPLLGWVVG 377
A4HMD6_LEIBR VVAMAPAGFFKPLSLQAHAMIAGAQPTGNTLVDMLIAKDASSLLVAWELLLFPFFGWMVG 406
             *.::************ *:*:*.. ******* *:*:***.**:.*:*:***.:**:.*

Consensus    VXXXAPAGFFKPLSLQAXAXIXGXXXTGNTLVDXLXAXDASXLLXXWXLXLFPXXGWXXG

Q9U5N8_LEIMA MSAFLRELIRNYTYAKSFILMYGVVGMYFASQSVRMMVMMAPVACIFTALLFRWALDYLL 480
E9BRZ2_LEIDB MSAFLTELVRNYTYTKSFMLMYGVVGLYFASQSVRMMVMMAPVACIFTALLFRWALDYLL 437
A4IB10_LEIIN MSAFLTELVRNYTYTKSFMLMYGVVGLYFASQSVRMMVMMAPVACIFTALLFRWALDYLL 437
E9B5Z4_LEIMU MSLFLTELVRNFTYAKSFILMYGVVGIYFASQSVRMMVMMAPVACIFTALLFRWTLDYLL 437
A4HMD6_LEIBR MGAFLTELVQSFTYTKSFMLMYGAVGMYFASQSVRMMVMMAPVACIFTALLFCLALDYAL 466
             *. ** **:.:**:***:****.**:************************   :*** *

Consensus    MXXFLXELXXXXTYXKSFXLMYGXVGXYFASQSVRMMVMMAPVACIFTALLFXXXLDYXL
```

Figure 8B

**Sequence alignment of Stt3 homologs from *Leishmania* (Cont.)**

```
Q9U5N8_LEIMA GSLFWAEMPPSFDTDAQRGRQQQTAEESEAETKRKEEEYNTMQVKKMSVRMLPFMLLLLL 540
E9BRZ2_LEIDB GSLFWAEMPPCFDTDAQRGRQQQTAEEAEAETKRKEEEYNTMQVKKMTTRMLPFMFLLLL 497
A4IB10_LEIIN GSLFWAEMPPCFDTDAQRGRQQQTAEEAEAETKRKEEEYNTMQVKKMTTRMLPFMFLLLL 497
E9B5Z4_LEIMU GSFFWAEMPLSLDTDAQRGRQQQTAEEAEAETKRKEEEYNTMQVKKMTVRMVPFMILLLL 497
A4HMD6_LEIBR GALFWAEIPPSIDSDAQQELHQQTAEAA-KTKKRKQEEYTTMQVKMISVRMMPLMLLVLL 525
             *::****:* .:*:***:  :***** :    .***:***.***** ::.**:*:*:*:**
Consensus    GXXFWAEXPXXXDXDAQXXXXQQTAEXXXXXXKRKXEEYXTMQVKXXXXRMXPXMXLXLL

Q9U5N8_LEIMA FRLSGFIEDVAAISRKMEAPGIVFPSEQVQGVSEKKVDDYYAGYLYLRDSTPEDARVLAW 600
E9BRZ2_LEIDB FRLSGFIEDVAAISREMEAPGIVFPSGQVQGVSEKKVDDYYAGYLYLRDNTPEDARILAW 557
A4IB10_LEIIN FRLSGFIEDVAAISREMEAPGIVFPSGQVQGVSEKKVDDYYSGYLYLRDNTPEDARILAW 557
E9B5Z4_LEIMU FRLSGFIEDVAAISREMESPGIIFPRGQVQGMPEDKVDDYYAGYLYLRENTPEDARILAW 557
A4HMD6_LEIBR FRFSGFIEDVAAISREIEVPGIVFPGSMVQGLSDDMIDDYYAGYLYLRDNTPADARVLSW 585
             **:************::* ***:**   ***: :. :****:******:.** ***:*:*
Consensus    FRXSGFIEDVAAISRXXEXPGIXFPXXXVQGXXXXXXDDYYXGYLYLRXXTPXDARXLXW

Q9U5N8_LEIMA WDYGYQITGIGNRTSLADGNTWNHEHIATIGKMLTSPVAEAHSLVRHMADYVLISAGDTY 660
E9BRZ2_LEIDB WDYGYQITGIGNRTSLADGNTWNHEHIATIGKMLTSPVAEAHSLVRHMADYVLIFAGDTY 617
A4IB10_LEIIN WDYGYQITGIGNRTSLADGNTWNHEHIATIGKMLTSPVAEAHSLVRHMADYVLIFAGDTY 617
E9B5Z4_LEIMU WDYGYQITGIGNRTSLADGNTWNHEHIATIGKMLTSPVAEAHSLVRHMADYVLIFSGDKY 617
A4HMD6_LEIBR WDYGYQITGIGNRTSLADGNTWNHEHIATIGKMLTSPVAEAHSLVRHMADYVLIFAGDMH 645
             ****************************************************** :** :
Consensus    WDYGYQITGIGNRTSLADGNTWNHEHIATIGKMLTSPVAEAHSLVRHMADYVLIXXGDXX

Q9U5N8_LEIMA FSDLNRSPMMARIGNSVYHDICPDDPLCSQFVLQKRPKAAAAKRSRHVSVDALEED-DTA 719
E9BRZ2_LEIDB FSDLNRSPHMARIGNSVYRDICPHDPLCSRFVLQKRPKAAAAKRSRHVSVDELEEE-DNA 676
A4IB10_LEIIN FSDLNRSPHMARIGNSVYRDICPHDPLCSRFVLQKRPKAAAAKRSRHVSVDELEEE-DNA 676
E9B5Z4_LEIMU FSDLNRSPMMARIGNSVYRDICPNDPLCSQFVLQKRRKVAAAKRSRHVTVNEQEED-DNP 676
A4HMD6_LEIBR FSDLINSPMMARIGNSVYHDICPNDPLCSRFVFQEKRKIAPARSGRHINLAKLGDDEEET 705
             **** .** *********:****.*****:**:*:: * * *: .**:.:    :: :
Consensus    FSDLXXSPXMARIGNSVYXDICPXDPLCSXFVXQXXXKXAXAXXXRHXXXXXXXXXXXXX
```

Figure 8C

**Sequence alignment of Stt3 homologs from *Leishmania* (Cont.)**

```
Q9U5N8_LEIMA    EHMVYEPSSLIAKSLIYHLHSTGVVTGVTLNETLFQHVFTSPQGLMRIFKVMNVSTESKK  779
E9BRZ2_LEIDB    EHVVYEPSSLMAKSLIYHLHSAGVVTGVTLNETLFQHVFTSAQGLIRIFKVMNVSEESKK  736
A4IB10_LEIIN    EHVVYEPSSLMAKSLIYHLHSAGVVKGVTLNETLFQHVFTSAQGLIRIFKVMNVSEESKK  736
E9B5Z4_LEIMU    ESVVYEPSSLMAKSLIYHLHSTGVVEGVMLDETLFQNVFTSTQGFMRIFKVMNVSAESKK  736
A4HMD6_LEIBR    QNVEYEPSPLMAKSLIYHLHSAGVKEGVTLNDKLFQHVYTSAHGLMRIFKVMNVSAESKK  765
                 :  * ****  *:************:**   ** *  :: *** . *:.* *  :*:.*********

Consensus       XXXXYEPSXLXAKSLIYHLHSXGVXXGVXLXXXLFQXVXTSXXGXXRIFKVMNVSXESKK

Q9U5N8_LEIMA    WVADSANRVCHPPGSWICPGQYPPAKEIQEMLAHQHTNFKDLLDPRTTWSGSRR-----   833
E9BRZ2_LEIDB    WVADPANRVCHPPGSWICPGQYPPAKEIQEMLAHQHTNFKDLLDAMNDLEREQALNKE    794
A4IB10_LEIIN    WVADPANRVCHPPGSWICPGQYPPAKEIQEMLAHQHTNFKDLLDAMNDLEREQALNKE    794
E9B5Z4_LEIMU    WVADPANRVCRPPGSWICPGQYPPAKEIQEMLAHQNTNFKDLLDAMNDLEQAQALNKV    794
A4HMD6_LEIBR    WVADPANRVCHPPGSWICPGQYPPAKEIQEMLAHRYTSLKDLVDSMSDSEREGTLNGE    823
                ****  ***** :***************************  . . .   .

Consensus       WVADXANRVCXPPGSWICPGQYPPAKEIQEMLAHXXTXXKDLXDXXXXXXXXXXXXXXX
```

Figure 8D

| UniProtKB Entry No. | Entry name | Protein names | Gene names | Organism | EMBL Acc. No. |
|---|---|---|---|---|---|
| Q2KJI2 | STT3A_BOVIN | Dolichyl-diphosphooligosaccharide--protein glycosyltransferase subunit STT3A (Oligosaccharyl transferase subunit STT3A) (STT3-A) (EC 2.4.1.119) | STT3A | Bos taurus (Bovine) | BC105328; |
| P46977 | STT3A_HUMAN | Dolichyl-diphosphooligosaccharide--protein glycosyltransferase subunit STT3A (Oligosaccharyl transferase subunit STT3A) (STT3-A) (EC 2.4.1.119) (B5) (Integral membrane protein 1) (Transmembrane protein TMC) | STT3A ITM1 TMC | Homo sapiens (Human) | L38961;L47337;AK290040;AK290657;BT007100;CH471065;BC020965;BC048348; |
| P46978 | STT3A_MOUSE | Dolichyl-diphosphooligosaccharide--protein glycosyltransferase subunit STT3A (Oligosaccharyl transferase subunit STT3A) (STT3-A) (EC 2.4.1.119) (B5) (Integral membrane protein 1) | Stt3a Itm1 | Mus musculus (Mouse) | L34260;BC037612; |
| Q5RCE2 | STT3A_PONAB | Dolichyl-diphosphooligosaccharide--protein glycosyltransferase subunit STT3A (Oligosaccharyl transferase subunit STT3A) (STT3-A) (EC 2.4.1.119) | STT3A | Pongo abelii (Sumatran orangutan) (Pongo pygmaeus abelii) | CR858329; |
| Q8TCJ2 | STT3B_HUMAN | Dolichyl-diphosphooligosaccharide--protein glycosyltransferase subunit STT3B (Oligosaccharyl transferase subunit STT3B) (STT3-B) (EC 2.4.1.119) (Source of immunodominant MHC-associated peptides homolog) | STT3B SIMP | Homo sapiens (Human) | AY074880;AK027789;AK075380;BC015880 |
| Q3TDQ1 | STT3B_MOUSE | Dolichyl-diphosphooligosaccharide--protein glycosyltransferase subunit STT3B (Oligosaccharyl transferase subunit STT3B) (STT3-B) (EC 2.4.1.119) (B6dom1 antigen) (Source of immunodominant MHC-associated peptides) | Stt3b Simp | Mus musculus (Mouse) | AK018758;AK145674;AK154979;AK152899;AK170079;BC003206;BC013054;BC052433; |
| P46975 | STT3_CAEEL | Oligosaccharyl transferase subunit STT3 homolog | T12A2.2 | Caenorhabditis elegans | FO080619; |
| Q54NM9 | STT3_DICDI | Dolichyl-diphosphooligosaccharide--protein glycosyltransferase subunit STT3 (Oligosaccharyl transferase subunit STT3) (EC 2.4.1.119) | stt3 DDB_G0285159 | Dictyostelium discoideum (Slime mold) | AAFI02000074; |

Figure 9A

| UniProtKB Entry No. | Entry name | Protein names | Gene names | Organism | EMBL Acc. No. |
|---|---|---|---|---|---|
| O94335 | STT3_SCHPO | Dolichyl-diphosphooligosaccharide--protein glycosyltransferase subunit stt3 (Oligosaccharyl transferase subunit stt3) (EC 2.4.1.119) | stt3 SPBC1271.02 | Schizosaccharomyces pombe (strain 972 / ATCC 24843) (Fission yeast) | AB015232;CU329671; |
| P39007 | STT3_YEAST | Dolichyl-diphosphooligosaccharide--protein glycosyltransferase subunit STT3 (Oligosaccharyl transferase subunit STT3) (EC 2.4.1.119) | STT3 YGL022W | Saccharomyces cerevisiae (strain ATCC 204508 / S288c) (Baker's yeast) | D28952;Z72544;BK006941; |
| Q5ALU8 | Q5ALU8_CANAL | Putative uncharacterized protein STT3 | STT3 CaO19.1478 CaO19.9053 orf19.1478 | Candida albicans (strain SC5314 / ATCC MYA-2876) (Yeast) | AACQ01000008;AACQ01000007; |
| J3NKV9 | J3NKV9_GAGT3 | Oligosaccharyl transferase STT3 subunit (Uncharacterized protein) | GGTG_01900 | Gaeumannomyces graminis var. tritici (strain R3-111a-1) (Wheat and barley take-all root rot fungus) | GL385395; |
| B2WCM5 | B2WCM5_PYRTR | Oligosaccharyl transferase stt3 subunit | PTRG_07734 | Pyrenophora tritici-repentis (strain Pt-1C-BFP) (Wheat tan spot fungus) (Drechslera tritici-repentis) | DS231622; |
| C0NFY5 | C0NFY5_AJECG | Oligosaccharyl transferase stt3 subunit | HCBG_01801 | Ajellomyces capsulata (strain G186AR / H82 / ATCC MYA-2454 / RMSCC 2432) (Darling's disease fungus) (Histoplasma capsulatum) | GG663364; |
| I7ZPM0 | I7ZPM0_ASPO3 | Oligosaccharyltransferase, STT3 subunit | | Aspergillus oryzae (strain 3.042) (Yellow koji mold) | AKHY01000199; |
| A1C3Y4 | A1C3Y4_ASPCL | Oligosaccharyl transferase subunit (Stt3), putative | ACLA_057800 | Aspergillus clavatus (strain ATCC 1007 / CBS 513.65 / DSM 816 / NCTC 3887 / NRRL 1) | DS026990; |

Figure 9B

| UniProtKB Entry No. | Entry name | Protein names | Gene names | Organism | EMBL Acc. No. |
|---|---|---|---|---|---|
| C5FX11 | C5FX11_ARTOC | Oligosaccharyl transferase stt3 subunit | MCYG_07670 | Arthroderma otae (strain ATCC MYA-4605 / CBS 113480) (Microsporum canis) | DS995707; |
| F2RXK5 | F2RXK5_TRIT1 | Oligosaccharyl transferase subunit Stt3 | TESG_03514 | Trichophyton tonsurans (strain CBS 112818) (Scalp ringworm fungus) | GG698492; |
| C6HL61 | C6HL61_AJECH | Oligosaccharyl transferase stt3 subunit | HCDG_06942 | Ajellomyces capsulata (strain H143) (Darling's disease fungus) (Histoplasma capsulatum) | GG692430; |
| F2SIZ8 | F2SIZ8_TRIRC | Oligosaccharyl transferase STT3 subunit | TERG_01982 | Trichophyton rubrum (strain ATCC MYA-4607 / CBS 118892) (Athlete's foot fungus) | GG700649; |
| H8WX50 | H8WX50_CANO9 | Stt3 oligosaccharyltransferase complex component | CORT_0A09700 | Candida orthopsilosis (strain 90-125) (Yeast) | HE681719; |
| G2WYZ0 | G2WYZ0_VERDV | Oligosaccharyl transferase STT3 subunit | VDAG_03232 | Verticillium dahliae (strain VdLs.17 / ATCC MYA-4575 / FGSC 10137) | DS572699; |
| C4QYM6 | C4QYM6_PICPG | Dolichyl-diphosphooligosaccharide--protein glycosyltransferase subunit STT3 | PAS_chr1-4_0685 | Pichia pastoris (strain GS115 / ATCC 20864) (Yeast) | FN392319; |
| C4JIH5 | C4JIH5_UNCRE | Oligosaccharyl transferase STT3 subunit | UREG_01512 | Uncinocarpus reesii (strain UAMH 1704) | CH476615; |
| G4MTS9 | G4MTS9_MAGO7 | Oligosaccharyl transferase STT3 subunit | MGG_04773 | Magnaporthe oryzae (strain 70-15 / ATCC MYA-4617 / FGSC 8958) (Rice blast fungus) (Pyricularia oryzae) | CM001232; |
| Q0D1X6 | Q0D1X6_ASPTN | Oligosaccharyl transferase stt3 subunit | ATEG_00058 | Aspergillus terreus (strain NIH 2624 / FGSC A1156) | CH476594; |

Figure 9C

| UniProtKB Entry No. | Entry name | Protein names | Gene names | Organism | EMBL Acc. No. |
|---|---|---|---|---|---|
| C5GUY5 | C5GUY5_AJEDR | Oligosaccharyl transferase STT3 subunit | BDCG_08079 | Ajellomyces dermatitidis (strain ER-3 / ATCC MYA-2586) (Blastomyces dermatitidis) | EQ999982; |
| G0SZE9 | G0SZE9_RHOG2 | Oligosaccharyl transferase STT3 subunit | RTG_02108 | Rhodotorula glutinis (strain ATCC 204091 / IIP 30 / MTCC 1151) (Yeast) | GL989651; |
| H1VV71 | H1VV71_9PEZI | Oligosaccharyl transferase STT3 subunit | CH063_03249 | Colletotrichum higginsianum | CACQ02006645; |
| I4YCS0 | I4YCS0_WALSC | STT3 subunit of Oligosaccharyl transferase | WALSEDRAFT_60231 | Wallemia sebi (strain ATCC MYA-4683 / CBS 633.66) | JH668230; |
| E4ZVS4 | E4ZVS4_LEPMJ | Similar to oligosaccharyl transferase subunit (Stt3) | LEMA_P028520.1 | Leptosphaeria maculans (strain JN3 / isolate v23.1.3 / race Av1-4-5-6-7-8) (Blackleg fungus) (Phoma lingam) | FP929127; |
| B6K602 | B6K602_SCHJY | Oligosaccharyltransferase subunit Stt3 | SJAG_04127 | Schizosaccharomyces japonicus (strain yFS275 / FY16936) (Fission yeast) | DS022228; |
| Q4WCH2 | Q4WCH2_ASPFU | Oligosaccharyl transferase subunit (Stt3), putative | AFUA_8G04430 | Neosartorya fumigata (strain ATCC MYA-4609 / Af293 / CBS 101355 / FGSC A1100) (Aspergillus fumigatus) | AAHF01000013; |
| C5M5Y0 | C5M5Y0_CANTT | Oligosaccharyl transferase STT3 subunit | CTRG_01261 | Candida tropicalis (strain ATCC MYA-3404 / T1) (Yeast) | GG692396; |
| B0CT90 | B0CT90_LACBS | Oligosaccharyl transferase STT3 subunit | STT3 LACBIDRAFT_305018 | Laccaria bicolor (strain S238N-H82 / ATCC MYA-4686) (Bicoloured deceiver) (Laccaria laccata var. bicolor) | DS547092; |
| J5K258 | J5K258_BEAB2 | Oligosaccharyl transferase STT3 subunit | | Beauveria bassiana (strain ARSEF 2860) (White muscardine disease fungus) (Tritirachium shiotae) | JH725150; |

Figure 9D

| UniProtKB Entry No. | Entry name | Protein names | Gene names | Organism | EMBL Acc. No. |
|---|---|---|---|---|---|
| Q6FXV8 | Q6FXV8_CANGA | Similar to uniprot\|P39007 Saccharomyces cerevisiae YGL022w STT3 | CAGL0A00209g | Candida glabrata (strain ATCC 2001 / CBS 138 / JCM 3761 / NBRC 0622 / NRRL Y-65) (Yeast) (Torulopsis glabrata) | CR380947; |
| E9DZX7 | E9DZX7_METAQ | Oligosaccharyl transferase STT3 subunit | MAC_03175 | Metarhizium acridum (strain CQMa 102) | GL698487; |
| E9EW71 | E9EW71_METAR | Oligosaccharyl transferase STT3 subunit | MAA_04270 | Metarhizium robertsii (strain ARSEF 23 / ATCC MYA-3075) (Metarhizium anisopliae) | GL698715; |
| Q5XWB6 | Q5XWB6_HORWE | Oligosaccharyl transferase subunit STT3 (Fragment) | | Hortaea werneckii | AY731090; |
| E9CTL6 | E9CTL6_COCPS | Oligosaccharyl transferase subunit Stt3 | CPSG_00060 | Coccidioides posadasii (strain RMSCC 757 / Silveira) (Valley fever fungus) | GL636486; |
| C9SME9 | C9SME9_VERA1 | Oligosaccharyl transferase STT3 subunit | VDBG_06073 | Verticillium albo-atrum (strain VaMs.102 / ATCC MYA-4576 / FGSC 10136) (Verticillium wilt) | DS985220; |
| B0YA20 | B0YA20_ASPFC | Oligosaccharyl transferase subunit (Stt3), putative | AFUB_083110 | Neosartorya fumigata (strain CEA10 / CBS 144.89 / FGSC A1163) (Aspergillus fumigatus) | DS499600; |
| A6QZB9 | A6QZB9_AJECN | Oligosaccharyl transferase STT3 subunit | HCAG_02726 | Ajellomyces capsulata (strain NAm1 / WU24) (Darling's disease fungus) (Histoplasma capsulatum) | CH476656; |
| B8NYJ0 | B8NYJ0_ASPFN | Oligosaccharyl transferase subunit (Stt3), putative | AFLA_011600 | Aspergillus flavus (strain ATCC 200026 / FGSC A1120 / NRRL 3357 / JCM 12722 / SRRC 167) | EQ963486; |
| F2TN10 | F2TN10_AJEDA | Oligosaccharyl transferase STT3 subunit | BDDG_07568 | Ajellomyces dermatitidis (strain ATCC 18188 / CBS 674.68) (Blastomyces dermatitidis) | GG749474; |

Figure 9E

| UniProtKB Entry No. | Entry name | Protein names | Gene names | Organism | EMBL Acc. No. |
|---|---|---|---|---|---|
| A1DB54 | A1DB54_NEOFI | Oligosaccharyl transferase subunit (Stt3), putative | NFIA_097170 | Neosartorya fischeri (strain ATCC 1020 / DSM 3700 / FGSC A1164 / NRRL 181) (Aspergillus fischerianus) | DS027694; |
| A7UW38 | A7UW38_NEUCR | Oligosaccharyl transferase STT3 subunit | NCU10497 | Neurospora crassa (strain ATCC 24698 / 74-OR23-1A / CBS 708.71 / DSM 1257 / FGSC 987) | AABX02000006; |
| E4UYC0 | E4UYC0_ARTGP | Oligosaccharyl transferase stt3 subunit | MGYG_05086 | Arthroderma gypseum (strain ATCC MYA-4604 / CBS 118893) (Microsporum gypseum) | DS989825; |
| C1G5L1 | C1G5L1_PARBD | Oligosaccharyl transferase stt3 subunit | PADG_02466 | Paracoccidioides brasiliensis (strain Pb18) | DS572752; |
| B6QM75 | B6QM75_PENMQ | Oligosaccharyl transferase subunit (Stt3), putative | PMAA_059810 | Penicillium marneffei (strain ATCC 18224 / CBS 334.59 / QM 7333) | DS995903; |
| C0RXC3 | C0RXC3_PARBP | Oligosaccharyltransferase subunit Stt3 | PABG_00078 | Paracoccidioides brasiliensis (strain Pb03) | DS544803; |
| A8N8M6 | A8N8M6_COPC7 | Oligosaccharyl transferase STT3 subunit | CC1G_15851 | Coprinopsis cinerea (strain Okayama-7 / 130 / ATCC MYA-4618 / FGSC 9003) (Inky cap fungus) (Hormographiella aspergillata) | AACS02000007; |
| G3JKC9 | G3JKC9_CORMM | Oligosaccharyl transferase STT3 subunit | CCM_06368 | Cordyceps militaris (strain CM01) (Caterpillar fungus) | JH126402; |
| E3QD87 | E3QD87_COLGM | Oligosaccharyl transferase STT3 subunit | GLRG_04003 | Colletotrichum graminicola (strain M1.001 / M2 / FGSC 10212) (Maize anthracnose fungus) (Glomerella graminicola) | GG697342; |

Figure 9F

| UniProtKB Entry No. | Entry name | Protein names | Gene names | Organism | EMBL Acc. No. |
|---|---|---|---|---|---|
| H0ERJ9 | H0ERJ9_GLAL7 | Putative Dolichyl-diphosphooligosaccharide--protein glycosyltransferase subunit stt3 | M7I_5318 | Glarea lozoyensis (strain ATCC 74030 / MF5533) | AGUE01000135; |
| B8MDZ2 | B8MDZ2_TALSN | Oligosaccharyl transferase subunit (Stt3), putative (EC 2.4.1.119) | TSTA_011780 | Talaromyces stipitatus (strain ATCC 10500 / CBS 375.48 / QM 6759 / NRRL 1006) (Penicillium stipitatum) | EQ962656; |
| E7RBB6 | E7RBB6_PICAD | Dolichyl-diphosphooligosaccharide-protein glycosyltransferase subunit STT3 | HPODL_3889 | Pichia angusta (strain ATCC 26012 / NRRL Y-7560 / DL-1) (Yeast) (Hansenula polymorpha) | AEOI01000013; |
| F2PGT2 | F2PGT2_TRIEC | Oligosaccharyl transferase stt3 subunit | TEQG_00154 | Trichophyton equinum (strain ATCC MYA-4606 / CBS 127.97) (Horse ringworm fungus) | DS995718; |
| C5JP67 | C5JP67_AJEDS | Oligosaccharyl transferase STT3 subunit | BDBG_04234 | Ajellomyces dermatitidis (strain SLH14081) (Blastomyces dermatitidis) | GG657454; |
| I2JW81 | I2JW81_DEKBR | Oligosaccharyl transferase stt3 subunit | AWRI1499_2864 | Dekkera bruxellensis AWRI1499 | AHIQ01000163; |
| C4YJC6 | C4YJC6_CANAW | Oligosaccharyl transferase STT3 subunit | CAWG_03939 | Candida albicans (strain WO-1) (Yeast) | CH672350; |
| B6KJL1 | B6KJL1_TOXGO | Oligosaccharyl transferase STT3, putative (EC 2.4.1.119) | TGME49_031430 TGVEG_024140 | Toxoplasma gondii | DS984734;EQ970680; |
| E1F7B3 | E1F7B3_GIAIA | Oligosaccharyl transferase STT3 subunit | GLP15_1743 | Giardia intestinalis (strain P15) (Giardia lamblia) | ACVC01000215; |
| E9CBA9 | E9CBA9_CAPO3 | Oligosaccharyl transferase STT3 subunit | CAOG_05399 | Capsaspora owczarzaki (strain ATCC 30864) | GG697250; |
| Q7YYI9 | Q7YYI9_CRYPV | Oligosaccharyl transferase stt3 protein, probable | 1MB.197 | Cryptosporidium parvum | BX538351; |
| Q8IIK0 | Q8IIK0_PLAF7 | Oligosaccharyl transferase STT3 subunit, putative | PF11_0173 | Plasmodium falciparum (isolate 3D7) | AE014186; |
| Q4YNV1 | Q4YNV1_PLABA | Oligosacharyl transferase STT3 subunit, putative (Fragment) | PB000857.03.0 | Plasmodium berghei (strain Anka) | CAAI01003269; |

Figure 9G

| UniProtKB Entry No. | Entry name | Protein names | Gene names | Organism | EMBL Acc. No. |
|---|---|---|---|---|---|
| F8QXJ9 | F8QXJ9_9EUCA | Oligosaccharyltransferase oligosaccharyl transferase STT3 subunit (Fragment) | | Scylla paramamosain (green mud crab) | HM217858; |
| F1KS44 | F1KS44_ASCSU | Oligosaccharyl transferase subunit STT3 | | Ascaris suum (Pig roundworm) (Ascaris lumbricoides) | JI164969; |
| F0ZGL1 | F0ZGL1_DICPU | STT3 subunit of oligosaccharyl transferase | DICPUDRAFT_150543 | Dictyostelium purpureum (Slime mold) | GL871013; |
| A2EPM4 | A2EPM4_TRIVA | Oligosaccharyl transferase STT3 subunit family protein | TVAG_131010 | Trichomonas vaginalis | DS113450; |
| A2EI94 | A2EI94_TRIVA | Oligosaccharyl transferase STT3 subunit family protein | TVAG_430200 | Trichomonas vaginalis | DS113395; |
| A2EDZ3 | A2EDZ3_TRIVA | Oligosaccharyl transferase STT3 subunit family protein | TVAG_230650 | Trichomonas vaginalis | DS113364; |
| A2FGM0 | A2FGM0_TRIVA | Oligosaccharyl transferase STT3 subunit family protein | TVAG_077860 | Trichomonas vaginalis | DS113781; |
| Q5CKU0 | Q5CKU0_CRYHO | Oligosaccharyl transferase stt3 protein | Chro.60239 | Cryptosporidium hominis | AAEL01000072; |
| F4Y9K6 | F4Y9K6_TRYBR | Putative oligosaccharyl transferase STT3 subunit | OSTI | Trypanosoma brucei rhodesiense | GU245936; |
| F4Y9K7 | F4Y9K7_TRYBR | Putative oligosaccharyl transferase STT3 subunit | OSTII | Trypanosoma brucei rhodesiense | GU245937; |
| F4YAX2 | F4YAX2_TRYBR | Putative oligosaccharyl transferase STT3 subunit (Fragment) | OSTII | Trypanosoma brucei rhodesiense | GU475126; |
| F4YAX1 | F4YAX1_TRYBR | Putative oligosaccharyl transferase STT3 subunit (Fragment) | OSTI | Trypanosoma brucei rhodesiense | GU475125; |
| O15615 | O15615_ENTHI | Oligosaccharyl transferase stt3 subunit homologue (Fragment) | | Entamoeba histolytica | AB002773; |
| Q7RMM7 | Q7RMM7_PLAYO | Stt3 protein-related | PY02151 | Plasmodium yoelii yoelii | AABL01000590; |
| Q5CX90 | Q5CX90_CRYPI | Oligosaccharyl transferase STT3 protein | cgd6_2040 | Cryptosporidium parvum (strain Iowa II) | AAEE01000002; |
| B3L4W9 | B3L4W9_PLAKH | Oligosacharyl transferase STT3 subunit,putative | PKH_091400 | Plasmodium knowlesi (strain H) | AM910991; |
| Q4XT08 | Q4XT08_PLACH | Oligosacharyl transferase STT3 subunit, putative (Fragment) | PC000621.03.0 | Plasmodium chabaudi | CAAJ01003402; |

Figure 9H

| UniProtKB Entry No. | Entry name | Protein names | Gene names | Organism | EMBL Acc. No. |
|---|---|---|---|---|---|
| A8NPF6 | A8NPF6_BRUMA | Oligosaccharyl transferase STT3 subunit homolog, putative | Bm1_06940 | Brugia malayi (Filarial nematode worm) | DS237740; |
| C1LIH8 | C1LIH8_SCHJA | STT3, subunit of the oligosaccharyltransferase complex, homolog B (EC 2.4.1.-) | STT3B | Schistosoma japonicum (Blood fluke) | FN318778; |
| C1LIH7 | C1LIH7_SCHJA | STT3, subunit of the oligosaccharyltransferase complex, homolog B (EC 2.4.1.-) | STT3B | Schistosoma japonicum (Blood fluke) | FN318777; |
| C1L600 | C1L600_SCHJA | STT3, subunit of the oligosaccharyltransferase complex, homolog B (EC 2.4.1.-) | STT3B | Schistosoma japonicum (Blood fluke) | FN314395; |
| C5KDG4 | C5KDG4_PERM5 | Stt3 protein, putative | Pmar_PMAR025427 | Perkinsus marinus (strain ATCC 50983 / TXsc) | GG672080; |
| C5K5U6 | C5K5U6_PERM5 | Stt3 protein, putative | Pmar_PMAR026732 | Perkinsus marinus (strain ATCC 50983 / TXsc) | GG670791; |
| A7ASS2 | A7ASS2_BABBO | Oligosaccharyl transferase STT3 subunit, putative | BBOV_II000220 | Babesia bovis | AAXT01000003; |
| Q9U5N8 | Q9U5N8_LEIMA | Hypothetical STT3 ortholog | stt3 | Leishmania major | AJ251127; |
| O97353 | O97353_TOXGO | Stt3 protein (Fragment) | stt3 | Toxoplasma gondii | AJ132382; |
| B9PGS3 | B9PGS3_TOXGO | Oligosaccharyl transferase STT3, putative (EC 2.4.1.119) | TGGT1_116240 | Toxoplasma gondii | EQ967475; |
| J9IDC3 | J9IDC3_9SPIT | Oligosaccharyl transferase STT3 subunit family protein | | Oxytricha trifallax | AMCR01018082; |
| A5K4H8 | A5K4H8_PLAVS | Oligosacharyl transferase STT3 subunit, putative | PVX_091460 | Plasmodium vivax (strain Salvador I) | AAKM01000005; |
| C8KI11 | C8KI11_BRAPC | Oligosacchary transferase STT3 subunit homolog (Fragment) | stt3 | Brachionus plicatilis (Marine rotifer) (Brachionus muelleri) | AB491800; |
| B6ADK3 | B6ADK3_CRYMR | Oligosaccharyl transferase STT3 subunit family protein (EC 2.4.1.119) | CMU_007850 | Cryptosporidium muris (strain RN66) | DS989729; |
| Q23H40 | Q23H40_TETTS | Oligosaccharyl transferase STT3 subunit family protein | TTHERM_00877020 | Tetrahymena thermophila (strain SB210) | GG662702; |
| G9KRR7 | G9KRR7_MUSPF | STT3, subunit of the oligosaccharyltransferase complex,-like protein B (Fragment) | | Mustela putorius furo (European domestic ferret) (Mustela furo) | JP018998; |

Figure 9I

| UniProtKB Entry No. | Entry name | Protein names | Gene names | Organism | EMBL Acc. No. |
|---|---|---|---|---|---|
| G9KRR6 | G9KRR6_MUSPF | STT3, subunit of the oligosaccharyltransferase complex,-like protein A (Fragment) | | Mustela putorius furo (European domestic ferret) (Mustela furo) | JP018997; |
| Q6F2Z1 | Q6F2Z1_ORYSJ | Os05g0519900 protein (Putative oligosaccharyl transferase STT3) (Putative oligosaccharyl transferase STT3 subunit) (cDNA clone:J013099L06, full insert sequence) | P0483D07.5 P0599F04.15 Os05g0519900 OsJ_19234 | Oryza sativa subsp. japonica (Rice) | AC130611;AC132491;AP008211;AK067224;CM000142; |
| Q93ZY3 | Q93ZY3_ARATH | Dolichyl-diphosphooligosaccharide--protein glycosyltransferase (Putative oligosaccharyl transferase STT3) | STT3A At5g19690 AT5G19690 | Arabidopsis thaliana (Mouse-ear cress) | AY056191;CP002688; |
| B7GE39 | B7GE39_PHATC | STT3 subunit-like protein | PHATRDRAFT_55198 | Phaeodactylum tricornutum (strain CCAP 1055/1) | CM000632; |
| B6T514 | B6T514_MAIZE | Oligosaccharyl transferase STT3 subunit | | Zea mays (Maize) | EU960079; |
| A8IH85 | A8IH85_CHLRE | Oligsaccharyl transferase STT3 subunit | GTR25 CHLREDRAFT_127991 | Chlamydomonas reinhardtii (Chlamydomonas smithii) | DS496117; |
| Q6XL70 | Q6XL70_VITVI | Putative oligosaccharyl transferase STT3 protein (Fragment) | ltm1 | Vitis vinifera (Grape) | AY226831; |
| D8S7P7 | D8S7P7_SELML | Oligosaccharyltransferase subunit STT3 | STT3B SELMODRAFT_110405 | Selaginella moellendorffii (Spikemoss) | GL377605; |
| D8SK97 | D8SK97_SELML | Oligosaccharyltransferase subunit STT3 (EC 2.4.1.119) | STT3A SELMODRAFT_452919 | Selaginella moellendorffii (Spikemoss) | GL377624; |
| I0Z4M4 | I0Z4M4_9CHLO | STT3 subunit of Oligosaccharyl transferase | | Coccomyxa subellipsoidea C-169 | AGSI01000004; |
| Q3U573 | Q3U573_MOUSE | STT3, subunit of the oligosaccharyltransferase complex, homolog A (S. cerevisiae) | Stt3a Itm1 mCG_4136 | Mus musculus (Mouse) | ;AK169669;CH466522; |
| Q5U412 | Q5U412_MOUSE | STT3, subunit of the oligosaccharyltransferase complex, homolog A (S. cerevisiae) | Stt3a Itm1 | Mus musculus (Mouse) | BC085313; |
| Q7ZTH5 | Q7ZTH5_DANRE | STT3, subunit of the oligosaccharyltransferase complex, homolog B (S. cerevisiae) | stt3b | Danio rerio (Zebrafish) (Brachydanio rerio) | BC052114; |

Figure 9J

SEQUENCE LISTING

```
<160> NUMBER OF SEQ ID NOS: 35

<210> SEQ ID NO 1
<211> LENGTH: 5
<212> TYPE: PRT
<213> ORGANISM: Artificial
<220> FEATURE:
<223> OTHER INFORMATION: Bacterial glycosylation motif
<220> FEATURE:
<221> NAME/KEY: MISC_FEATURE
<222> LOCATION: (1)..(1)
<223> OTHER INFORMATION: X at position 1 is D or E
<220> FEATURE:
<221> NAME/KEY: MISC_FEATURE
<222> LOCATION: (2)..(2)
<223> OTHER INFORMATION: X at position 2 is any amino acid except
      proline
<220> FEATURE:
<221> NAME/KEY: MISC_FEATURE
<222> LOCATION: (4)..(4)
<223> OTHER INFORMATION: X at position 4 is any amino acid except
      proline
<220> FEATURE:
<221> NAME/KEY: MISC_FEATURE
<222> LOCATION: (5)..(5)
<223> OTHER INFORMATION: X at position 5 is S or T

<400> SEQUENCE: 1

Xaa Xaa Asn Xaa Xaa
1               5


<210> SEQ ID NO 2
<211> LENGTH: 664
```

<212> TYPE: PRT
<213> ORGANISM: Campylobacter jejuni

<400> SEQUENCE: 2

```
Ile Ile Ser Asn Asp Gly Tyr Ala Phe Ala Glu Gly Ala Arg Asp Met
1               5                   10                  15

Ile Ala Gly Phe His Gln Pro Asn Asp Leu Ser Tyr Tyr Gly Ser Ser
            20                  25                  30

Leu Ser Thr Leu Thr Tyr Trp Leu Tyr Lys Ile Thr Pro Phe Ser Phe
        35                  40                  45

Glu Ser Ile Ile Leu Tyr Met Ser Thr Phe Leu Ser Ser Leu Val Val
    50                  55                  60

Ile Pro Ile Ile Leu Leu Ala Asn Glu Tyr Lys Arg Pro Leu Met Gly
65                  70                  75                  80

Phe Val Ala Ala Leu Leu Ala Ser Ile Ala Asn Ser Tyr Tyr Asn Arg
                85                  90                  95

Thr Met Ser Gly Tyr Tyr Asp Thr Asp Met Leu Val Ile Val Leu Pro
            100                 105                 110

Met Phe Ile Leu Phe Phe Met Val Arg Met Ile Leu Lys Lys Asp Phe
        115                 120                 125

Phe Ser Leu Ile Ala Leu Pro Leu Phe Ile Gly Ile Tyr Leu Trp Trp
    130                 135                 140

Tyr Pro Ser Ser Tyr Thr Leu Asn Val Ala Leu Ile Gly Leu Phe Leu
145                 150                 155                 160

Ile Tyr Thr Leu Ile Phe His Arg Lys Glu Lys Ile Phe Tyr Ile Ala
                165                 170                 175

Val Ile Leu Ser Ser Leu Thr Leu Ser Asn Ile Ala Trp Phe Tyr Gln
            180                 185                 190

Ser Thr Ile Ile Val Ile Leu Phe Ala Leu Phe Ala Leu Glu Gln Lys
        195                 200                 205

Arg Leu Asn Phe Val Ile Ile Gly Ile Leu Ala Ser Val Thr Leu Ile
    210                 215                 220

Phe Leu Ile Leu Ser Gly Gly Val Asp Pro Ile Leu Tyr Gln Leu Lys
225                 230                 235                 240

Phe Tyr Ile Phe Arg Ser Asp Glu Ser Ala Asn Leu Thr Gln Gly Phe
                245                 250                 255

Met Tyr Phe Asn Val Asn Gln Thr Ile Gln Glu Val Glu Asn Val Asp
            260                 265                 270

Leu Ser Glu Phe Met Arg Arg Ile Ser Gly Ser Glu Ile Val Phe Leu
        275                 280                 285

Phe Ser Leu Phe Gly Phe Val Trp Leu Leu Arg Lys His Lys Ser Met
    290                 295                 300

Ile Met Ala Leu Pro Ile Leu Val Leu Gly Phe Leu Ala Leu Lys Gly
305                 310                 315                 320

Gly Leu Arg Phe Thr Ile Tyr Ser Val Pro Val Met Ala Leu Gly Phe
                325                 330                 335

Gly Phe Leu Leu Ser Glu Phe Lys Ala Ile Leu Val Lys Lys Tyr Ser
            340                 345                 350

Gln Leu Thr Ser Asn Val Cys Ile Val Phe Ala Thr Ile Leu Thr Leu
        355                 360                 365

Ala Pro Val Phe Ile His Ile Tyr Asn Tyr Lys Ala Pro Thr Val Phe
    370                 375                 380

Ser Gln Asn Glu Ala Ser Leu Leu Asn Gln Leu Lys Asn Ile Ala Asn
385                 390                 395                 400
```

```
Arg Glu Asp Tyr Val Val Thr Trp Trp Asp Tyr Gly Tyr Pro Val Arg
            405                 410                 415

Tyr Tyr Ser Asp Val Lys Thr Leu Val Asp Gly Gly Lys His Leu Gly
            420                 425                 430

Lys Asp Asn Phe Phe Pro Ser Phe Ala Leu Ser Lys Asp Glu Gln Ala
        435                 440                 445

Ala Ala Asn Met Ala Arg Leu Ser Val Glu Tyr Thr Glu Lys Ser Phe
    450                 455                 460

Tyr Ala Pro Gln Asn Asp Ile Leu Lys Thr Asp Ile Leu Gln Ala Met
465                 470                 475                 480

Met Lys Asp Tyr Asn Gln Ser Asn Val Asp Leu Phe Leu Ala Ser Leu
            485                 490                 495

Ser Lys Pro Asp Phe Lys Ile Asp Thr Pro Lys Thr Arg Asp Ile Tyr
            500                 505                 510

Leu Tyr Met Pro Ala Arg Met Ser Leu Ile Phe Ser Thr Val Ala Ser
        515                 520                 525

Phe Ser Phe Ile Asn Leu Asp Thr Gly Val Leu Asp Lys Pro Phe Thr
    530                 535                 540

Phe Ser Thr Ala Tyr Pro Leu Asp Val Lys Asn Gly Glu Ile Tyr Leu
545                 550                 555                 560

Ser Asn Gly Val Val Leu Ser Asp Asp Phe Arg Ser Phe Lys Ile Gly
            565                 570                 575

Asp Asn Val Val Ser Val Asn Ser Ile Val Glu Ile Asn Ser Ile Lys
            580                 585                 590

Gln Gly Glu Tyr Lys Ile Thr Pro Ile Asp Asp Lys Ala Gln Phe Tyr
        595                 600                 605

Ile Phe Tyr Leu Lys Asp Ser Ala Ile Pro Tyr Ala Gln Phe Ile Leu
    610                 615                 620

Met Asp Lys Thr Met Phe Asn Ser Ala Tyr Val Gln Met Phe Phe Leu
625                 630                 635                 640

Gly Asn Tyr Asp Lys Asn Leu Phe Asp Leu Val Ile Asn Ser Arg Asp
            645                 650                 655

Ala Lys Val Phe Lys Leu Lys Ile
            660


<210> SEQ ID NO 3
<211> LENGTH: 1995
<212> TYPE: DNA
<213> ORGANISM: Campylobacter jejuni

<400> SEQUENCE: 3

atcatttcaa acgatggtta tgcttttgct gagggtgcaa gagatatgat agcaggtttt      60

catcagccta atgatttgag ttattatgga tcttctttat ctacgcttac ttattggctt     120

tataaaatca caccttttc tttcgaaagt attattttat atatgagtac tttttatct     180

tctttggtgg tgattcctat tattttacta gctaatgaat acaaacgtcc tttaatgggc     240

tttgtagctg ctcttttagc aagtatagca aacagttatt ataatcgcac tatgagtggg     300

tattatgata cggatatgct ggtaattgtt ttacctatgt ttattttatt ttttatggta     360

agaatgattt taaaaaaaga ctttttttca ttgattgcct taccgttatt tataggaatt     420

tatctttggt ggtatccttc aagctatact ttaaatgtag ctttaattgg actttttta     480

atttatacac ttatttttca tagaaaagaa aagatttttt atatagctgt gattttgtct     540

tctcttactc tttcaaatat agcatggttt tatcaaagta ctattatagt aatactttt     600
```

```
gctttatttg ctttagagca aaaacgctta aattttgtaa ttataggaat tttagctagt    660

gtaactttga tatttttgat tttaagtgga ggggttgatc ctatacttta tcagcttaaa    720

ttttatattt ttagaagtga tgaaagtgcg aatttaacgc agggttttat gtattttaat    780

gtcaatcaaa ccatacaaga agttgaaaat gtagatctta gcgaatttat gcgaagaatt    840

agtggtagtg aaattgtttt tttgttttct ttgtttggtt ttgtatggct tttgagaaaa    900

cataaaagta tgattatggc tttacctata ttggtgcttg ggtttttagc cttaaaaggg    960

gggcttagat ttaccattta ttctgtacct gtaatggcct taggatttgg tttttttattg  1020

agcgagttta aggctatatt ggttaaaaaa tatagccaat taacttcaaa tgtttgtatt   1080

gtttttgcaa ctattttgac tttagctcca gtatttatcc atatttacaa ctataaagca   1140

ccaacagttt tttctcaaaa tgaagcatca ttattaaatc aattaaaaaa tatagccaat   1200

agagaagatt atgtggtaac ttggtgggat tatggttatc ctgtgcgtta ttatagtgat   1260

gtgaaaactt tagtagatgg tggaaagcat ttaggtaagg ataatttttt cccttctttt   1320

gctttaagca aagatgaaca agctgcagct aatatggcaa gacttagtgt agaatataca   1380

gaaaaaagct tttatgctcc gcaaaatgat attttaaaaa cagacatttt acaagccatg   1440

atgaaagatt ataatcaaag caatgtggat ttgtttctag cttcattatc aaaacctgat   1500

tttaaaatcg atacaccaaa aactcgtgat atttatcttt atatgcccgc tagaatgtct   1560

ttgatttttt ctacggtggc tagtttttct tttattaatt tagatacagg agttttggat   1620

aaacctttta cctttagcac agcttatcca cttgatgtta aaaatggaga aatttatctt   1680

agcaacggag tggttttaag cgatgatttt agaagtttta aaataggtga taatgtggtt   1740

tctgtaaata gtatcgtaga gattaattct attaaacaag gtgaatacaa aatcactcca   1800

attgatgata aggctcagtt ttatattttt tatttaaagg atagtgctat tccttacgca   1860

caatttattt taatggataa aaccatgttt aatagtgctt atgtgcaaat gtttttttta   1920

ggaaattatg ataagaattt atttgacttg gtgattaatt ctagagatgc taaggttttt   1980

aaacttaaaa tttaa                                                    1995
```

<210> SEQ ID NO 4
<211> LENGTH: 711
<212> TYPE: PRT
<213> ORGANISM: Campylobacter lari

<400> SEQUENCE: 4

```
Met Lys Leu Gln Gln Asn Phe Thr Asp Asn Asn Ser Ile Lys Tyr Thr
1               5                   10                  15

Cys Ile Leu Ile Leu Ile Ala Phe Ala Phe Ser Val Leu Cys Arg Leu
            20                  25                  30

Tyr Trp Val Ala Trp Ala Ser Glu Phe Tyr Glu Phe Phe Phe Asn Asp
        35                  40                  45

Gln Leu Met Ile Thr Thr Asn Asp Gly Tyr Ala Phe Ala Glu Gly Ala
    50                  55                  60

Arg Asp Met Ile Ala Gly Phe His Gln Pro Asn Asp Leu Ser Tyr Phe
65                  70                  75                  80

Gly Ser Ser Leu Ser Thr Leu Thr Tyr Trp Leu Tyr Ser Ile Leu Pro
                85                  90                  95

Phe Ser Phe Glu Ser Ile Ile Leu Tyr Met Ser Ala Phe Phe Ala Ser
            100                 105                 110

Leu Ile Val Val Pro Ile Ile Leu Ile Ala Arg Glu Tyr Lys Leu Thr
```

-continued

```
        115                 120                 125

Thr Tyr Gly Phe Ile Ala Ala Leu Leu Gly Ser Ile Ala Asn Ser Tyr
    130                 135                 140

Tyr Asn Arg Thr Met Ser Gly Tyr Tyr Asp Thr Asp Met Leu Val Leu
145                 150                 155                 160

Val Leu Pro Met Leu Ile Leu Leu Thr Phe Ile Arg Leu Thr Ile Asn
                165                 170                 175

Lys Asp Ile Phe Thr Leu Leu Leu Ser Pro Val Phe Ile Met Ile Tyr
            180                 185                 190

Leu Trp Trp Tyr Pro Ser Ser Tyr Ser Leu Asn Phe Ala Met Ile Gly
        195                 200                 205

Leu Phe Gly Leu Tyr Thr Leu Val Phe His Arg Lys Glu Lys Ile Phe
    210                 215                 220

Tyr Leu Thr Ile Ala Leu Met Ile Ile Ala Leu Ser Met Leu Ala Trp
225                 230                 235                 240

Gln Tyr Lys Leu Ala Leu Ile Val Leu Leu Phe Ala Ile Phe Ala Phe
                245                 250                 255

Lys Glu Glu Lys Ile Asn Phe Tyr Met Ile Trp Ala Leu Ile Phe Ile
            260                 265                 270

Ser Ile Leu Ile Leu His Leu Ser Gly Gly Leu Asp Pro Val Leu Tyr
        275                 280                 285

Gln Leu Lys Phe Tyr Val Phe Lys Ala Ser Asp Val Gln Asn Leu Lys
    290                 295                 300

Asp Ala Ala Phe Met Tyr Phe Asn Val Asn Glu Thr Ile Met Glu Val
305                 310                 315                 320

Asn Thr Ile Asp Pro Glu Val Phe Met Gln Arg Ile Ser Ser Ser Val
                325                 330                 335

Leu Val Phe Ile Leu Ser Phe Ile Gly Phe Ile Leu Leu Cys Lys Asp
            340                 345                 350

His Lys Ser Met Leu Leu Ala Leu Pro Met Leu Ala Leu Gly Phe Met
        355                 360                 365

Ala Leu Arg Ala Gly Leu Arg Phe Thr Ile Tyr Ala Val Pro Val Met
    370                 375                 380

Ala Leu Gly Phe Gly Tyr Phe Leu Tyr Ala Phe Phe Asn Phe Leu Glu
385                 390                 395                 400

Lys Lys Gln Ile Lys Leu Ser Leu Arg Asn Lys Asn Ile Leu Leu Ile
                405                 410                 415

Leu Ile Ala Phe Phe Ser Ile Ser Pro Ala Leu Met His Ile Tyr Tyr
            420                 425                 430

Tyr Lys Ser Ser Thr Val Phe Thr Ser Tyr Glu Ala Ser Ile Leu Asn
        435                 440                 445

Asp Leu Lys Asn Lys Ala Gln Arg Glu Asp Tyr Val Val Ala Trp Trp
    450                 455                 460

Asp Tyr Gly Tyr Pro Ile Arg Tyr Tyr Ser Asp Val Lys Thr Leu Ile
465                 470                 475                 480

Asp Gly Gly Lys His Leu Gly Lys Asp Asn Phe Phe Ser Ser Phe Val
                485                 490                 495

Leu Ser Lys Glu Gln Ile Pro Ala Ala Asn Met Ala Arg Leu Ser Val
            500                 505                 510

Glu Tyr Thr Glu Lys Ser Phe Lys Glu Asn Tyr Pro Asp Val Leu Lys
        515                 520                 525

Ala Met Val Lys Asp Tyr Asn Lys Thr Ser Ala Lys Asp Phe Leu Glu
    530                 535                 540
```

-continued

Ser Leu Asn Asp Lys Asp Phe Lys Phe Asp Thr Asn Lys Thr Arg Asp
545 550 555 560

Val Tyr Ile Tyr Met Pro Tyr Arg Met Leu Arg Ile Met Pro Val Val
565 570 575

Ala Gln Phe Ala Asn Thr Asn Pro Asp Asn Gly Glu Gln Glu Lys Ser
580 585 590

Leu Phe Phe Ser Gln Ala Asn Ala Ile Ala Gln Asp Lys Thr Thr Gly
595 600 605

Ser Val Met Leu Asp Asn Gly Val Glu Ile Ile Asn Asp Phe Arg Ala
610 615 620

Leu Lys Val Glu Gly Ala Ser Ile Pro Leu Lys Ala Phe Val Asp Ile
625 630 635 640

Glu Ser Ile Thr Asn Gly Lys Phe Tyr Tyr Asn Glu Ile Asp Ser Lys
645 650 655

Ala Gln Ile Tyr Leu Leu Phe Leu Arg Glu Tyr Lys Ser Phe Val Ile
660 665 670

Leu Asp Glu Ser Leu Tyr Asn Ser Ser Tyr Ile Gln Met Phe Leu Leu
675 680 685

Asn Gln Tyr Asp Gln Asp Leu Phe Glu Gln Ile Thr Asn Asp Thr Arg
690 695 700

Ala Lys Ile Tyr Arg Leu Lys
705 710

<210> SEQ ID NO 5
<211> LENGTH: 2139
<212> TYPE: DNA
<213> ORGANISM: Campylobacter lari

<400> SEQUENCE: 5
atgaaactac aacaaaattt cacggataat aattctataa aatatacctg tattttaatc 60
cttatagcct ttgcttttag tgttttgtgt agattatact gggtagcttg ggcaagtgag 120
ttttatgagt ttttctttaa tgatcaactc atgattacta ctaatgatgg ctatgctttt 180
gcagaaggtg caagagatat gatagcaggt tttcatcaac ctaatgactt atcttatttt 240
ggaagctcac tttctacttt gacttattgg ctttatagta ttttgccttt tagctttgaa 300
agtattattt tatatatgag tgcttttttt gcttctttga ttgttgtgcc tattatatta 360
atcgcaagag agtataaact cactacctat ggctttatag cagctttact tggaagcatt 420
gcaaatagtt attataaccg cactatgagt gggtattacg atacagatat gctagtgtta 480
gttttaccaa tgcttatttt gcttaccttt atacgcttaa ctattaataa agacattttc 540
accctacttt taagtccggt ttttatcatg atttatttgt ggtggtatcc atcaagttat 600
tctttaaatt ttgctatgat aggacttttt ggactttata ctttagtatt tcatagaaaa 660
gaaaagattt tttatctaac tattgctttg atgatcatag ctttaagtat gctagcatgg 720
caatataagc ttgctttgat tgtattatta tttgctattt ttgcttttaa agaagaaaaa 780
atcaattttt atatgatttg ggctttgatt tttattagca ttttgatatt gcatttaagt 840
ggcggcttag atcctgtttt ataccaactt aaattttatg tatttaaagc ttctgatgtg 900
caaaatttaa aagatgctgc ctttatgtat tttaatgtca atgaaaccat tatggaagta 960
aatactatcg atcctgaagt atttatgcaa agaattagct ctagtgtttt agtatttatc 1020
ctttctttta taggttttat cttactttgc aaagatcaca aaagcatgct tttggctcta 1080
cctatgcttg cactaggttt tatggcttta agagctggac ttagatttac catttatgca 1140

```
gttcctgtga tggctttggg ttttgggtat tttttatatg catttttttaa tttttagaa   1200

aaaaaacaaa tcaaacttag cctaagaaat aaaaatatct tacttatact cattgcattt   1260

tttagtataa gccctgcttt gatgcatatt tattattata aatcctctac tgtttttact   1320

tcttatgaag ctagtatttt aaatgattta aaaaataaag ctcaaagaga agattatgtt   1380

gttgcttggt gggattatgg ttatccaata cgctattata gcgatgtaaa aaccttaatc   1440

gatggtggaa aacacctagg aaaagataat tttttctcat cttttgtctt aagcaaagaa   1500

caaattccag cagccaatat ggcaagactt agcgtagaat acactgaaaa atctttcaaa   1560

gaaaactatc ctgatgtttt aaaagctatg gttaaagatt ataataaaac aagtgctaaa   1620

gattttttag aaagtttaaa tgataaagat tttaaatttg ataccaataa aactagagat   1680

gtatacattt atatgcctta tagaatgttg cgtatcatgc ctgtggtggc acaatttgca   1740

aatacaaatc ctgataatgg agagcaagaa aaaagtttat ttttctccca agctaatgcc   1800

atagctcaag ataaaaccac aggttctgtt atgcttgata atggagtaga aattattaat   1860

gattttagag ccttaaaagt agaaggtgca agcatacctt taaaagcttt tgtggatata   1920

gaatccatta ctaatggcaa attttattac aatgaaattg attcaaaagc tcaaatttat   1980

ttgctctttt taagagaata taaaagcttt gtgattttag atgaaagtct ttataatagt   2040

tcttatatac aaatgttttt gttaaatcaa tacgatcaag atttatttga acaaattact   2100

aatgatacaa gagcaaaaat ttataggcta aaaagatga                          2139
```

<210> SEQ ID NO 6
<211> LENGTH: 714
<212> TYPE: PRT
<213> ORGANISM: Campylobacter coli

<400> SEQUENCE: 6

```
Met Leu Lys Lys Glu Tyr Phe Lys Asn Pro Thr Phe Ile Leu Leu Ala
1               5                   10                  15

Phe Ile Ile Leu Ala Tyr Val Phe Ser Val Leu Cys Arg Phe Tyr Trp
            20                  25                  30

Ile Phe Trp Ala Ser Glu Phe Asn Glu Tyr Phe Phe Asn Asn Glu Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Phe Tyr Lys Ile Thr Pro Phe Ser
                85                  90                  95

Leu Glu Ser Ile Phe Ile Tyr Ile Ser Thr Phe Leu Ser Ser Leu Val
            100                 105                 110

Val Ile Pro Leu Ile Leu Ile Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Ala Met Met Ile Val Phe Phe Met Ile Arg Leu Ile Leu Lys Lys Asp
                165                 170                 175

Leu Leu Ser Leu Ile Thr Leu Pro Leu Phe Val Gly Ile Tyr Leu Trp
            180                 185                 190
```

```
Trp Tyr Pro Ser Ser Tyr Thr Leu Asn Val Ala Leu Leu Gly Leu Phe
        195                 200                 205

Phe Ile Tyr Thr Leu Val Phe His Ile Lys Glu Lys Thr Leu Tyr Met
    210                 215                 220

Ala Ile Ile Leu Ala Ser Ile Thr Leu Ser Asn Ile Ala Trp Phe Tyr
225                 230                 235                 240

Gln Ser Ala Ile Ile Val Ile Leu Phe Ser Leu Phe Val Leu Gln Asn
                245                 250                 255

Lys Arg Phe Ser Phe Ala Leu Leu Gly Ile Leu Gly Leu Ala Thr Leu
            260                 265                 270

Val Phe Leu Ile Leu Ser Gly Gly Ile Asp Pro Ile Leu Tyr Gln Leu
        275                 280                 285

Lys Phe Tyr Ile Phe Arg Ser Asp Glu Ser Ala Asn Leu Ala Gln Gly
    290                 295                 300

Phe Met Tyr Phe Asn Val Asn Gln Thr Ile Gln Glu Val Glu Ser Ile
305                 310                 315                 320

Asp Leu Ser Ile Phe Met Gln Arg Ile Ser Gly Ser Glu Leu Val Phe
                325                 330                 335

Phe Val Ser Leu Ile Gly Phe Ile Phe Leu Val Arg Lys His Lys Ser
            340                 345                 350

Met Ile Leu Ala Leu Pro Met Leu Ala Leu Gly Phe Leu Ala Leu Lys
        355                 360                 365

Ser Gly Leu Arg Phe Thr Ile Tyr Ala Val Pro Val Leu Ala Leu Gly
    370                 375                 380

Phe Gly Phe Leu Met Ser Leu Leu Gln Glu Arg Lys Gln Lys Asn Asn
385                 390                 395                 400

Asn Thr Tyr Trp Trp Ala Asn Ile Gly Val Phe Ile Phe Thr Phe Leu
                405                 410                 415

Ser Leu Ile Pro Met Phe Tyr His Ile Asn Asn Tyr Lys Ala Pro Thr
            420                 425                 430

Val Phe Ser Gln Asn Glu Ala Thr Lys Leu Asp Glu Leu Lys Lys Ile
        435                 440                 445

Ala Gln Arg Glu Asp Tyr Val Val Thr Trp Trp Asp Tyr Gly Tyr Pro
    450                 455                 460

Ile Arg Tyr Tyr Ser Asp Val Lys Thr Leu Ala Asp Gly Gly Lys His
465                 470                 475                 480

Leu Gly Lys Asp Asn Phe Phe Pro Ser Phe Val Leu Ser Lys Asp Gln
                485                 490                 495

Val Ala Ala Ala Asn Met Ala Arg Leu Ser Val Glu Tyr Thr Glu Lys
            500                 505                 510

Ser Phe Tyr Ala Pro Leu Asn Asp Ile Leu Lys Asn Asp Leu Leu Gln
        515                 520                 525

Ala Met Met Lys Asp Tyr Asn Gln Asn Asn Val Asp Leu Phe Leu Ala
    530                 535                 540

Ser Leu Ser Lys Pro Asp Phe Lys Ile Asn Thr Pro Lys Thr Arg Asp
545                 550                 555                 560

Val Tyr Ile Tyr Met Pro Ala Arg Met Ser Leu Ile Phe Ser Thr Val
                565                 570                 575

Ala Ser Phe Ser Phe Val Asp Leu Glu Thr Gly Glu Ile Asn Lys Pro
            580                 585                 590

Phe Thr Phe Ser Ala Ala Tyr Pro Leu Asp Val Lys Asn Gly Glu Ile
        595                 600                 605

Tyr Leu Ser Asn Gly Ile Ala Leu Ser Asp Asp Phe Arg Ser Phe Lys
```

-continued 610 615 620

Ile Asn Asn Ser Thr Ile Ser Val Asn Ser Ile Ile Glu Ile Asn Ser
625 630 635 640

Ile Lys Gln Gly Glu Tyr Lys Ile Thr Pro Ile Asp Asp Met Ala Gln
645 650 655

Phe Tyr Ile Phe Tyr Leu Lys Asp Ser Thr Ile Pro Tyr Ala Gln Phe
660 665 670

Ile Leu Met Asp Lys Thr Met Phe Asn Ser Ala Tyr Val Gln Met Phe
675 680 685

Phe Leu Gly Asn Tyr Asp Lys Asn Leu Tyr Asp Leu Val Ile Asn Ala
690 695 700

Arg Asp Ala Lys Val Phe Lys Leu Lys Ile
705 710

<210> SEQ ID NO 7
<211> LENGTH: 2145
<212> TYPE: DNA
<213> ORGANISM: Campylobacter coli

<400> SEQUENCE: 7
atgttaaaaa aagaatactt taaaaaccca acttttattt tattggcttt tataatttta 60
gcgtatgtct ttagtgtttt atgtaggttt tattggattt tttgggcaag tgagtttaat 120
gaatattttt tcaataacga gcttatgatt atctcaaatg atggatatgc ttttgcagag 180
ggtgcaagag atatgatagc gggttttcat caacctaatg atttgagtta ttatggttct 240
tcgctttcaa cgctcacata ttggttttat aaaataactc ctttttcttt agaaagcatt 300
tttatatata tcagtacttt tttatcttct ttggtggtta tacctttgat tttgattgct 360
aatgaataca aacgcccttt aatggggttt gttgcagcat tgctagccag tatagctaat 420
agctattata atcgcacgat gagcggatat tatgatactg atatgcttgt tatagttctt 480
gcaatgatga tagttttctt tatgataagg ctgattttga aaaaagattt attatcttta 540
ataacactgc ctttgtttgt aggaatttat ctttggtggt atccatcaag ctatacttta 600
aatgttgctt tactaggact tttctttatt tataccttgg tttttcatat aaaagaaaaa 660
acgctttata tggctattat cctagcttct atcacacttt caaatatagc ttggttttat 720
caaagcgcca tcattgtcat acttttttagt ctttttgttt tgcaaaataa gcgttttagc 780
tttgctttgc ttggaatttt aggtttggca actttggtat ttttgatact aagcggtgga 840
attgatccta tactctatca acttaaattt tatattttta gaagtgatga gagtgcaaat 900
ttggctcaag gttttatgta ttttaatgta aatcaaacca tacaagaggt agaaagtata 960
gatttaagta tttttatgca aaggattagc ggaagcgagc ttgtattttt tgtatcttta 1020
atcggcttta ttttccttgt tagaaaacat aaaagtatga ttttggcttt gccgatgtta 1080
gctttaggat ttttagcact taagagtgga cttcgtttta ctatttatgc agtacctgtt 1140
ttagcacttg gatttggttt tttaatgagt cttttgcaag aaagaaaaca aaaaaaacaat 1200 aatacctatt ggtgggccaa tataggcgtt tttattttta ctttttttaag tttaattcct 1260 atgttctatc atatcaacaa ttataaagca ccaactgttt tttctcaaaa tgaggctacg 1320
aaattagatg agcttaaaaa aattgcacaa agagaagatt atgtagtaac ttggtgggat 1380
tatggatatc ctattaggta ttacagcgat gttaaaactt tggctgatgg gggtaagcat 1440
ttaggcaagg ataatttttt cccatctttt gttctaagta aagatcaagt ggctgctgca 1500
aatatggcaa gacttagtgt agaatacaca gaaaaaagtt tttacgcccc tttaaatgat 1560

```
attttaaaaa atgatctttt acaagccatg atgaaagatt ataatcaaaa taatgtggat   1620

ttgtttttag cttcgctttc caagcctgat tttaaaatca atacgccaaa aacacgcgat   1680

gtgtatatct atatgccagc tagaatgtct ttgatttttt caactgtggc tagtttttct   1740

tttgtggatt tggagacagg tgagataaat aaacctttta cttttagtgc agcttatcca   1800

cttgatgtta aaaatggaga aatttatctt agcaatggta ttgcattaag tgatgatttt   1860

agaagtttta aaataaataa tagtactata tccgtaaata gtatcataga gattaattct   1920

atcaaacaag gtgaatataa aatcactcct attgatgata tggctcaatt ttatattttt   1980

tatcttaaag atagcaccat accttatgct cagtttattt taatggataa aactatgttt   2040

aatagtgctt atgtgcaaat gtttttcctt ggaaattatg ataaaaattt gtatgattta   2100

gtgattaatg ctagagatgc aaaagttttt aaactcaaaa tttaa                   2145


<210> SEQ ID NO 8
<211> LENGTH: 785
<212> TYPE: PRT
<213> ORGANISM: Campylobacter upsaliensis

<400> SEQUENCE: 8

Met Lys Asn Glu Ala Val Lys Asn Ala Asn Leu Arg Leu Val Phe Phe
1               5                   10                  15

Ile Leu Leu Ala Phe Gly Phe Ser Val Leu Cys Arg Phe Tyr Trp Ile
            20                  25                  30

Tyr Trp Ala Ser Asp Phe Asn Glu Tyr Phe Phe Asn Asn Gln Leu Met
        35                  40                  45

Ile Ser Ser Asn Asp Gly Tyr Thr Phe Ala Glu Gly Ala Arg Asp Lys
    50                  55                  60

Ile Ala Gly Phe His Gln Glu Asn Asp Leu Ser Phe Ile Asn Ser Ser
65                  70                  75                  80

Leu Ser Ile Leu Thr Tyr Val Leu Tyr Lys Ile Thr Pro Phe Ser Phe
                85                  90                  95

Glu Ser Ile Ile Leu Tyr Met Ser Val Phe Phe Ser Ser Leu Ile Val
            100                 105                 110

Val Pro Leu Ile Leu Ile Ala Asn Glu Leu Lys Arg Pro Leu Met Gly
        115                 120                 125

Leu Phe Ala Ala Phe Leu Ala Ser Ile Ala Lys Ser Tyr Tyr Asn Arg
    130                 135                 140

Thr Met Ala Gly Tyr Tyr Asp Thr Asp Met Leu Ala Ile Val Leu Pro
145                 150                 155                 160

Met Phe Ile Leu Tyr Phe Phe Ile Arg Leu Ile Leu Arg Lys Asp Asp
                165                 170                 175

Phe Ser Leu Leu Ala Leu Pro Phe Phe Met Gly Leu Tyr Leu Trp Trp
            180                 185                 190

Tyr Pro Ser Ser Tyr Thr Leu Asn Val Ala Phe Ile Ala Leu Phe Thr
        195                 200                 205

Leu Tyr Val Leu Ile Tyr His Arg Lys Glu Arg Ser Phe Tyr Met Ala
    210                 215                 220

Ala Leu Leu Cys Ala Ile Thr Leu Ser Asn Ile Ala Trp Phe Tyr Gln
225                 230                 235                 240

Ser Ala Ile Ile Val Leu Leu Phe Ala Leu Phe Met Leu Lys Asn Ser
                245                 250                 255

Phe Phe Asn Phe Lys Phe Ile Ala Leu Leu Ala Leu Gly Val Leu Val
            260                 265                 270
```

```
Phe Leu Ala Leu Ser Gly Gly Ile Asp Pro Ile Leu Tyr Gln Leu Lys
        275                 280                 285

Phe Tyr Leu Leu Arg Ser Asp Glu Ser Ala Ser Leu Ala Arg Gly Phe
    290                 295                 300

Ala Tyr Phe Asn Val Asn Leu Thr Ile Gln Glu Val Glu Ser Ile Asp
305                 310                 315                 320

Leu Ser Thr Phe Met Gln Arg Ile Ser Gly Ser Glu Leu Val Phe Leu
                325                 330                 335

Leu Ser Leu Phe Gly Phe Leu Trp Leu Leu Lys Lys His Lys Val Met
            340                 345                 350

Leu Leu Thr Leu Pro Met Leu Leu Leu Gly Phe Leu Ala Leu Arg Gly
        355                 360                 365

Gly Leu Arg Phe Thr Ile Tyr Ala Val Pro Ile Met Ala Leu Gly Phe
    370                 375                 380

Gly Phe Leu Ser Val Gln Ile Leu Ser Leu Ile Gln Lys Met Arg Pro
385                 390                 395                 400

Leu Lys Glu Thr Arg Lys Leu Arg Ile Phe Phe Tyr Gly Ile Phe Pro
                405                 410                 415

Leu Phe Val Leu Val Leu Gly Ala Tyr Phe Tyr Phe Ser Gln Ser Ala
            420                 425                 430

Ile Tyr Glu Ser Met Gly Val Glu Phe Gln Lys Asn Phe Val Ser Phe
        435                 440                 445

Phe Val Glu Asp Thr Leu Leu Phe Ser Leu Leu Ile Leu Ala Ile Phe
    450                 455                 460

Thr Pro Leu Ile Phe Glu Leu Leu Trp Arg Lys Lys Asp Ile Arg Phe
465                 470                 475                 480

Val Cys Ser Phe Tyr Ile Val Gly Val Leu Leu Phe Ser Leu Trp Ala
                485                 490                 495

Asn Leu Ser His Ile Tyr Asn Tyr Arg Ala His Thr Val Phe Ser Tyr
            500                 505                 510

Asn Glu Ala Ser Ile Leu Asp Asn Leu Lys Ala Asn Val Ser Arg Glu
        515                 520                 525

Asp Tyr Ile Val Ala Trp Trp Asp Tyr Gly Tyr Pro Ile Arg Tyr Tyr
    530                 535                 540

Ser Asp Val Lys Thr Leu Ala Asp Gly Gly Lys His Leu Gly Lys Asp
545                 550                 555                 560

Asn Phe Phe Pro Ser Phe Val Leu Ser Gln Asn Pro Arg Ala Ala Ala
                565                 570                 575

Asn Met Ala Arg Leu Ser Val Glu Tyr Thr Glu Lys Gly Phe Lys Thr
            580                 585                 590

Pro Tyr Asn Asp Leu Leu Glu Ala Met Met Lys Asp Tyr Asn Tyr Ser
        595                 600                 605

Asn Val Asn Leu Phe Leu Ala Ala Leu Ser Lys Glu Asp Phe Thr Leu
    610                 615                 620

Gln Thr Pro Lys Thr Arg Asp Ile Tyr Ile Tyr Met Pro Ser Arg Met
625                 630                 635                 640

Ala Ala Ile Phe Gly Thr Val Ala Ser Phe Ser Tyr Met Ser Leu Glu
                645                 650                 655

Thr Gly Glu Leu Glu Asn Pro Phe Val Tyr Ser Val Ala Tyr Tyr Leu
            660                 665                 670

Gly Asn Glu Asp Gly Lys Leu Val Leu Ser Asn Asn Met Leu Leu His
        675                 680                 685
```

```
Ser Asp Phe Arg Ser Phe Asp Leu Asn Gly Lys Asn Tyr Ala Ile Asn
    690                 695                 700

Ser Leu Val Glu Phe Thr Ser Val Gln Gln Lys Tyr Tyr Ser Val Val
705                 710                 715                 720

Glu Ile Asp Lys Asn Ala Lys Tyr Tyr Leu Phe His Ile Lys Asp Ala
                725                 730                 735

Asn Ile Pro Asn Val Gln Phe Ile Leu Met Asp Lys Ala Met Tyr Glu
            740                 745                 750

Ser Ala Phe Val Gln Met Phe Phe Phe Gly Lys Tyr Asp Glu Ser Leu
        755                 760                 765

Tyr Glu Leu Ile Val Asp Ser Lys Glu Ala Lys Val Tyr Lys Leu Lys
    770                 775                 780

Leu
785


<210> SEQ ID NO 9
<211> LENGTH: 2358
<212> TYPE: DNA
<213> ORGANISM: Campylobacter upsaliensis

<400> SEQUENCE: 9

atgaaaaacg aggctgtgaa aaatgcgaat ttgaggctag tattttttat cttactagct     60

tttggtttta gtgttttatg tcgcttttat tggatttatt gggcgagtga ttttaacgaa    120

tattttttta ataatcagct tatgataagc tcaaatgacg gctacacttt tgcagagggt    180

gctagagata agatagcggg ctttcatcag gaaaatgatt taagctttat taattcctct    240

ctttctattt tgacttatgt gctttataaa atcacgcctt ttagttttga aagcattatt    300

ttatatatga gtgtattttt ttcttcactt atagttgtgc cgcttatttt aattgcaaat    360

gagcttaaac gccctttaat gggacttttt gcggcatttt tagcaagtat tgcaaaaagc    420

tattataacc gcactatggc aggatattat gatacagata tgttagccat tgtgcttcct    480

atgtttattt tatatttttt catcaggctt attttaagaa aagatgattt ttctttactt    540

gccttgccgt tttttatggg actttatctt tggtggtatc catcaagcta tactctaaat    600

gtcgctttta tcgcactttt taccctttat gttttgattt atcatagaaa agaaaggtct    660

ttttatatgg cagcactttt gtgtgccatt accctttcaa atattgcttg gttttatcaa    720

agtgctatta ttgttttact ttttgctctt tttatgctta aaaattcgtt ttttaatttt    780

aaatttatcg cacttttagc cttaggagtt ttagtttttt tggctttaag tgggggggata    840

gaccccatac tttatcagct taaattttat cttttaagaa gtgatgaaag tgcaagttta    900

gcgcgtggtt ttgcgtattt taatgtaaat ttaaccatac aagaggttga aagtatcgat    960

ttaagcactt ttatgcaaag aattagcgga agtgagcttg tgtttttact ttctcttttt   1020

ggctttttat ggcttttaaa aaagcataag gtgatgcttt taaccctacc tatgcttttg   1080

ctcggttttt tagcacttag aggtgggctt agatttacta tttatgctgt gcctattatg   1140

gcgcttggct ttggcttttt aagcgttcaa attttaagct taatccaaaa aatgcgtccc   1200

ttaaaagaaa ctcgaaaatt aagaatattt ttttatggaa tctttccgct tttgtgcttt   1260

gttttggggg cttattttta ttttagtcaa agtgctattt atgagagtat gggagtggaa   1320

tttcaaaaga actttgtgag cttttttgta gaagatactt tgcttttttc tttgctgatt   1380

ttggctattt ttacgccttt aatttttgag cttttgtgga gaaaaaagga cattcgtttt   1440

gtgtgtagct tttatattgt gggggttttg ctttttttctt tatgggcaaa tttaagtcat   1500
```

```
atttataatt atagagcaca caccgttttt agctacaatg aagcgagtat tttggataat   1560

cttaaagcta atgtttctag ggaagattat attgtggctt ggtgggatta tggctatcct   1620

attcgttatt atagcgatgt gaaaacctta gctgatgggg gtaagcattt gggtaaggat   1680

aatttttcc cttcttttgt tttaagtcaa aatccacgcg cagcggcaaa tatggcaaga   1740

cttagcgtag aatacacaga aaaaggcttt aaaacgcctt ataatgatct tttagaagcg   1800

atgatgaagg attataatta tagcaatgta aatttatttt tagcggcact ttctaaggag   1860

gattttactc ttcaaacgcc caaaactaga gatatttaca tctatatgcc ttctcgtatg   1920

gcggcgattt ttggcacggt ggcaagtttt tcttatatga gcttagaaac gggtgagctt   1980

gaaaatcctt ttgtttatag tgtggcgtat tatttgggaa atgaggacgg caaactcgtc   2040

ttaagtaata atatgctcct tcatagcgac tttagaagct ttgaccttaa tggcaagaat   2100

tatgctatta attctttggt tgaatttact tcggtgcagc aaaaatatta tagtgttgtg   2160

gagattgata aaaatgctaa atattatctc tttcacatca aagacgctaa tatccctaat   2220

gtgcaattta tcctaatgga taaggcgatg tatgagagtg ctttcgtgca aatgtttttc   2280

tttggtaagt atgatgagag tttgtatgaa ttaattgtag atagtaaaga agcaaaggtg   2340

tataaattaa aattatga                                                   2358
```

```
<210> SEQ ID NO 10
<211> LENGTH: 661
<212> TYPE: PRT
<213> ORGANISM: Artificial
<220> FEATURE:
<223> OTHER INFORMATION: Campylobacter Pg1B Consensus Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
```

<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(60)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (107)..(108)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(124)
<223> OTHER INFORMATION: Xaa can be any naturally occurring amino acid
<220> FEATURE:
<221> NAME/KEY: misc_feature
<222> LOCATION: (127)..(129)
<223> OTHER INFORMATION: Xaa can be any naturally occurring amino acid
<220> FEATURE:

<221> NAME/KEY: misc_feature
<222> LOCATION: (131)..(133)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (137)..(139)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(156)
<223> OTHER INFORMATION: Xaa can be any naturally occurring amino acid
<220> FEATURE:
<221> NAME/KEY: misc_feature
<222> LOCATION: (159)..(160)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (164)..(165)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (170)..(172)
<223> OTHER INFORMATION: Xaa can be any naturally occurring amino acid
<220> FEATURE:
<221> NAME/KEY: misc_feature
<222> LOCATION: (174)..(177)
<223> OTHER INFORMATION: Xaa can be any naturally occurring amino acid
<220> FEATURE:
<221> NAME/KEY: misc_feature
<222> LOCATION: (179)..(182)
<223> OTHER INFORMATION: Xaa can be any naturally occurring amino acid
<220> FEATURE:
<221> NAME/KEY: misc_feature
<222> LOCATION: (185)..(186)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (191)..(194)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (203)..(210)
<223> OTHER INFORMATION: Xaa can be any naturally occurring amino acid
<220> FEATURE:
<221> NAME/KEY: misc_feature
<222> LOCATION: (212)..(216)
<223> OTHER INFORMATION: Xaa can be any naturally occurring amino acid
<220> FEATURE:
<221> NAME/KEY: misc_feature
<222> LOCATION: (218)..(224)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (242)..(250)
<223> OTHER INFORMATION: Xaa can be any naturally occurring amino acid
<220> FEATURE:
<221> NAME/KEY: misc_feature
<222> LOCATION: (252)..(255)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (269)..(271)
<223> OTHER INFORMATION: Xaa can be any naturally occurring amino acid
<220> FEATURE:
<221> NAME/KEY: misc_feature
<222> LOCATION: (273)..(275)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (291)..(292)
<223> OTHER INFORMATION: Xaa can be any naturally occurring amino acid
<220> FEATURE:
<221> NAME/KEY: misc_feature
<222> LOCATION: (295)..(296)
<223> OTHER INFORMATION: Xaa can be any naturally occurring amino acid
<220> FEATURE:
<221> NAME/KEY: misc_feature
<222> LOCATION: (298)..(301)
<223> OTHER INFORMATION: Xaa can be any naturally occurring amino acid
<220> FEATURE:
<221> NAME/KEY: misc_feature
<222> LOCATION: (303)..(303)

<223> OTHER INFORMATION: Xaa can be any naturally occurring amino acid
<220> FEATURE:
<221> NAME/KEY: misc_feature
<222> LOCATION: (305)..(307)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid
<220> FEATURE:
<221> NAME/KEY: misc_feature
<222> LOCATION: (319)..(320)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (331)..(332)
<223> OTHER INFORMATION: Xaa can be any naturally occurring amino acid
<220> FEATURE:
<221> NAME/KEY: misc_feature
<222> LOCATION: (338)..(348)
<223> OTHER INFORMATION: Xaa can be any naturally occurring amino acid
<220> FEATURE:
<221> NAME/KEY: misc_feature
<222> LOCATION: (350)..(373)
<223> OTHER INFORMATION: Xaa can be any naturally occurring amino acid
<220> FEATURE:
<221> NAME/KEY: misc_feature
<222> LOCATION: (376)..(377)
<223> OTHER INFORMATION: Xaa can be any naturally occurring amino acid
<220> FEATURE:
<221> NAME/KEY: misc_feature
<222> LOCATION: (379)..(381)
<223> OTHER INFORMATION: Xaa can be any naturally occurring amino acid
<220> FEATURE:
<221> NAME/KEY: misc_feature
<222> LOCATION: (385)..(387)
<223> OTHER INFORMATION: Xaa can be any naturally occurring amino acid
<220> FEATURE:
<221> NAME/KEY: misc_feature
<222> LOCATION: (390)..(391)
<223> OTHER INFORMATION: Xaa can be any naturally occurring amino acid
<220> FEATURE:
<221> NAME/KEY: misc_feature
<222> LOCATION: (393)..(394)
<223> OTHER INFORMATION: Xaa can be any naturally occurring amino acid
<220> FEATURE:
<221> NAME/KEY: misc_feature
<222> LOCATION: (397)..(400)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (415)..(415)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (441)..(441)
<223> OTHER INFORMATION: Xaa can be any naturally occurring amino acid
<220> FEATURE:
<221> NAME/KEY: misc_feature
<222> LOCATION: (444)..(448)
<223> OTHER INFORMATION: Xaa can be any naturally occurring amino acid
<220> FEATURE:
<221> NAME/KEY: misc_feature
<222> LOCATION: (463)..(463)
<223> OTHER INFORMATION: Xaa can be any naturally occurring amino acid
<220> FEATURE:
<221> NAME/KEY: misc_feature
<222> LOCATION: (465)..(469)
<223> OTHER INFORMATION: Xaa can be any naturally occurring amino acid
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
<222> LOCATION: (475)..(476)
<223> OTHER INFORMATION: Xaa can be any naturally occurring amino acid
<220> FEATURE:
<221> NAME/KEY: misc_feature
<222> LOCATION: (481)..(486)
<223> OTHER INFORMATION: Xaa can be any naturally occurring amino acid
<220> FEATURE:
<221> NAME/KEY: misc_feature
<222> LOCATION: (489)..(490)
<223> OTHER INFORMATION: Xaa can be any naturally occurring amino acid
<220> FEATURE:
<221> NAME/KEY: misc_feature
<222> LOCATION: (492)..(494)
<223> OTHER INFORMATION: Xaa can be any naturally occurring amino acid
<220> FEATURE:
<221> NAME/KEY: misc_feature
<222> LOCATION: (497)..(499)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (508)..(508)
<223> OTHER INFORMATION: Xaa can be any naturally occurring amino acid
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (515)..(516)
<223> OTHER INFORMATION: Xaa can be any naturally occurring amino acid
<220> FEATURE:
<221> NAME/KEY: misc_feature
<222> LOCATION: (518)..(520)
<223> OTHER INFORMATION: Xaa can be any naturally occurring amino acid
<220> FEATURE:
<221> NAME/KEY: misc_feature
<222> LOCATION: (523)..(523)
<223> OTHER INFORMATION: Xaa can be any naturally occurring amino acid
<220> FEATURE:

<221> NAME/KEY: misc_feature
<222> LOCATION: (525)..(531)
<223> OTHER INFORMATION: Xaa can be any naturally occurring amino acid
<220> FEATURE:
<221> NAME/KEY: misc_feature
<222> LOCATION: (533)..(540)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (544)..(552)
<223> OTHER INFORMATION: Xaa can be any naturally occurring amino acid
<220> FEATURE:
<221> NAME/KEY: misc_feature
<222> LOCATION: (554)..(556)
<223> OTHER INFORMATION: Xaa can be any naturally occurring amino acid
<220> FEATURE:
<221> NAME/KEY: misc_feature
<222> LOCATION: (558)..(558)
<223> OTHER INFORMATION: Xaa can be any naturally occurring amino acid
<220> FEATURE:
<221> NAME/KEY: misc_feature
<222> LOCATION: (560)..(565)
<223> OTHER INFORMATION: Xaa can be any naturally occurring amino acid
<220> FEATURE:
<221> NAME/KEY: misc_feature
<222> LOCATION: (569)..(586)
<223> OTHER INFORMATION: Xaa can be any naturally occurring amino acid
<220> FEATURE:
<221> NAME/KEY: misc_feature
<222> LOCATION: (588)..(601)
<223> OTHER INFORMATION: Xaa can be any naturally occurring amino acid
<220> FEATURE:
<221> NAME/KEY: misc_feature
<222> LOCATION: (603)..(604)
<223> OTHER INFORMATION: Xaa can be any naturally occurring amino acid
<220> FEATURE:
<221> NAME/KEY: misc_feature
<222> LOCATION: (606)..(618)
<223> OTHER INFORMATION: Xaa can be any naturally occurring amino acid
<220> FEATURE:
<221> NAME/KEY: misc_feature
<222> LOCATION: (620)..(622)
<223> OTHER INFORMATION: Xaa can be any naturally occurring amino acid
<220> FEATURE:
<221> NAME/KEY: misc_feature
<222> LOCATION: (624)..(628)
<223> OTHER INFORMATION: Xaa can be any naturally occurring amino acid
<220> FEATURE:
<221> NAME/KEY: misc_feature
<222> LOCATION: (630)..(632)
<223> OTHER INFORMATION: Xaa can be any naturally occurring amino acid
<220> FEATURE:
<221> NAME/KEY: misc_feature
<222> LOCATION: (636)..(639)
<223> OTHER INFORMATION: Xaa can be any naturally occurring amino acid
<220> FEATURE:
<221> NAME/KEY: misc_feature
<222> LOCATION: (642)..(643)
<223> OTHER INFORMATION: Xaa can be any naturally occurring amino acid
<220> FEATURE:
<221> NAME/KEY: misc_feature
<222> LOCATION: (645)..(653)
<223> OTHER INFORMATION: Xaa can be any naturally occurring amino acid
<220> FEATURE:
<221> NAME/KEY: misc_feature
<222> LOCATION: (656)..(661)
<223> OTHER INFORMATION: Xaa can be any naturally occurring amino acid

<400> SEQUENCE: 10

```
Xaa Xaa Asn Asp Gly Tyr Xaa Phe Ala Glu Gly Ala Arg Asp Xaa Ile
1               5                   10                  15

Ala Gly Phe His Gln Xaa Asn Asp Leu Ser Xaa Xaa Xaa Ser Ser Leu
            20                  25                  30
```

```
Ser Xaa Leu Thr Tyr Xaa Xaa Tyr Xaa Ile Leu Pro Phe Ser Xaa Glu
        35                  40                  45

Ser Ile Xaa Xaa Tyr Xaa Ser Xaa Phe Xaa Xaa Xaa Leu Xaa Val Xaa
    50                  55                  60

Pro Xaa Ile Leu Xaa Ala Xaa Glu Xaa Lys Xaa Xaa Xaa Xaa Gly Xaa
65                  70                  75                  80

Xaa Ala Ala Xaa Leu Xaa Ser Ile Ala Xaa Ser Tyr Tyr Asn Arg Thr
                85                  90                  95

Met Xaa Gly Tyr Tyr Asp Thr Asp Met Leu Xaa Xaa Val Leu Xaa Met
            100                 105                 110

Xaa Ile Xaa Xaa Xaa Xaa Xaa Xaa Xaa Xaa Xaa Xaa Lys Asp Xaa Xaa
        115                 120                 125

Xaa Leu Xaa Xaa Xaa Pro Xaa Phe Xaa Xaa Xaa Tyr Leu Trp Trp Tyr
    130                 135                 140

Pro Ser Ser Tyr Xaa Leu Asn Xaa Ala Xaa Xaa Xaa Leu Phe Xaa Xaa
145                 150                 155                 160

Tyr Xaa Leu Xaa Xaa His Xaa Lys Glu Xaa Xaa Xaa Tyr Xaa Xaa Xaa
                165                 170                 175

Xaa Leu Xaa Xaa Xaa Xaa Leu Ser Xaa Xaa Ala Trp Xaa Tyr Xaa Xaa
            180                 185                 190

Xaa Xaa Ile Val Xaa Leu Phe Xaa Xaa Phe Xaa Xaa Xaa Xaa Xaa Xaa
        195                 200                 205

Xaa Xaa Phe Xaa Xaa Xaa Xaa Xaa Leu Xaa Xaa Xaa Xaa Xaa Xaa Xaa
    210                 215                 220

Leu Xaa Leu Ser Gly Gly Xaa Asp Pro Xaa Leu Tyr Gln Leu Lys Xaa
225                 230                 235                 240

Tyr Xaa Xaa Xaa Xaa Xaa Xaa Xaa Xaa Xaa Leu Xaa Xaa Xaa Xaa Phe
                245                 250                 255

Xaa Tyr Phe Asn Val Asn Xaa Thr Ile Xaa Glu Val Xaa Xaa Xaa Asp
            260                 265                 270

Xaa Xaa Xaa Phe Met Xaa Arg Ile Ser Xaa Ser Xaa Xaa Val Phe Xaa
        275                 280                 285

Xaa Ser Xaa Xaa Gly Phe Xaa Xaa Leu Xaa Xaa Xaa Xaa Lys Xaa Met
    290                 295                 300

Xaa Xaa Xaa Leu Pro Xaa Leu Xaa Leu Gly Phe Xaa Ala Leu Xaa Xaa
305                 310                 315                 320

Gly Leu Arg Phe Thr Ile Tyr Xaa Val Pro Xaa Xaa Ala Leu Gly Phe
                325                 330                 335

Gly Xaa Xaa Xaa Xaa Xaa Xaa Xaa Xaa Xaa Xaa Xaa Lys Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa His Ile Xaa Xaa Tyr Xaa Xaa Xaa Thr Val Phe
    370                 375                 380

Xaa Xaa Xaa Glu Ala Xaa Xaa Leu Xaa Xaa Leu Lys Xaa Xaa Xaa Xaa
385                 390                 395                 400

Arg Glu Asp Tyr Xaa Val Xaa Trp Trp Asp Tyr Gly Tyr Pro Xaa Arg
                405                 410                 415

Tyr Tyr Ser Asp Xaa Lys Thr Leu Xaa Asp Gly Gly Lys His Leu Gly
            420                 425                 430

Lys Asp Asn Phe Phe Xaa Ser Phe Xaa Leu Ser Xaa Xaa Xaa Xaa Xaa
        435                 440                 445
```

Ala Ala Asn Met Ala Arg Leu Ser Val Glu Tyr Thr Glu Lys Xaa Phe
450 455 460

Xaa Xaa Xaa Xaa Xaa Asp Xaa Leu Xaa Ala Xaa Xaa Lys Asp Tyr Asn
465 470 475 480

Xaa Xaa Xaa Xaa Xaa Xaa Phe Leu Xaa Xaa Leu Xaa Xaa Xaa Asp Phe
485 490 495

Xaa Xaa Xaa Thr Xaa Lys Thr Arg Asp Xaa Tyr Xaa Tyr Met Pro Xaa
500 505 510

Arg Met Xaa Xaa Ile Xaa Xaa Xaa Val Ala Xaa Phe Xaa Xaa Xaa Xaa
515 520 525

Xaa Xaa Xaa Gly Xaa Xaa Xaa Xaa Xaa Xaa Xaa Xaa Ser Xaa Ala Xaa
530 535 540

Xaa Xaa Xaa Xaa Xaa Xaa Xaa Xaa Gly Xaa Xaa Xaa Leu Xaa Asn Xaa
545 550 555 560

Xaa Xaa Xaa Xaa Xaa Asp Phe Arg Xaa Xaa Xaa Xaa Xaa Xaa Xaa Xaa
565 570 575

Xaa Xaa Xaa Xaa Xaa Xaa Xaa Xaa Xaa Xaa Ser Xaa Xaa Xaa Xaa Xaa
580 585 590

Xaa Xaa Xaa Xaa Xaa Xaa Xaa Xaa Xaa Ala Xaa Xaa Tyr Xaa Xaa Xaa
595 600 605

Xaa Xaa Xaa Xaa Xaa Xaa Xaa Xaa Xaa Xaa Phe Xaa Xaa Xaa Asp Xaa
610 615 620

Xaa Xaa Xaa Xaa Ser Xaa Xaa Xaa Gln Met Phe Xaa Xaa Xaa Xaa Tyr
625 630 635 640

Asp Xaa Xaa Leu Xaa Xaa Xaa Xaa Xaa Xaa Xaa Xaa Xaa Ala Lys Xaa
645 650 655

Xaa Xaa Xaa Xaa Xaa
660

<210> SEQ ID NO 11
<211> LENGTH: 967
<212> TYPE: PRT
<213> ORGANISM: Pyrococcus furiosus

<400> SEQUENCE: 11

Met Val Lys Thr Gln Ile Lys Glu Lys Lys Lys Asp Glu Lys Val Thr
1 5 10 15

Ile Pro Leu Pro Gly Lys Ile Lys Thr Val Leu Ala Phe Leu Val Val
20 25 30

Leu Ala Phe Ala Ala Tyr Gly Phe Tyr Ile Arg His Leu Thr Ala Gly
35 40 45

Lys Tyr Phe Ser Asp Pro Asp Thr Phe Tyr His Phe Glu Ile Tyr Lys
50 55 60

Leu Val Leu Lys Glu Gly Leu Pro Arg Tyr Tyr Pro Met Ala Asp Ala
65 70 75 80

Pro Phe Gly Ser Leu Ile Gly Glu Pro Leu Gly Leu Tyr Ile Leu Pro
85 90 95

Ala Ile Phe Tyr Lys Ile Ile Ser Ile Phe Gly Tyr Asn Glu Leu Glu
100 105 110

Ala Phe Leu Leu Trp Pro Pro Phe Val Gly Phe Leu Ser Val Ile Gly
115 120 125

Val Tyr Leu Leu Gly Arg Lys Val Leu Asn Glu Trp Ala Gly Met Trp
130 135 140

Gly Ala Ile Ile Leu Ser Val Leu Thr Ala Asn Phe Ser Arg Thr Phe
145 150 155 160

-continued

```
Ser Gly Asn Ala Arg Gly Asp Gly Pro Phe Met Met Leu Phe Thr Phe
                165                 170                 175

Ser Ala Val Leu Met Leu Tyr Tyr Leu Thr Glu Glu Asn Lys Asn Lys
            180                 185                 190

Lys Ile Ile Trp Gly Thr Leu Phe Val Leu Leu Ala Gly Ile Ser Thr
        195                 200                 205

Ala Ala Trp Asn Gly Ser Pro Phe Gly Leu Met Val Leu Leu Gly Phe
    210                 215                 220

Ala Ser Phe Gln Thr Ile Ile Leu Phe Ile Phe Gly Lys Ile Asn Glu
225                 230                 235                 240

Leu Arg Glu Phe Ile Lys Glu Tyr Tyr Pro Ala Tyr Leu Gly Ile Leu
                245                 250                 255

Ala Ile Ser Tyr Leu Leu Thr Ile Pro Gly Ile Gly Lys Ile Gly Gly
            260                 265                 270

Phe Val Arg Phe Ala Phe Glu Val Phe Leu Gly Leu Val Phe Leu Ala
        275                 280                 285

Ile Val Met Leu Tyr Gly Gly Lys Tyr Leu Asn Tyr Ser Asp Lys Lys
    290                 295                 300

His Arg Phe Ala Val Val Ala Val Ile Val Ile Ala Gly Phe Ala Gly
305                 310                 315                 320

Ala Tyr Ile Tyr Val Gly Pro Lys Leu Phe Thr Leu Met Gly Gly Ala
                325                 330                 335

Tyr Gln Ser Thr Gln Val Tyr Glu Thr Val Gln Glu Leu Ala Lys Thr
            340                 345                 350

Asp Trp Gly Asp Val Lys Val Tyr Tyr Gly Val Glu Lys Pro Asn Gly
        355                 360                 365

Ile Val Phe Phe Leu Gly Leu Val Gly Ala Met Ile Val Thr Ala Arg
    370                 375                 380

Tyr Leu Tyr Lys Leu Phe Lys Asp Gly Arg Arg Pro His Glu Glu Leu
385                 390                 395                 400

Phe Ala Ile Thr Phe Tyr Val Met Ser Ile Tyr Leu Leu Trp Thr Ala
                405                 410                 415

Ala Arg Phe Leu Phe Leu Ala Ser Tyr Ala Ile Ala Leu Met Ser Gly
            420                 425                 430

Val Phe Ala Gly Tyr Val Leu Glu Thr Val Glu Lys Met Lys Glu Ser
        435                 440                 445

Ile Pro Ile Lys Ala Ala Leu Gly Gly Val Ile Ala Ile Met Leu Leu
    450                 455                 460

Leu Ile Pro Leu Thr His Gly Pro Leu Leu Ala Gln Ser Ala Lys Ser
465                 470                 475                 480

Met Arg Thr Thr Glu Ile Glu Thr Ser Gly Trp Glu Asp Ala Leu Lys
                485                 490                 495

Trp Leu Arg Glu Asn Thr Pro Glu Tyr Ser Thr Ala Thr Ser Trp Trp
            500                 505                 510

Asp Tyr Gly Tyr Trp Ile Glu Ser Ser Leu Leu Gly Gln Arg Arg Ala
        515                 520                 525

Ser Ala Asp Gly Gly His Ala Arg Asp Arg Asp His Ile Leu Ala Leu
    530                 535                 540

Phe Leu Ala Arg Asp Gly Asn Ile Ser Glu Val Asp Phe Glu Ser Trp
545                 550                 555                 560

Glu Leu Asn Tyr Phe Leu Val Tyr Leu Asn Asp Trp Ala Lys Phe Asn
                565                 570                 575
```

-continued

```
Ala Ile Ser Tyr Leu Gly Gly Ala Ile Thr Arg Arg Glu Tyr Asn Gly
            580                 585                 590

Asp Glu Ser Gly Arg Gly Ala Val Thr Thr Leu Leu Pro Leu Pro Arg
        595                 600                 605

Tyr Gly Glu Lys Tyr Val Asn Leu Tyr Ala Lys Val Ile Val Asp Val
    610                 615                 620

Ser Asn Ser Ser Val Lys Val Thr Val Gly Asp Arg Glu Cys Asp Pro
625                 630                 635                 640

Leu Met Val Thr Phe Thr Pro Ser Gly Lys Thr Ile Lys Gly Thr Gly
                645                 650                 655

Thr Cys Ser Asp Gly Asn Ala Phe Pro Tyr Val Leu His Leu Thr Pro
            660                 665                 670

Thr Ile Gly Val Leu Ala Tyr Tyr Lys Val Ala Thr Ala Asn Phe Ile
        675                 680                 685

Lys Leu Ala Phe Gly Val Pro Ala Ser Thr Ile Pro Gly Phe Ser Asp
    690                 695                 700

Lys Leu Phe Ser Asn Phe Glu Pro Val Tyr Glu Ser Gly Asn Val Ile
705                 710                 715                 720

Val Tyr Arg Phe Thr Pro Phe Gly Ile Tyr Lys Ile Glu Glu Asn Ile
                725                 730                 735

Asn Gly Thr Trp Lys Gln Val Tyr Asn Leu Thr Pro Gly Lys His Glu
            740                 745                 750

Leu Lys Leu Tyr Ile Ser Ala Phe Gly Arg Asp Ile Glu Asn Ala Thr
        755                 760                 765

Leu Tyr Ile Tyr Ala Ile Asn Asn Glu Lys Ile Ile Glu Lys Ile Lys
    770                 775                 780

Ile Ala Glu Ile Ser His Met Asp Tyr Leu Asn Glu Tyr Pro Ile Ala
785                 790                 795                 800

Val Asn Val Thr Leu Pro Asn Ala Thr Ser Tyr Arg Phe Val Leu Val
                805                 810                 815

Gln Lys Gly Pro Ile Gly Val Leu Leu Asp Ala Pro Lys Val Asn Gly
            820                 825                 830

Glu Ile Arg Ser Pro Thr Asn Ile Leu Arg Glu Gly Glu Ser Gly Glu
        835                 840                 845

Ile Glu Leu Lys Val Gly Val Asp Lys Asp Tyr Thr Ala Asp Leu Tyr
    850                 855                 860

Leu Arg Ala Thr Phe Ile Tyr Leu Val Arg Lys Ser Gly Lys Asp Asn
865                 870                 875                 880

Glu Asp Tyr Asp Ala Ala Phe Glu Pro Gln Met Asp Val Phe Phe Ile
                885                 890                 895

Thr Lys Ile Gly Glu Asn Ile Gln Leu Lys Glu Gly Glu Asn Thr Val
            900                 905                 910

Lys Val Arg Ala Glu Leu Pro Glu Gly Val Ile Ser Ser Tyr Lys Asp
        915                 920                 925

Glu Leu Gln Arg Lys Tyr Gly Asp Lys Leu Ile Ile Arg Gly Ile Arg
    930                 935                 940

Val Glu Pro Val Phe Ile Ala Glu Lys Glu Tyr Leu Met Leu Glu Val
945                 950                 955                 960

Ser Ala Ser Ala Pro His His
                965
```

<210> SEQ ID NO 12
<211> LENGTH: 2904
<212> TYPE: DNA

<213> ORGANISM: Pyrococcus furiosus

<400> SEQUENCE: 12

```
atggtgaaaa cccaaataaa ggagaaaaag aaagatgaaa aagttactat tccacttcct     60
gggaagataa aaactgtttt ggccttccta gtcgttttgg catttgccgc atatggattt    120
tacattagac atttaacagc cggaaagtat ttctcagatc cagatacctt ctaccatttc    180
gaaatttata agctagtcct caaagagggc cttcctaggt attacccaat ggcagatgct    240
ccatttggaa gtctcatagg agaacctctt ggactataca tccttccagc aatattctac    300
aaaataatct caatatttgg gtacaatgag ctagaggcat ttcttctttg gcccccattc    360
gtaggatttc tcagtgttat aggtgtttac ttactcggaa gaaaagttct gaacgaatgg    420
gcagggatgt ggggtgctat aattctctca gtcctcacgg caaacttttc aagaacattc    480
tcaggcaacg caagaggcga cggcccattc atgatgttgt ttacgttttc agcagtccta    540
atgctctatt atctaaccga ggaaaataaa aacaagaaaa taatctgggg aacactgttt    600
gtactcttgg caggaatatc aactgcagca tggaacggtt caccatttgg actaatggtt    660
ctccttggat tcgcatcgtt ccagacaata atcctcttta tttttggaaa gatcaatgag    720
cttagagaat tcataaagga atactaccca gcatacctgg gaattttagc tataagctac    780
cttctaacga tcccaggaat tggaaaaata ggaggatttg taagatttgc atttgaggtt    840
ttcttagggt tagttttctt agccatcgtc atgctctatg gaggaaaata cttgaactat    900
tctgacaaga agcacaggtt cgcagtggtt gcagttatag ttattgcggg gttcgcagga    960
gcttatattt acgttggtcc aaaactcttc actctaatgg gtggagctta tcagtcaacg   1020
caagtttatg aaacagtaca ggagctcgca aaaactgatt ggggagatgt aaaagtctat   1080
tatggagtag aaaagccaaa cggaatagtc ttcttccttg gattagttgg agcaatgatt   1140
gttacagcta ggtacctcta caaattattt aaagatggaa ggcgcccaca cgaagagtta   1200
tttgcaataa ctttctatgt aatgtcaatt tacctcctct ggacagctgc tagattccta   1260
ttcctagcga gttatgcgat agcattgatg tcaggtgtct ttgcaggata cgtcctagag   1320
actgtagaaa agatgaaaga gagtatacca ataaaagcag cactaggagg agtaattgct   1380
attatgcttc ttctaatacc cttaactcat ggcccactct tagctcaaag cgctaaaagt   1440
atgagaacaa ccgagatcga gactagtgga tgggaagatg cgctcaaatg gctcagagaa   1500
aacactccag aatattcgac cgcaacctct tggtgggact atggatattg gatagagtca   1560
agcctcctag gacagagaag ggccagtgct gatggtggac atgcaagaga tagagatcat   1620
atcttagccc tatttctagc cagagacggt aacattagtg aagtagactt tgagagttgg   1680
gagcttaact acttcctagt ttaccttaat gattgggcaa agttcaatgc aatcagctat   1740
ctaggcgggg ctataacgag gagagaatac aatggagatg aaagtggaag aggagccgta   1800
actacgctac ttcctctccc aaggtatgga gagaaatacg tcaacctcta tgccaaagtt   1860
atagttgatg tttcaaactc gagcgtaaag gttactgtag gagacagaga gtgtgatcca   1920
ctaatggtta cgtttactcc aagtggaaag acgataaaag gaactggaac ctgtagtgat   1980
ggcaacgcct tcccatatgt tttacactta actccaacaa ttggagtact tgcatactac   2040
aaagtagcaa ctgcaaactt cattaagtta gccttcggtg ttccagcttc aacaattcca   2100
ggattctctg ataagctatt ctcaaacttt gagccagtgt atgagtcagg aaacgtaata   2160
gtatatcgct tcacaccatt tggaatatac aaaattgagg aaaacattaa cggaacttgg   2220
aagcaagttt ataacctaac tcctggaaaa cacgagctca aactgtacat ttcagcattc   2280
```

ggaagagaca tcgaaaatgc aacgctgtac atttacgcca taaacaacga gaagatcata 2340
gagaaaatta agattgccga gatatcccac atggactatc taaatgaata cccgatagca 2400
gtgaacgtaa ccctaccaaa tgctacaagc tacaggtttg tactagttca aaaaggccca 2460
ataggtgttc ttctagatgc accaaaagtc aatggtgaga taagaagtcc aaccaacata 2520
ctaagggaag gagaaagtgg agaaatagag cttaaagttg gggttgataa agactacact 2580
gccgatctat acttaagggc tacgttcata tatttagtca gaaaaagtgg aaaggataac 2640
gaagattatg acgcagcgtt tgagccccaa atggatgttt tctttatcac aaagatcgga 2700
gaaaacattc aacttaaaga aggagagaat acagtaaagg ttagggcgga gcttccagaa 2760
ggagttatat ctagctacaa agatgaacta cagagaaaat acggagacaa gttgataatc 2820
agaggaataa gagtagagcc agtgttcata gcagaaaaag agtacctaat gctcgaggtc 2880
agtgcatcgg ctcctcatca ctaa 2904

<210> SEQ ID NO 13
<211> LENGTH: 980
<212> TYPE: PRT
<213> ORGANISM: Artificial
<220> FEATURE:
<223> OTHER INFORMATION: Pyrococcus sp. ST04 OST

<400> SEQUENCE: 13

Met Lys Ser Leu Val Lys Val Glu Val Lys Arg Glu Lys Lys Asp Arg
1 5 10 15

Lys Glu Lys Arg Glu Ile Gly Asn Ile Ser Arg His Tyr Gly Lys Ile
20 25 30

Lys Leu Ala Leu Thr Phe Ile Val Thr Leu Ile Phe Ala Trp Tyr Ala
35 40 45

Phe His Ile Arg His Leu Thr Ala Gly Lys Tyr Phe Pro Asp Pro Asp
50 55 60

Thr Phe Tyr His Tyr Glu Ile Tyr Lys Leu Val Leu Lys Glu Gly Leu
65 70 75 80

Pro Lys Tyr Tyr Pro Met Ser Asp Ala Pro Phe Gly Ser Leu Ile Gly
85 90 95

Glu Pro Leu Gly Leu Tyr Ile Leu Pro Ala Ile Phe Tyr Lys Ile Leu
100 105 110

Ser Ala Phe Gly Tyr Asn Glu Phe Gln Ala Phe Leu Leu Trp Pro Pro
115 120 125

Phe Val Gly Phe Leu Ser Val Ile Gly Val Tyr Leu Leu Gly Arg Lys
130 135 140

Ile Leu Asn Glu Trp Ala Gly Leu Trp Ala Ala Ala Ile Leu Ala Val
145 150 155 160

Ser Thr Ala Asn Phe Ser Arg Thr Phe Ser Gly Asn Ala Arg Gly Asp
165 170 175

Gly Pro Phe Met Met Leu Phe Val Phe Ser Met Val Ala Leu Leu Tyr
180 185 190

Tyr Leu Glu Glu Ala Arg Ile Lys Arg Lys Ala Val Trp Gly Ala Leu
195 200 205

Phe Val Ile Leu Ala Gly Leu Ser Thr Met Ala Trp Asn Gly Ser Pro
210 215 220

Phe Gly Leu Met Val Leu Leu Gly Phe Ala Ser Leu Gln Thr Ile Ala
225 230 235 240

Leu Phe Ile Phe Gly Lys Ile Asp Glu Leu Lys Lys Phe Ile Lys Glu

```
                245                 250                 255

Phe Tyr Pro Ala Tyr Val Ser Val Leu Ile Leu Ser Tyr Leu Leu Thr
            260                 265                 270

Ile Pro Gly Leu Ala Lys Ile Gln Ser Phe Ile Arg Phe Ala Phe Glu
        275                 280                 285

Val Phe Leu Gly Leu Val Phe Leu Ala Ile Val Met Leu Tyr Gly Glu
    290                 295                 300

Lys Phe Leu Asn Tyr Ser Asp Lys Lys His Arg Phe Leu Val Val Ala
305                 310                 315                 320

Ile Ile Val Leu Ile Gly Phe Ala Gly Ala Tyr Ala Tyr Val Gly Pro
                325                 330                 335

Lys Leu Phe Arg Leu Met Gly Gly Ala Tyr Gln Ser Thr Gln Val Tyr
            340                 345                 350

Gln Thr Val Gln Glu Leu Ala Lys Thr Ser Met Gln Asp Ile Lys Leu
        355                 360                 365

Tyr Tyr Gly Val Glu Lys Ala Asn Gly Leu Ile Phe Phe Leu Ser Ile
    370                 375                 380

Pro Gly Phe Leu Ile Met Leu Ser Leu Tyr Leu Ile Gly Leu Trp Ser
385                 390                 395                 400

Lys Ser Glu Ser Pro Asn Lys Glu Leu Leu Gly Ile Thr Phe Tyr Val
                405                 410                 415

Met Ser Ile Tyr Leu Met Ser Leu Ala Val Arg Phe Leu Phe Leu Ala
            420                 425                 430

Ser Tyr Ala Ile Ala Leu Phe Ala Gly Ile Leu Val Gly Tyr Gly Leu
        435                 440                 445

Glu Val Ile Glu Lys Met Lys Glu Asn Val Gly Ile Lys Ala Ala Leu
    450                 455                 460

Ala Ile Val Ile Ser Ile Met Ile Leu Leu Ile Pro Ile Thr His Gly
465                 470                 475                 480

Pro Val Leu Ala Arg Ser Ala Lys Ala Met Ser Lys Thr Glu Val Glu
                485                 490                 495

Thr Ser Gly Trp Glu Gln Ala Leu Lys Trp Leu Arg Asn Asn Thr Pro
            500                 505                 510

Lys Tyr Ala Thr Ala Thr Ser Trp Trp Asp Tyr Gly Tyr Trp Ile Glu
        515                 520                 525

Ser Ser Leu Leu Gly Asn Arg Arg Ala Ser Ala Asp Gly Gly His Ala
    530                 535                 540

Arg Asp Arg Asp His Ile Leu Ala Leu Phe Leu Ala Arg Asp Gly Asn
545                 550                 555                 560

Val Ser Glu Val Asp Phe Glu Ser Trp Glu Leu Asn Tyr Phe Ile Val
                565                 570                 575

Tyr Leu Asn Asp Trp Ala Lys Phe Asn Ala Ile Ser Tyr Leu Gly Gly
            580                 585                 590

Ala Ile Thr Lys Arg Glu Tyr Ser Gly Asp Glu Lys Gly Arg Gly Ser
        595                 600                 605

Ile Pro Thr Ile Ile Leu Ala Pro Arg Phe Gly Glu Gln Tyr Ile Asn
    610                 615                 620

Pro Tyr Asn Gly Val Ser Ile Lys Val Leu Asn Asn Ser Gln Val Thr
625                 630                 635                 640

Val Thr Ile Gly Ser Thr Thr Cys Ser Pro Leu Met Thr Val Phe Ile
                645                 650                 655

Pro Gly Asn Lys Lys Val Lys Gly Gln Gly Ser Cys Thr Asn Gly Gly
            660                 665                 670
```

```
Ser Phe Pro Phe Val Val Tyr Leu Thr Pro Thr Leu Gly Val Ile Ser
        675                 680                 685

Tyr Tyr Lys Val Ala Thr Ser Asn Phe Leu Lys Leu Ala Tyr Gly Ile
    690                 695                 700

Pro Ala Ser Lys Glu Pro Gly Phe Thr Asp Lys Leu Phe Ser Asn Phe
705                 710                 715                 720

Lys Met Val Tyr Gln Glu Gly Asn Val Val Ile Tyr Glu Phe Arg Pro
                725                 730                 735

Phe Ala Ile Tyr Lys Leu Gln Glu Phe Thr Asn Gly Thr Trp Lys Thr
            740                 745                 750

Ile Thr Thr Leu Ser Pro Gly Lys His Thr Leu Lys Leu Tyr Ile Ser
        755                 760                 765

Ala Phe Gly Arg Asp Ile Lys Asn Ala Thr Leu Tyr Ile Asp Ala Ile
    770                 775                 780

Lys Asp Asn Arg Thr Ile Gln Arg Ile Lys Ile Gly Glu Ile Lys Tyr
785                 790                 795                 800

Met Ser His Leu Asn Glu Thr Pro Ile Thr Val Asn Val Thr Leu Pro
                805                 810                 815

Asp Ala Asp Lys Tyr Lys Phe Val Leu Val Gln Lys Gly Pro Val Gly
            820                 825                 830

Val Leu Thr Ala Pro Pro Lys Val Asn Gly Lys Ile Ala Asn Pro Val
        835                 840                 845

Arg Val Leu Asn Asp Gly Glu Ser Gly Arg Leu Glu Leu Lys Val Gly
    850                 855                 860

Val Asp Lys Asp Tyr Lys Ala Asp Leu Tyr Leu Arg Ala Thr Phe Ile
865                 870                 875                 880

Tyr Leu Val Arg Lys Ser Gly Thr Ser Asn Asp Asp Tyr Asn Ala Ala
                885                 890                 895

Phe Glu Pro His Met Asp Val Phe Phe Ile Thr Lys Leu Lys Ser Gly
            900                 905                 910

Ile Ser Leu His Lys Gly Glu Asn Glu Val Thr Val Glu Ala Lys Met
        915                 920                 925

Pro Glu Asn Val Ile Ser Asp Tyr Lys Lys Lys Leu Glu Ala Glu Tyr
    930                 935                 940

Gly Asp Lys Leu Ile Ile Arg Gly Ile Arg Val Glu Pro Val Phe Ile
945                 950                 955                 960

Ala Glu Lys Glu Tyr Val Met Leu Glu Val Arg Ala Ser Ala Pro His
                965                 970                 975

His Ser Ser Glu
            980
```

<210> SEQ ID NO 14
<211> LENGTH: 973
<212> TYPE: PRT
<213> ORGANISM: Artificial
<220> FEATURE:
<223> OTHER INFORMATION: Pyrococcus strain NA2 OST

<400> SEQUENCE: 14

```
Met Val Lys Arg Lys Lys Glu Glu Lys Glu Ile Lys Gly Glu Lys Arg
1               5                   10                  15

Glu Phe Tyr Ser Lys Ile Lys Arg Met Ile Ile Pro Ile Ile Val Leu
            20                  25                  30

Gly Phe Ala Thr Tyr Gly Phe Tyr Leu Arg His Leu Thr Ala Gly Arg
        35                  40                  45
```

```
Tyr Phe Pro Asp Pro Asp Thr Phe Tyr His Phe Glu Ile Tyr Lys Leu
    50                  55                  60

Val Ile Lys Glu Gly Leu Pro Lys Tyr Tyr Pro Leu Ser Asp Ala Pro
65                  70                  75                  80

Phe Gly Ser Leu Ile Gly Glu Pro Leu Gly Leu Tyr Ile Leu Pro Ala
                85                  90                  95

Ile Phe Tyr Lys Val Ile Ser Ala Phe Gly Tyr Asn Glu Phe Gln Ala
            100                 105                 110

Phe Leu Leu Trp Pro Pro Phe Val Gly Phe Leu Ser Val Val Gly Ile
        115                 120                 125

Tyr Leu Leu Gly Arg Lys Val Leu Asn Glu Trp Ala Gly Leu Trp Ala
    130                 135                 140

Ala Val Ile Leu Ser Val Ser Thr Ala Asn Phe Ser Arg Thr Phe Ser
145                 150                 155                 160

Gly Asn Ala Arg Gly Asp Gly Pro Phe Met Met Leu Phe Val Phe Ser
                165                 170                 175

Ala Ile Leu Met Phe His Tyr Leu Arg Glu Thr Ser Lys Thr Lys Lys
            180                 185                 190

Val Leu Tyr Gly Thr Leu Phe Val Ile Leu Ala Ser Ile Ser Leu Gly
        195                 200                 205

Ala Trp Asn Gly Ser Pro Phe Gly Leu Met Val Leu Leu Gly Phe Ala
    210                 215                 220

Ser Phe Gln Thr Ile Ala Leu Phe Ile Phe Gly Lys Ile Ser Glu Leu
225                 230                 235                 240

Lys Lys Phe Ala Thr Glu Phe Tyr Pro Ala Tyr Leu Gly Ile Leu Ala
                245                 250                 255

Leu Gly Tyr Leu Leu Thr Ile Pro Gly Ile Val Lys Ile Gly Ser Phe
            260                 265                 270

Ile Lys Phe Ala Phe Glu Val Phe Leu Gly Leu Val Val Leu Leu Thr
        275                 280                 285

Ile Met Leu Tyr Gly Gly Arg Tyr Leu Asn Tyr Ser Asp Lys Lys His
    290                 295                 300

Arg Phe Leu Val Val Ala Val Val Val Leu Ile Gly Phe Ala Gly Ala
305                 310                 315                 320

Tyr Ala Tyr Val Gly Pro Lys Leu Phe Arg Leu Met Gly Gly Ala Tyr
                325                 330                 335

Gln Ser Thr Gln Val Tyr Glu Thr Val Gln Glu Leu Ala Lys Thr Thr
            340                 345                 350

Met Arg Asp Ile Lys Val Tyr Tyr Gly Val Glu Asn Pro Asn Gly Leu
        355                 360                 365

Ile Phe Phe Leu Ser Ile Pro Gly Ile Ile Ile Ile Leu Val Lys Tyr
    370                 375                 380

Leu Val Asp Leu Phe Arg Lys Ser Glu Ser Ser Asn Glu Thr Leu Phe
385                 390                 395                 400

Ala Ala Val Phe Tyr Ile Met Ser Ile Tyr Leu Leu Ser Leu Ala Val
                405                 410                 415

Arg Phe Leu Phe Leu Ala Ser Tyr Ala Ile Ala Leu Phe Ala Gly Ile
            420                 425                 430

Phe Ala Gly Phe Val Ile Glu Ile Val Glu Lys Met Lys Glu Ser Ile
        435                 440                 445

Gly Ile Lys Ala Ala Leu Gly Ile Val Ile Ser Ile Met Ile Leu Met
    450                 455                 460
```

-continued

```
Ile Pro Ile Thr His Ala Pro Val Leu Ala Arg Ser Ala Arg Ser Leu
465                 470                 475                 480

Ser Arg Thr Glu Val Glu Thr Thr Gly Trp Glu Gln Val Leu Lys Trp
                485                 490                 495

Leu Arg Ser Asn Thr Ser Gln Tyr Ala Thr Ala Thr Ser Trp Trp Asp
            500                 505                 510

Tyr Gly Tyr Trp Ile Glu Ser Ser Leu Leu Gly Asn Arg Arg Ala Ser
        515                 520                 525

Ala Asp Gly Gly His Ala Arg Asp Arg Asp His Ile Leu Ala Leu Phe
    530                 535                 540

Leu Ala Arg Asp Gly Asn Val Ser Glu Val Asp Phe Glu Ser Trp Glu
545                 550                 555                 560

Leu Asn Tyr Phe Ile Val Tyr Leu Asn Asp Trp Ala Lys Phe Asn Ala
                565                 570                 575

Ile Ser Tyr Leu Gly Gly Ala Leu Thr Arg Arg Glu Tyr Lys Gly Asp
            580                 585                 590

Glu Thr Gly Arg Gly Ser Val Thr Ser Ile Leu Ile Thr Gln Gly Ala
        595                 600                 605

Gly Asn Val Tyr Val Asn Pro Tyr Ala Gly Ile Thr Ile Lys Val Val
    610                 615                 620

Glu Glu Asn Lys Thr Arg Lys Val Val Val Asn Ile Gly Arg Leu Glu
625                 630                 635                 640

Cys Ser Pro Met Thr Thr Val Val Phe Pro Gly Asn Ile His Ile Lys
                645                 650                 655

Gly Thr Gly Ser Cys Asn Asn Gly Ser Ser Phe Pro Tyr Val Val Tyr
            660                 665                 670

Leu Thr Pro Ser Leu Gly Ile Ile Ala Tyr Tyr Lys Val Ala Thr Ser
        675                 680                 685

Asn Phe Ile Lys Leu Ala Phe Gly Ile Pro Val Ser Asn Tyr Lys Gly
    690                 695                 700

Phe Thr Glu Lys Leu Phe Ser Asn Phe Val Pro Val Tyr Gln Ala Gly
705                 710                 715                 720

Asn Val Ile Val Tyr Glu Phe Arg Pro Phe Ala Ile Tyr Gly Met Glu
                725                 730                 735

Glu Leu Val Asn Gly Ser Trp Arg Tyr Ile Gly Tyr Leu Thr Pro Gly
            740                 745                 750

Lys His Thr Leu Arg Leu Tyr Ile Ser Ala Phe Gly Arg Asp Ile Lys
        755                 760                 765

Asn Ala Thr Leu Tyr Val Tyr Ala Ile Asn Gly Thr Glu Ile Thr Ala
    770                 775                 780

Lys Ile Arg Leu Thr Lys Ile Asp Tyr Met Asn His Leu Asn Glu Tyr
785                 790                 795                 800

Pro Ile Thr Val Asn Val Thr Leu Pro Pro Ala Gln Lys Tyr Arg Phe
                805                 810                 815

Val Leu Val Gln Lys Gly Pro Val Gly Val Leu Thr Gly Pro Pro Lys
            820                 825                 830

Leu Asn Gly Lys Ile Val Asn Pro Ile Ser Val Leu Lys Glu Gly Glu
        835                 840                 845

Glu Gly Glu Leu Glu Leu Lys Val Gly Val Asp Lys Asn Tyr Thr Ala
    850                 855                 860

Asp Leu Tyr Leu Arg Ala Thr Phe Ile Tyr Leu Val Arg Lys Gly Gly
865                 870                 875                 880

Thr Ser Asn Glu Asp Tyr Asn Ala Ala Phe Glu Pro His Met Asp Val
```

-continued

```
                885                 890                 895

Phe Phe Ile Ser Arg Val Lys Glu Gly Ile Lys Leu His Pro Gly Asp
            900                 905                 910

Asn Tyr Val Lys Ala His Val Glu Met Pro Lys Gly Val Ile Ser Ser
        915                 920                 925

Tyr Lys Glu Glu Leu Glu Lys Lys Tyr Gly Asp Arg Leu Ile Ile Arg
    930                 935                 940

Gly Ile Arg Val Glu Pro Val Phe Ile Ala Glu Lys Glu Tyr Thr Met
945                 950                 955                 960

Leu Glu Val Ser Ala Ser Ala Pro His His Ser Ser Glu
                965                 970


<210> SEQ ID NO 15
<211> LENGTH: 976
<212> TYPE: PRT
<213> ORGANISM: Pyrococcus horikoshii

<400> SEQUENCE: 15

Met Val Lys Ser Lys Val Lys Lys Val Glu Lys Gly Lys Glu Gly Glu
1               5                   10                  15

Glu Lys Arg Ser Thr Tyr Val Leu Leu Lys Lys Val Leu Ile Pro Ile
            20                  25                  30

Leu Val Phe Gly Phe Ala Ile Tyr Ala Phe Tyr Leu Arg His Leu Thr
        35                  40                  45

Ala Gly Lys Tyr Phe Pro Asp Pro Asp Thr Phe Tyr His Phe Glu Ile
    50                  55                  60

Tyr Lys Leu Val Leu Lys Glu Gly Leu Pro Arg Tyr Tyr Pro Met Ser
65                  70                  75                  80

Asp Ala Pro Phe Gly Ser Leu Ile Gly Glu Pro Leu Gly Leu Tyr Leu
                85                  90                  95

Leu Pro Ala Ala Phe Tyr Lys Val Val Ser Leu Phe Gly Tyr Asn Glu
            100                 105                 110

Leu Gln Ala Phe Leu Leu Trp Pro Pro Phe Val Gly Phe Leu Gly Val
        115                 120                 125

Ile Ala Val Tyr Leu Leu Gly Arg Lys Val Leu Asn Glu Trp Thr Gly
    130                 135                 140

Leu Trp Gly Ala Val Val Leu Thr Val Ser Thr Ala Asn Phe Ser Arg
145                 150                 155                 160

Thr Phe Ser Gly Asn Ala Arg Gly Asp Gly Pro Phe Met Ala Leu Phe
                165                 170                 175

Ile Phe Ala Ser Val Ala Met Leu Tyr Tyr Leu Lys Glu Ser Asn Lys
            180                 185                 190

Thr Arg Lys Ile Ile Tyr Gly Thr Leu Phe Val Leu Leu Thr Val Ile
        195                 200                 205

Ser Leu Gly Ala Trp Asn Gly Ser Pro Phe Gly Leu Met Val Leu Leu
    210                 215                 220

Gly Phe Ala Ser Leu Gln Thr Ile Ile Leu Phe Ile Phe Gly Lys Leu
225                 230                 235                 240

Glu Glu Leu Lys Lys Phe Val Lys Glu Phe Tyr Pro Ala Tyr Leu Ala
                245                 250                 255

Ile Leu Ala Phe Gly Tyr Ala Leu Thr Phe Pro Gly Ile Val Lys Ile
            260                 265                 270

Gly Gly Phe Ile Arg Phe Ala Phe Glu Val Phe Leu Gly Leu Ile Phe
        275                 280                 285
```

-continued

```
Leu Leu Val Ile Met Leu Tyr Gly Gly Arg Tyr Leu Asn Tyr Ser Asp
    290                 295                 300

Lys Lys His Arg Phe Leu Val Val Thr Ile Ile Val Leu Leu Gly Phe
305                 310                 315                 320

Gly Gly Ala Tyr Ala Tyr Val Gly Pro Lys Leu Phe Arg Leu Met Gly
                325                 330                 335

Gly Ala Tyr Gln Ser Thr Gln Val Tyr Glu Thr Val Gln Glu Leu Ala
            340                 345                 350

Lys Thr Thr Ile Gly Asp Val Lys Ala Tyr Tyr Gly Val Glu Ser Gly
        355                 360                 365

Asn Gly Leu Ile Phe Phe Leu Ser Ile Pro Gly Leu Leu Ile Leu Leu
    370                 375                 380

Thr Lys Tyr Leu Tyr Asp Leu Phe Lys Lys Ala Lys Ser Asp Asn Glu
385                 390                 395                 400

Thr Leu Phe Ala Leu Val Phe Tyr Thr Met Ser Leu Tyr Leu Leu Tyr
                405                 410                 415

Leu Ala Val Arg Phe Leu Phe Leu Ala Ser Tyr Ala Val Ala Leu Phe
            420                 425                 430

Phe Gly Ile Phe Ile Gly Phe Ser Met Asp Val Ile Glu Lys Met Lys
        435                 440                 445

Glu Asn Ile Gly Ile Lys Ala Ala Leu Gly Ile Val Leu Ser Leu Met
    450                 455                 460

Ile Leu Val Ile Pro Phe Val His Ala Pro Val Leu Ala Arg Ser Ala
465                 470                 475                 480

Arg Ala Leu Lys Asn Thr Glu Ile Glu Val Thr Gly Trp Glu Gln Ala
                485                 490                 495

Leu Lys Trp Leu Arg Ser Asn Thr Ser Lys Tyr Ala Thr Ala Thr Ser
            500                 505                 510

Trp Trp Asp Tyr Gly Tyr Trp Ile Glu Ser Ser Leu Leu Gly Asn Arg
        515                 520                 525

Arg Ala Ser Ala Asp Gly Gly His Ala Arg Asp Arg Asp His Ile Leu
    530                 535                 540

Ala Leu Phe Leu Ala Arg Asp Gly Asn Ile Ser Glu Val Asp Phe Glu
545                 550                 555                 560

Ser Trp Glu Leu Asn Tyr Phe Ile Ile Tyr Leu Asn Asp Trp Ala Lys
                565                 570                 575

Phe Asn Ala Ile Ser Tyr Leu Gly Gly Ala Ile Thr Arg Lys Glu Tyr
            580                 585                 590

Asn Gly Asp Glu Asn Gly Arg Gly Arg Val Thr Thr Ile Leu Leu Thr
        595                 600                 605

Gln Ala Ala Gly Asn Val Tyr Val Asn Pro Tyr Ala Arg Ile Val Ile
    610                 615                 620

Lys Val Ile Gln Gln Asn Lys Thr Arg Arg Ile Ala Val Asn Ile Gly
625                 630                 635                 640

Gln Leu Glu Cys Ser Pro Ile Leu Ser Val Ala Phe Pro Gly Asn Ile
                645                 650                 655

Lys Ile Lys Gly Ser Gly Arg Cys Ser Asp Gly Ser Pro Phe Pro Tyr
            660                 665                 670

Val Val Tyr Leu Thr Pro Ser Leu Gly Val Leu Ala Tyr Tyr Lys Val
        675                 680                 685

Ala Thr Ser Asn Phe Val Lys Leu Ala Phe Gly Ile Pro Thr Ser Ser
    690                 695                 700

Tyr Ser Glu Phe Ala Glu Lys Leu Phe Ser Asn Phe Ile Pro Val Tyr
```

-continued

```
705                 710                 715                 720

Gln Tyr Gly Ser Val Ile Val Tyr Glu Phe Arg Pro Phe Ala Ile Tyr
                725                 730                 735

Lys Ile Glu Asp Phe Ile Asn Gly Thr Trp Arg Glu Val Gly Lys Leu
            740                 745                 750

Ser Pro Gly Lys His Thr Leu Arg Leu Tyr Ile Ser Ala Phe Gly Arg
        755                 760                 765

Asp Ile Lys Asn Ala Thr Leu Tyr Val Tyr Ala Leu Asn Gly Thr Lys
    770                 775                 780

Ile Ile Lys Arg Ile Lys Val Gly Glu Ile Lys Tyr Met Asn His Leu
785                 790                 795                 800

Glu Glu Tyr Pro Ile Ile Val Asn Val Thr Leu Pro Thr Ala Gln Lys
                805                 810                 815

Tyr Arg Phe Ile Leu Ala Gln Lys Gly Pro Val Gly Val Leu Thr Gly
            820                 825                 830

Pro Val Arg Val Asn Gly Lys Ile Thr Asn Pro Ala Tyr Ile Met Arg
        835                 840                 845

Glu Gly Glu Ser Gly Arg Leu Glu Leu Lys Val Gly Val Asp Lys Glu
    850                 855                 860

Tyr Thr Ala Asp Leu Tyr Leu Arg Ala Thr Phe Ile Tyr Leu Val Arg
865                 870                 875                 880

Lys Gly Gly Lys Ser Asn Glu Asp Tyr Asp Ala Ser Phe Glu Pro His
                885                 890                 895

Met Asp Thr Phe Phe Ile Thr Lys Leu Lys Glu Gly Ile Lys Leu Arg
            900                 905                 910

Pro Gly Glu Asn Glu Ile Val Val Asn Ala Glu Met Pro Lys Asn Ala
        915                 920                 925

Ile Ser Ser Tyr Lys Glu Lys Leu Glu Lys Glu His Gly Asp Lys Leu
    930                 935                 940

Ile Ile Arg Gly Ile Arg Val Glu Pro Val Phe Ile Val Glu Lys Glu
945                 950                 955                 960

Tyr Thr Met Ile Glu Val Ser Ala Ser Ala Pro His His Ser Ser Glu
                965                 970                 975


<210> SEQ ID NO 16
<211> LENGTH: 976
<212> TYPE: PRT
<213> ORGANISM: Pyrococcus abyssi

<400> SEQUENCE: 16

Met Val Lys Thr Lys Val Lys Glu Glu Lys Glu Glu Lys Ser Glu Lys
1               5                   10                  15

Ser Glu Gly Lys Ser Leu Tyr Pro Leu Leu Lys Arg Ile Leu Ile Pro
            20                  25                  30

Leu Ala Val Ile Gly Phe Gly Ile Tyr Ala Tyr Tyr Leu Arg His Leu
        35                  40                  45

Thr Ala Gly Lys Tyr Phe Pro Asp Pro Asp Thr Phe Tyr His Phe Glu
    50                  55                  60

Ile Tyr Lys Leu Val Leu Lys Glu Gly Leu Pro Lys Tyr Tyr Pro Met
65                  70                  75                  80

Ala Glu Ala Pro Phe Gly Ser Leu Ile Gly Glu Pro Leu Gly Leu Tyr
                85                  90                  95

Ile Leu Pro Ala Ile Phe Tyr Lys Val Val Ser Val Phe Gly Tyr Asn
            100                 105                 110
```

```
Glu Phe Gln Ala Phe Leu Met Trp Pro Pro Phe Val Gly Phe Leu Gly
        115                 120                 125

Val Ile Ala Val Tyr Leu Leu Gly Arg Lys Val Leu Asn Glu Trp Ala
    130                 135                 140

Gly Leu Trp Ala Ala Val Ile Leu Ser Val Ser Thr Ala Asn Phe Ser
145                 150                 155                 160

Arg Thr Phe Ser Gly Asn Ala Arg Gly Asp Gly Pro Phe Met Thr Leu
                165                 170                 175

Phe Leu Phe Ser Leu Val Ala Met Leu Tyr Tyr Leu Lys Glu Asn Asp
            180                 185                 190

Ile Lys Lys Lys Ser Leu Trp Gly Ala Val Phe Val Leu Leu Ala Ser
        195                 200                 205

Ile Ser Leu Gly Ala Trp Asn Gly Ser Pro Phe Gly Leu Met Val Leu
    210                 215                 220

Ile Gly Phe Ala Ser Phe Gln Thr Ile Ala Leu Phe Ile Phe Gly Lys
225                 230                 235                 240

Ile Lys Glu Leu Lys Lys Phe Val Lys Glu Phe Tyr Pro Ala Tyr Leu
                245                 250                 255

Ala Ile Leu Ala Ile Gly Tyr Gly Leu Thr Ile Pro Gly Ile Ala Lys
            260                 265                 270

Ile Gly Gly Phe Ile Lys Phe Ala Phe Glu Val Phe Leu Gly Leu Val
        275                 280                 285

Leu Leu Val Thr Ile Met Leu Tyr Gly Gly Lys Phe Leu Asn Tyr Ser
    290                 295                 300

Asp Lys Lys His Arg Phe Ala Val Val Ala Val Ile Val Leu Leu Gly
305                 310                 315                 320

Phe Ala Gly Ala Tyr Ala Tyr Val Gly Pro Lys Leu Phe Arg Leu Met
                325                 330                 335

Gly Gly Ala Tyr Gln Ser Thr Gln Val Tyr Gln Thr Val Gln Glu Leu
            340                 345                 350

Ala Lys Thr Thr Leu Ser Asp Ile Lys Leu Tyr Tyr Gly Val Glu Gly
        355                 360                 365

Asn Asn Gly Leu Val Phe Phe Leu Ser Ile Pro Gly Phe Leu Ile Ile
    370                 375                 380

Leu Gly Leu Tyr Leu Asn Ala Leu Leu Lys Lys Ser Glu Ser Ser Asn
385                 390                 395                 400

Glu Tyr Met Leu Ser Leu Val Phe Tyr Ile Met Ser Leu Tyr Leu Leu
                405                 410                 415

Ser Leu Ala Val Arg Phe Leu Phe Leu Ala Ser Tyr Ala Ile Ala Leu
            420                 425                 430

Phe Ser Gly Ile Phe Ala Gly Phe Thr Met Glu Val Ile Glu Lys Met
        435                 440                 445

Lys Glu Asn Val Gly Ile Lys Ala Ala Leu Gly Ile Ala Ile Ala Val
    450                 455                 460

Met Ile Leu Met Val Pro Ile Thr His Gly Pro Val Ile Ala Arg Asn
465                 470                 475                 480

Ala Lys Ala Leu Lys Val Ser Glu Ile Glu Thr Thr Gly Trp Glu Gln
                485                 490                 495

Val Leu Lys Trp Leu Asn Glu Asn Thr Ser Lys Tyr Ala Thr Ala Thr
            500                 505                 510

Ser Trp Trp Asp Tyr Gly Tyr Trp Ile Glu Ser Ser Leu Leu Gly His
        515                 520                 525

Arg Arg Ala Ser Ala Asp Gly Gly His Ala Arg Asp Arg Asp His Ile
```

```
    530                 535                 540

Leu Ala Leu Phe Leu Ala Arg Asp Gly Asn Val Ser Glu Val Asp Phe
545                 550                 555                 560

Glu Ser Trp Glu Leu Asn Tyr Phe Ile Ile Tyr Leu Asn Asp Trp Ala
                565                 570                 575

Lys Phe Asn Ala Ile Ser Tyr Leu Gly Gly Ala Ile Thr Arg Arg Glu
            580                 585                 590

Tyr Asn Gly Asp Glu Thr Gly Arg Gly Gln Val Thr Thr Ile Leu Pro
        595                 600                 605

Leu Gln Gly Ser Gly Gly Ile Tyr Val Asn Pro Tyr Ala Gly Ile Ser
    610                 615                 620

Val Arg Val Val Gln Ser Asn Thr Thr Ser Lys Val Thr Val Asn Val
625                 630                 635                 640

Arg Gly Arg Ala Glu Cys Ser Pro Ile Tyr Thr Leu Leu Ile Pro Gly
                645                 650                 655

Asn Lys Lys Ile Pro Gly Asn Gly Arg Cys Ser Asp Gly Ser Pro Phe
            660                 665                 670

Pro Tyr Val Leu Tyr Leu Ala Pro Asn Phe Gly Leu Ile Thr Tyr Tyr
        675                 680                 685

Lys Val Ala Thr Ser Asn Phe Ile Lys Leu Ala Phe Asn Ile Pro Ile
    690                 695                 700

Ser Lys Tyr Ser Gly Phe Thr Glu Lys Leu Tyr Ser Asn Phe Val Pro
705                 710                 715                 720

Val Tyr Gly Tyr Gly Asn Val Ile Val Tyr Glu Phe Arg Pro Phe Ala
                725                 730                 735

Ile Tyr Arg Ile Glu Glu Leu Ile Asn Gly Thr Trp Lys Ala Val Asn
            740                 745                 750

Ser Leu Thr Pro Gly Lys His Glu Leu Lys Leu Tyr Ile Ser Ala Phe
        755                 760                 765

Gly Arg Asp Ile Arg Asn Ala Thr Leu Tyr Val Tyr Ala Ile Gly Asn
    770                 775                 780

Lys Thr Glu Lys Ile Lys Ile Gly Glu Ile Glu Tyr Met Asn His Leu
785                 790                 795                 800

Asn Glu Lys Pro Ile Ile Val Asn Val Thr Leu Pro Lys Ala Glu Lys
                805                 810                 815

Tyr Arg Leu Val Leu Val Gln Lys Gly Pro Val Gly Val Leu Thr Gly
            820                 825                 830

Pro Pro Lys Leu Asn Gly Glu Ile Ala Asn Pro Ile Arg Ile Ala Arg
        835                 840                 845

Glu Gly Glu Lys Gly Thr Leu Ser Leu Lys Val Gly Val Asp Lys Asp
    850                 855                 860

Tyr Thr Ala Asp Leu Tyr Leu Arg Ala Thr Phe Ile Tyr Leu Val Arg
865                 870                 875                 880

Lys Glu Gly Lys Ser Asn Asp Asp Tyr Asn Ala Ala Phe Glu Pro His
                885                 890                 895

Met Asp Thr Phe Phe Ile Thr Lys Leu Lys Gly Gly Ile Lys Leu His
            900                 905                 910

Lys Gly Asp Asn Val Val Thr Ala Glu Leu Asn Met Pro Asn Gly Val
        915                 920                 925

Ile Ser Ser Tyr Lys Glu Lys Leu Glu Lys Glu Tyr Gly Asp Lys Leu
    930                 935                 940

Ile Ile Arg Gly Ile Arg Val Glu Pro Val Phe Ile Ala Glu Lys Glu
945                 950                 955                 960
```

```
Tyr Val Met Ala Glu Val Arg Ala Ser Ala Pro His His Gly Ser Glu
                965                 970                 975


<210> SEQ ID NO 17
<211> LENGTH: 972
<212> TYPE: PRT
<213> ORGANISM: Pyrococcus yayanossi

<400> SEQUENCE: 17

Met Val Lys Thr Lys Val Lys Arg Glu Lys Arg Glu Glu Lys Ala Pro
1               5                   10                  15

Glu His Arg Pro Lys Thr Leu Val Val Phe Phe Lys Arg Phe Gly Ile
            20                  25                  30

Pro Leu Ile Val Leu Ala Phe Ala Thr Leu Gly Phe Tyr Ile Arg Tyr
        35                  40                  45

Leu Pro Gly Thr Gly Lys Tyr Phe Ile Asp Pro Asp Thr Tyr Tyr His
    50                  55                  60

Tyr Glu Ile Tyr Lys Leu Val Leu Lys Glu Gly Leu Pro Arg Tyr Tyr
65                  70                  75                  80

Ser Met Ala Glu Ala Pro Phe Gly Ser Leu Ile Gly Glu Pro Leu Gly
                85                  90                  95

Leu Tyr Leu Leu Pro Ala Ile Phe Tyr Lys Leu Ile Ser Ala Phe Gly
            100                 105                 110

Tyr Thr Thr Leu Gln Ala Phe Lys Leu Trp Pro Pro Thr Val Gly Phe
        115                 120                 125

Leu Ser Ile Ile Ala Thr Tyr Leu Leu Ala Arg Lys Ile His Gly Glu
    130                 135                 140

Trp Ala Gly Leu Trp Ser Ala Ala Ile Met Ser Phe Leu Leu Ala His
145                 150                 155                 160

Phe Thr Arg Thr Phe Ser Gly Asn Ala Arg Gly Asp Gly Pro Phe Leu
                165                 170                 175

Met Leu Phe Leu Phe Ala Ser Val Ala Met Leu Tyr Tyr Leu Glu Ala
            180                 185                 190

Lys Asp Val Lys Arg Lys Met Val Tyr Gly Thr Leu Phe Val Ala Leu
        195                 200                 205

Ser Val Ile Ala Leu Ser Ala Trp Asn Gly Ser Pro Phe Ser Leu Met
    210                 215                 220

Val Phe Leu Gly Phe Gly Ala Leu Gln Ala Ile Val Leu Phe Val Phe
225                 230                 235                 240

Gly Arg Ile Glu Glu Leu Arg Glu Phe Ile Lys Leu Tyr Tyr Pro Thr
                245                 250                 255

Tyr Leu Thr Val Leu Leu Leu Gly Tyr Leu Leu Thr Phe Pro Arg Ile
            260                 265                 270

Val Ala Val Lys Gly His Ile Leu Phe Ala Leu Lys Val Phe Leu Gly
        275                 280                 285

Leu Ala Gly Leu Thr Val Leu Met Leu Tyr Gly Gly Lys Trp Leu Asn
    290                 295                 300

Tyr Ser Asp Arg Arg His Arg Phe Ala Val Val Ala Val Val Thr Leu
305                 310                 315                 320

Leu Gly Phe Val Gly Ala Tyr Ile Tyr Val Gly Pro Lys Leu Phe Ser
                325                 330                 335

Leu Met Ala Gly Ala Tyr Gln Ser Thr Gln Val Tyr Glu Thr Val Gln
            340                 345                 350

Glu Leu Ala Lys Thr Thr Leu Gly Asp Ile Lys Ala Tyr Tyr Gly Ile
```

-continued

```
        355                 360                 365

Lys Gly Thr Asp Gly Ile Val Phe Phe Met Ser Leu Ala Gly Val Leu
    370                 375                 380

Val Leu Leu Tyr Arg Tyr Leu Thr Thr Leu Leu Arg Glu Gly Arg Ser
385                 390                 395                 400

Ser His Glu Tyr Leu Phe Ala Leu Thr Leu Tyr Gly Met Ser Leu Tyr
                405                 410                 415

Leu Val Trp Ser Ala Val Arg Phe Leu Phe Leu Ala Ser Gly Ala Val
            420                 425                 430

Ile Leu Met Ala Gly Val Phe Ala Gly Glu Leu Phe Arg Ile Ile Glu
        435                 440                 445

Asp Met Lys Glu Lys Ala Thr Thr Lys Ile Thr Leu Gly Leu Ala Leu
    450                 455                 460

Thr Val Met Leu Leu Leu Met Pro Val Thr Gly Val Pro Leu Met Ile
465                 470                 475                 480

Asn Thr Ala Lys Ala Met Lys Thr Ser Glu Val Glu Arg Ser Gly Trp
                485                 490                 495

Glu Asp Ala Leu Met Trp Leu Arg Glu Asn Thr Ser Glu Tyr Ala Thr
            500                 505                 510

Ala Thr Ser Trp Trp Asp Tyr Gly Tyr Trp Ile Glu Ser Ser Leu Leu
        515                 520                 525

Gly Asn Arg Arg Ala Ser Ala Asp Gly Gly His Ala Arg Asp Arg Asp
    530                 535                 540

His Ile Leu Ala Leu Phe Leu Ala Arg Asp Gly Asn Val Ser Glu Val
545                 550                 555                 560

Asp Phe Glu Ser Trp Glu Leu Asn Tyr Phe Ile Ala Tyr Met Gln Asp
                565                 570                 575

Trp Arg Lys Phe Asn Ala Ile Ser Tyr Leu Gly Gly Ala Ile Thr Arg
            580                 585                 590

Arg Glu Tyr Lys Gly Asp Glu Ser Gly Arg Gly Gly Val Thr Thr Ile
        595                 600                 605

Val Leu Leu Pro Gly Ala Asn Gly Val Tyr Ser Asn Pro Tyr Met Gly
    610                 615                 620

Leu Thr Leu Arg Val Glu Asn Arg Thr Val Lys Val Asn Gly Tyr Cys
625                 630                 635                 640

Glu Pro Met Glu Ser Val Ile Leu Pro Ser Asn Thr His Ile Lys Gly
                645                 650                 655

Ser Gly Gln Cys Glu Thr Gly Ser Tyr Phe Pro Tyr Val Ala Tyr Val
            660                 665                 670

Thr Pro Thr Phe Ala Val Leu Ala Tyr Tyr Lys Val Ala Thr Ser Asn
        675                 680                 685

Phe Leu Lys Leu Ala Phe Gly Ile Pro Ala Ser Lys Glu Ala Asn Phe
    690                 695                 700

Thr Glu Lys Leu Tyr Ala Asn Phe Glu Leu Val Phe Gln Ser Gly Asp
705                 710                 715                 720

Val Ile Val Tyr Glu Phe Lys Pro Phe Ala Val Tyr Lys Ala Glu Glu
                725                 730                 735

Leu Val Asn Gly Thr Trp Arg Ala Val Glu Thr Leu Thr Pro Gly Glu
            740                 745                 750

His Thr Leu Lys Leu Tyr Ile Ser Ala Phe Gly Arg Asp Val Lys Asn
        755                 760                 765

Ala Thr Leu Tyr Val Glu Ala Leu Lys Asp Gly Lys Val Val Glu Arg
    770                 775                 780
```

```
Ile Lys Val Ala Glu Gly Leu Tyr Ile Asp His Leu Asn Glu Lys Pro
785                 790                 795                 800

Ile Glu Val Lys Val Asn Leu Pro Glu Ala Asp Glu Tyr Arg Phe Val
                805                 810                 815

Leu Val Gln Lys Gly Pro Val Gly Val Leu Thr Ser Ala Pro Arg Val
            820                 825                 830

Asn Gly Ser Ile Ala Asn Pro Ile Lys Val Leu Gly Glu Gly Gln Ser
        835                 840                 845

Gly Thr Leu Glu Leu Lys Ala Ala Phe Asp Arg Asp Tyr Thr Ala Asp
    850                 855                 860

Leu Tyr Leu Arg Val Thr Phe Ile Tyr Leu Val Arg Lys Ser Gly Arg
865                 870                 875                 880

Ser Asn Asp Asp Ile Asp Ala Ala Phe Glu Pro His Met Asp Thr Phe
                885                 890                 895

Phe Ala Ala Lys Leu Ala Glu Gly Leu Lys Leu Lys Lys Gly Glu Asp
            900                 905                 910

Thr Ile Thr Val Asn Ala Gly Leu Pro Ala Gly Val Ile Ser Ser Tyr
        915                 920                 925

Glu Glu Lys Leu Lys Ala Leu Tyr Gly Asp Arg Leu Ile Ile Arg Gly
    930                 935                 940

Ile Arg Val Glu Pro Val Phe Ile Ala Asp Lys Ala Tyr Thr Ile Trp
945                 950                 955                 960

Glu Val Arg Ala Ser Ala Pro His His Gly Ser Glu
                965                 970
```

```
<210> SEQ ID NO 18
<211> LENGTH: 982
<212> TYPE: PRT
<213> ORGANISM: Artificial
<220> FEATURE:
<223> OTHER INFORMATION: Pyrococcus STT3 consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(29)
<223> OTHER INFORMATION: Xaa can be any naturally occurring amino acid
<220> FEATURE:
<221> NAME/KEY: misc_feature
<222> LOCATION: (31)..(40)
<223> OTHER INFORMATION: Xaa can be any naturally occurring amino acid
<220> FEATURE:
<221> NAME/KEY: misc_feature
<222> LOCATION: (42)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (64)..(64)
```

<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(86)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (116)..(119)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (132)..(136)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (143)..(145)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(160)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (178)..(179)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (184)..(190)
<223> OTHER INFORMATION: Xaa can be any naturally occurring amino acid
<220> FEATURE:
<221> NAME/KEY: misc_feature
<222> LOCATION: (193)..(199)
<223> OTHER INFORMATION: Xaa can be any naturally occurring amino acid
<220> FEATURE:
<221> NAME/KEY: misc_feature
<222> LOCATION: (201)..(203)
<223> OTHER INFORMATION: Xaa can be any naturally occurring amino acid
<220> FEATURE:
<221> NAME/KEY: misc_feature
<222> LOCATION: (205)..(206)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (211)..(216)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (228)..(229)
<223> OTHER INFORMATION: Xaa can be any naturally occurring amino acid
<220> FEATURE:
<221> NAME/KEY: misc_feature
<222> LOCATION: (232)..(234)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (244)..(246)
<223> OTHER INFORMATION: Xaa can be any naturally occurring amino acid
<220> FEATURE:
<221> NAME/KEY: misc_feature
<222> LOCATION: (249)..(250)
<223> OTHER INFORMATION: Xaa can be any naturally occurring amino acid
<220> FEATURE:
<221> NAME/KEY: misc_feature
<222> LOCATION: (252)..(255)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (260)..(262)
<223> OTHER INFORMATION: Xaa can be any naturally occurring amino acid
<220> FEATURE:

<221> NAME/KEY: misc_feature
<222> LOCATION: (264)..(266)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(282)
<223> OTHER INFORMATION: Xaa can be any naturally occurring amino acid
<220> FEATURE:
<221> NAME/KEY: misc_feature
<222> LOCATION: (285)..(286)
<223> OTHER INFORMATION: Xaa can be any naturally occurring amino acid
<220> FEATURE:
<221> NAME/KEY: misc_feature
<222> LOCATION: (292)..(293)
<223> OTHER INFORMATION: Xaa can be any naturally occurring amino acid
<220> FEATURE:
<221> NAME/KEY: misc_feature
<222> LOCATION: (295)..(297)
<223> OTHER INFORMATION: Xaa can be any naturally occurring amino acid
<220> FEATURE:
<221> NAME/KEY: misc_feature
<222> LOCATION: (302)..(304)
<223> OTHER INFORMATION: Xaa can be any naturally occurring amino acid
<220> FEATURE:
<221> NAME/KEY: misc_feature
<222> LOCATION: (310)..(311)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid
<220> FEATURE:
<221> NAME/KEY: misc_feature
<222> LOCATION: (318)..(323)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (330)..(330)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (360)..(362)
<223> OTHER INFORMATION: Xaa can be any naturally occurring amino acid
<220> FEATURE:
<221> NAME/KEY: misc_feature
<222> LOCATION: (364)..(364)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (370)..(374)
<223> OTHER INFORMATION: Xaa can be any naturally occurring amino acid
<220> FEATURE:
<221> NAME/KEY: misc_feature
<222> LOCATION: (376)..(377)
<223> OTHER INFORMATION: Xaa can be any naturally occurring amino acid
<220> FEATURE:
<221> NAME/KEY: misc_feature
<222> LOCATION: (380)..(383)
<223> OTHER INFORMATION: Xaa can be any naturally occurring amino acid
<220> FEATURE:
<221> NAME/KEY: misc_feature
<222> LOCATION: (385)..(391)
<223> OTHER INFORMATION: Xaa can be any naturally occurring amino acid
<220> FEATURE:
<221> NAME/KEY: misc_feature
<222> LOCATION: (394)..(395)
<223> OTHER INFORMATION: Xaa can be any naturally occurring amino acid
<220> FEATURE:
<221> NAME/KEY: misc_feature
<222> LOCATION: (397)..(412)
<223> OTHER INFORMATION: Xaa can be any naturally occurring amino acid
<220> FEATURE:
<221> NAME/KEY: misc_feature
<222> LOCATION: (414)..(414)
<223> OTHER INFORMATION: Xaa can be any naturally occurring amino acid
<220> FEATURE:
<221> NAME/KEY: misc_feature
<222> LOCATION: (417)..(417)
<223> OTHER INFORMATION: Xaa can be any naturally occurring amino acid
<220> FEATURE:
<221> NAME/KEY: misc_feature
<222> LOCATION: (420)..(422)
<223> OTHER INFORMATION: Xaa can be any naturally occurring amino acid
<220> FEATURE:
<221> NAME/KEY: misc_feature
<222> LOCATION: (424)..(424)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (434)..(435)
<223> OTHER INFORMATION: Xaa can be any naturally occurring amino acid
<220> FEATURE:
<221> NAME/KEY: misc_feature
<222> LOCATION: (437)..(438)
<223> OTHER INFORMATION: Xaa can be any naturally occurring amino acid
<220> FEATURE:
<221> NAME/KEY: misc_feature
<222> LOCATION: (440)..(442)
<223> OTHER INFORMATION: Xaa can be any naturally occurring amino acid
<220> FEATURE:
<221> NAME/KEY: misc_feature
<222> LOCATION: (444)..(449)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (455)..(458)
<223> OTHER INFORMATION: Xaa can be any naturally occurring amino acid
<220> FEATURE:
<221> NAME/KEY: misc_feature
<222> LOCATION: (460)..(461)
<223> OTHER INFORMATION: Xaa can be any naturally occurring amino acid
<220> FEATURE:
<221> NAME/KEY: misc_feature
<222> LOCATION: (463)..(468)
<223> OTHER INFORMATION: Xaa can be any naturally occurring amino acid
<220> FEATURE:
<221> NAME/KEY: misc_feature
<222> LOCATION: (470)..(470)
<223> OTHER INFORMATION: Xaa can be any naturally occurring amino acid
<220> FEATURE:
<221> NAME/KEY: misc_feature
<222> LOCATION: (472)..(473)

<223> OTHER INFORMATION: Xaa can be any naturally occurring amino acid
<220> FEATURE:
<221> NAME/KEY: misc_feature
<222> LOCATION: (475)..(478)
<223> OTHER INFORMATION: Xaa can be any naturally occurring amino acid
<220> FEATURE:
<221> NAME/KEY: misc_feature
<222> LOCATION: (480)..(484)
<223> OTHER INFORMATION: Xaa can be any naturally occurring amino acid
<220> FEATURE:
<221> NAME/KEY: misc_feature
<222> LOCATION: (486)..(491)
<223> OTHER INFORMATION: Xaa can be any naturally occurring amino acid
<220> FEATURE:
<221> NAME/KEY: misc_feature
<222> LOCATION: (493)..(493)
<223> OTHER INFORMATION: Xaa can be any naturally occurring amino acid
<220> FEATURE:
<221> NAME/KEY: misc_feature
<222> LOCATION: (495)..(496)
<223> OTHER INFORMATION: Xaa can be any naturally occurring amino acid
<220> FEATURE:
<221> NAME/KEY: misc_feature
<222> LOCATION: (500)..(501)
<223> OTHER INFORMATION: Xaa can be any naturally occurring amino acid
<220> FEATURE:
<221> NAME/KEY: misc_feature
<222> LOCATION: (503)..(503)
<223> OTHER INFORMATION: Xaa can be any naturally occurring amino acid
<220> FEATURE:
<221> NAME/KEY: misc_feature
<222> LOCATION: (506)..(507)
<223> OTHER INFORMATION: Xaa can be any naturally occurring amino acid
<220> FEATURE:
<221> NAME/KEY: misc_feature
<222> LOCATION: (510)..(511)
<223> OTHER INFORMATION: Xaa can be any naturally occurring amino acid
<220> FEATURE:
<221> NAME/KEY: misc_feature
<222> LOCATION: (513)..(513)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: misc_feature
<222> LOCATION: (573)..(574)
<223> OTHER INFORMATION: Xaa can be any naturally occurring amino acid
<220> FEATURE:
<221> NAME/KEY: misc_feature
<222> LOCATION: (576)..(577)
<223> OTHER INFORMATION: Xaa can be any naturally occurring amino acid
<220> FEATURE:
<221> NAME/KEY: misc_feature
<222> LOCATION: (580)..(580)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (594)..(595)
<223> OTHER INFORMATION: Xaa can be any naturally occurring amino acid
<220> FEATURE:
<221> NAME/KEY: misc_feature
<222> LOCATION: (598)..(598)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid
<220> FEATURE:
<221> NAME/KEY: misc_feature
<222> LOCATION: (606)..(619)
<223> OTHER INFORMATION: Xaa can be any naturally occurring amino acid
<220> FEATURE:
<221> NAME/KEY: misc_feature
<222> LOCATION: (621)..(621)
<223> OTHER INFORMATION: Xaa can be any naturally occurring amino acid
<220> FEATURE:
<221> NAME/KEY: misc_feature
<222> LOCATION: (623)..(623)
<223> OTHER INFORMATION: Xaa can be any naturally occurring amino acid
<220> FEATURE:
<221> NAME/KEY: misc_feature
<222> LOCATION: (625)..(630)
<223> OTHER INFORMATION: Xaa can be any naturally occurring amino acid
<220> FEATURE:
<221> NAME/KEY: misc_feature
<222> LOCATION: (632)..(649)
<223> OTHER INFORMATION: Xaa can be any naturally occurring amino acid
<220> FEATURE:
<221> NAME/KEY: misc_feature
<222> LOCATION: (651)..(651)
<223> OTHER INFORMATION: Xaa can be any naturally occurring amino acid
<220> FEATURE:
<221> NAME/KEY: misc_feature
<222> LOCATION: (653)..(658)
<223> OTHER INFORMATION: Xaa can be any naturally occurring amino acid
<220> FEATURE:
<221> NAME/KEY: misc_feature
<222> LOCATION: (660)..(665)
<223> OTHER INFORMATION: Xaa can be any naturally occurring amino acid
<220> FEATURE:
<221> NAME/KEY: misc_feature
<222> LOCATION: (667)..(667)
<223> OTHER INFORMATION: Xaa can be any naturally occurring amino acid
<220> FEATURE:
<221> NAME/KEY: misc_feature
<222> LOCATION: (669)..(669)
<223> OTHER INFORMATION: Xaa can be any naturally occurring amino acid
<220> FEATURE:
<221> NAME/KEY: misc_feature
<222> LOCATION: (671)..(672)
<223> OTHER INFORMATION: Xaa can be any naturally occurring amino acid
<220> FEATURE:
<221> NAME/KEY: misc_feature
<222> LOCATION: (674)..(675)
<223> OTHER INFORMATION: Xaa can be any naturally occurring amino acid
<220> FEATURE:
<221> NAME/KEY: misc_feature
<222> LOCATION: (678)..(678)
<223> OTHER INFORMATION: Xaa can be any naturally occurring amino acid
<220> FEATURE:
<221> NAME/KEY: misc_feature
<222> LOCATION: (680)..(683)
<223> OTHER INFORMATION: Xaa can be any naturally occurring amino acid
<220> FEATURE:
<221> NAME/KEY: misc_feature
<222> LOCATION: (685)..(690)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (700)..(700)
<223> OTHER INFORMATION: Xaa can be any naturally occurring amino acid
<220> FEATURE:
<221> NAME/KEY: misc_feature
<222> LOCATION: (704)..(706)
<223> OTHER INFORMATION: Xaa can be any naturally occurring amino acid
<220> FEATURE:
<221> NAME/KEY: misc_feature
<222> LOCATION: (708)..(708)
<223> OTHER INFORMATION: Xaa can be any naturally occurring amino acid
<220> FEATURE:
<221> NAME/KEY: misc_feature
<222> LOCATION: (710)..(713)
<223> OTHER INFORMATION: Xaa can be any naturally occurring amino acid
<220> FEATURE:

<221> NAME/KEY: misc_feature
<222> LOCATION: (715)..(716)
<223> OTHER INFORMATION: Xaa can be any naturally occurring amino acid
<220> FEATURE:
<221> NAME/KEY: misc_feature
<222> LOCATION: (719)..(720)
<223> OTHER INFORMATION: Xaa can be any naturally occurring amino acid
<220> FEATURE:
<221> NAME/KEY: misc_feature
<222> LOCATION: (723)..(724)
<223> OTHER INFORMATION: Xaa can be any naturally occurring amino acid
<220> FEATURE:
<221> NAME/KEY: misc_feature
<222> LOCATION: (726)..(728)
<223> OTHER INFORMATION: Xaa can be any naturally occurring amino acid
<220> FEATURE:
<221> NAME/KEY: misc_feature
<222> LOCATION: (730)..(730)
<223> OTHER INFORMATION: Xaa can be any naturally occurring amino acid
<220> FEATURE:
<221> NAME/KEY: misc_feature
<222> LOCATION: (732)..(733)
<223> OTHER INFORMATION: Xaa can be any naturally occurring amino acid
<220> FEATURE:
<221> NAME/KEY: misc_feature
<222> LOCATION: (735)..(735)
<223> OTHER INFORMATION: Xaa can be any naturally occurring amino acid
<220> FEATURE:
<221> NAME/KEY: misc_feature
<222> LOCATION: (737)..(737)
<223> OTHER INFORMATION: Xaa can be any naturally occurring amino acid
<220> FEATURE:
<221> NAME/KEY: misc_feature
<222> LOCATION: (740)..(741)
<223> OTHER INFORMATION: Xaa can be any naturally occurring amino acid
<220> FEATURE:
<221> NAME/KEY: misc_feature
<222> LOCATION: (743)..(748)
<223> OTHER INFORMATION: Xaa can be any naturally occurring amino acid
<220> FEATURE:
<221> NAME/KEY: misc_feature
<222> LOCATION: (751)..(751)
<223> OTHER INFORMATION: Xaa can be any naturally occurring amino acid
<220> FEATURE:
<221> NAME/KEY: misc_feature
<222> LOCATION: (753)..(757)
<223> OTHER INFORMATION: Xaa can be any naturally occurring amino acid
<220> FEATURE:
<221> NAME/KEY: misc_feature
<222> LOCATION: (759)..(759)
<223> OTHER INFORMATION: Xaa can be any naturally occurring amino acid
<220> FEATURE:
<221> NAME/KEY: misc_feature
<222> LOCATION: (762)..(762)
<223> OTHER INFORMATION: Xaa can be any naturally occurring amino acid
<220> FEATURE:
<221> NAME/KEY: misc_feature
<222> LOCATION: (764)..(764)
<223> OTHER INFORMATION: Xaa can be any naturally occurring amino acid
<220> FEATURE:
<221> NAME/KEY: misc_feature
<222> LOCATION: (766)..(766)
<223> OTHER INFORMATION: Xaa can be any naturally occurring amino acid
<220> FEATURE:
<221> NAME/KEY: misc_feature
<222> LOCATION: (776)..(777)
<223> OTHER INFORMATION: Xaa can be any naturally occurring amino acid
<220> FEATURE:
<221> NAME/KEY: misc_feature
<222> LOCATION: (783)..(784)
<223> OTHER INFORMATION: Xaa can be any naturally occurring amino acid
<220> FEATURE:
<221> NAME/KEY: misc_feature
<222> LOCATION: (786)..(794)
<223> OTHER INFORMATION: Xaa can be any naturally occurring amino acid
<220> FEATURE:
<221> NAME/KEY: misc_feature
<222> LOCATION: (796)..(805)
<223> OTHER INFORMATION: Xaa can be any naturally occurring amino acid
<220> FEATURE:
<221> NAME/KEY: misc_feature
<222> LOCATION: (807)..(807)
<223> OTHER INFORMATION: Xaa can be any naturally occurring amino acid
<220> FEATURE:
<221> NAME/KEY: misc_feature
<222> LOCATION: (809)..(809)
<223> OTHER INFORMATION: Xaa can be any naturally occurring amino acid
<220> FEATURE:
<221> NAME/KEY: misc_feature
<222> LOCATION: (812)..(812)
<223> OTHER INFORMATION: Xaa can be any naturally occurring amino acid
<220> FEATURE:
<221> NAME/KEY: misc_feature
<222> LOCATION: (814)..(814)
<223> OTHER INFORMATION: Xaa can be any naturally occurring amino acid
<220> FEATURE:
<221> NAME/KEY: misc_feature
<222> LOCATION: (816)..(816)
<223> OTHER INFORMATION: Xaa can be any naturally occurring amino acid
<220> FEATURE:
<221> NAME/KEY: misc_feature
<222> LOCATION: (819)..(819)
<223> OTHER INFORMATION: Xaa can be any naturally occurring amino acid
<220> FEATURE:
<221> NAME/KEY: misc_feature
<222> LOCATION: (821)..(822)
<223> OTHER INFORMATION: Xaa can be any naturally occurring amino acid
<220> FEATURE:
<221> NAME/KEY: misc_feature
<222> LOCATION: (824)..(826)
<223> OTHER INFORMATION: Xaa can be any naturally occurring amino acid
<220> FEATURE:
<221> NAME/KEY: misc_feature
<222> LOCATION: (828)..(828)
<223> OTHER INFORMATION: Xaa can be any naturally occurring amino acid
<220> FEATURE:
<221> NAME/KEY: misc_feature
<222> LOCATION: (833)..(833)
<223> OTHER INFORMATION: Xaa can be any naturally occurring amino acid
<220> FEATURE:
<221> NAME/KEY: misc_feature
<222> LOCATION: (837)..(842)
<223> OTHER INFORMATION: Xaa can be any naturally occurring amino acid
<220> FEATURE:
<221> NAME/KEY: misc_feature
<222> LOCATION: (845)..(845)
<223> OTHER INFORMATION: Xaa can be any naturally occurring amino acid
<220> FEATURE:
<221> NAME/KEY: misc_feature
<222> LOCATION: (847)..(848)
<223> OTHER INFORMATION: Xaa can be any naturally occurring amino acid
<220> FEATURE:
<221> NAME/KEY: misc_feature
<222> LOCATION: (850)..(855)
<223> OTHER INFORMATION: Xaa can be any naturally occurring amino acid
<220> FEATURE:
<221> NAME/KEY: misc_feature
<222> LOCATION: (857)..(858)
<223> OTHER INFORMATION: Xaa can be any naturally occurring amino acid
<220> FEATURE:
<221> NAME/KEY: misc_feature
<222> LOCATION: (860)..(862)
<223> OTHER INFORMATION: Xaa can be any naturally occurring amino acid
<220> FEATURE:
<221> NAME/KEY: misc_feature
<222> LOCATION: (865)..(867)
<223> OTHER INFORMATION: Xaa can be any naturally occurring amino acid
<220> FEATURE:
<221> NAME/KEY: misc_feature
<222> LOCATION: (869)..(870)
<223> OTHER INFORMATION: Xaa can be any naturally occurring amino acid
<220> FEATURE:
<221> NAME/KEY: misc_feature
<222> LOCATION: (872)..(872)
<223> OTHER INFORMATION: Xaa can be any naturally occurring amino acid
<220> FEATURE:
<221> NAME/KEY: misc_feature
<222> LOCATION: (879)..(879)

<223> OTHER INFORMATION: Xaa can be any naturally occurring amino acid
<220> FEATURE:
<221> NAME/KEY: misc_feature
<222> LOCATION: (888)..(888)
<223> OTHER INFORMATION: Xaa can be any naturally occurring amino acid
<220> FEATURE:
<221> NAME/KEY: misc_feature
<222> LOCATION: (890)..(891)
<223> OTHER INFORMATION: Xaa can be any naturally occurring amino acid
<220> FEATURE:
<221> NAME/KEY: misc_feature
<222> LOCATION: (893)..(893)
<223> OTHER INFORMATION: Xaa can be any naturally occurring amino acid
<220> FEATURE:
<221> NAME/KEY: misc_feature
<222> LOCATION: (895)..(896)
<223> OTHER INFORMATION: Xaa can be any naturally occurring amino acid
<220> FEATURE:
<221> NAME/KEY: misc_feature
<222> LOCATION: (898)..(898)
<223> OTHER INFORMATION: Xaa can be any naturally occurring amino acid
<220> FEATURE:
<221> NAME/KEY: misc_feature
<222> LOCATION: (902)..(902)
<223> OTHER INFORMATION: Xaa can be any naturally occurring amino acid
<220> FEATURE:
<221> NAME/KEY: misc_feature
<222> LOCATION: (905)..(905)
<223> OTHER INFORMATION: Xaa can be any naturally occurring amino acid
<220> FEATURE:
<221> NAME/KEY: misc_feature
<222> LOCATION: (908)..(916)
<223> OTHER INFORMATION: Xaa can be any naturally occurring amino acid
<220> FEATURE:
<221> NAME/KEY: misc_feature
<222> LOCATION: (918)..(919)
<223> OTHER INFORMATION: Xaa can be any naturally occurring amino acid
<220> FEATURE:
<221> NAME/KEY: misc_feature
<222> LOCATION: (921)..(930)
<223> OTHER INFORMATION: Xaa can be any naturally occurring amino acid
<220> FEATURE:
<221> NAME/KEY: misc_feature
<222> LOCATION: (932)..(934)
<223> OTHER INFORMATION: Xaa can be any naturally occurring amino acid
<220> FEATURE:
<221> NAME/KEY: misc_feature
<222> LOCATION: (937)..(937)
<223> OTHER INFORMATION: Xaa can be any naturally occurring amino acid
<220> FEATURE:
<221> NAME/KEY: misc_feature
<222> LOCATION: (939)..(941)
<223> OTHER INFORMATION: Xaa can be any naturally occurring amino acid
<220> FEATURE:
<221> NAME/KEY: misc_feature
<222> LOCATION: (943)..(946)
<223> OTHER INFORMATION: Xaa can be any naturally occurring amino acid
<220> FEATURE:
<221> NAME/KEY: misc_feature
<222> LOCATION: (949)..(949)
<223> OTHER INFORMATION: Xaa can be any naturally occurring amino acid
<220> FEATURE:
<221> NAME/KEY: misc_feature
<222> LOCATION: (963)..(964)
<223> OTHER INFORMATION: Xaa can be any naturally occurring amino acid
<220> FEATURE:
<221> NAME/KEY: misc_feature
<222> LOCATION: (966)..(966)
<223> OTHER INFORMATION: Xaa can be any naturally occurring amino acid
<220> FEATURE:
<221> NAME/KEY: misc_feature
<222> LOCATION: (968)..(970)
<223> OTHER INFORMATION: Xaa can be any naturally occurring amino acid
<220> FEATURE:
<221> NAME/KEY: misc_feature
<222> LOCATION: (973)..(973)
<223> OTHER INFORMATION: Xaa can be any naturally occurring amino acid
<220> FEATURE:
<221> NAME/KEY: misc_feature
<222> LOCATION: (980)..(982)
<223> OTHER INFORMATION: Xaa can be any naturally occurring amino acid

<400> SEQUENCE: 18

Xaa Val Lys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Lys Xaa Xaa
            20                  25                  30

Xaa Xaa Xaa Xaa Xaa Xaa Xaa Xaa Phe Xaa Xaa Xaa Xaa Xaa Xaa Xaa
        35                  40                  45

Arg Xaa Leu Xaa Xaa Xaa Gly Xaa Tyr Phe Xaa Asp Pro Asp Thr Xaa
    50                  55                  60

Tyr His Xaa Glu Ile Tyr Lys Leu Val Xaa Lys Glu Gly Leu Pro Xaa
65                  70                  75                  80

Tyr Tyr Xaa Xaa Xaa Xaa Ala Pro Phe Gly Ser Leu Ile Gly Glu Pro
                85                  90                  95

Leu Gly Leu Tyr Xaa Leu Pro Ala Xaa Phe Tyr Lys Xaa Xaa Ser Xaa
            100                 105                 110

Phe Gly Tyr Xaa Xaa Xaa Xaa Ala Phe Xaa Xaa Trp Pro Pro Xaa Val
        115                 120                 125

Gly Phe Leu Xaa Xaa Xaa Xaa Xaa Tyr Leu Leu Xaa Arg Lys Xaa Xaa
    130                 135                 140

Xaa Glu Trp Xaa Gly Xaa Trp Xaa Ala Xaa Xaa Xaa Xaa Xaa Xaa Xaa
145                 150                 155                 160

Ala Xaa Phe Xaa Arg Thr Phe Ser Gly Asn Ala Arg Gly Asp Gly Pro
                165                 170                 175

Phe Xaa Xaa Leu Phe Xaa Phe Xaa Xaa Xaa Xaa Xaa Xaa Xaa Tyr Leu
            180                 185                 190

Xaa Xaa Xaa Xaa Xaa Xaa Xaa Lys Xaa Xaa Xaa Gly Xaa Xaa Phe Val
        195                 200                 205

Xaa Leu Xaa Xaa Xaa Xaa Xaa Xaa Ala Trp Asn Gly Ser Pro Phe Xaa
    210                 215                 220

Leu Met Val Xaa Xaa Gly Phe Xaa Xaa Xaa Gln Xaa Ile Xaa Leu Phe
225                 230                 235                 240

Xaa Phe Gly Xaa Xaa Xaa Glu Leu Xaa Xaa Phe Xaa Xaa Xaa Xaa Tyr
                245                 250                 255

Pro Xaa Tyr Xaa Xaa Xaa Leu Xaa Xaa Xaa Tyr Xaa Leu Thr Xaa Pro
            260                 265                 270

Xaa Xaa Xaa Xaa Xaa Xaa Xaa Xaa Xaa Xaa Phe Ala Xaa Xaa Val Phe
        275                 280                 285

Leu Gly Leu Xaa Xaa Leu Xaa Xaa Xaa Met Leu Tyr Gly Xaa Xaa Xaa
    290                 295                 300

Leu Asn Tyr Ser Asp Xaa Xaa His Arg Phe Xaa Val Val Xaa Xaa Xaa
305                 310                 315                 320

Xaa Xaa Xaa Gly Phe Xaa Gly Ala Tyr Xaa Tyr Val Gly Pro Lys Leu
                325                 330                 335

Phe Xaa Leu Met Xaa Gly Ala Tyr Gln Ser Thr Gln Val Tyr Xaa Thr
            340                 345                 350

Val Gln Glu Leu Ala Lys Lys Xaa Xaa Xaa Asp Xaa Lys Xaa Tyr Tyr
        355                 360                 365

Gly Xaa Xaa Xaa Xaa Xaa Gly Xaa Xaa Phe Phe Xaa Xaa Xaa Xaa Gly
    370                 375                 380

Xaa Xaa Xaa Xaa Xaa Xaa Xaa Tyr Leu Xaa Xaa Leu Xaa Xaa Xaa Xaa
385                 390                 395                 400

-continued

```
Xaa Xaa Xaa Xaa Xaa Xaa Xaa Xaa Xaa Xaa Xaa Xaa Tyr Xaa Met Ser
                405                 410                 415

Xaa Tyr Leu Xaa Xaa Xaa Ala Xaa Arg Phe Leu Phe Leu Ala Ser Xaa
            420                 425                 430

Ala Xaa Xaa Leu Xaa Xaa Gly Xaa Xaa Xaa Gly Xaa Xaa Xaa Xaa Xaa
        435                 440                 445

Xaa Glu Xaa Met Lys Glu Xaa Xaa Xaa Xaa Lys Xaa Xaa Leu Xaa Xaa
    450                 455                 460

Xaa Xaa Xaa Xaa Met Xaa Leu Xaa Xaa Pro Xaa Xaa Xaa Xaa Pro Xaa
465                 470                 475                 480

Xaa Xaa Xaa Xaa Ala Xaa Xaa Xaa Xaa Xaa Xaa Glu Xaa Glu Xaa Xaa
                485                 490                 495

Gly Trp Glu Xaa Xaa Leu Xaa Trp Leu Xaa Xaa Asn Thr Xaa Xaa Tyr
            500                 505                 510

Xaa Thr Ala Thr Ser Trp Trp Asp Tyr Gly Tyr Trp Ile Glu Ser Ser
        515                 520                 525

Leu Leu Gly Xaa Arg Arg Ala Ser Ala Asp Gly Gly His Ala Arg Asp
    530                 535                 540

Arg Asp His Ile Leu Ala Leu Phe Leu Ala Arg Asp Gly Asn Xaa Ser
545                 550                 555                 560

Glu Val Asp Phe Glu Ser Trp Glu Leu Asn Tyr Phe Xaa Xaa Tyr Xaa
                565                 570                 575

Xaa Asp Trp Xaa Lys Phe Asn Ala Ile Ser Tyr Leu Gly Gly Ala Xaa
            580                 585                 590

Thr Xaa Xaa Glu Tyr Xaa Gly Asp Glu Xaa Gly Arg Gly Xaa Xaa Xaa
        595                 600                 605

Xaa Xaa Xaa Xaa Xaa Xaa Xaa Xaa Xaa Xaa Xaa Tyr Xaa Asn Xaa Tyr
    610                 615                 620

Xaa Xaa Xaa Xaa Xaa Xaa Val Xaa Xaa Xaa Xaa Xaa Xaa Xaa Xaa Xaa
625                 630                 635                 640

Xaa Xaa Xaa Xaa Xaa Xaa Xaa Xaa Xaa Cys Xaa Pro Xaa Xaa Xaa Xaa
                645                 650                 655

Xaa Xaa Pro Xaa Xaa Xaa Xaa Xaa Xaa Gly Xaa Gly Xaa Cys Xaa Xaa
            660                 665                 670

Gly Xaa Xaa Phe Pro Xaa Val Xaa Xaa Xaa Xaa Pro Xaa Xaa Xaa Xaa
        675                 680                 685

Xaa Xaa Tyr Tyr Lys Val Ala Thr Xaa Asn Phe Xaa Lys Leu Ala Xaa
    690                 695                 700

Xaa Xaa Pro Xaa Ser Xaa Xaa Xaa Xaa Phe Xaa Xaa Lys Leu Xaa Xaa
705                 710                 715                 720

Asn Phe Xaa Xaa Val Xaa Xaa Xaa Gly Xaa Val Xaa Xaa Tyr Xaa Phe
                725                 730                 735

Xaa Pro Phe Xaa Xaa Tyr Xaa Xaa Xaa Xaa Xaa Xaa Asn Gly Xaa Trp
            740                 745                 750

Xaa Xaa Xaa Xaa Xaa Leu Xaa Pro Gly Xaa His Xaa Leu Xaa Leu Tyr
        755                 760                 765

Ile Ser Ala Phe Gly Arg Asp Xaa Xaa Asn Ala Thr Leu Tyr Xaa Xaa
    770                 775                 780

Ala Xaa Xaa Xaa Xaa Xaa Xaa Xaa Xaa Xaa Ile Xaa Xaa Xaa Xaa Xaa
785                 790                 795                 800

Xaa Xaa Xaa Xaa Xaa Leu Xaa Glu Xaa Pro Ile Xaa Val Xaa Val Xaa
                805                 810                 815
```

-continued

```
Leu Pro Xaa Ala Xaa Xaa Tyr Xaa Xaa Xaa Leu Xaa Gln Lys Gly Pro
            820                 825                 830

Xaa Gly Val Leu Xaa Xaa Xaa Xaa Xaa Xaa Asn Gly Xaa Ile Xaa Xaa
        835                 840                 845

Pro Xaa Xaa Xaa Xaa Xaa Xaa Gly Xaa Xaa Gly Xaa Xaa Xaa Leu Lys
    850                 855                 860

Xaa Xaa Xaa Asp Xaa Xaa Tyr Xaa Ala Asp Leu Tyr Leu Arg Xaa Thr
865                 870                 875                 880

Phe Ile Tyr Leu Val Arg Lys Xaa Gly Xaa Xaa Asn Xaa Asp Xaa Xaa
                885                 890                 895

Ala Xaa Phe Glu Pro Xaa Met Asp Xaa Phe Phe Xaa Xaa Xaa Xaa Xaa
            900                 905                 910

Xaa Xaa Xaa Xaa Leu Xaa Xaa Gly Xaa Xaa Xaa Xaa Xaa Xaa Xaa Xaa
        915                 920                 925

Xaa Xaa Pro Xaa Xaa Xaa Ile Ser Xaa Tyr Xaa Xaa Xaa Leu Xaa Xaa
    930                 935                 940

Xaa Xaa Gly Asp Xaa Leu Ile Ile Arg Gly Ile Arg Val Glu Pro Val
945                 950                 955                 960

Phe Ile Xaa Xaa Lys Xaa Tyr Xaa Xaa Xaa Glu Val Xaa Ala Ser Ala
                965                 970                 975

Pro His His Xaa Xaa Xaa
            980


<210> SEQ ID NO 19
<211> LENGTH: 833
<212> TYPE: PRT
<213> ORGANISM: Leishmania major

<400> SEQUENCE: 19

Met Ala Ala Ala Ser Asn Val Asn Ala Pro Glu Ser Asn Val Met Thr
1               5                   10                  15

Thr Arg Ser Ala Val Ala Pro Pro Ser Thr Ala Ala Pro Lys Glu Ala
            20                  25                  30

Ser Ser Glu Thr Leu Leu Ile Gly Leu Tyr Lys Met Pro Ser Gln Thr
        35                  40                  45

Arg Ser Leu Ile Tyr Ser Ser Cys Phe Ala Val Ala Met Ala Ile Ala
    50                  55                  60

Leu Pro Ile Ala Tyr Asp Met Arg Val Arg Ser Ile Gly Val Tyr Gly
65                  70                  75                  80

Tyr Leu Phe His Ser Ser Asp Pro Trp Phe Asn Tyr Arg Ala Ala Glu
                85                  90                  95

Tyr Met Ser Thr His Gly Trp Ser Ala Phe Phe Ser Trp Phe Asp Tyr
            100                 105                 110

Met Ser Trp Tyr Pro Leu Gly Arg Pro Val Gly Ser Thr Thr Tyr Pro
        115                 120                 125

Gly Leu Gln Leu Thr Ala Val Ala Ile His Arg Ala Leu Ala Ala Ala
    130                 135                 140

Gly Met Pro Met Ser Leu Asn Asn Val Cys Val Leu Met Pro Ala Trp
145                 150                 155                 160

Phe Ser Leu Val Ser Ser Ala Met Ala Ala Leu Leu Ala His Glu Met
                165                 170                 175

Ser Gly Asn Met Ala Val Ala Ser Ile Ser Ser Ile Leu Phe Ser Val
            180                 185                 190

Val Pro Ala His Leu Met Arg Ser Met Ala Gly Glu Phe Asp Asn Glu
        195                 200                 205
```

-continued

```
Cys Ile Ala Val Ala Ala Met Leu Leu Thr Phe Tyr Cys Trp Val Arg
    210                 215                 220

Ser Leu Arg Thr Arg Ser Ser Trp Pro Ile Gly Val Leu Thr Gly Val
225                 230                 235                 240

Ala Tyr Gly Tyr Met Ala Ala Ala Trp Gly Gly Tyr Ile Phe Val Leu
                245                 250                 255

Asn Met Val Ala Met His Ala Gly Ile Ser Ser Met Val Asp Trp Ala
            260                 265                 270

Arg Asn Thr Tyr Asn Pro Ser Leu Leu Arg Ala Tyr Thr Leu Phe Tyr
        275                 280                 285

Val Val Gly Thr Ala Ile Ala Val Cys Val Pro Pro Val Gly Met Ser
    290                 295                 300

Pro Phe Lys Ser Leu Glu Gln Leu Gly Ala Leu Leu Val Leu Val Phe
305                 310                 315                 320

Ile Phe Gly Gln Ser Val Cys Glu Ala Gln Arg Arg Arg Leu Gly Ile
                325                 330                 335

Ala Arg Leu Ser Lys Glu Gly Val Ala Leu Leu Ile Arg Ile Asp Ala
            340                 345                 350

Ala Phe Phe Val Gly Ile Val Ala Val Ala Thr Ile Ala Pro Ala Gly
        355                 360                 365

Phe Phe Lys Pro Leu Ser Leu Gln Ala Asn Ala Ile Ile Thr Gly Val
    370                 375                 380

Ser Arg Thr Gly Asn Thr Leu Val Asp Ile Leu Leu Ala Gln Asp Ala
385                 390                 395                 400

Ser Asn Leu Leu Met Val Trp Gln Leu Phe Leu Phe Pro Phe Leu Gly
                405                 410                 415

Trp Val Ala Gly Met Ser Ala Phe Leu Arg Glu Leu Ile Arg Asn Tyr
            420                 425                 430

Thr Tyr Ala Lys Ser Phe Ile Leu Met Tyr Gly Val Val Gly Met Tyr
        435                 440                 445

Phe Ala Ser Gln Ser Val Arg Met Met Val Met Met Ala Pro Val Ala
    450                 455                 460

Cys Ile Phe Thr Ala Leu Leu Phe Arg Trp Ala Leu Asp Tyr Leu Leu
465                 470                 475                 480

Gly Ser Leu Phe Trp Ala Glu Met Pro Pro Ser Phe Asp Thr Asp Ala
                485                 490                 495

Gln Arg Gly Arg Gln Gln Gln Thr Ala Glu Glu Ser Glu Ala Glu Thr
            500                 505                 510

Lys Arg Lys Glu Glu Glu Tyr Asn Thr Met Gln Val Lys Lys Met Ser
        515                 520                 525

Val Arg Met Leu Pro Phe Met Leu Leu Leu Leu Leu Phe Arg Leu Ser
    530                 535                 540

Gly Phe Ile Glu Asp Val Ala Ala Ile Ser Arg Lys Met Glu Ala Pro
545                 550                 555                 560

Gly Ile Val Phe Pro Ser Glu Gln Val Gln Gly Val Ser Glu Lys Lys
                565                 570                 575

Val Asp Asp Tyr Tyr Ala Gly Tyr Leu Tyr Leu Arg Asp Ser Thr Pro
            580                 585                 590

Glu Asp Ala Arg Val Leu Ala Trp Trp Asp Tyr Gly Tyr Gln Ile Thr
        595                 600                 605

Gly Ile Gly Asn Arg Thr Ser Leu Ala Asp Gly Asn Thr Trp Asn His
    610                 615                 620
```

-continued

```
Glu His Ile Ala Thr Ile Gly Lys Met Leu Thr Ser Pro Val Ala Glu
625                 630                 635                 640

Ala His Ser Leu Val Arg His Met Ala Asp Tyr Val Leu Ile Ser Ala
                645                 650                 655

Gly Asp Thr Tyr Phe Ser Asp Leu Asn Arg Ser Pro Met Met Ala Arg
            660                 665                 670

Ile Gly Asn Ser Val Tyr His Asp Ile Cys Pro Asp Asp Pro Leu Cys
        675                 680                 685

Ser Gln Phe Val Leu Gln Lys Arg Pro Lys Ala Ala Ala Ala Lys Arg
    690                 695                 700

Ser Arg His Val Ser Val Asp Ala Leu Glu Glu Asp Asp Thr Ala Glu
705                 710                 715                 720

His Met Val Tyr Glu Pro Ser Ser Leu Ile Ala Lys Ser Leu Ile Tyr
                725                 730                 735

His Leu His Ser Thr Gly Val Val Thr Gly Val Thr Leu Asn Glu Thr
            740                 745                 750

Leu Phe Gln His Val Phe Thr Ser Pro Gln Gly Leu Met Arg Ile Phe
        755                 760                 765

Lys Val Met Asn Val Ser Thr Glu Ser Lys Lys Trp Val Ala Asp Ser
    770                 775                 780

Ala Asn Arg Val Cys His Pro Pro Gly Ser Trp Ile Cys Pro Gly Gln
785                 790                 795                 800

Tyr Pro Pro Ala Lys Glu Ile Gln Glu Met Leu Ala His Gln His Thr
                805                 810                 815

Asn Phe Lys Asp Leu Leu Asp Pro Arg Thr Thr Trp Ser Gly Ser Arg
            820                 825                 830

Arg
```

<210> SEQ ID NO 20
<211> LENGTH: 2502
<212> TYPE: DNA
<213> ORGANISM: Leishmania major

<400> SEQUENCE: 20

```
atggcggcag cgtcaaacgt gaatgccccc gaaagcaacg tgatgacaac gagaagtgcc      60

gttgcaccac cgtcgacggc tgcacccaaa gaggcttcaa gtgaaacgct gctcattggc     120

ctatacaaga tgccctcgca aactcgtagc ctcatctact cctcctgctt tgcggtggcc     180

atggccattg ccctccctat cgcgtacgac atgcgtgtcc gctccatcgg cgtgtacggg     240

tacctcttcc acagcagtga cccgtggttc aactaccgcg ctgccgagta catgtccacg     300

cacggctggt ccgccttctt cagctggttc gactacatga gctggtaccc gctgggccgc     360

cccgtcggct ccaccacgta cccgggcctg cagctcactg ccgtcgccat tcaccgcgca     420

ctggcggctg ccggcatgcc gatgtctctc aacaacgtgt gcgtgctgat gccagcgtgg     480

ttttcacttg tctcttcagc gatggcggca ctgctggcgc atgagatgag cggcaatatg     540

gcggtagcca gcatctcgtc tatcttattc agtgtggttc cagcccacct gatgcggtcc     600

atggcgggtg agttcgacaa cgagtgtatc gccgtcgcag ccatgctcct caccttctac     660

tgctgggtgc gctcgctgcg cacgcggtcc tcgtggccca tcggtgtcct caccggtgtc     720

gcctacggct acatggcggc ggcgtggggc ggctacattt tcgtgctcaa catggttgcc     780

atgcatgccg gcatatcatc gatggtggac tgggcccgca acacgtacaa cccgtcgctg     840

ctgcgtgcat acacgctgtt ctacgtcgtg ggcaccgcca tcgccgtgtg cgtgccgcca     900
```

-continued

```
gtggggatgt cgcccttcaa gtcgctggag cagctgggtg cgctgctggt gcttgtcttc    960

attttcggtc agtctgtgtg tgaggcccag cgcagacgat tgggaatcgc gcgcctttca   1020

aaggagggcg tggcgctgct catccgcatc gacgcagcct tcttcgtcgg tatcgttgcc   1080

gtggccacca ttgccccggc tggattcttc aagccgctct ccctgcaagc gaacgcgata   1140

atcactggcg tatctcgtac cggaaacaca ctcgtagaca ttctgcttgc gcaagacgcg   1200

tccaacctac tcatggtgtg gcagcttttt ctctttccct tcttaggttg ggtggcgggc   1260

atgagcgcct tccttagaga gttgatccgg aactacacct acgcgaagag tttcatcctg   1320

atgtacggcg tggtcggtat gtacttcgcc agccagtctg tccgaatgat ggtgatgatg   1380

gcccccgtgg cgtgcatctt tactgccctc ttgttccgct gggcactgga ctacctcctc   1440

gggtctttgt tttgggctga gatgccacct tcctttgaca ccgacgcaca gcgtgggcgg   1500

cagcaacaga ccgccgagga gtcggaggca gagaccaagc gtaaggagga agagtacaac   1560

accatgcagg tcaagaagat gtcggtgcgc atgttgccct tcatgctgtt gctcttactg   1620

tttcgtcttt cggggttcat cgaagatgtg gcggcgatat cgcgcaagat ggaggcgccg   1680

ggtatagttt ttcccagtga acaggtgcaa ggcgtgtcgg agaaaaaggt cgacgactac   1740

tatgcggggt acctgtatct gcgcgacagc acgccagagg acgcgcgcgt tttggcctgg   1800

tgggactacg gctaccagat cacaggcatc ggcaaccgca cctcgctggc cgatggcaac   1860

acctggaacc acgagcacat cgccacgatc ggcaagatgc tgacgtcgcc cgtggcggag   1920

gcgcactcgc tggtgcgcca catggccgac tatgttctga tttctgctgg agacacatat   1980

ttttccgacc tgaatcgctc accgatgatg gcgcgcatcg gcaacagcgt gtaccacgac   2040

atctgccccg acgacccact ttgtagtcag ttcgtgttgc agaaaagacc gaaagctgct   2100

gcagcgaagc gcagtcggca cgtcagcgtt gacgcactag aggaggatga cactgcagag   2160

catatggtat acgagccgtc atcactcata gccaagtcgc tcatatatca cctgcactcc   2220

acaggggtgg tgacgggggt cacgctgaat gagacgctct tccagcacgt cttcacctca   2280

ccgcagggtc tcatgcgcat cttcaaggtc atgaacgtga gcacggagag caaaaagtgg   2340

gttgctgact cggcaaaccg cgtgtgccac ccgcctgggt cgtggatctg ccccgggcag   2400

tacccgccgg cgaaggagat ccaggagatg ctggcacacc aacacaccaa cttcaaggac   2460

cttcttgatc ccagaacgac ttggagcggg agcaggcgct ga                      2502
```

```
<210> SEQ ID NO 21
<211> LENGTH: 794
<212> TYPE: PRT
<213> ORGANISM: Leishmania donovani

<400> SEQUENCE: 21

Met Ser Ser Gln Thr Arg Ser Ile Ile Tyr Ser Ser Cys Phe Ala Val
1               5                   10                  15

Ala Met Ala Ile Ala Leu Pro Ile Ala Tyr Asp Met Arg Val Arg Ser
            20                  25                  30

Ile Gly Val Tyr Gly Tyr Leu Phe His Arg Ser Asp Pro Trp Phe Asn
        35                  40                  45

Tyr Arg Ala Ala Glu Tyr Met Ser Thr His Gly Trp Ser Ala Phe Phe
    50                  55                  60

Ser Trp Phe Asp Tyr Met Ser Trp Tyr Pro Leu Gly Arg Pro Val Gly
65                  70                  75                  80

Ser Thr Thr Tyr Pro Gly Leu Gln Leu Thr Ala Val Ala Ile His Arg
                85                  90                  95
```

```
Ala Leu Ala Ala Ala Gly Met Pro Met Ser Leu Asn Asn Val Cys Val
            100                 105                 110

Leu Met Pro Ala Trp Phe Ser Leu Val Ser Ser Ala Met Val Ala Leu
        115                 120                 125

Leu Ala His Glu Leu Ser Gly Asn Met Ala Val Ala Ser Ile Ser Ser
    130                 135                 140

Ile Leu Phe Ser Val Val Pro Ala His Leu Met Arg Ser Met Ala Gly
145                 150                 155                 160

Glu Phe Asp Asn Glu Cys Ile Ala Val Ala Ala Met Leu Leu Thr Phe
                165                 170                 175

Tyr Cys Trp Val Arg Ser Leu Arg Thr Arg Ser Ser Trp Pro Ile Gly
            180                 185                 190

Val Leu Thr Gly Val Ala Tyr Gly Tyr Met Val Ala Ala Trp Gly Gly
        195                 200                 205

Tyr Ile Phe Val Leu Asn Met Val Ala Met His Ala Gly Ile Ser Ser
    210                 215                 220

Met Val Asp Trp Ala Arg Asn Thr Tyr Asn Pro Ser Leu Leu Arg Ala
225                 230                 235                 240

Tyr Thr Leu Phe Tyr Val Val Gly Thr Ala Ile Ala Val Cys Val Pro
                245                 250                 255

Pro Val Gly Met Ser Pro Phe Lys Ser Leu Glu Gln Leu Gly Ala Leu
            260                 265                 270

Leu Val Leu Leu Phe Ile Phe Gly Gln Ser Val Cys Glu Ala Gln Arg
        275                 280                 285

Arg Arg Leu Glu Ile Ala Arg Phe Ser Lys Glu Gly Val Ala Leu Leu
    290                 295                 300

Ile Arg Ile Tyr Ala Ala Phe Phe Val Gly Ile Val Ala Val Ala Thr
305                 310                 315                 320

Ile Ala Pro Ala Gly Phe Phe Lys Pro Leu Ser Leu Gln Ala Ser Ala
                325                 330                 335

Ile Ile Thr Gly Val Ser Arg Thr Gly Asn Thr Leu Val Asp Thr Leu
            340                 345                 350

Ile Ala Gln Asp Ala Ser Asn Leu Leu Ile Val Trp Gln Leu Phe Leu
        355                 360                 365

Phe Pro Val Phe Gly Trp Val Ala Gly Met Ser Ala Phe Leu Thr Glu
    370                 375                 380

Leu Val Arg Asn Tyr Thr Tyr Thr Lys Ser Phe Met Leu Met Tyr Gly
385                 390                 395                 400

Val Val Gly Leu Tyr Phe Ala Ser Gln Ser Val Arg Met Met Val Met
                405                 410                 415

Met Ala Pro Val Ala Cys Ile Phe Thr Ala Leu Leu Phe Arg Trp Ala
            420                 425                 430

Leu Asp Tyr Leu Leu Gly Ser Leu Phe Trp Ala Glu Met Pro Pro Cys
        435                 440                 445

Phe Asp Thr Asp Ala Gln Arg Gly Arg Gln Gln Gln Thr Ala Glu Glu
    450                 455                 460

Ala Glu Ala Glu Thr Lys Arg Lys Glu Glu Glu Tyr Asn Thr Met Gln
465                 470                 475                 480

Val Lys Lys Met Thr Thr Arg Met Leu Pro Phe Met Phe Leu Leu Leu
                485                 490                 495

Leu Phe Arg Leu Ser Gly Phe Ile Glu Asp Val Ala Ala Ile Ser Arg
            500                 505                 510
```

-continued

```
Glu Met Glu Ala Pro Gly Ile Val Phe Pro Ser Gly Gln Val Gln Gly
        515                 520                 525

Val Ser Glu Lys Lys Val Asp Asp Tyr Tyr Ala Gly Tyr Leu Tyr Leu
    530                 535                 540

Arg Asp Asn Thr Pro Glu Asp Ala Arg Ile Leu Ala Trp Trp Asp Tyr
545                 550                 555                 560

Gly Tyr Gln Ile Thr Gly Ile Gly Asn Arg Thr Ser Leu Ala Asp Gly
                565                 570                 575

Asn Thr Trp Asn His Glu His Ile Ala Thr Ile Gly Lys Met Leu Thr
            580                 585                 590

Ser Pro Val Ala Glu Ala His Ser Leu Val Arg His Met Ala Asp Tyr
        595                 600                 605

Val Leu Ile Phe Ala Gly Asp Thr Tyr Phe Ser Asp Leu Asn Arg Ser
    610                 615                 620

Pro His Met Ala Arg Ile Gly Asn Ser Val Tyr Arg Asp Ile Cys Pro
625                 630                 635                 640

His Asp Pro Leu Cys Ser Arg Phe Val Leu Gln Lys Arg Pro Lys Ala
                645                 650                 655

Ala Ala Ala Lys Arg Ser Arg His Val Ser Val Asp Glu Leu Glu Glu
            660                 665                 670

Glu Asp Asn Ala Glu His Val Val Tyr Glu Pro Ser Ser Leu Met Ala
        675                 680                 685

Lys Ser Leu Ile Tyr His Leu His Ser Ala Gly Val Val Thr Gly Val
    690                 695                 700

Thr Leu Asn Glu Thr Leu Phe Gln His Val Phe Thr Ser Ala Gln Gly
705                 710                 715                 720

Leu Ile Arg Ile Phe Lys Val Met Asn Val Ser Glu Glu Ser Lys Lys
                725                 730                 735

Trp Val Ala Asp Pro Ala Asn Arg Val Cys His Pro Pro Gly Ser Trp
            740                 745                 750

Ile Cys Pro Gly Gln Tyr Pro Pro Ala Lys Glu Ile Gln Glu Met Leu
        755                 760                 765

Ala His Gln His Thr Asn Phe Lys Asp Leu Leu Asp Ala Met Asn Asp
    770                 775                 780

Leu Glu Arg Glu Gln Ala Leu Asn Lys Glu
785                 790


<210> SEQ ID NO 22
<211> LENGTH: 794
<212> TYPE: PRT
<213> ORGANISM: Leishmania infantum

<400> SEQUENCE: 22

Met Ser Ser Gln Thr Arg Ser Ile Ile Tyr Ser Ser Cys Phe Ala Val
1               5                   10                  15

Ala Met Ala Ile Ala Leu Pro Ile Ala Tyr Asp Met Arg Val Arg Ser
            20                  25                  30

Ile Gly Val Tyr Gly Tyr Leu Phe His Arg Ser Asp Pro Trp Phe Asn
        35                  40                  45

Tyr Arg Ala Ala Glu Tyr Met Ser Thr His Gly Trp Ser Ala Phe Phe
    50                  55                  60

Ser Trp Phe Asp Tyr Met Ser Trp Tyr Pro Leu Gly Arg Pro Val Gly
65                  70                  75                  80

Ser Thr Thr Tyr Pro Gly Leu Gln Leu Thr Ala Val Ala Ile His Arg
                85                  90                  95
```

```
Ala Leu Ala Ala Ala Gly Met Pro Met Ser Leu Asn Asn Val Cys Val
                100                 105                 110

Leu Met Pro Ala Trp Phe Ser Leu Val Ser Ser Ala Met Val Ala Leu
            115                 120                 125

Leu Ala His Glu Leu Ser Gly Asn Met Ala Val Ala Ser Ile Ser Ser
    130                 135                 140

Ile Leu Phe Ser Val Ile Pro Ala His Leu Met Arg Ser Met Ala Gly
145                 150                 155                 160

Glu Phe Asp Asn Glu Cys Ile Ala Val Ala Ala Met Leu Leu Thr Phe
                165                 170                 175

Tyr Cys Trp Val Arg Ser Leu Arg Thr Arg Ser Ser Trp Pro Ile Gly
                180                 185                 190

Val Leu Thr Gly Val Ala Tyr Gly Tyr Met Val Ala Ala Trp Gly Gly
            195                 200                 205

Tyr Ile Phe Val Leu Asn Met Val Ala Met His Ala Gly Ile Ser Ser
    210                 215                 220

Met Val Asp Trp Ala Arg Asn Thr Tyr Asn Pro Ser Leu Leu Arg Ala
225                 230                 235                 240

Tyr Thr Leu Phe Tyr Val Val Gly Thr Ala Ile Ala Val Cys Val Pro
                245                 250                 255

Pro Val Gly Met Ser Pro Phe Lys Ser Leu Glu Gln Leu Gly Ala Leu
                260                 265                 270

Leu Val Leu Leu Phe Ile Phe Gly Gln Ser Val Cys Glu Ala Gln Arg
            275                 280                 285

Arg Arg Leu Glu Ile Ala Arg Phe Ser Lys Glu Gly Val Ala Leu Leu
    290                 295                 300

Ile Arg Ile Tyr Ala Ala Phe Phe Val Gly Ile Val Ala Val Ala Thr
305                 310                 315                 320

Ile Ala Pro Ala Gly Phe Phe Lys Pro Leu Ser Leu Gln Ala Ser Ala
                325                 330                 335

Ile Ile Thr Gly Val Ser Arg Thr Gly Asn Thr Leu Val Asp Thr Leu
                340                 345                 350

Ile Ala Gln Asp Ala Ser Asn Leu Leu Ile Val Trp Gln Leu Phe Leu
            355                 360                 365

Phe Pro Val Phe Gly Trp Val Ala Gly Met Ser Ala Phe Leu Thr Glu
    370                 375                 380

Leu Val Arg Asn Tyr Thr Tyr Thr Lys Ser Phe Met Leu Met Tyr Gly
385                 390                 395                 400

Val Val Gly Leu Tyr Phe Ala Ser Gln Ser Val Arg Met Met Val Met
                405                 410                 415

Met Ala Pro Val Ala Cys Ile Phe Thr Ala Leu Leu Phe Arg Trp Ala
                420                 425                 430

Leu Asp Tyr Leu Leu Gly Ser Leu Phe Trp Ala Glu Met Pro Pro Cys
            435                 440                 445

Phe Asp Thr Asp Ala Gln Arg Gly Arg Gln Gln Gln Thr Ala Glu Glu
    450                 455                 460

Ala Glu Ala Glu Thr Lys Arg Lys Glu Glu Glu Tyr Asn Thr Met Gln
465                 470                 475                 480

Val Lys Lys Met Thr Thr Arg Met Leu Pro Phe Met Phe Leu Leu Leu
                485                 490                 495

Leu Phe Arg Leu Ser Gly Phe Ile Glu Asp Val Ala Ala Ile Ser Arg
                500                 505                 510
```

Glu Met Glu Ala Pro Gly Ile Val Phe Pro Ser Gly Gln Val Gln Gly
515 520 525

Val Ser Glu Lys Lys Val Asp Asp Tyr Tyr Ser Gly Tyr Leu Tyr Leu
530 535 540

Arg Asp Asn Thr Pro Glu Asp Ala Arg Ile Leu Ala Trp Trp Asp Tyr
545 550 555 560

Gly Tyr Gln Ile Thr Gly Ile Gly Asn Arg Thr Ser Leu Ala Asp Gly
565 570 575

Asn Thr Trp Asn His Glu His Ile Ala Thr Ile Gly Lys Met Leu Thr
580 585 590

Ser Pro Val Ala Glu Ala His Ser Leu Val Arg His Met Ala Asp Tyr
595 600 605

Val Leu Ile Phe Ala Gly Asp Thr Tyr Phe Ser Asp Leu Asn Arg Ser
610 615 620

Pro His Met Ala Arg Ile Gly Asn Ser Val Tyr Arg Asp Ile Cys Pro
625 630 635 640

His Asp Pro Leu Cys Ser Arg Phe Val Leu Gln Lys Arg Pro Lys Ala
645 650 655

Ala Ala Ala Lys Arg Ser Arg His Val Ser Val Asp Glu Leu Glu Glu
660 665 670

Glu Asp Asn Ala Glu His Val Val Tyr Glu Pro Ser Ser Leu Met Ala
675 680 685

Lys Ser Leu Ile Tyr His Leu His Ser Ala Gly Val Val Lys Gly Val
690 695 700

Thr Leu Asn Glu Thr Leu Phe Gln His Val Phe Thr Ser Ala Gln Gly
705 710 715 720

Leu Ile Arg Ile Phe Lys Val Met Asn Val Ser Glu Glu Ser Lys Lys
725 730 735

Trp Val Ala Asp Pro Ala Asn Arg Val Cys His Pro Pro Gly Ser Trp
740 745 750

Ile Cys Pro Gly Gln Tyr Pro Pro Ala Lys Glu Ile Gln Glu Met Leu
755 760 765

Ala His Gln His Thr Asn Phe Lys Asp Leu Leu Asp Ala Met Asn Asp
770 775 780

Leu Glu Arg Glu Gln Ala Leu Asn Lys Glu
785 790

<210> SEQ ID NO 23
<211> LENGTH: 794
<212> TYPE: PRT
<213> ORGANISM: Leishmania Mexicana

<400> SEQUENCE: 23

Met Ser Ser Gln Thr Arg Ser Leu Ile Tyr Ser Ser Cys Phe Ala Val
1 5 10 15

Val Met Ala Ile Gly Leu Ser Ile Ala Tyr Asp Met Arg Val Arg Ser
20 25 30

Ile Gly Val Tyr Gly Tyr Leu Phe His Ser Ser Asp Pro Trp Phe Asn
35 40 45

Tyr Arg Ala Ala Glu Tyr Met Ser Thr His Gly Trp Ser Ala Phe Phe
50 55 60

Ser Trp Phe Asp Tyr Met Ser Trp Tyr Pro Leu Gly Arg Pro Val Gly
65 70 75 80

Ser Thr Thr Tyr Pro Gly Leu Gln Phe Thr Ala Val Ala Ile His Arg
85 90 95

-continued

```
Ala Leu Ala Ala Ala Gly Met Pro Met Ser Leu Asn Asp Val Cys Val
            100                 105                 110

Leu Ile Pro Ala Trp Phe Ser Leu Leu Ser Ser Ala Met Val Ala Leu
        115                 120                 125

Leu Ala His Glu Ile Ser Gly Asn Met Ala Val Ala Ser Val Ser Ser
    130                 135                 140

Ile Leu Phe Ser Val Val Pro Ala His Leu Met Arg Ser Met Ala Gly
145                 150                 155                 160

Glu Phe Asp Asn Glu Cys Ile Ala Val Thr Ala Met Leu Leu Thr Phe
                165                 170                 175

Tyr Cys Trp Val Arg Ser Leu Arg Thr Arg Ser Ser Trp Pro Ile Gly
            180                 185                 190

Val Leu Thr Gly Val Ala Tyr Gly Tyr Met Val Ala Ala Trp Gly Gly
        195                 200                 205

Tyr Ile Phe Val Leu Asn Met Val Ala Met His Ala Gly Ile Ser Ser
    210                 215                 220

Met Val Asp Trp Ala Arg Asn Thr Tyr Asn Pro Ser Leu Leu Arg Ala
225                 230                 235                 240

Tyr Thr Leu Phe Tyr Val Val Gly Thr Ala Ile Ala Val Cys Val Pro
                245                 250                 255

Pro Val Gly Met Ser Pro Phe Lys Ser Leu Glu Gln Leu Gly Ala Leu
            260                 265                 270

Leu Val Leu Leu Phe Ile Phe Gly Gln Ala Leu Cys Glu Ala Gln Arg
        275                 280                 285

Ser Arg Leu Gly Ile Glu Arg Phe Ser Lys Glu Gly Val Ala Leu Leu
    290                 295                 300

Ile Arg Ile Tyr Ala Ala Phe Phe Val Gly Ile Val Ala Val Ala Ala
305                 310                 315                 320

Val Ala Pro Ala Gly Phe Phe Lys Pro Leu Ser Leu Gln Ala Thr Ala
                325                 330                 335

Ile Ile Ala Gly Val Ser Arg Thr Gly Asn Thr Leu Val Asp Ile Leu
            340                 345                 350

Ile Ala Gln Asp Ala Ser Asn Leu Leu Ile Val Trp Gln Leu Phe Leu
        355                 360                 365

Phe Pro Leu Leu Gly Trp Val Val Gly Met Ser Leu Phe Leu Thr Glu
    370                 375                 380

Leu Val Arg Asn Phe Thr Tyr Ala Lys Ser Phe Ile Leu Met Tyr Gly
385                 390                 395                 400

Val Val Gly Ile Tyr Phe Ala Ser Gln Ser Val Arg Met Met Val Met
                405                 410                 415

Met Ala Pro Val Ala Cys Ile Phe Thr Ala Leu Leu Phe Arg Trp Thr
            420                 425                 430

Leu Asp Tyr Leu Leu Gly Ser Phe Phe Trp Ala Glu Met Pro Leu Ser
        435                 440                 445

Leu Asp Thr Asp Ala Gln Arg Gly Arg Gln Gln Gln Thr Ala Glu Glu
    450                 455                 460

Ala Glu Ala Glu Thr Lys Arg Lys Glu Glu Glu Tyr Asn Thr Met Gln
465                 470                 475                 480

Val Lys Lys Met Thr Val Arg Met Val Pro Phe Met Ile Leu Leu Leu
                485                 490                 495

Leu Phe Arg Leu Ser Gly Phe Ile Glu Asp Val Ala Ala Ile Ser Arg
            500                 505                 510
```

```
Glu Met Glu Ser Pro Gly Ile Ile Phe Pro Arg Gly Gln Val Gln Gly
        515                 520                 525

Met Pro Glu Asp Lys Val Asp Asp Tyr Tyr Ala Gly Tyr Leu Tyr Leu
    530                 535                 540

Arg Glu Asn Thr Pro Glu Asp Ala Arg Ile Leu Ala Trp Trp Asp Tyr
545                 550                 555                 560

Gly Tyr Gln Ile Thr Gly Ile Gly Asn Arg Thr Ser Leu Ala Asp Gly
                565                 570                 575

Asn Thr Trp Asn His Glu His Ile Ala Thr Ile Gly Lys Met Leu Thr
            580                 585                 590

Ser Pro Val Ala Glu Ala His Ser Leu Val Arg His Met Ala Asp Tyr
        595                 600                 605

Val Leu Ile Phe Ser Gly Asp Lys Tyr Phe Ser Asp Leu Asn Arg Ser
    610                 615                 620

Pro Met Met Ala Arg Ile Gly Asn Ser Val Tyr Arg Asp Ile Cys Pro
625                 630                 635                 640

Asn Asp Pro Leu Cys Ser Gln Phe Val Leu Gln Lys Arg Arg Lys Val
                645                 650                 655

Ala Ala Ala Lys Arg Ser Arg His Val Thr Val Asn Glu Gln Glu Glu
            660                 665                 670

Asp Asp Asn Pro Glu Ser Val Val Tyr Glu Pro Ser Ser Leu Met Ala
        675                 680                 685

Lys Ser Leu Ile Tyr His Leu His Ser Thr Gly Val Val Glu Gly Val
    690                 695                 700

Met Leu Asp Glu Thr Leu Phe Gln Asn Val Phe Thr Ser Thr Gln Gly
705                 710                 715                 720

Phe Met Arg Ile Phe Lys Val Met Asn Val Ser Ala Glu Ser Lys Lys
                725                 730                 735

Trp Val Ala Asp Pro Ala Asn Arg Val Cys Arg Pro Pro Gly Ser Trp
            740                 745                 750

Ile Cys Pro Gly Gln Tyr Pro Pro Ala Lys Glu Ile Gln Glu Met Leu
        755                 760                 765

Ala His Gln Asn Thr Asn Phe Lys Asp Leu Leu Asp Ala Met Asn Asp
    770                 775                 780

Leu Glu Gln Ala Gln Ala Leu Asn Lys Val
785                 790


<210> SEQ ID NO 24
<211> LENGTH: 823
<212> TYPE: PRT
<213> ORGANISM: Leishmania braziliensis

<400> SEQUENCE: 24

Met Val Thr Glu Arg Gly Ala Ala Thr Pro Ser Thr Ala Ala Ser Gly
1               5                   10                  15

Glu Ala Pro Ser Glu Thr Leu Leu Leu Gly Glu Tyr Lys Val Ser Leu
            20                  25                  30

His Ala Arg Ser Thr Ile Tyr Thr Ala Cys Phe Ala Val Pro Met Ala
        35                  40                  45

Ile Leu Phe Pro Ile Ala Tyr Lys Met Arg Val Arg Ser Ile Asp Val
    50                  55                  60

Tyr Gly Tyr Leu Phe His Arg Asn Asp Pro Trp Phe Asn Tyr Arg Ala
65                  70                  75                  80

Ala Glu Tyr Met Ser Ala His Gly Trp Ser Ala Phe Phe Ser Trp Phe
                85                  90                  95
```

-continued

```
Asp Tyr Met Ser Trp Tyr Pro Leu Gly Arg Pro Val Gly Thr Thr Thr
            100                 105                 110

Tyr Pro Gly Leu Gln Leu Thr Ala Val Ala Ile His Arg Ala Leu Ala
        115                 120                 125

Ala Ala Gly Val Pro Met Ser Leu Asn Asn Val Cys Val Leu Ile Pro
    130                 135                 140

Ala Trp Phe Ser Leu Val Ser Ser Ala Met Val Ala Leu Leu Ala His
145                 150                 155                 160

Glu Met Thr Gly Asn Met Ala Thr Ser Ser Ile Ser Ser Ile Leu Phe
                165                 170                 175

Ser Val Val Pro Ala His Leu Met Arg Ser Met Ala Gly Glu Phe Asp
            180                 185                 190

Asn Glu Cys Ile Ala Val Ala Ala Met Leu Leu Thr Phe Tyr Leu Trp
        195                 200                 205

Val Arg Ser Leu Arg Thr Arg Cys Ser Trp Pro Ile Gly Ile Leu Thr
    210                 215                 220

Gly Ile Ala Tyr Gly Tyr Met Val Ala Ala Trp Gly Gly Tyr Ile Phe
225                 230                 235                 240

Val Leu Asn Met Val Ala Met His Ala Gly Ile Ser Ser Met Val Asp
                245                 250                 255

Trp Ala Arg Asn Thr Tyr Asn Pro Ser Leu Leu Arg Ala Tyr Ala Leu
            260                 265                 270

Phe Tyr Val Val Gly Thr Ala Ile Ala Thr Arg Val Pro Pro Val Gly
        275                 280                 285

Met Ser Pro Phe Arg Ser Leu Glu Gln Leu Gly Ala Leu Val Val Leu
    290                 295                 300

Leu Phe Leu Cys Gly Leu Gln Ala Cys Glu Thr Gln Arg Ser Arg Leu
305                 310                 315                 320

Gly Val Glu Arg Phe Ser Thr Glu Gly Val Ser Leu Leu Val Arg Ile
                325                 330                 335

Tyr Ala Ala Phe Phe Val Gly Ile Val Ala Val Val Ala Met Ala Pro
            340                 345                 350

Ala Gly Phe Phe Lys Pro Leu Ser Leu Gln Ala His Ala Met Ile Ala
        355                 360                 365

Gly Ala Gln Pro Thr Gly Asn Thr Leu Val Asp Met Leu Ile Ala Lys
    370                 375                 380

Asp Ala Ser Ser Leu Leu Val Ala Trp Glu Leu Leu Leu Phe Pro Phe
385                 390                 395                 400

Phe Gly Trp Met Val Gly Met Gly Ala Phe Leu Thr Glu Leu Val Gln
                405                 410                 415

Ser Phe Thr Tyr Thr Lys Ser Phe Met Leu Met Tyr Gly Ala Val Gly
            420                 425                 430

Met Tyr Phe Ala Ser Gln Ser Val Arg Met Met Val Met Met Ala Pro
        435                 440                 445

Val Ala Cys Ile Phe Thr Ala Leu Leu Phe Cys Leu Ala Leu Asp Tyr
    450                 455                 460

Ala Leu Gly Ala Leu Phe Trp Ala Glu Ile Pro Pro Ser Ile Asp Ser
465                 470                 475                 480

Asp Ala Gln Gln Glu Leu His Gln Gln Thr Ala Glu Ala Ala Lys Thr
                485                 490                 495

Lys Lys Arg Lys Gln Glu Glu Tyr Thr Thr Met Gln Val Lys Met Ile
            500                 505                 510
```

```
Ser Val Arg Met Met Pro Leu Met Leu Leu Val Leu Leu Phe Arg Phe
        515                 520                 525

Ser Gly Phe Ile Glu Asp Val Ala Ala Ile Ser Arg Glu Ile Glu Val
    530                 535                 540

Pro Gly Ile Val Phe Pro Gly Ser Met Val Gln Gly Leu Ser Asp Asp
545                 550                 555                 560

Met Ile Asp Asp Tyr Tyr Ala Gly Tyr Leu Tyr Leu Arg Asp Asn Thr
                565                 570                 575

Pro Ala Asp Ala Arg Val Leu Ser Trp Trp Asp Tyr Gly Tyr Gln Ile
            580                 585                 590

Thr Gly Ile Gly Asn Arg Thr Ser Leu Ala Asp Gly Asn Thr Trp Asn
        595                 600                 605

His Glu His Ile Ala Thr Ile Gly Lys Met Leu Thr Ser Pro Val Ala
    610                 615                 620

Glu Ala His Ser Leu Val Arg His Met Ala Asp Tyr Val Leu Ile Phe
625                 630                 635                 640

Ala Gly Asp Met His Phe Ser Asp Leu Ile Asn Ser Pro Met Met Ala
                645                 650                 655

Arg Ile Gly Asn Ser Val Tyr His Asp Ile Cys Pro Asn Asp Pro Leu
            660                 665                 670

Cys Ser Arg Phe Val Phe Gln Glu Lys Arg Lys Ile Ala Pro Ala Arg
        675                 680                 685

Ser Gly Arg His Ile Asn Leu Ala Lys Leu Gly Asp Asp Glu Glu Glu
    690                 695                 700

Thr Gln Asn Val Glu Tyr Glu Pro Ser Pro Leu Met Ala Lys Ser Leu
705                 710                 715                 720

Ile Tyr His Leu His Ser Ala Gly Val Lys Glu Gly Val Thr Leu Asn
                725                 730                 735

Asp Lys Leu Phe Gln His Val Tyr Thr Ser Ala His Gly Leu Met Arg
            740                 745                 750

Ile Phe Lys Val Met Asn Val Ser Ala Glu Ser Lys Lys Trp Val Ala
        755                 760                 765

Asp Pro Ala Asn Arg Val Cys His Pro Pro Gly Ser Trp Ile Cys Pro
    770                 775                 780

Gly Gln Tyr Pro Pro Ala Lys Glu Ile Gln Glu Met Leu Ala His Arg
785                 790                 795                 800

Tyr Thr Ser Leu Lys Asp Leu Val Asp Ser Met Ser Asp Ser Glu Arg
                805                 810                 815

Glu Gly Thr Leu Asn Gly Glu
            820
```

<210> SEQ ID NO 25
<211> LENGTH: 795
<212> TYPE: PRT
<213> ORGANISM: Artificial
<220> FEATURE:
<223> OTHER INFORMATION: Leishmania STT3 consensus sequence
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (133)..(134)
<223> OTHER INFORMATION: Xaa can be any naturally occurring amino acid
<220> FEATURE:
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (193)..(193)

<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (253)..(254)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (278)..(279)
<223> OTHER INFORMATION: Xaa can be any naturally occurring amino acid
<220> FEATURE:
<221> NAME/KEY: misc_feature
<222> LOCATION: (281)..(283)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (292)..(294)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (319)..(321)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (341)..(343)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (362)..(363)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (367)..(367)
<223> OTHER INFORMATION: Xaa can be any naturally occurring amino acid
<220> FEATURE:
<221> NAME/KEY: misc_feature
<222> LOCATION: (371)..(372)
<223> OTHER INFORMATION: Xaa can be any naturally occurring amino acid
<220> FEATURE:
<221> NAME/KEY: misc_feature
<222> LOCATION: (375)..(376)
<223> OTHER INFORMATION: Xaa can be any naturally occurring amino acid
<220> FEATURE:
<221> NAME/KEY: misc_feature
<222> LOCATION: (379)..(380)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (386)..(389)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
<221> NAME/KEY: misc_feature
<222> LOCATION: (430)..(432)
<223> OTHER INFORMATION: Xaa can be any naturally occurring amino acid
<220> FEATURE:

<221> NAME/KEY: misc_feature
<222> LOCATION: (436)..(436)
<223> OTHER INFORMATION: Xaa can be any naturally occurring amino acid
<220> FEATURE:
<221> NAME/KEY: misc_feature
<222> LOCATION: (439)..(440)
<223> OTHER INFORMATION: Xaa can be any naturally occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (447)..(449)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (455)..(458)
<223> OTHER INFORMATION: Xaa can be any naturally occurring amino acid
<220> FEATURE:
<221> NAME/KEY: misc_feature
<222> LOCATION: (464)..(469)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
<222> LOCATION: (477)..(477)
<223> OTHER INFORMATION: Xaa can be any naturally occurring amino acid
<220> FEATURE:
<221> NAME/KEY: misc_feature
<222> LOCATION: (483)..(486)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid
<220> FEATURE:
<221> NAME/KEY: misc_feature
<222> LOCATION: (491)..(491)
<223> OTHER INFORMATION: Xaa can be any naturally occurring amino acid
<220> FEATURE:
<221> NAME/KEY: misc_feature
<222> LOCATION: (493)..(493)
<223> OTHER INFORMATION: Xaa can be any naturally occurring amino acid
<220> FEATURE:
<221> NAME/KEY: misc_feature
<222> LOCATION: (495)..(495)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (513)..(514)
<223> OTHER INFORMATION: Xaa can be any naturally occurring amino acid
<220> FEATURE:
<221> NAME/KEY: misc_feature
<222> LOCATION: (516)..(516)
<223> OTHER INFORMATION: Xaa can be any naturally occurring amino acid
<220> FEATURE:
<221> NAME/KEY: misc_feature
<222> LOCATION: (520)..(520)
<223> OTHER INFORMATION: Xaa can be any naturally occurring amino acid
<220> FEATURE:
<221> NAME/KEY: misc_feature
<222> LOCATION: (523)..(525)
<223> OTHER INFORMATION: Xaa can be any naturally occurring amino acid
<220> FEATURE:
<221> NAME/KEY: misc_feature
<222> LOCATION: (529)..(534)
<223> OTHER INFORMATION: Xaa can be any naturally occurring amino acid
<220> FEATURE:
<221> NAME/KEY: misc_feature
<222> LOCATION: (539)..(539)
<223> OTHER INFORMATION: Xaa can be any naturally occurring amino acid
<220> FEATURE:
<221> NAME/KEY: misc_feature
<222> LOCATION: (546)..(547)
<223> OTHER INFORMATION: Xaa can be any naturally occurring amino acid
<220> FEATURE:
<221> NAME/KEY: misc_feature
<222> LOCATION: (550)..(550)
<223> OTHER INFORMATION: Xaa can be any naturally occurring amino acid
<220> FEATURE:
<221> NAME/KEY: misc_feature
<222> LOCATION: (554)..(554)
<223> OTHER INFORMATION: Xaa can be any naturally occurring amino acid
<220> FEATURE:
<221> NAME/KEY: misc_feature
<222> LOCATION: (556)..(556)
<223> OTHER INFORMATION: Xaa can be any naturally occurring amino acid
<220> FEATURE:
<221> NAME/KEY: misc_feature
<222> LOCATION: (612)..(613)
<223> OTHER INFORMATION: Xaa can be any naturally occurring amino acid
<220> FEATURE:
<221> NAME/KEY: misc_feature
<222> LOCATION: (616)..(617)
<223> OTHER INFORMATION: Xaa can be any naturally occurring amino acid
<220> FEATURE:
<221> NAME/KEY: misc_feature
<222> LOCATION: (622)..(623)
<223> OTHER INFORMATION: Xaa can be any naturally occurring amino acid
<220> FEATURE:
<221> NAME/KEY: misc_feature
<222> LOCATION: (626)..(626)
<223> OTHER INFORMATION: Xaa can be any naturally occurring amino acid
<220> FEATURE:
<221> NAME/KEY: misc_feature
<222> LOCATION: (636)..(636)
<223> OTHER INFORMATION: Xaa can be any naturally occurring amino acid
<220> FEATURE:
<221> NAME/KEY: misc_feature
<222> LOCATION: (641)..(641)
<223> OTHER INFORMATION: Xaa can be any naturally occurring amino acid
<220> FEATURE:
<221> NAME/KEY: misc_feature
<222> LOCATION: (647)..(647)
<223> OTHER INFORMATION: Xaa can be any naturally occurring amino acid
<220> FEATURE:
<221> NAME/KEY: misc_feature
<222> LOCATION: (650)..(650)
<223> OTHER INFORMATION: Xaa can be any naturally occurring amino acid
<220> FEATURE:
<221> NAME/KEY: misc_feature
<222> LOCATION: (652)..(654)
<223> OTHER INFORMATION: Xaa can be any naturally occurring amino acid
<220> FEATURE:
<221> NAME/KEY: misc_feature
<222> LOCATION: (656)..(656)
<223> OTHER INFORMATION: Xaa can be any naturally occurring amino acid
<220> FEATURE:
<221> NAME/KEY: misc_feature
<222> LOCATION: (658)..(658)
<223> OTHER INFORMATION: Xaa can be any naturally occurring amino acid
<220> FEATURE:
<221> NAME/KEY: misc_feature
<222> LOCATION: (660)..(662)
<223> OTHER INFORMATION: Xaa can be any naturally occurring amino acid
<220> FEATURE:
<221> NAME/KEY: misc_feature
<222> LOCATION: (665)..(681)
<223> OTHER INFORMATION: Xaa can be any naturally occurring amino acid
<220> FEATURE:
<221> NAME/KEY: misc_feature
<222> LOCATION: (686)..(686)
<223> OTHER INFORMATION: Xaa can be any naturally occurring amino acid
<220> FEATURE:
<221> NAME/KEY: misc_feature
<222> LOCATION: (688)..(688)

<223> OTHER INFORMATION: Xaa can be any naturally occurring amino acid
<220> FEATURE:
<221> NAME/KEY: misc_feature
<222> LOCATION: (699)..(699)
<223> OTHER INFORMATION: Xaa can be any naturally occurring amino acid
<220> FEATURE:
<221> NAME/KEY: misc_feature
<222> LOCATION: (702)..(703)
<223> OTHER INFORMATION: Xaa can be any naturally occurring amino acid
<220> FEATURE:
<221> NAME/KEY: misc_feature
<222> LOCATION: (706)..(706)
<223> OTHER INFORMATION: Xaa can be any naturally occurring amino acid
<220> FEATURE:
<221> NAME/KEY: misc_feature
<222> LOCATION: (708)..(710)
<223> OTHER INFORMATION: Xaa can be any naturally occurring amino acid
<220> FEATURE:
<221> NAME/KEY: misc_feature
<222> LOCATION: (714)..(714)
<223> OTHER INFORMATION: Xaa can be any naturally occurring amino acid
<220> FEATURE:
<221> NAME/KEY: misc_feature
<222> LOCATION: (716)..(716)
<223> OTHER INFORMATION: Xaa can be any naturally occurring amino acid
<220> FEATURE:
<221> NAME/KEY: misc_feature
<222> LOCATION: (719)..(720)
<223> OTHER INFORMATION: Xaa can be any naturally occurring amino acid
<220> FEATURE:
<221> NAME/KEY: misc_feature
<222> LOCATION: (722)..(723)
<223> OTHER INFORMATION: Xaa can be any naturally occurring amino acid
<220> FEATURE:
<221> NAME/KEY: misc_feature
<222> LOCATION: (733)..(733)
<223> OTHER INFORMATION: Xaa can be any naturally occurring amino acid
<220> FEATURE:
<221> NAME/KEY: misc_feature
<222> LOCATION: (742)..(742)
<223> OTHER INFORMATION: Xaa can be any naturally occurring amino acid
<220> FEATURE:
<221> NAME/KEY: misc_feature
<222> LOCATION: (748)..(748)
<223> OTHER INFORMATION: Xaa can be any naturally occurring amino acid
<220> FEATURE:
<221> NAME/KEY: misc_feature
<222> LOCATION: (772)..(773)
<223> OTHER INFORMATION: Xaa can be any naturally occurring amino acid
<220> FEATURE:
<221> NAME/KEY: misc_feature
<222> LOCATION: (775)..(776)
<223> OTHER INFORMATION: Xaa can be any naturally occurring amino acid
<220> FEATURE:
<221> NAME/KEY: misc_feature
<222> LOCATION: (780)..(780)
<223> OTHER INFORMATION: Xaa can be any naturally occurring amino acid
<220> FEATURE:
<221> NAME/KEY: misc_feature
<222> LOCATION: (782)..(795)
<223> OTHER INFORMATION: Xaa can be any naturally occurring amino acid

<400> SEQUENCE: 25

```
Xaa Xaa Xaa Xaa Xaa Xaa Ser Thr Xaa Tyr Thr Xaa Xaa Phe Ala Val
1               5                   10                  15

Pro Met Ala Ile Xaa Xaa Xaa Ile Ala Tyr Xaa Met Arg Val Arg Ser
            20                  25                  30

Ile Xaa Val Tyr Gly Tyr Leu Phe His Xaa Xaa Asp Pro Trp Phe Asn
        35                  40                  45

Tyr Arg Ala Ala Glu Tyr Met Ser Xaa His Gly Trp Ser Ala Phe Phe
    50                  55                  60

Ser Trp Phe Asp Tyr Met Ser Trp Tyr Pro Leu Gly Arg Pro Val Gly
65                  70                  75                  80
```

-continued

```
Xaa Thr Thr Tyr Pro Gly Leu Gln Xaa Thr Ala Val Ala Ile His Arg
                85                  90                  95

Ala Leu Ala Ala Ala Gly Xaa Pro Met Ser Leu Asn Xaa Val Cys Val
            100                 105                 110

Leu Xaa Pro Ala Trp Phe Ser Leu Xaa Ser Ser Ala Met Xaa Ala Leu
        115                 120                 125

Leu Ala His Glu Xaa Xaa Gly Asn Met Ala Xaa Xaa Ser Xaa Ser Ser
    130                 135                 140

Ile Leu Phe Ser Val Xaa Pro Ala His Leu Met Arg Ser Met Ala Gly
145                 150                 155                 160

Glu Phe Asp Asn Glu Cys Ile Ala Val Xaa Ala Met Leu Leu Thr Phe
                165                 170                 175

Tyr Xaa Trp Val Arg Ser Leu Arg Thr Arg Xaa Ser Trp Pro Ile Gly
            180                 185                 190

Xaa Leu Thr Gly Xaa Ala Tyr Gly Tyr Met Xaa Ala Ala Trp Gly Gly
        195                 200                 205

Tyr Ile Phe Val Leu Asn Met Val Ala Met His Ala Gly Ile Ser Ser
    210                 215                 220

Met Val Asp Trp Ala Arg Asn Thr Tyr Asn Pro Ser Leu Leu Arg Ala
225                 230                 235                 240

Tyr Xaa Leu Phe Tyr Val Val Gly Thr Ala Ile Ala Xaa Xaa Val Pro
                245                 250                 255

Pro Val Gly Met Ser Pro Phe Xaa Arg Ser Leu Glu Gln Leu Gly Ala
            260                 265                 270

Xaa Val Val Xaa Leu Xaa Xaa Cys Xaa Xaa Xaa Ala Cys Xaa Thr Gln
        275                 280                 285

Xaa Ser Arg Xaa Xaa Xaa Glu Xaa Phe Xaa Thr Glu Gly Xaa Ser Leu
    290                 295                 300

Xaa Arg Ile Xaa Ala Ala Phe Phe Val Gly Ile Val Ala Val Xaa Xaa
305                 310                 315                 320

Xaa Ala Pro Ala Gly Phe Phe Lys Pro Leu Ser Leu Gln Ala Xaa Ala
                325                 330                 335

Xaa Ile Xaa Gly Xaa Xaa Xaa Thr Gly Asn Thr Leu Val Asp Xaa Leu
            340                 345                 350

Xaa Ala Xaa Asp Ala Ser Xaa Leu Leu Xaa Xaa Trp Xaa Leu Xaa Leu
        355                 360                 365

Phe Pro Xaa Xaa Gly Trp Xaa Xaa Gly Met Xaa Xaa Phe Leu Xaa Glu
    370                 375                 380

Leu Xaa Xaa Xaa Xaa Thr Tyr Xaa Lys Ser Phe Xaa Leu Met Tyr Gly
385                 390                 395                 400

Xaa Val Gly Xaa Tyr Phe Ala Ser Gln Ser Val Arg Met Met Val Met
                405                 410                 415

Met Ala Pro Val Ala Cys Ile Phe Thr Ala Leu Leu Phe Xaa Xaa Xaa
            420                 425                 430

Leu Asp Tyr Xaa Leu Gly Xaa Xaa Phe Trp Ala Glu Xaa Pro Xaa Xaa
        435                 440                 445

Xaa Asp Xaa Asp Ala Gln Xaa Xaa Xaa Xaa Gln Gln Thr Ala Glu Xaa
    450                 455                 460

Xaa Xaa Xaa Xaa Xaa Lys Arg Lys Xaa Glu Glu Tyr Xaa Thr Met Gln
465                 470                 475                 480

Val Lys Xaa Xaa Xaa Xaa Arg Met Xaa Pro Xaa Met Xaa Leu Xaa Leu
                485                 490                 495

Leu Phe Arg Xaa Ser Gly Phe Ile Glu Asp Val Ala Ala Ile Ser Arg
```

```
            500                 505                 510

Xaa Xaa Glu Xaa Pro Gly Ile Xaa Phe Pro Xaa Xaa Xaa Val Gln Gly
        515                 520                 525

Xaa Xaa Xaa Xaa Xaa Xaa Asp Asp Tyr Tyr Xaa Gly Tyr Leu Tyr Leu
    530                 535                 540

Arg Xaa Xaa Thr Pro Xaa Asp Ala Arg Xaa Leu Xaa Trp Trp Asp Tyr
545                 550                 555                 560

Gly Tyr Gln Ile Thr Gly Ile Gly Asn Arg Thr Ser Leu Ala Asp Gly
                565                 570                 575

Asn Thr Trp Asn His Glu His Ile Ala Thr Ile Gly Lys Met Leu Thr
            580                 585                 590

Ser Pro Val Ala Glu Ala His Ser Leu Val Arg His Met Ala Asp Tyr
        595                 600                 605

Val Leu Ile Xaa Xaa Gly Asp Xaa Xaa Phe Ser Asp Leu Xaa Xaa Ser
    610                 615                 620

Pro Xaa Met Ala Arg Ile Gly Asn Ser Val Tyr Xaa Asp Ile Cys Pro
625                 630                 635                 640

Xaa Asp Pro Leu Cys Ser Xaa Phe Val Xaa Gln Xaa Xaa Xaa Lys Xaa
                645                 650                 655

Ala Xaa Ala Xaa Xaa Xaa Arg His Xaa Xaa Xaa Xaa Xaa Xaa Xaa Xaa
            660                 665                 670

Xaa Xaa Xaa Xaa Xaa Xaa Xaa Xaa Xaa Tyr Glu Pro Ser Xaa Leu Xaa
        675                 680                 685

Ala Lys Ser Leu Ile Tyr His Leu His Ser Xaa Gly Val Xaa Xaa Gly
    690                 695                 700

Val Xaa Leu Xaa Xaa Xaa Leu Phe Gln Xaa Val Xaa Thr Ser Xaa Xaa
705                 710                 715                 720

Gly Xaa Xaa Arg Ile Phe Lys Val Met Asn Val Ser Xaa Glu Ser Lys
                725                 730                 735

Lys Trp Val Ala Asp Xaa Ala Asn Arg Val Cys Xaa Pro Pro Gly Ser
            740                 745                 750

Trp Ile Cys Pro Gly Gln Tyr Pro Pro Ala Lys Glu Ile Gln Glu Met
        755                 760                 765

Leu Ala His Xaa Xaa Thr Xaa Xaa Lys Asp Leu Xaa Asp Xaa Xaa Xaa
    770                 775                 780

Xaa Xaa Xaa Xaa Xaa Xaa Xaa Xaa Xaa Xaa Xaa
785                 790                 795
```

<210> SEQ ID NO 26
<211> LENGTH: 718
<212> TYPE: PRT
<213> ORGANISM: Saccharomyces cerevisiae

<400> SEQUENCE: 26

```
Met Gly Ser Asp Arg Ser Cys Val Leu Ser Val Phe Gln Thr Ile Leu
1               5                   10                  15

Lys Leu Val Ile Phe Val Ala Ile Phe Gly Ala Ala Ile Ser Ser Arg
            20                  25                  30

Leu Phe Ala Val Ile Lys Phe Glu Ser Ile Ile His Glu Phe Asp Pro
        35                  40                  45

Trp Phe Asn Tyr Arg Ala Thr Lys Tyr Leu Val Asn Asn Ser Phe Tyr
    50                  55                  60

Lys Phe Leu Asn Trp Phe Asp Asp Arg Thr Trp Tyr Pro Leu Gly Arg
65                  70                  75                  80
```

-continued

```
Val Thr Gly Gly Thr Leu Tyr Pro Gly Leu Met Thr Thr Ser Ala Phe
                85                  90                  95

Ile Trp His Ala Leu Arg Asn Trp Leu Gly Leu Pro Ile Asp Ile Arg
            100                 105                 110

Asn Val Cys Val Leu Phe Ala Pro Leu Phe Ser Gly Val Thr Ala Trp
        115                 120                 125

Ala Thr Tyr Glu Phe Thr Lys Glu Ile Lys Asp Ala Ser Ala Gly Leu
    130                 135                 140

Leu Ala Ala Gly Phe Ile Ala Ile Val Pro Gly Tyr Ile Ser Arg Ser
145                 150                 155                 160

Val Ala Gly Ser Tyr Asp Asn Glu Ala Ile Ala Ile Thr Leu Leu Met
                165                 170                 175

Val Thr Phe Met Phe Trp Ile Lys Ala Gln Lys Thr Gly Ser Ile Met
            180                 185                 190

His Ala Thr Cys Ala Ala Leu Phe Tyr Phe Tyr Met Val Ser Ala Trp
        195                 200                 205

Gly Gly Tyr Val Phe Ile Thr Asn Leu Ile Pro Leu His Val Phe Leu
    210                 215                 220

Leu Ile Leu Met Gly Arg Tyr Ser Ser Lys Leu Tyr Ser Ala Tyr Thr
225                 230                 235                 240

Thr Trp Tyr Ala Ile Gly Thr Val Ala Ser Met Gln Ile Pro Phe Val
                245                 250                 255

Gly Phe Leu Pro Ile Arg Ser Asn Asp His Met Ala Ala Leu Gly Val
            260                 265                 270

Phe Gly Leu Ile Gln Ile Val Ala Phe Gly Asp Phe Val Lys Gly Gln
        275                 280                 285

Ile Ser Thr Ala Lys Phe Lys Val Ile Met Met Val Ser Leu Phe Leu
    290                 295                 300

Ile Leu Val Leu Gly Val Val Gly Leu Ser Ala Leu Thr Tyr Met Gly
305                 310                 315                 320

Leu Ile Ala Pro Trp Thr Gly Arg Phe Tyr Ser Leu Trp Asp Thr Asn
                325                 330                 335

Tyr Ala Lys Ile His Ile Pro Ile Ile Ala Ser Val Ser Glu His Gln
            340                 345                 350

Pro Val Ser Trp Pro Ala Phe Phe Phe Asp Thr His Phe Leu Ile Trp
        355                 360                 365

Leu Phe Pro Ala Gly Val Phe Leu Leu Phe Leu Asp Leu Lys Asp Glu
    370                 375                 380

His Val Phe Val Ile Ala Tyr Ser Val Leu Cys Ser Tyr Phe Ala Gly
385                 390                 395                 400

Val Met Val Arg Leu Met Leu Thr Leu Thr Pro Val Ile Cys Val Ser
                405                 410                 415

Ala Ala Val Ala Leu Ser Lys Ile Phe Asp Ile Tyr Leu Asp Phe Lys
            420                 425                 430

Thr Ser Asp Arg Lys Tyr Ala Ile Lys Pro Ala Ala Leu Leu Ala Lys
        435                 440                 445

Leu Ile Val Ser Gly Ser Phe Ile Phe Tyr Leu Tyr Leu Phe Val Phe
    450                 455                 460

His Ser Thr Trp Val Thr Arg Thr Ala Tyr Ser Ser Pro Ser Val Val
465                 470                 475                 480

Leu Pro Ser Gln Thr Pro Asp Gly Lys Leu Ala Leu Ile Asp Asp Phe
                485                 490                 495

Arg Glu Ala Tyr Tyr Trp Leu Arg Met Asn Ser Asp Glu Asp Ser Lys
```

-continued

```
            500                 505                 510

Val Ala Ala Trp Trp Asp Tyr Gly Tyr Gln Ile Gly Gly Met Ala Asp
        515                 520                 525

Arg Thr Thr Leu Val Asp Asn Asn Thr Trp Asn Asn Thr His Ile Ala
    530                 535                 540

Ile Val Gly Lys Ala Met Ala Ser Pro Glu Glu Lys Ser Tyr Glu Ile
545                 550                 555                 560

Leu Lys Glu His Asp Val Asp Tyr Val Leu Val Ile Phe Gly Gly Leu
                565                 570                 575

Ile Gly Phe Gly Gly Asp Asp Ile Asn Lys Phe Leu Trp Met Ile Arg
            580                 585                 590

Ile Ser Glu Gly Ile Trp Pro Glu Glu Ile Lys Glu Arg Tyr Phe Tyr
        595                 600                 605

Thr Ala Glu Gly Glu Tyr Arg Val Asp Ala Arg Ala Ser Glu Thr Met
    610                 615                 620

Arg Asn Ser Leu Leu Tyr Lys Met Ser Tyr Lys Asp Phe Pro Gln Leu
625                 630                 635                 640

Phe Asn Gly Gly Gln Ala Thr Asp Arg Val Arg Gln Gln Met Ile Thr
                645                 650                 655

Pro Leu Asp Val Pro Pro Leu Asp Tyr Phe Asp Glu Val Phe Thr Ser
            660                 665                 670

Glu Asn Trp Met Val Arg Ile Tyr Gln Leu Lys Lys Asp Asp Ala Gln
        675                 680                 685

Gly Arg Thr Leu Arg Asp Val Gly Glu Leu Thr Arg Ser Ser Thr Lys
    690                 695                 700

Thr Arg Arg Ser Ile Lys Arg Pro Glu Leu Gly Leu Arg Val
705                 710                 715
```

<210> SEQ ID NO 27
<211> LENGTH: 2157
<212> TYPE: DNA
<213> ORGANISM: Saccharomyces cerevisiae

<400> SEQUENCE: 27

```
atgggatccg accggtcgtg tgttttgtct gtgtttcaga ccatcctcaa gctcgtcatc     60

ttcgtggcga tttttggggc tgccatatca tcacgtttgt ttgcagtcat caaatttgag    120

tctattatcc atgaattcga cccctggttc aattataggg ctaccaaata tctcgtcaac    180

aattcgtttt acaagttttt gaactggttt gacgaccgta cctggtaccc cctcggaagg    240

gttactggag ggactttata tcctggtttg atgacgacta gtgcgttcat ctggcacgcc    300

ctgcgcaact ggttgggctt gcccattgac atcagaaacg tttgtgtgct atttgcgcca    360

ctattttctg ggtcaccgc  ctgggcgact tacgaattta cgaaagagat taaagatgcc    420

agcgctgggc ttttggctgc tggttttata gccattgtcc ccggttatat atctagatca    480

gtggcggggt cctacgataa tgaggccatt gccattacac tattaatggt cactttcatg    540

ttttggatta aggcccaaaa gactggctct atcatgcacg caacgtgtgc agctttattc    600

tacttctaca tggtgtcggc ttggggtgga tacgtgttca tcaccaactt gatcccactc    660

catgtctttt tgctgatttt gatgggcaga tattcgtcca aactgtattc tgcctacacc    720

acttggtacg ctattggaac tgttgcatcc atgcagatcc catttgtcgg tttcctacct    780

atcaggtcta acgaccacat ggccgcattg ggtgttttcg gtttgattca gattgtcgcc    840

ttcggtgact tcgtgaaggg ccaaatcagc acagctaagt ttaaagtcat catgatggtt    900
```

-continued

```
tctctgtttt tgatcttggt ccttggtgtg gtcggacttt ctgccttgac ctatatgggg    960
ttgattgccc cttggactgg tagattttat tcgttatggg ataccaacta cgcaaagatc   1020
cacattccta tcattgcctc cgtttccgaa catcaacccg tttcgtggcc cgctttcttc   1080
tttgataccc actttttgat ctggctattc cccgccggtg tattcctact attcctcgac   1140
ttgaaagacg agcacgtttt tgtcatcgct tactccgttc tgtgttcgta ctttgccggt   1200
gttatggtta gattgatgtt gactttgaca ccagtcatct gtgtgtccgc cgccgtcgca   1260
ttgtccaaga tatttgacat ctacctggat ttcaagacaa gtgaccgcaa atacgccatc   1320
aaacctgcgg cactactggc caaattgatt gtttccggat cattcatctt ttatttgtat   1380
cttttcgtct tccattctac ttgggtaaca agaactgcat actcttctcc ttctgttgtt   1440
ttgccatcac aaaccccaga tggtaaattg gcgttgatcg acgacttcag ggaagcgtac   1500
tattggttaa gaatgaactc tgatgaggac agtaaggttg cagcgtggtg ggattacggt   1560
taccaaattg gtggcatggc agacagaacc actttagtcg ataacaacac gtggaacaat   1620
actcacatcg ccatcgttgg taaagccatg gcttcccctg aagagaaatc ttacgaaatt   1680
ctaaaagagc atgatgtcga ttatgtcttg gtcatctttg gtggtctaat tgggtttggt   1740
ggtgatgaca tcaacaaatt cttgtggatg atcagaatta gcgagggaat ctggccagaa   1800
gagataaaag agcgttattt ctataccgca gagggagaat acagagtaga tgcaagggct   1860
tctgagacca tgaggaactc gctactttac aagatgtcct acaaagattt cccacaatta   1920
ttcaatggtg gccaagccac tgacagagtg cgtcaacaaa tgatcacacc attagacgtc   1980
ccaccattag actacttcga cgaagttttt acttccgaaa actggatggt tagaatatat   2040
caattgaaga aggatgatgc ccaaggtaga actttgaggg acgttggtga gttaaccagg   2100
tcttctacga aaaccagaag gtccataaag agacctgaat taggcttgag agtctaa      2157
```

<210> SEQ ID NO 28
<211> LENGTH: 749
<212> TYPE: PRT
<213> ORGANISM: Schizosaccharomyces pombe

<400> SEQUENCE: 28

```
Met Ala Asn Ser Ala Thr Ile Thr Ser Lys Lys Gly Val Lys Ser His
1               5                   10                  15

Gln Lys Asp Trp Lys Ile Pro Leu Lys Val Leu Ile Leu Ile Cys Ile
            20                  25                  30

Ala Val Ala Ser Val Ser Ser Arg Leu Phe Ser Val Ile Arg Tyr Glu
        35                  40                  45

Ser Ile Ile His Glu Phe Asp Pro Trp Phe Asn Phe Arg Ala Ser Lys
    50                  55                  60

Ile Leu Val Glu Gln Gly Phe Tyr Asn Phe Leu Asn Trp Phe Asp Glu
65                  70                  75                  80

Arg Ser Trp Tyr Pro Leu Gly Arg Val Ala Gly Gly Thr Leu Tyr Pro
                85                  90                  95

Gly Leu Met Val Thr Ser Gly Ile Ile Phe Lys Val Leu His Leu Leu
            100                 105                 110

Arg Ile Asn Val Asn Ile Arg Asp Val Cys Val Leu Leu Ala Pro Ala
        115                 120                 125

Phe Ser Gly Ile Thr Ala Ile Ala Thr Tyr Tyr Leu Ala Arg Glu Leu
    130                 135                 140

Lys Ser Asp Ala Cys Gly Leu Leu Ala Ala Ala Phe Met Gly Ile Ala
145                 150                 155                 160
```

-continued

```
Pro Gly Tyr Thr Ser Arg Ser Val Ala Gly Ser Tyr Asp Asn Glu Ala
                165                 170                 175

Ile Ala Ile Thr Leu Leu Met Ser Thr Phe Ala Leu Trp Ile Lys Ala
            180                 185                 190

Val Lys Ser Gly Ser Ser Phe Trp Gly Ala Cys Thr Gly Leu Leu Tyr
        195                 200                 205

Phe Tyr Met Val Thr Ala Trp Gly Gly Tyr Val Phe Ile Thr Asn Met
    210                 215                 220

Ile Pro Leu His Val Phe Val Leu Leu Leu Met Gly Arg Tyr Thr Ser
225                 230                 235                 240

Lys Leu Tyr Ile Ala Tyr Thr Thr Tyr Tyr Val Ile Gly Thr Leu Ala
                245                 250                 255

Ser Met Gln Val Pro Phe Val Gly Phe Gln Pro Val Ser Thr Ser Glu
            260                 265                 270

His Met Ser Ala Leu Gly Val Phe Gly Leu Leu Gln Leu Phe Ala Phe
        275                 280                 285

Tyr Asn Tyr Val Lys Gly Leu Val Ser Ser Lys Gln Phe Gln Ile Leu
    290                 295                 300

Ile Arg Phe Ala Leu Val Cys Leu Val Gly Leu Ala Thr Val Val Leu
305                 310                 315                 320

Phe Ala Leu Ser Ser Thr Gly Val Ile Ala Pro Trp Thr Gly Arg Phe
                325                 330                 335

Tyr Ser Leu Trp Asp Thr Asn Tyr Ala Lys Ile His Ile Pro Ile Ile
            340                 345                 350

Ala Ser Val Ser Glu His Gln Pro Pro Thr Trp Ser Ser Leu Phe Phe
        355                 360                 365

Asp Leu Gln Phe Leu Ile Trp Leu Leu Pro Val Gly Val Tyr Leu Cys
    370                 375                 380

Phe Lys Glu Leu Arg Asn Glu His Val Phe Ile Ile Ile Tyr Pro Val
385                 390                 395                 400

Leu Gly Thr Tyr Phe Cys Gly Val Met Val Arg Leu Val Leu Thr Leu
                405                 410                 415

Thr Pro Cys Val Cys Ile Ala Ala Ala Val Ala Ile Ser Thr Leu Leu
            420                 425                 430

Asp Thr Tyr Met Gly Pro Glu Val Glu Glu Asp Lys Val Ser Glu Glu
        435                 440                 445

Ala Ala Ser Ala Lys Ser Lys Asn Lys Lys Gly Ile Ser Ser Ile Leu
    450                 455                 460

Ser Phe Phe Thr Ser Gly Ser Lys Asn Ile Gly Ile Tyr Ser Leu Leu
465                 470                 475                 480

Ser Arg Val Leu Val Ile Ser Ser Thr Ala Tyr Phe Leu Ile Met Phe
                485                 490                 495

Val Tyr His Ser Ser Trp Val Thr Ser Asn Ala Tyr Ser Ser Pro Thr
            500                 505                 510

Val Val Leu Ser Thr Val Leu Asn Asp Gly Ser Leu Met Tyr Ile Asp
        515                 520                 525

Asp Phe Arg Glu Ala Tyr Asp Trp Leu Arg Arg Asn Thr Pro Tyr Asp
    530                 535                 540

Thr Lys Val Met Ser Trp Trp Asp Tyr Gly Tyr Gln Ile Ala Gly Met
545                 550                 555                 560

Ala Asp Arg Ile Thr Leu Val Asp Asn Asn Thr Trp Asn Asn Thr His
                565                 570                 575
```

-continued

```
Ile Ala Thr Val Gly Lys Ala Met Ser Ser Pro Glu Glu Lys Ala Tyr
            580                 585                 590

Pro Ile Leu Arg Lys His Asp Val Asp Tyr Ile Leu Ile Ile Tyr Gly
        595                 600                 605

Gly Thr Leu Gly Tyr Ser Ser Asp Asp Met Asn Lys Phe Leu Trp Met
    610                 615                 620

Ile Arg Ile Ser Gln Gly Leu Trp Pro Asp Glu Ile Val Glu Arg Asn
625                 630                 635                 640

Phe Phe Thr Pro Asn Gly Glu Tyr Arg Thr Asp Asp Ala Ala Thr Pro
                645                 650                 655

Thr Met Arg Glu Ser Leu Leu Tyr Lys Met Ser Tyr His Gly Ala Trp
            660                 665                 670

Lys Leu Phe Pro Pro Asn Gln Gly Tyr Asp Arg Ala Arg Asn Gln Lys
        675                 680                 685

Leu Pro Ser Lys Asp Pro Gln Leu Phe Thr Ile Glu Glu Ala Phe Thr
    690                 695                 700

Thr Val His His Leu Val Arg Leu Tyr Lys Val Lys Lys Pro Asp Thr
705                 710                 715                 720

Leu Gly Arg Asp Leu Lys Gln Val Thr Leu Phe Glu Glu Gly Lys Arg
                725                 730                 735

Lys Lys Ser Ala Val Leu Gln Lys Leu Thr Lys Phe Leu
            740                 745
```

```
<210> SEQ ID NO 29
<211> LENGTH: 2250
<212> TYPE: DNA
<213> ORGANISM: Schizosaccharomyces pombe

<400> SEQUENCE: 29

atggctaatt ctgctacaat tacgagtaaa aaaggcgtga agtctcatca gaaggactgg      60

aaaattccac ttaaagtgct cattcttata tgtattgctg tggcttctgt ctcttcgagg     120

ctttttttctg tcattcgtta cgagtccatt attcatgaat ttgatccttg gttcaatttc     180

cgagcttcca aaatattggt ggaacaaggt ttttataact ttttaaattg gtttgatgaa     240

agaagttggt acccgttggg tcgtgtagcg ggtggtactt tgtacccagg acttatggtc     300

acgtctggta ttattttcaa agttttacat cttttaagaa ttaacgtgaa catccgtgat     360

gtatgtgttt tacttgcccc tgctttctct ggaatcactg cgattgctac ctattatctg     420

gctagagaat tgaaaagtga tgcatgtggc cttttagctg ccgcatttat gggtattgct     480

cctggataca cctcccgttc cgtcgctggt tcttacgata atgaagcaat tgctattacc     540

cttttgatgt caacgtttgc tttgtggatc aaggcagtga agtctggctc ctctttctgg     600

ggtgcctgca caggattgct ctacttctat atggtaactg cgtggggtgg ttatgtattc     660

atcacaaaca tgatacctt acacgtattt gttcttctac ttatgggtcg ctatactagc     720

aaattataca ttgcttacac aacatactat gttattggaa cgctggcttc tatgcaagtt     780

ccgtttgttg gtttccaacc cgtgtcgact agtgagcata tgtccgcttt aggagtgttt     840

ggcctgttac agctttttgc attctacaat tatgttaaag gtctagtttc atccaagcaa     900

ttccaaatac ttattcgttt tgccttggtt tgcttagtgg gtctagcaac agtcgtcctt     960

tttgctttat cttcaacagg tgttatcgct ccttggacag gacgtttcta ttctctttgg    1020

gatacaaact acgccaagat tcatattcct atcattgctt cggtatcaga acatcagcct    1080

cctacttgga gttcgttgtt ctttgatctt caatttttga tttggttatt gccagttggt    1140
```

```
gtttacttgt gtttcaagga acttcgtaat gaacatgtct ttattattat atatcctgtc   1200

ttaggaacat atttttgtgg tgtgatggtt cgtttggttt taaccttaac tccttgtgtt   1260

tgcatagctg ctgctgtagc aatttccact cttttagaca catatatggg tcctgaagtt   1320

gaagaggaca aagtgagcga agaagccgct tcagccaaat ctaagaacaa gaaaggtatt   1380

tcctctattc ttagtttctt cacttctggc tcaaaaaata ttggaattta cagtttgctt   1440

tccagagtat tagtcatttc ctctaccgca tatttcctaa taatgtttgt ttatcattcc   1500

agttgggtga cttctaatgc ttactcttcc cctaccgtgg ttttgtctac cgtgttaaac   1560

gatggtagtt taatgtatat tgatgacttc cgtgaagctt atgactggct tcgtagaaac   1620

actccttatg acacaaaggt tatgagttgg tgggattatg gttaccaaat tgctggtatg   1680

gctgatcgta ttactttagt cgacaacaat acgtggaaca acacacatat tgccacagtt   1740

ggaaaagcca tgtcttcacc tgaagaaaaa gcttacccta tcctccgtaa acacgatgtt   1800

gattatattc ttattatata tggtggtact cttggataca gcagcgacga catgaacaag   1860

ttcctttgga tgatccgaat ttctcaggga ttatggcccg atgaaatagt agagcgtaac   1920

ttttttactc ctaatggaga atatcgaact gacgatgcgg ctactcccac tatgcgtgag   1980

tctttattat ataagatgtc atatcacggt gcttggaaac ttttccctcc caatcaagga   2040

tatgaccgtg ctcgcaatca aaaactacca tcgaaagatc ctcaactatt tactatcgaa   2100

gaagcattca ctaccgttca tcatttagtt cgtttgtata aggttaagaa accggataca   2160

cttggacgcg atttgaaaca agtgacatta tttgaagaag gcaaaagaaa gaagtccgcc   2220

gtcctgcaaa aactaacgaa attcctttga                                   2250


<210> SEQ ID NO 30
<211> LENGTH: 714
<212> TYPE: PRT
<213> ORGANISM: Dictyostelium discoideum

<400> SEQUENCE: 30

Met Lys Arg Ser Glu Lys Ser Ser Thr Ser Val Val Ser Asn Asn Lys
1               5                   10                  15

Gln Gln Asp Val Asn Ile Ile Ser Ser Asn Glu Val Gly Val Lys Glu
            20                  25                  30

Glu Asn Lys Gly His Gln Glu Phe Leu Leu Lys Val Leu Ile Leu Ser
        35                  40                  45

Val Ile Tyr Val Leu Ala Phe Ser Thr Arg Leu Phe Ser Val Leu Arg
    50                  55                  60

Tyr Glu Ser Val Ile His Glu Phe Asp Pro Tyr Phe Asn Tyr Arg Ser
65                  70                  75                  80

Thr Ile Tyr Leu Val Gln Glu Gly Phe Tyr Asn Phe Leu Asn Trp Phe
                85                  90                  95

Asp Glu Arg Ala Trp Tyr Pro Leu Gly Arg Ile Val Gly Gly Thr Ile
            100                 105                 110

Tyr Pro Gly Leu Met Ala Thr Ala Ser Leu Val His Trp Ser Leu Asn
        115                 120                 125

Ser Leu Asn Ile Thr Val Asn Ile Arg Asn Val Cys Val Leu Leu Ser
    130                 135                 140

Pro Trp Phe Ala Ser Asn Thr Ala Met Val Thr Tyr Lys Phe Ala Lys
145                 150                 155                 160

Glu Val Lys Asp Thr Gln Thr Gly Leu Val Ala Ala Ala Met Ile Ala
                165                 170                 175
```

-continued

```
Ile Val Pro Gly Tyr Ile Ser Arg Ser Val Ala Gly Ser Phe Asp Asn
            180                 185                 190

Glu Gly Ile Ala Ile Phe Ala Leu Ile Phe Thr Tyr Tyr Cys Trp Ile
        195                 200                 205

Lys Ser Val Asn Thr Gly Ser Leu Met Trp Ala Ala Ile Cys Ser Leu
    210                 215                 220

Ala Tyr Phe Tyr Met Ala Ser Ala Trp Gly Gly Tyr Val Phe Ile Ile
225                 230                 235                 240

Asn Leu Ile Pro Leu His Ala Phe Phe Leu Leu Leu Thr Gly Arg Tyr
                245                 250                 255

Ser His Arg Leu Tyr Ile Ala Tyr Ser Thr Met Phe Val Ile Gly Thr
            260                 265                 270

Ile Leu Ser Met Gln Ile Thr Phe Ile Ser Phe Gln Pro Val Gln Ser
        275                 280                 285

Ser Glu His Leu Ala Ala Ile Gly Ile Phe Gly Leu Leu Gln Leu Tyr
    290                 295                 300

Ala Gly Leu Ser Trp Val Lys Ser His Leu Thr Asn Glu Ala Phe Lys
305                 310                 315                 320

Lys Leu Gln Arg Leu Thr Val Leu Phe Val Leu Ser Cys Ala Ala Ala
                325                 330                 335

Val Leu Val Val Gly Thr Leu Thr Gly Tyr Ile Ser Pro Phe Asn Gly
            340                 345                 350

Arg Phe Tyr Ser Leu Leu Asp Pro Thr Tyr Ala Arg Asp His Ile Pro
        355                 360                 365

Ile Ile Ala Ser Val Ser Glu His Gln Pro Thr Thr Trp Ala Ser Tyr
    370                 375                 380

Phe Phe Asp Leu His Ile Leu Val Phe Leu Phe Pro Ala Gly Leu Tyr
385                 390                 395                 400

Phe Cys Phe Gln Lys Leu Thr Asp Ala Asn Ile Phe Leu Ile Leu Tyr
                405                 410                 415

Gly Val Thr Ser Ile Tyr Phe Ser Gly Val Met Val Arg Leu Met Leu
            420                 425                 430

Val Leu Ala Pro Val Ala Cys Ile Leu Ala Ala Val Ala Val Ser Ala
        435                 440                 445

Thr Leu Thr Thr Tyr Met Lys Lys Leu Lys Ala Pro Ser Ser Pro Ser
    450                 455                 460

Asp Ala Asn Asn Ser Lys Glu Ser Gly Gly Val Met Val Ala Val Leu
465                 470                 475                 480

Thr Val Leu Leu Ile Leu Tyr Ala Phe His Cys Thr Trp Val Thr Ser
                485                 490                 495

Glu Ala Tyr Ser Ser Pro Ser Ile Val Leu Ser Ala Lys Gln Asn Asp
            500                 505                 510

Gly Ser Arg Val Ile Phe Asp Asp Phe Arg Glu Ala Tyr Arg Trp Ile
        515                 520                 525

Gly Gln Asn Thr Ala Asp Asp Ala Arg Ile Met Ser Trp Trp Asp Tyr
    530                 535                 540

Gly Tyr Gln Leu Ser Ala Met Ala Asn Arg Thr Val Leu Val Asp Asn
545                 550                 555                 560

Asn Thr Trp Asn Asn Ser His Ile Ala Gln Val Gly Lys Ala Phe Ala
                565                 570                 575

Ser Thr Glu Glu Asp Ala Tyr Ile Gln Met Lys Ala Leu Asp Val Asp
            580                 585                 590

Tyr Val Leu Val Ile Phe Gly Gly Leu Thr Gly Tyr Ser Ser Asp Asp
```

```
        595                 600                 605

Ile Asn Lys Phe Leu Trp Met Val Arg Ile Gly Gly Ser Cys Asp Pro
    610                 615                 620

Asn Ile Lys Glu Gln Asp Tyr Leu Thr Asn Gly Gln Tyr Arg Ile Asp
625                 630                 635                 640

Lys Gly Ala Ser Pro Thr Met Leu Asn Ser Leu Met Tyr Lys Leu Ser
                645                 650                 655

Tyr Tyr Arg Phe Ser Glu Val His Thr Asp Tyr Gln Arg Pro Thr Gly
            660                 665                 670

Phe Asp Arg Val Arg Asn Val Glu Ile Gly Asn Lys Asn Phe Asp Leu
        675                 680                 685

Thr Tyr Leu Glu Glu Ala Phe Thr Ser Val His Trp Leu Val Arg Val
    690                 695                 700

Tyr Lys Val Lys Asp Phe Asp Asn Arg Ala
705                 710


<210> SEQ ID NO 31
<211> LENGTH: 2145
<212> TYPE: DNA
<213> ORGANISM: Dictyostelium discoideum

<400> SEQUENCE: 31

atgaaaagat cagaaaaatc aagtacatct gttgttagta ataacaaaca acaagatgta     60

aatatcatca gttcaaatga agttggtgtt aaagaagaaa ataaaggaca tcaagaattc    120

ttattaaaag ttttaattct atcagtcatt tatgttttag cattttcaac tcgtttattc    180

tcagtattac gttatgaaag tgttattcat gaatttgatc catattttaa ttatagatca    240

acaatatatc ttgttcaaga aggtttttat aattttttaa attggtttga tgaaagagca    300

tggtatccat taggacgtat tgtaggtggt acaatttacc caggtttaat ggcaacagca    360

agtttagttc attggtcatt gaattcattg aatattacag ttaatattag aaatgtatgt    420

gtattgttat caccatggtt tgcatcaaat acagcaatgg taacctataa atttgccaaa    480

gaagttaagg atacacaaac tggtttggtt gcagcagcca tgattgcaat tgttccaggt    540

tatatttcac gttcagtagc aggttcattc gataatgaag gtattgcaat ctttgcattg    600

attttcacat attattgttg gattaagtca gtaaacacag gctcattgat gtgggctgcc    660

atctgttcat tggcctactt ttatatggca agtgcctggg gtggttatgt attcatcatt    720

aatttaatcc cattgcatgc ctttttcttg cttttgacag gccgttattc acatcgtctc    780

tacatagcct acagcacaat gtttgtcatt ggtacaatcc tctctatgca aattacattc    840

attagtttcc aaccagttca atcatctgaa catttggctg ccattggtat ctttggtctc    900

ctccaattgt acgctggttt gtcatgggta aagagtcacc tcaccaatga agccttcaag    960

aaacttcaac gtttgacagt gttattcgtt ttatcttgtg ctgctgccgt acttgtcgtt   1020

ggtacattaa ctggttacat ctcaccattc aatggtcgtt tctattcatt gttggatcca   1080

acctatgctc gtgaccacat tccaatcatt gcatcagtat cagagcatca accaaccact   1140

tgggcatcat actttttcga tctccatatc ttggtattcc ttttcccagc cggtttatac   1200

ttttgtttcc aaaaattaac cgatgctaat attttcctca ttctctacgg tgtcacctcc   1260

atttatttct ctggtgtaat ggtacgtctt atgttggttt tagcaccagt tgcatgtatt   1320

ttagccgccg ttgccgtcag tgcaaccctc accacctata tgaagaagtt aaaggctcca   1380

tcatcaccaa gtgatgctaa taattccaaa gagagtggtg gtgttatggt tgcagtctta   1440
```

-continued

```
actgttcttt taattctcta cgctttccat tgtacttggg tcactagtga agcctactca   1500

tctccatcca ttgtactctc tgccaaacaa aacgatggta gtcgtgtgat tttcgatgat   1560

ttccgtgaag cctaccgttg gattggtcaa aatactgccg acgacgctcg tattatgtct   1620

tggtgggatt atggttatca attatctgca atggccaatc gtaccgtatt ggttgataat   1680

aacacttgga acaatagtca tatcgctcaa gttggtaaag catttgcatc cactgaagaa   1740

gatgcttaca tacaaatgaa agcattggat gtcgattatg ttttagttat ttttggtggt   1800

ttaactggtt acagttctga tgatatcaat aaattccttt ggatggttag aattggtggt   1860

agttgtgatc caaatattaa agaacaagat tatctcacca atggtcaata tagaatagat   1920

aaaggtgcct caccaacaat gttaaattct ctcatgtaca aacttagtta ctatcgtttc   1980

tctgaagttc acactgacta tcaaagacca acaggtttcg atcgtgtaag aaatgttgaa   2040

attggtaata aaaatttcga tttaacttat ttagaagaag ctttcacatc tgttcattgg   2100

ttagttagag tttataaagt taaagatttt gataatagag cttaa                   2145
```

<210> SEQ ID NO 32
<211> LENGTH: 206
<212> TYPE: PRT
<213> ORGANISM: Pseudomonas aeruginosa

<400> SEQUENCE: 32

```
Met Ser Leu Ala Ser Ser Leu Glu Ser Leu Arg Lys Ile Asp Ile Asn
1               5                   10                  15

Asp Leu Asp Leu Asn Asn Ile Gly Ser Trp Pro Ala Ala Val Lys Val
            20                  25                  30

Ile Val Cys Val Leu Leu Thr Ala Ala Val Leu Ala Leu Gly Tyr Asn
        35                  40                  45

Phe His Leu Ser Asp Met Gln Ala Gln Leu Glu Gln Gln Ala Ala Glu
    50                  55                  60

Glu Glu Thr Leu Lys Gln Gln Phe Ser Thr Lys Ala Phe Gln Ala Ala
65                  70                  75                  80

Asn Leu Glu Ala Tyr Lys Ala Gln Met Lys Glu Met Glu Glu Ser Phe
                85                  90                  95

Gly Ala Leu Leu Arg Gln Leu Pro Ser Asp Thr Glu Val Pro Gly Leu
            100                 105                 110

Leu Glu Asp Ile Thr Arg Thr Gly Leu Gly Ser Gly Leu Glu Phe Glu
        115                 120                 125

Glu Ile Lys Leu Leu Pro Glu Val Ala Gln Gln Phe Tyr Ile Glu Leu
    130                 135                 140

Pro Ile Gln Ile Ser Val Val Gly Gly Tyr His Asp Leu Ala Thr Val
145                 150                 155                 160

Ser Gly Val Ser Ser Leu Pro Arg Ile Val Thr Leu His Asp Phe Glu
                165                 170                 175

Ile Lys Pro Val Ala Pro Gly Ser Thr Ser Lys Leu Arg Met Ser Ile
            180                 185                 190

Leu Ala Lys Thr Tyr Arg Tyr Asn Asp Lys Gly Leu Lys Lys
        195                 200                 205
```

<210> SEQ ID NO 33
<211> LENGTH: 624
<212> TYPE: DNA
<213> ORGANISM: Pseudomonas aeruginosa

<400> SEQUENCE: 33

-continued

```
atgagtctgg ccagttccct ggaaagtctg cgcaagatcg atatcaacga tctcgacctg      60

aacaacatcg gttcctggcc ggcggcggtc aaggtcatcg tctgcgtgct gctgaccgcg     120

gcggtcctgg cgctgggcta caacttccat ctgagtgaca tgcaggctca gctcgaacag     180

caggccgcgg aagaggagac gctcaagcag cagttctcca ccaaggcctt ccaggccgcg     240

aacctggaag cctacaaggc acagatgaag gagatggaag agtcctttgg cgccttgctg     300

cggcagttgc ccagcgacac cgaggtaccc gggctgctcg aggacatcac tcgtaccggc     360

ctgggcagcg gcctggagtt cgaggaaatc aagctgcttc ccgaggttgc ccagcagttc     420

tacatcgagc tgccgatcca gatcagcgtg gtcggcggct accacgactt ggcgaccttc     480

gtcagcggcg tgtccagcct gccgcggatc gtcaccctgc atgacttcga gatcaagccg     540

gtcgcgcccg gcagcacgtc caagctgcgc atgagcatcc tggccaagac ctatcgctac     600

aacgacaagg ggctgaagaa atga                                            624


<210> SEQ ID NO 34
<211> LENGTH: 604
<212> TYPE: PRT
<213> ORGANISM: Neisseria meningitidis

<400> SEQUENCE: 34

Met Pro Ala Glu Thr Thr Val Ser Gly Ala His Pro Ala Ala Lys Leu
1               5                   10                  15

Pro Ile Tyr Ile Leu Pro Cys Phe Leu Trp Ile Gly Ile Val Pro Phe
            20                  25                  30

Thr Phe Ala Leu Lys Leu Lys Pro Ser Pro Asp Phe Tyr His Asp Ala
        35                  40                  45

Ala Ala Ala Ala Gly Leu Ile Val Leu Leu Phe Leu Thr Ala Gly Lys
    50                  55                  60

Lys Leu Phe Asp Val Lys Ile Pro Ala Ile Ser Phe Leu Leu Phe Ala
65                  70                  75                  80

Met Ala Ala Phe Trp Tyr Leu Gln Ala Arg Leu Met Asn Leu Ile Tyr
                85                  90                  95

Pro Gly Met Asn Asp Ile Val Ser Trp Ile Phe Ile Leu Leu Ala Val
            100                 105                 110

Ser Ala Trp Ala Cys Arg Ser Leu Val Ala His Phe Gly Gln Glu Arg
        115                 120                 125

Ile Val Thr Leu Phe Ala Trp Ser Leu Leu Ile Gly Ser Leu Leu Gln
    130                 135                 140

Ser Cys Ile Val Val Ile Gln Phe Ala Gly Trp Glu Asp Thr Pro Leu
145                 150                 155                 160

Phe Gln Asn Ile Ile Val Tyr Ser Gly Gln Gly Val Ile Gly His Ile
                165                 170                 175

Gly Gln Arg Asn Asn Leu Gly His Tyr Leu Met Trp Gly Ile Leu Ala
            180                 185                 190

Ala Ala Tyr Leu Asn Gly Gln Arg Lys Ile Pro Ala Ala Leu Gly Val
        195                 200                 205

Ile Cys Leu Ile Met Gln Thr Ala Val Leu Gly Leu Val Asn Ser Arg
    210                 215                 220

Thr Ile Leu Thr Tyr Ile Ala Ala Ile Ala Leu Ile Leu Pro Phe Trp
225                 230                 235                 240

Tyr Phe Arg Ser Asp Lys Ser Asn Arg Arg Thr Met Leu Gly Ile Ala
                245                 250                 255

Ala Ala Val Phe Leu Thr Ala Leu Phe Gln Phe Ser Met Asn Thr Ile
```

```
            260                 265                 270

Leu Glu Thr Phe Thr Gly Ile Arg Tyr Glu Thr Ala Val Glu Arg Val
        275                 280                 285

Ala Asn Gly Gly Phe Thr Asp Leu Pro Arg Gln Ile Glu Trp Asn Lys
    290                 295                 300

Ala Leu Ala Ala Phe Gln Ser Ala Pro Ile Phe Gly His Gly Trp Asn
305                 310                 315                 320

Ser Phe Ala Gln Gln Thr Phe Leu Ile Asn Ala Glu Gln His Asn Ile
                325                 330                 335

Tyr Asp Asn Leu Leu Ser Asn Leu Phe Thr His Ser His Asn Ile Val
            340                 345                 350

Leu Gln Leu Leu Ala Glu Met Gly Ile Ser Gly Thr Leu Leu Val Ala
        355                 360                 365

Ala Thr Leu Leu Thr Gly Ile Ala Gly Leu Leu Lys Arg Pro Leu Thr
    370                 375                 380

Pro Ala Ser Leu Phe Leu Ile Cys Thr Leu Ala Val Ser Met Cys His
385                 390                 395                 400

Ser Met Leu Glu Tyr Pro Leu Trp Tyr Val Tyr Phe Leu Ile Pro Phe
                405                 410                 415

Gly Leu Met Leu Phe Leu Ser Pro Ala Glu Ala Ser Asp Gly Ile Ala
            420                 425                 430

Phe Lys Lys Ala Ala Asn Leu Gly Ile Leu Thr Ala Ser Ala Ala Ile
        435                 440                 445

Phe Ala Gly Leu Leu His Leu Asp Trp Thr Tyr Thr Arg Leu Val Asn
    450                 455                 460

Ala Phe Ser Pro Ala Thr Asp Asp Ser Ala Lys Thr Leu Asn Arg Lys
465                 470                 475                 480

Ile Asn Glu Leu Arg Tyr Ile Ser Ala Asn Ser Pro Met Leu Ser Phe
                485                 490                 495

Tyr Ala Asp Phe Ser Leu Val Asn Phe Ala Leu Pro Glu Tyr Pro Glu
            500                 505                 510

Thr Gln Thr Trp Ala Glu Glu Ala Thr Leu Lys Ser Leu Lys Tyr Arg
        515                 520                 525

Pro His Ser Ala Thr Tyr Arg Ile Ala Leu Tyr Leu Met Arg Gln Gly
    530                 535                 540

Lys Val Ala Glu Ala Lys Gln Trp Met Arg Ala Thr Gln Ser Tyr Tyr
545                 550                 555                 560

Pro Tyr Leu Met Pro Arg Tyr Ala Asp Glu Ile Arg Lys Leu Pro Val
                565                 570                 575

Trp Ala Pro Leu Leu Pro Glu Leu Leu Lys Asp Cys Lys Ala Phe Ala
            580                 585                 590

Ala Ala Pro Gly His Pro Glu Ala Lys Pro Cys Lys
        595                 600


<210> SEQ ID NO 35
<211> LENGTH: 1815
<212> TYPE: DNA
<213> ORGANISM: Neisseria meningitidis

<400> SEQUENCE: 35

atgcccgctg aaacgaccgt atccggcgcg caccccgccg ccaaactgcc gatttacatc      60

ctgccctgct tcctttggat aggcatcgtc ccctttacct tcgcgctcaa actgaaaccg     120

tcgcccgact tttaccacga tgccgccgcc gcagccggcc tgattgtcct gttgttcctc     180
```

-continued

```
acggcaggaa aaaaactgtt tgatgtcaaa atccccgcca tcagcttcct tctgtttgca    240
atggcggcgt tttggtatct tcaggcacgc ctgatgaacc tgatttaccc cggtatgaac    300
gacatcgtct cttggatttt catcttgctc gccgtcagcg cgtgggcctg ccggagcttg    360
gtcgcacact tcggacaaga acgcatcgtg accctgtttg cctggtcgct gcttatcggc    420
tccctgcttc aatcctgcat cgtcgtcatc cagtttgccg gctgggaaga cacccctctg    480
tttcaaaaca tcatcgttta cagcgggcaa ggcgtaatcg gacacatcgg gcagcgcaac    540
aacctcggac actacctcat gtggggcata ctcgccgccg cctacctcaa cggacaacga    600
aaaatccccg ccgccctcgg cgtaatctgc ctgattatgc agaccgccgt tttaggtttg    660
gtcaactcgc gcaccatctt gacctacata gccgccatcg ccctcatcct tcccttctgg    720
tatttccgtt cggacaaatc caacaggcgg acgatgctcg gcatagccgc agccgtattc    780
cttaccgcgc tgttccaatt ttccatgaac accattctgg aaacctttac tggcatccgc    840
tacgaaactg ccgtcgaacg cgtcgccaac ggcggtttca cagacttgcc gcgccaaatc    900
gaatggaata aagcccttgc cgccttccag tccgccccga tattcgggca cggctggaac    960
agttttgccc aacaaacctt cctcatcaat gccgaacagc acaacatata cgacaacctc   1020
ctcagcaact tgttcaccca ttcccacaac atcgtcctcc aactccttgc agagatggga   1080
atcagcggca cgcttctggt tgccgcaacc ctgctgacgg gcattgccgg gctgcttaaa   1140
cgcccccctga cccccgcatc gcttttccta atctgcacgc ttgccgtcag tatgtgccac   1200
agtatgctcg aatatccttt gtggtatgtc tatttcctca tccctttcgg actgatgctc   1260
ttcctgtccc ccgcagaggc ttcagacggc atcgccttca aaaaagccgc caatctcggc   1320
atactgaccg cctccgccgc catattcgca ggattgctgc acttggactg gacatacacc   1380
cggctggtta acgccttttc ccccgccact gacgacagtg ccaaaaccct caaccggaaa   1440
atcaacgagt tgcgctatat ttccgcaaac agtccgatgc tgtcctttta tgccgacttc   1500
tccctcgtaa acttcgccct gccggaatac cccgaaaccc agacttgggc ggaagaagca   1560
accctcaaat cactaaaata ccgcccccac tccgccacct accgcatcgc cctctacctg   1620
atgcggcaag gcaaagttgc agaagcaaaa caatggatgc gggcgacaca gtcctattac   1680
ccctacctga tgccccgata cgccgacgaa atccgcaaac tgcccgtatg ggcgccgctg   1740
ctacccgaac tgctcaaaga ctgcaaagcc ttcgccgccg cgcccggtca tccggaagca   1800
aaaccctgca aatga                                                     1815
```

PROKARYOTE-BASED CELL-FREE SYSTEM FOR THE SYNTHESIS OF GLYCOPROTEINS

This application is a national stage application under 35 U.S.C. § 371 from PCT Application No. PCT/US2012/063590, filed Nov. 5, 2012, which claims the benefit of U.S. Provisional Patent Application Ser. No. 61/555,854, filed Nov. 5, 2011, both of which are hereby incorporated by reference in their entirety.

FIELD OF THE INVENTION

The present invention relates to cell-free systems, kits, and methods for producing a glycosylated protein or peptide.

BACKGROUND OF THE INVENTION

Cell-free protein-synthesizing systems are emerging as an attractive alternative to conventional expression systems that rely on living cells (Katzen et al., "The Past, Present and Future of Cell-Free Protein Synthesis," *Trends Biotechnol.* 23:150-156 (2005)). This is because, over the past decade, cell-free protein synthesis reactions: (i) can be completed in less than a day; (ii) use reagents whose costs are down; (iii) fold complex proteins by routinely forming disulfide bonds; and (iv) can be scaled to 100 L. Two main approaches have been used for in vitro transcription/translation: one is based on cell-free extracts (CFEs), often derived from *Escherichia coli*, rabbit reticulocytes or wheat germ, and the second is based on reconstituted protein synthesis from purified components (Shimizu et al., "Cell-Free Translation Reconstituted With Purified Components," *Nat. Biotechnol.* 19:751-755 (2001)). Because of their ability to co-activate multiple biochemical networks in a single integrated platform (Jewett et al., "An Integrated Cell-Free Metabolic Platform for Protein Production and Synthetic Biology," *Mol. Syst. Biol.* 4:220 (2008)), cell free systems are increasingly used in many important biotechnology and synthetic biology applications (Ryabova et al., "Functional Antibody Production Using Cell-Free Translation: Effects of Protein Disulfide Isomerase and Chaperones," *Nat. Biotechnol.* 15:79-84 (1997); Noireaux et al., "Principles of Cell-Free Genetic Circuit Assembly," *Proc. Nat'l. Acad. Sci. U.S.A.* 100:12672-12677 (2003); Yang et al., "Rapid Expression of Vaccine Proteins for B-Cell Lymphoma in a Cell-Free System," *Biotechnol. Bioeng.* 89:503-511 (2005)).

The ability to accurately and efficiently glycosylate proteins in a cell-free system would have advantages for many areas of basic and applied research, especially given the importance of N-linked glycosylation in protein folding, quality control, sorting, degradation, secretion and activity (Helenius & Aebi, "Roles of N-Linked Glycans in the Endoplasmic Reticulum," *Annu. Rev. Biochem.* 73:1019-1049 (2004)). Unfortunately, the best characterized and most widely used cell-free translation systems based on *E. coli* are incapable of making glycoproteins because *E. coli* lack glycosylation machinery. Likewise, rabbit reticulocyte and wheat germ CFE systems cannot perform this post-translational modification because they lack microsomes (Tarui et al., "A Novel Cell-Free Translation/Glycosylation System Prepared From Insect Cells," *J. Biosci. Bioeng.* 90:508-514 (2000)). This can be overcome by supplementing eukaryotic CFEs with microsomal vesicles (e.g., canine pancreas microsomes) (Lingappa et al., "Coupled Cell-Free Synthesis, Segregation, and Core Glycosylation of a Secretory Protein," *Proc. Nat'l. Acad. Sci. U.S.A.* 75:2338-2342 (1978); Rothblatt & Meyer, "Secretion in Yeast: Reconstitution of the Translocation and Glycosylation of Alpha-Factor and Invertase in a Homologous Cell-Free System," *Cell* 44:619-628 (1986)), but the resulting systems do not always faithfully process the target protein due to poor compatibility between some CFEs and microsomal vesicles (Rothblatt & Meyer, "Secretion in Yeast: Reconstitution of the Translocation and Glycosylation of Alpha-Factor and Invertase in a Homologous Cell-Free System," *Cell* 44:619-628 (1986); Moreno et al., "An mRNA-Dependent in Vitro Translation System from *Trypanosoma* brucei," *Mol. Biochem. Parasitol.* 46:265-274 (1991)). An alternative strategy for creating a cell-free translation system that can execute N-linked glycosylation is to prepare CFEs from specialized cells such as hybridomas (Mikami et al., "A Hybridoma-Based in Vitro Translation System That Efficiently Synthesizes Glycoproteins," *J. Biotechnol.* 127:65-78 (2006)), trypanosomes (Moreno et al., "An mRNA-Dependent in Vitro Translation System from *Trypanosoma brucei*," *Mol. Biochem. Parasitol.* 46:265-274 (1991)), insect cells (Tarui et al., "A Novel Cell-Free Translation/Glycosylation System Prepared From Insect Cells," *J. Biosci. Bioeng.* 90:508-514 (2000)) or mammalian cells (Shibutani et al., "Preparation of a Cell-Free Translation System From PC12 Cell," *Neurochem. Res.* 21:801-807 (1996)). However, these systems are technically difficult to prepare and typically result in inefficient glycosylation and low product yields. Moreover, in all the above systems, the glycosylation process is effectively a "black-box" and thus difficult to control.

The present invention is directed at overcoming these and other deficiencies in the art.

SUMMARY OF THE INVENTION

A first aspect of the present invention is directed to a cell-free system for producing a glycosylated protein. This system comprises an isolated oligosaccharyltransferase (OST) capable of transferring a glycan from a lipid carrier molecule to a glycoprotein target; one or more isolated glycans, wherein each glycan is linked to a lipid carrier molecule; and a glycoprotein target comprising one or more glycan acceptor amino acid residues, or a nucleic acid molecule encoding said glycoprotein target.

Another aspect of the present invention is directed to a kit comprising an isolated oligosaccharyltransferase capable of transferring a glycan from a lipid carrier molecule to a glycoprotein target, and one or more isolated glycans, wherein each glycan is linked to a lipid carrier molecule.

Another aspect of the present invention relates to a method for producing a glycosylated protein in a cell-free system. This method involves providing an isolated oligosaccharyltransferase capable of transferring a glycan from a lipid carrier molecule to a glycoprotein target, providing one or more isolated glycans, wherein each glycan is linked to a lipid carrier molecule, and providing a glycoprotein target comprising one or more glycan acceptor amino acid residues. This method further involves combining the oligosaccharyltransferase, one or more isolated glycans, and glycoprotein target to form a cell-free glycosylation reaction mixture, and subjecting the cell-free glycosylation reaction mixture to conditions effective for the oligosaccharyltransferase to transfer the glycan from the lipid carrier molecule to the one or more glycan acceptor residues of the glycoprotein target to produce a glycosylated protein.

To address the failure of other cell-free systems to accurately and efficiently glycosylate proteins, two novel cell-free translation/glycosylation systems—termed "glycoCFE" and "glycoPURE"—were created as described herein. These systems combine existing in vitro translation systems with a reconstituted N-linked glycosylation pathway. Purified glycosylation components were derived from the protein glycosylation locus (pgl) present in the genome of the Gram-negative bacterium *Campylobacter jejuni* (FIG. 1A). This gene cluster encodes an N-linked glycosylation system that is functionally similar to that of eukaryotes and archaea, involving an oligosaccharyltransferase that catalyzes the en bloc transfer of preassembled oligosaccharides from lipid carriers onto asparagine residues in a conserved motif [N-$X_1$-S/T in eukaryotes and D/E-$X_1$-N-$X_2$-S/T (SEQ ID NO: 1) in bacteria (Kowarik et al., "Definition of the Bacterial N-Glycosylation Site Consensus Sequence," *EMBO J.* 25:1957-1966 (2006), which is hereby incorporated by reference in its entirety), where $X_1$ and $X_2$ are any residues except proline] within polypeptides (FIG. 1B). *C. jejuni* glycosylation machinery is ideally suited for use in a cell-free translation/glycosylation system for the following reasons. First, *E. coli* transformed with the entire pgl gene cluster can perform N-linked protein glycosylation (Wacker et al., "N-Linked Glycosylation in *Campylobacter jejuni* and its Functional Transfer Into *E. coli,*" *Science* 298:1790-1793 (2002), which is hereby incorporated by reference in its entirety), thereby providing a convenient host for producing the necessary components in a pure and active form. Since *E. coli* lacks native glycosylation machinery, the potential for contamination from background N- or O-linked systems is eliminated. Second, *C. jejuni* OST, named PglB (CjPglB), is a single-subunit enzyme that is active when solubilized in detergent (Lizak et al., "X-ray Structure of a Bacterial Oligosaccharyltransferase," *Nature* 474:350-355 (2011), which is hereby incorporated by reference in its entirety), and does not require any accessory components for its activity. Third, CjPglB can transfer sugars post-translationally to locally flexible structures in folded proteins (Kowarik et al., "N-Linked Glycosylation of Folded Proteins by the Bacterial Oligosaccharyltransferase," *Science* 314:1148-1150 (2006), which is hereby incorporated by reference in its entirety), indicating that protein glycosylation can be achieved without supplementing a functional membrane system (e.g. microsomes).

BRIEF DESCRIPTION OF THE DRAWINGS

FIG. 1A shows the 17-kb pgl locus of *C. jejuni* encoding the N-linked glycosylation machinery that has been fully reconstituted in *E. coli*. FIG. 1B shows a comparison of N-linked glycosylation in prokaryotes (left) and eukaryotes (right). In both systems, several glycosyltransferases synthesize the glycan by sequential addition of nucleotide-activated sugars on a lipid carrier on the cytoplasmic face of the inner membrane. Once assembled, a flippase transfers the lipid-linked glycans (also referred to as lipid-linked oligosaccharides or LLOs) across the membrane where the oligosaccharyltransferase catalyzes the transfer to Asn residues of periplasmic or endoplasmic reticulum substrate proteins. PglB is a single-subunit, integral membrane protein that is homologous to the catalytic subunit of the eukaryotic OST STT3 (note that PglB and STT3 complex are not drawn to scale). Whereas eukaryotes and archaea use an N-X-S/T acceptor sequence (where X is any amino acid but Pro), PglB requires an extended motif that includes an Asp or Glu residue in the −2 position (D/E-$X_1$-N-$X_2$-S/T (SEQ ID NO:1), where $X_1$ and $X_2$ can be any amino acid except Pro). PglB can transfer sugars post-translationally to locally flexible structures in folded proteins.

In FIG. 3A, the in vitro glycosylation assay was carried out using purified OST, extracted LLOs and purified acceptor proteins produced in *E. coli*. The immunoblots of FIG. 3A show the detection of acceptor protein AcrA and scFv13-R4-GT (both anti-His) or glycans (anti-glycan). Reactions included 3 μg wild-type CjPglB, 5 (+) or 10 (++) μL of LLOs and 5 μg of acceptor protein. Controls included the omission of different components (−), inactivated PglB (mut) and LLOs from SCM6 cells with empty pACYC (+/−). Glycosylation yields a mobility shift from the unmodified (g0) to the glycosylated forms (g1 and g2). FIG. 3B is the same assay as described in FIG. 3A but with purified PglB from *Campylobacter lari* (ClPglB). FIG. 3C shows immunoblots detecting AcrA following in vitro glycosylation using 3-month-old freeze thawed components.

FIG. 4A is an immunoblot detecting different AcrA constructs (anti-AcrA) produced by in vitro translation using either *E. coli* CFEs or purified translation components (PURE). AcrA concentration was estimated by comparing band intensities to that of purified AcrA loaded in lane 1. FIG. 4B is an immunoblot detecting ΔssAcrA expression (anti-AcrA) and glycosylation (anti-glycan). ΔssAcrAwas produced by cell-free translation/glycosylation using either the CFE or the PURE systems that were primed with pET24(AcrA-cyt). Controls included the omission of different components (−) or LLOs from SCM6 cells with empty pACYC (+/−).

FIG. 5A is an immunoblot detecting different scFv13-R4-GT (anti-FLAG) produced by in vitro translation using either *E. coli* cell-free extracts (CFE) or purified translation components (PURE). Estimates of the scFv13-R4-GT concentration were determined by comparison of band intensities to that of the purified scFv13-R4-GT sample loaded in lane 1. FIG. 5B is an immunoblot detecting scFv13-R4-GT expression (anti-FLAG) and glycosylation (anti-glycan). The scFv13-R4-GT protein was produced by cell-free translation/glycosylation using either the CFE or PURE systems that were primed with pET24-ssDsbAscFv13-R4-GT. Controls included omission of different components (−).

FIGS. 6A-6C show an amino acid sequence alignment of various *Campylobacter* PglB proteins that are suitable for use in the systems, kits, and methods of the present invention. The PglB amino acid sequences are derived from *C. jejuni* (SEQ ID NO: 2), *C. lari* (SEQ ID NO:4), *C. coli* (SEQ ID NO: 6), and *C. upsaliensis* (SEQ ID NO: 8). An (*) indicates positions which have a single, fully conserved residue; (:) indicates conservation between groups of strongly similar properties; and (.) indicates conservation between groups of weakly similar properties. A PglB consensus sequence based on the alignment of *Campylobacter* PglB sequences is presented as SEQ ID NO: 10. Residues that are not fully conserved between the four *Campylobacter* sequences are depicted as X, where X can be any amino acid residue. Alternatively, X is selected from an amino acid residue at that corresponding position in one of the four depicted *Campylobacter* sequences.

FIGS. 7A-7E shows an amino acid sequence alignment of various *Pyrococcus* OST STT3 subunit proteins that are suitable for use in the systems, kits, and methods of the present invention. The OST amino acid sequences are derived from *P. furiosus* (SEQ ID NO: 11), *Pyrococcus* sp. ST04 (SEQ ID NO: 13), *Pyrococcus* sp. (strain NA2) (SEQ ID NO: 14), *P. horikoshii* (SEQ ID NO:15), *P. abyssi* (SEQ ID NO: 16), and *P. yayanosii* (SEQ ID NO: 17). An (*) indicates positions which have a single, fully conserved residue; (:) indicates conservation between groups of strongly similar properties; and (.) indicates conservation between groups of weakly similar properties. A STT3 consensus sequence based on the alignment of *Pyrococcus* STT3 sequences is presented as SEQ ID NO: 18. Residues that are not fully conserved between the six *Pyrococcus* sequences are depicted as X, where X can be any amino acid residue. Alternatively, X is selected from an amino acid residue at the corresponding position in one of the six depicted *Pyrococcus* sequences.

FIGS. 8A-8D shows an amino acid sequence alignment of various *Leishmania* OST STT3 subunit related proteins that are suitable for use in the systems, kits, and methods of the present invention. The OST amino acid sequences are derived from *L. major* (SEQ ID NO: 19), *L. donovani* (SEQ ID NO: 21), *L. infantum* (SEQ ID NO: 22), *L. mexicana* (SEQ ID NO: 23), and *L. braziliensis* (SEQ ID NO: 24). An (*) indicates positions which have a single, fully conserved residue; (:) indicates conservation between groups of strongly similar properties; and (.) indicates conservation between groups of weakly similar properties. A STT3 consensus sequence based on the alignment of *Leishmania* STT3 sequences is presented as SEQ ID NO: 25. Residues that are not fully conserved between the five *Leishmania* sequences are depicted as X, where X can be any amino acid residue. Alternatively, X is selected from an amino acid residue at the corresponding position in one of the five depicted *Leishmania* sequences.

FIGS. 9A-9J contain a listing of eukaryotic STT3 oligosaccharyltransferases that are suitable for use in the methods, systems, and kits of the present invention. The oligosaccharyltransferases are identified by UniProtKB Entry number (col. 1), which provides the amino acid sequence of the protein, UniProtKB Entry name (col. 2), protein name (col. 3), gene name (col. 4), organism (col. 5) and European Molecular Biology Laboratory (EMBL) database accession number (col. 6) which provides the encoding nucleotide sequence of the protein.

DETAILED DESCRIPTION OF THE INVENTION

Figures 1A, 1B:
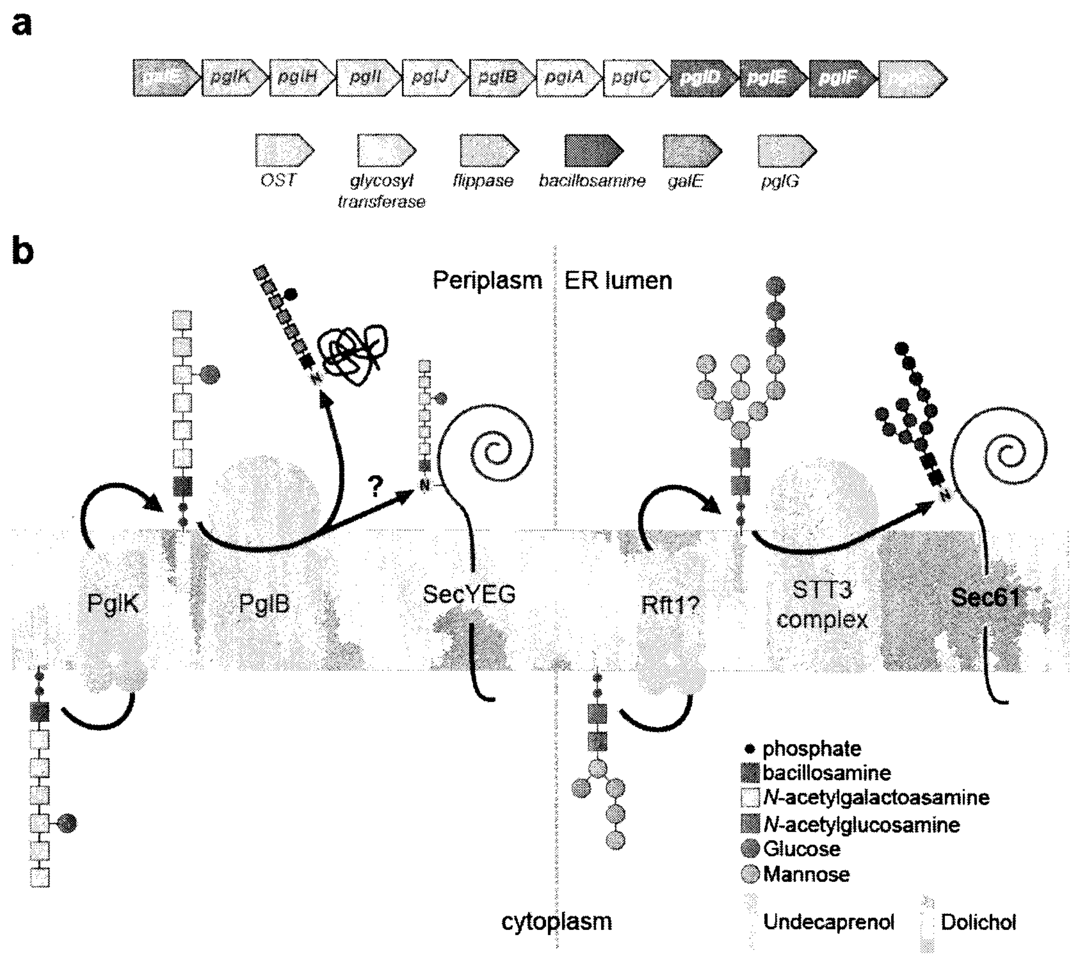
FIGS. 1A-1B depict aspects of bacterial and eukaryotic N-linked glycosylation.

A first aspect of the present invention is directed to a cell-free system for producing a glycosylated protein. This system comprises an isolated oligosaccharyltransferase capable of transferring a glycan from a lipid carrier molecule to a glycoprotein target; one or more isolated glycans, wherein each glycan is linked to a lipid carrier molecule; and a glycoprotein target comprising one or more glycan acceptor amino acid residue, or a nucleic acid molecule encoding said glycoprotein target.

In accordance with this and all aspects of the present invention, "oligosaccharyltransferase" ("OST") refers generally to a glycosylation enzyme or subunit of a glycosylation enzyme complex that is capable of transferring a glycan, i.e., an oligosaccharide or polysaccharide, from a donor substrate to a particular acceptor substrate. The donor substrate is typically a lipid carrier molecule linked to the glycan, and the acceptor substrate is typically a particular amino acid residue of a target glycoprotein. Suitable OSTs include those enzymes that transfer a glycan to an asparagine residue, i.e., an OST involved in N-linked glycosylation, and those enzymes that transfer a glycan or activated sugar moiety to a hydroxyl oxygen molecule of an amino acid residue, i.e., an OST involved in O-linked glycosylation. An isolated OST of the present invention can be a single-subunit enzyme, a multi-subunit enzyme complex, or a single subunit derived from a multi-subunit enzyme complex. While a number of exemplary OST enzymes are described below, one of skill in the art readily appreciates that any oligosaccharyltransferase enzyme known in the art is suitable for use in the present invention.

In accordance with this and all aspects of the present invention, the OST can be a prokaryotic OST. By way of example only, PglB, a single, integral membrane OST protein derived from *Campylobacter jejuni* is suitable for use in the present invention. PglB attaches a heptasaccharide to an asparagine residue of a glycoprotein target (Kowarik et al., "Definition of the Bacterial N-glycosylation Site Consensus Sequence," *Embo J.* 25:1957-66 (2006), which is hereby incorporated by reference in its entirety). The amino acid sequence encoding *C. jejuni* PglB (UniProtKB Accession No. Q9S4V7) is shown below as SEQ ID NO: 2:

```
Ile Ile Ser Asn Asp Gly Tyr Ala Phe Ala Glu Gly Ala Arg Asp Met
1               5                   10                  15

Ile Ala Gly Phe His Gln Pro Asn Asp Leu Ser Tyr Tyr Gly Ser Ser
            20                  25                  30

Leu Ser Thr Leu Thr Tyr Trp Leu Tyr Lys Ile Thr Pro Phe Ser Phe
        35                  40                  45

Glu Ser Ile Ile Leu Tyr Met Ser Thr Phe Leu Ser Ser Leu Val Val
    50                  55                  60

Ile Pro Ile Ile Leu Leu Ala Asn Glu Tyr Lys Arg Pro Leu Met Gly
65                  70                  75                  80

Phe Val Ala Ala Leu Leu Ala Ser Ile Ala Asn Ser Tyr Tyr Asn Arg
                85                  90                  95

Thr Met Ser Gly Tyr Tyr Asp Thr Asp Met Leu Val Ile Val Leu Pro
            100                 105                 110
```

-continued

```
Met Phe Ile Leu Phe Phe Met Val Arg Met Ile Leu Lys Lys Asp Phe
        115                 120                 125

Phe Ser Leu Ile Ala Leu Pro Leu Phe Ile Gly Ile Tyr Leu Trp Trp
    130                 135                 140

Tyr Pro Ser Ser Tyr Thr Leu Asn Val Ala Leu Ile Gly Leu Phe Leu
145                 150                 155                 160

Ile Tyr Thr Leu Ile Phe His Arg Lys Glu Lys Ile Phe Tyr Ile Ala
                165                 170                 175

Val Ile Leu Ser Ser Leu Thr Leu Ser Asn Ile Ala Trp Phe Tyr Gln
            180                 185                 190

Ser Thr Ile Ile Val Ile Leu Phe Ala Leu Phe Ala Leu Glu Gln Lys
        195                 200                 205

Arg Leu Asn Phe Val Ile Ile Gly Ile Leu Ala Ser Val Thr Leu Ile
    210                 215                 220

Phe Leu Ile Leu Ser Gly Gly Val Asp Pro Ile Leu Tyr Gln Leu Lys
225                 230                 235                 240

Phe Tyr Ile Phe Arg Ser Asp Glu Ser Ala Asn Leu Thr Gln Gly Phe
                245                 250                 255

Met Tyr Phe Asn Val Asn Gln Thr Ile Gln Glu Val Glu Asn Val Asp
            260                 265                 270

Leu Ser Glu Phe Met Arg Arg Ile Ser Gly Ser Glu Ile Val Phe Leu
        275                 280                 285

Phe Ser Leu Phe Gly Phe Val Trp Leu Leu Arg Lys His Lys Ser Met
    290                 295                 300

Ile Met Ala Leu Pro Ile Leu Val Leu Gly Phe Leu Ala Leu Lys Gly
305                 310                 315                 320

Gly Leu Arg Phe Thr Ile Tyr Ser Val Pro Val Met Ala Leu Gly Phe
                325                 330                 335

Gly Phe Leu Leu Ser Glu Phe Lys Ala Ile Leu Val Lys Lys Tyr Ser
            340                 345                 350

Gln Leu Thr Ser Asn Val Cys Ile Val Phe Ala Thr Ile Leu Thr Leu
        355                 360                 365

Ala Pro Val Phe Ile His Ile Tyr Asn Tyr Lys Ala Pro Thr Val Phe
    370                 375                 380

Ser Gln Asn Glu Ala Ser Leu Leu Asn Gln Leu Lys Asn Ile Ala Asn
385                 390                 395                 400

Arg Glu Asp Tyr Val Val Thr Trp Trp Asp Tyr Gly Tyr Pro Val Arg
                405                 410                 415

Tyr Tyr Ser Asp Val Lys Thr Leu Val Asp Gly Gly Lys His Leu Gly
            420                 425                 430

Lys Asp Asn Phe Phe Pro Ser Phe Ala Leu Ser Lys Asp Glu Gln Ala
        435                 440                 445

Ala Ala Asn Met Ala Arg Leu Ser Val Glu Tyr Thr Glu Lys Ser Phe
    450                 455                 460

Tyr Ala Pro Gln Asn Asp Ile Leu Lys Thr Asp Ile Leu Gln Ala Met
465                 470                 475                 480

Met Lys Asp Tyr Asn Gln Ser Asn Val Asp Leu Phe Leu Ala Ser Leu
                485                 490                 495

Ser Lys Pro Asp Phe Lys Ile Asp Thr Pro Lys Thr Arg Asp Ile Tyr
            500                 505                 510

Leu Tyr Met Pro Ala Arg Met Ser Leu Ile Phe Ser Thr Val Ala Ser
        515                 520                 525

Phe Ser Phe Ile Asn Leu Asp Thr Gly Val Leu Asp Lys Pro Phe Thr
    530                 535                 540
```

-continued

```
Phe Ser Thr Ala Tyr Pro Leu Asp Val Lys Asn Gly Glu Ile Tyr Leu
545                 550                 555                 560

Ser Asn Gly Val Val Leu Ser Asp Asp Phe Arg Ser Phe Lys Ile Gly
                565                 570                 575

Asp Asn Val Val Ser Val Asn Ser Ile Val Glu Ile Asn Ser Ile Lys
            580                 585                 590

Gln Gly Glu Tyr Lys Ile Thr Pro Ile Asp Asp Lys Ala Gln Phe Tyr
        595                 600                 605

Ile Phe Tyr Leu Lys Asp Ser Ala Ile Pro Tyr Ala Gln Phe Ile Leu
    610                 615                 620

Met Asp Lys Thr Met Phe Asn Ser Ala Tyr Val Gln Met Phe Phe Leu
625                 630                 635                 640

Gly Asn Tyr Asp Lys Asn Leu Phe Asp Leu Val Ile Asn Ser Arg Asp
                645                 650                 655

Ala Lys Val Phe Lys Leu Lys Ile
            660
```

The nucleic acid sequence encoding the amino acid sequence of SEQ ID NO: 2 is provided below as SEQ ID NO: 3 (EMBL Nucleotide Sequence Database No. AAD51383):

```
atcatttcaa acgatggtta tgcttttgct gagggtgcaa gagatatgat agcaggtttt   60

catcagccta atgatttgag ttattatgga tcttctttat ctacgcttac ttattggctt  120

tataaaatca cacctttttc tttcgaaagt attattttat atatgagtac ttttttatct  180

tctttggtgg tgattcctat tattttacta gctaatgaat acaaacgtcc tttaatgggc  240

tttgtagctg ctcttttagc aagtatagca aacagttatt ataatcgcac tatgagtggg  300

tattatgata cggatatgct ggtaattgtt ttacctatgt ttattttatt ttttatggta  360

agaatgattt taaaaaaaga cttttttca ttgattgcct taccgttatt tataggaatt  420

tatctttggt ggtatccttc aagctatact ttaaatgtag ctttaattgg actttttta  480

atttatacac ttatttttca tagaaaagaa aagatttttt atatagctgt gattttgtct  540

tctcttactc tttcaaatat agcatggttt tatcaaagta ctattatagt aatacttttt  600

gctttatttg ctttagagca aaaacgctta aattttgtaa ttataggaat tttagctagt  660

gtaactttga tatttttgat tttaagtgga ggggttgatc ctatacttta tcagcttaaa  720

ttttatattt ttagaagtga tgaaagtgcg aatttaacgc agggttttat gtattttaat  780

gtcaatcaaa ccatacaaga agttgaaaat gtagatctta gcgaatttat gcgaagaatt  840

agtggtagtg aaattgtttt tttgttttct ttgtttggtt ttgtatggct tttgagaaaa  900

cataaaagta tgattatggc tttacctata ttggtgcttg ggtttttagc cttaaaaggg  960

gggcttagat ttaccattta ttctgtacct gtaatggcct taggatttgg tttttattg 1020

agcgagttta aggctatatt ggttaaaaaa tatagccaat taacttcaaa tgtttgtatt 1080

gtttttgcaa ctattttgac tttagctcca gtatttatcc atatttacaa ctataaagca 1140

ccaacagttt tttctcaaaa tgaagcatca ttattaaatc aattaaaaaa tatagccaat 1200

agagaagatt atgtggtaac ttggtgggat tatggttatc ctgtgcgtta ttatagtgat 1260

gtgaaaactt tagtagatgg tggaaagcat ttaggtaagg ataatttttt cccttcttt 1320

gctttaagca aagatgaaca agctgcagct aatatggcaa gacttagtgt agaatataca 1380

gaaaaaagct tttatgctcc gcaaaatgat attttaaaaa cagacatttt acaagccatg 1440

atgaaagatt ataatcaaag caatgtggat ttgtttctag cttcattatc aaaacctgat 1500
```

-continued

```
tttaaaatcg atacaccaaa aactcgtgat atttatcttt atatgcccgc tagaatgtct 1560
ttgatttttt ctacggtggc tagtttttct tttattaatt tagatacagg agttttggat 1620
aaacctttta cctttagcac agcttatcca cttgatgtta aaaatggaga aatttatctt 1680
agcaacggag tggttttaag cgatgatttt agaagtttta aaataggtga taatgtggtt 1740
tctgtaaata gtatcgtaga gattaattct attaaacaag gtgaatacaa aatcactcca 1800
attgatgata aggctcagtt ttatattttt tatttaaagg atagtgctat tccttacgca 1860
caatttattt taatggataa aaccatgttt aatagtgctt atgtgcaaat gttttttta 1920
ggaaattatg ataagaattt atttgacttg gtgattaatt ctagagatgc taaggttttt 1980
aaacttaaaa tttaa                                                   1995
```

The amino acid and nucleotide sequences of SEQ ID NOs: 2 and 3, respectively, are representative *C. jejuni* PglB protein and nucleic acid sequences. It is appreciated by one of skill in the art that there are at least 70 subspecies of *C. jejuni* having a PglB protein that may vary in sequence identity from the amino acid sequence of SEQ ID NO: 2, but retain the same function. Accordingly, homologous PglB protein sequences from other subspecies and strains of *C. jejuni* that are characterized by an amino acid sequence identity of at least about 70 percent, more preferably at least about 75 percent or 80 percent, most preferably at least about 85 percent or 90 percent or 95 percent as compared to the *C. jejuni* amino acid sequence of SEQ ID NO: 2 are also suitable for use in the present invention. The amino acid sequences of related *C. jejuni* PglB proteins and nucleotide sequences encoding the same are known and readily available to one of skill in the art.

OSTs from other species of *Campylobacter* that share sequence identity to *C. jejuni* PglB and/or are capable of transferring an oligosaccharide moiety to a target glycoprotein are also suitable for use in this and all aspects of the present invention. For example, as demonstrated herein, PglB from *Campylobacter lari* (ClPglB), which shares only 56% sequence identity to the amino acid sequence of *C. jejuni* (Schwarz et al., "Relaxed Acceptor Site Specificity of Bacterial Oligosaccharyltransferase in Vivo," *Glycobiology* 21:45-54 (2011), which is hereby incorporated by reference in its entirety), is capable of transferring a glycan to an acceptor amino acid residue (i.e., asparagine) of a target glycoprotein in the cell-free glycosylation system of the present invention. The amino acid sequence encoding *C. lari* PglB (UniProtKB Accession No. B9 KDD4) is shown below as SEQ ID NO: 4:

```
Met Lys Leu Gln Gln Asn Phe Thr Asp Asn Asn Ser Ile Lys Tyr Thr
1               5                   10                  15

Cys Ile Leu Ile Leu Ile Ala Phe Ala Phe Ser Val Leu Cys Arg Leu
            20                  25                  30

Tyr Trp Val Ala Trp Ala Ser Glu Phe Tyr Glu Phe Phe Phe Asn Asp
        35                  40                  45

Gln Leu Met Ile Thr Thr Asn Asp Gly Tyr Ala Phe Ala Glu Gly Ala
    50                  55                  60

Arg Asp Met Ile Ala Gly Phe His Gln Pro Asn Asp Leu Ser Tyr Phe
65                  70                  75                  80

Gly Ser Ser Leu Ser Thr Leu Thr Tyr Trp Leu Tyr Ser Ile Leu Pro
                85                  90                  95

Phe Ser Phe Glu Ser Ile Ile Leu Tyr Met Ser Ala Phe Phe Ala Ser
            100                 105                 110

Leu Ile Val Val Pro Ile Ile Leu Ile Ala Arg Glu Tyr Lys Leu Thr
        115                 120                 125

Thr Tyr Gly Phe Ile Ala Ala Leu Leu Gly Ser Ile Ala Asn Ser Tyr
    130                 135                 140

Tyr Asn Arg Thr Met Ser Gly Tyr Tyr Asp Thr Asp Met Leu Val Leu
145                 150                 155                 160

Val Leu Pro Met Leu Ile Leu Leu Thr Phe Ile Arg Leu Thr Ile Asn
                165                 170                 175

Lys Asp Ile Phe Thr Leu Leu Leu Ser Pro Val Phe Ile Met Ile Tyr
            180                 185                 190

Leu Trp Trp Tyr Pro Ser Ser Tyr Ser Leu Asn Phe Ala Met Ile Gly
        195                 200                 205
```

-continued

Leu Phe Gly Leu Tyr Thr Leu Val Phe His Arg Lys Glu Lys Ile Phe
    210                 215                 220

Tyr Leu Thr Ile Ala Leu Met Ile Ile Ala Leu Ser Met Leu Ala Trp
225                 230                 235                 240

Gln Tyr Lys Leu Ala Leu Ile Val Leu Leu Phe Ala Ile Phe Ala Phe
                245                 250                 255

Lys Glu Glu Lys Ile Asn Phe Tyr Met Ile Trp Ala Leu Ile Phe Ile
            260                 265                 270

Ser Ile Leu Ile Leu His Leu Ser Gly Gly Leu Asp Pro Val Leu Tyr
        275                 280                 285

Gln Leu Lys Phe Tyr Val Phe Lys Ala Ser Asp Val Gln Asn Leu Lys
    290                 295                 300

Asp Ala Ala Phe Met Tyr Phe Asn Val Asn Glu Thr Ile Met Glu Val
305                 310                 315                 320

Asn Thr Ile Asp Pro Glu Val Phe Met Gln Arg Ile Ser Ser Ser Val
                325                 330                 335

Leu Val Phe Ile Leu Ser Phe Ile Gly Phe Ile Leu Leu Cys Lys Asp
            340                 345                 350

His Lys Ser Met Leu Leu Ala Leu Pro Met Leu Ala Leu Gly Phe Met
        355                 360                 365

Ala Leu Arg Ala Gly Leu Arg Phe Thr Ile Tyr Ala Val Pro Val Met
    370                 375                 380

Ala Leu Gly Phe Gly Tyr Phe Leu Tyr Ala Phe Phe Asn Phe Leu Glu
385                 390                 395                 400

Lys Lys Gln Ile Lys Leu Ser Leu Arg Asn Lys Asn Ile Leu Leu Ile
                405                 410                 415

Leu Ile Ala Phe Phe Ser Ile Ser Pro Ala Leu Met His Ile Tyr Tyr
            420                 425                 430

Tyr Lys Ser Ser Thr Val Phe Thr Ser Tyr Glu Ala Ser Ile Leu Asn
        435                 440                 445

Asp Leu Lys Asn Lys Ala Gln Arg Glu Asp Tyr Val Val Ala Trp Trp
    450                 455                 460

Asp Tyr Gly Tyr Pro Ile Arg Tyr Tyr Ser Asp Val Lys Thr Leu Ile
465                 470                 475                 480

Asp Gly Gly Lys His Leu Gly Lys Asp Asn Phe Phe Ser Ser Phe Val
                485                 490                 495

Leu Ser Lys Glu Gln Ile Pro Ala Ala Asn Met Ala Arg Leu Ser Val
            500                 505                 510

Glu Tyr Thr Glu Lys Ser Phe Lys Glu Asn Tyr Pro Asp Val Leu Lys
        515                 520                 525

Ala Met Val Lys Asp Tyr Asn Lys Thr Ser Ala Lys Asp Phe Leu Glu
    530                 535                 540

Ser Leu Asn Asp Lys Asp Phe Lys Phe Asp Thr Asn Lys Thr Arg Asp
545                 550                 555                 560

Val Tyr Ile Tyr Met Pro Tyr Arg Met Leu Arg Ile Met Pro Val Val
                565                 570                 575

Ala Gln Phe Ala Asn Thr Asn Pro Asp Asn Gly Glu Gln Glu Lys Ser
            580                 585                 590

Leu Phe Phe Ser Gln Ala Asn Ala Ile Ala Gln Asp Lys Thr Thr Gly
        595                 600                 605

Ser Val Met Leu Asp Asn Gly Val Glu Ile Ile Asn Asp Phe Arg Ala
    610                 615                 620

Leu Lys Val Glu Gly Ala Ser Ile Pro Leu Lys Ala Phe Val Asp Ile
625                 630                 635                 640

-continued

```
Glu Ser Ile Thr Asn Gly Lys Phe Tyr Tyr Asn Glu Ile Asp Ser Lys
                645                 650                 655

Ala Gln Ile Tyr Leu Leu Phe Leu Arg Glu Tyr Lys Ser Phe Val Ile
            660                 665                 670

Leu Asp Glu Ser Leu Tyr Asn Ser Ser Tyr Ile Gln Met Phe Leu Leu
        675                 680                 685

Asn Gln Tyr Asp Gln Asp Leu Phe Glu Gln Ile Thr Asn Asp Thr Arg
    690                 695                 700

Ala Lys Ile Tyr Arg Leu Lys
705                 710
```

Amino acid sequences sharing at least about 70 percent, more preferably at least about 75 percent or 80 percent, most preferably at least about 85 percent or 90 percent or 95 percent as compared to the *C. lari* amino acid sequence of SEQ ID NO: 4 are also suitable for use in the present invention. The nucleic acid sequence encoding the amino acid sequence of SEQ ID NO: 4 is provided below as SEQ ID NO: 5 (EMBL Nucleotide Sequence Database No. ACM64573.1):

```
atgaaactac aacaaaattt cacggataat aattctataa aatatacctg tattttaatc   60
cttatagcct ttgcttttag tgttttgtgt agattatact gggtagcttg ggcaagtgag  120
ttttatgagt ttttctttaa tgatcaactc atgattacta ctaatgatgg ctatgctttt  180
gcagaaggtg caagagatat gatagcaggt tttcatcaac ctaatgactt atcttatttt  240
ggaagctcac tttctacttt gacttattgg ctttatagta ttttgccttt tagctttgaa  300
agtattattt tatatatgag tgcttttttt gcttctttga ttgttgtgcc tattatatta  360
atcgcaagag agtataaact cactacctat ggctttatag cagctttact tggaagcatt  420
gcaaatagtt attataaccg cactatgagt gggtattacg atacagatat gctagtgtta  480
gttttaccaa tgcttatttt gcttaccttt atacgcttaa ctattaataa agacattttc  540
accctacttt taagtccggt ttttatcatg atttatttgt ggtggtatcc atcaagttat  600
tctttaaatt ttgctatgat aggacttttt ggactttata ctttagtatt tcatagaaaa  660
gaaaagattt tttatctaac tattgctttg atgatcatag ctttaagtat gctagcatgg  720
caatataagc ttgctttgat tgtattatta tttgctattt ttgcttttaa agaagaaaaa  780
atcaattttt atatgatttg ggctttgatt tttattagca ttttgatatt gcatttaagt  840
ggcggcttag atcctgtttt ataccaactt aaattttatg tatttaaagc ttctgatgtg  900
caaaatttaa aagatgctgc ctttatgtat tttaatgtca atgaaaccat tatggaagta  960
aatactatcg atcctgaagt atttatgcaa agaattagct ctagtgtttt agtatttatc 1020
ctttctttta taggttttat cttactttgc aaagatcaca aaagcatgct tttggctcta 1080
cctatgcttg cactaggttt tatggcttta agagctggac ttagatttac catttatgca 1140
gttcctgtga tggctttggg ttttgggtat tttttatatg catttttttaa ttttttagaa 1200
aaaaaacaaa tcaaacttag cctaagaaat aaaaatatct tacttatact cattgcattt 1260
tttagtataa gccctgcttt gatgcatatt tattattata aatcctctac tgtttttact 1320
tcttatgaag ctagtatttt aaatgattta aaaaataaag ctcaaagaga agattatgtt 1380
gttgcttggt gggattatgg ttatccaata cgctattata gcgatgtaaa aaccttaatc 1440
gatggtggaa aacacctagg aaaagataat tttttctcat cttttgtctt aagcaaagaa 1500
caaattccag cagccaatat ggcaagactt agcgtagaat acactgaaaa atctttcaaa 1560
gaaaactatc ctgatgtttt aaaagctatg gttaaagatt ataataaaac aagtgctaaa 1620
gatttttttag aaagtttaaa tgataaagat tttaaatttg ataccaataa aactagagat 1680
```

-continued

```
gtatacattt atatgcctta tagaatgttg cgtatcatgc ctgtggtggc acaatttgca 1740

aatacaaatc ctgataatgg agagcaagaa aaaagtttat ttttctccca agctaatgcc 1800

atagctcaag ataaaaccac aggttctgtt atgcttgata atggagtaga aattattaat 1860

gattttagag ccttaaaagt agaaggtgca agcatacctt taaaagcttt tgtggatata 1920

gaatccatta ctaatggcaa attttattac aatgaaattg attcaaaagc tcaaatttat 1980

ttgctctttt taagagaata taaaagcttt gtgattttag atgaaagtct ttataatagt 2040

tcttatatac aaatgttttt gttaaatcaa tacgatcaag atttatttga acaaattact 2100

aatgatacaa gagcaaaaat ttataggcta aaaagatga                        2139
```

Another N-linked OST from *Campylobacter* that is suitable for use in this and all aspects of the present invention is PglB from *C. Coli*. The amino acid sequence encoding PglB from *C. coli* (UniProtKB Accession No. H7WI6), which is 81% identical to that of *C. jejuni*, is provided below as SEQ ID NO: 6

```
Met Leu Lys Lys Glu Tyr Phe Lys Asn Pro Thr Phe Ile Leu Leu Ala
1               5                   10                  15

Phe Ile Ile Leu Ala Tyr Val Phe Ser Val Leu Cys Arg Phe Tyr Trp
            20                  25                  30

Ile Phe Trp Ala Ser Glu Phe Asn Glu Tyr Phe Phe Asn Asn Glu Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Phe Tyr Lys Ile Thr Pro Phe Ser
                85                  90                  95

Leu Glu Ser Ile Phe Ile Tyr Ile Ser Thr Phe Leu Ser Ser Leu Val
            100                 105                 110

Val Ile Pro Leu Ile Leu Ile Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Ala Met Met Ile Val Phe Phe Met Ile Arg Leu Ile Leu Lys Lys Asp
                165                170                      175

Leu Leu Ser Leu Ile Thr Leu Pro Leu Phe Val Gly Ile Tyr Leu Trp
            180                 185                 190

Trp Tyr Pro Ser Ser Tyr Thr Leu Asn Val Ala Leu Leu Gly Leu Phe
        195                 200                 205

Phe Ile Tyr Thr Leu Val Phe His Ile Lys Glu Lys Thr Leu Tyr Met
    210                 215                 220

Ala Ile Ile Leu Ala Ser Ile Thr Leu Ser Asn Ile Ala Trp Phe Tyr
225                 230                 235                 240

Gln Ser Ala Ile Ile Val Ile Leu Phe Ser Leu Phe Val Leu Gln Asn
                245                 250                 255

Lys Arg Phe Ser Phe Ala Leu Leu Gly Ile Leu Gly Leu Ala Thr Leu
            260                265                      270

Val Phe Leu Ile Leu Ser Gly Gly Ile Asp Pro Ile Leu Tyr Gln Leu
        275                 280                 285

Lys Phe Tyr Ile Phe Arg Ser Asp Glu Ser Ala Asn Leu Ala Gln Gly
    290                 295                 300
```

-continued

```
Phe Met Tyr Phe Asn Val Asn Gln Thr Ile Gln Glu Val Glu Ser Ile
305                 310                 315                 320

Asp Leu Ser Ile Phe Met Gln Arg Ile Ser Gly Ser Glu Leu Val Phe
                325                 330                 335

Phe Val Ser Leu Ile Gly Phe Ile Phe Leu Val Arg Lys His Lys Ser
            340                 345                 350

Met Ile Leu Ala Leu Pro Met Leu Ala Leu Gly Phe Leu Ala Leu Lys
        355                 360                 365

Ser Gly Leu Arg Phe Thr Ile Tyr Ala Val Pro Val Leu Ala Leu Gly
    370                 375                 380

Phe Gly Phe Leu Met Ser Leu Leu Gln Glu Arg Lys Gln Lys Asn Asn
385                 390                 395                 400

Asn Thr Tyr Trp Trp Ala Asn Ile Gly Val Phe Ile Phe Thr Phe Leu
                405                 410                 415

Ser Leu Ile Pro Met Phe Tyr His Ile Asn Asn Tyr Lys Ala Pro Thr
            420                 425                 430

Val Phe Ser Gln Asn Glu Ala Thr Lys Leu Asp Glu Leu Lys Lys Ile
        435                 440                 445

Ala Gln Arg Glu Asp Tyr Val Val Thr Trp Trp Asp Tyr Gly Tyr Pro
    450                 455                 460

Ile Arg Tyr Tyr Ser Asp Val Lys Thr Leu Ala Asp Gly Gly Lys His
465                 470                 475                 480

Leu Gly Lys Asp Asn Phe Phe Pro Ser Phe Val Leu Ser Lys Asp Gln
                485                 490                 495

Val Ala Ala Ala Asn Met Ala Arg Leu Ser Val Glu Tyr Thr Glu Lys
            500                 505                 510

Ser Phe Tyr Ala Pro Leu Asn Asp Ile Leu Lys Asn Asp Leu Leu Gln
        515                 520                 525

Ala Met Met Lys Asp Tyr Asn Gln Asn Asn Val Asp Leu Phe Leu Ala
    530                 535                 540

Ser Leu Ser Lys Pro Asp Phe Lys Ile Asn Thr Pro Lys Thr Arg Asp
545                 550                 555                 560

Val Tyr Ile Tyr Met Pro Ala Arg Met Ser Leu Ile Phe Ser Thr Val
                565                 570                 575

Ala Ser Phe Ser Phe Val Asp Leu Glu Thr Gly Glu Ile Asn Lys Pro
            580                 585                 590

Phe Thr Phe Ser Ala Ala Tyr Pro Leu Asp Val Lys Asn Gly Glu Ile
        595                 600                 605

Tyr Leu Ser Asn Gly Ile Ala Leu Ser Asp Asp Phe Arg Ser Phe Lys
    610                 615                 620

Ile Asn Asn Ser Thr Ile Ser Val Asn Ser Ile Ile Glu Ile Asn Ser
625                 630                 635                 640

Ile Lys Gln Gly Glu Tyr Lys Ile Thr Pro Ile Asp Asp Met Ala Gln
                645                 650                 655

Phe Tyr Ile Phe Tyr Leu Lys Asp Ser Thr Ile Pro Tyr Ala Gln Phe
            660                 665                 670

Ile Leu Met Asp Lys Thr Met Phe Asn Ser Ala Tyr Val Gln Met Phe
        675                 680                 685

Phe Leu Gly Asn Tyr Asp Lys Asn Leu Tyr Asp Leu Val Ile Asn Ala
    690                 695                 700

Arg Asp Ala Lys Val Phe Lys Leu Lys Ile
705                 710
```

Amino acid sequences sharing at least about 70 percent, more preferably at least about 75 percent or 80 percent, most preferably at least about 85 percent or 90 percent or 95 percent as compared to the *C. coli* amino acid sequence of SEQ ID NO: 6 are also suitable for use in the present invention. The nucleic acid sequence encoding the amino acid sequence of SEQ ID NO: 6 is provided below as SEQ ID NO: 7 (EMBL Nucleotide Sequence Database No. EIB 14175):

```
atgttaaaaa aagaatactt taaaaaccca acttttattt tattggcttt tataatttta   60
gcgtatgtct ttagtgtttt atgtaggttt tattggattt tttgggcaag tgagtttaat  120
gaatattttt tcaataacga gcttatgatt atctcaaatg atggatatgc ttttgcagag  180
ggtgcaagag atatgatagc gggttttcat caacctaatg atttgagtta ttatggttct  240
tcgctttcaa cgctcacata ttggttttat aaaataactc ctttttcttt agaaagcatt  300
tttatatata tcagtacttt tttatcttct ttggtggtta tacctttgat tttgattgct  360
aatgaataca aacgcccttt aatggggttt gttgcagcat tgctagccag tatagctaat  420
agctattata atcgcacgat gagcggatat tatgatactg atatgcttgt tatagttctt  480
gcaatgatga tagttttctt tatgataagg ctgattttga aaaaagattt attatcttta  540
ataacactgc ctttgtttgt aggaatttat ctttggtggt atccatcaag ctatacttta  600
aatgttgctt tactaggact tttctttatt tataccttgg tttttcatat aaaagaaaaa  660
acgctttata tggctattat cctagcttct atcacacttt caaatatagc ttggttttat  720
caaagcgcca tcattgtcat actttttagt ctttttgttt tgcaaaataa gcgttttagc  780
tttgctttgc ttggaatttt aggtttggca actttggtat ttttgatact aagcggtgga  840
attgatccta tactctatca acttaaattt tatattttta gaagtgatga gagtgcaaat  900
ttggctcaag gttttatgta ttttaatgta aatcaaacca tacaagaggt agaaagtata  960
gatttaagta tttttatgca aaggattagc ggaagcgagc ttgtattttt tgtatcttta 1020
atcggcttta ttttccttgt tagaaaacat aaaagtatga ttttggcttt gccgatgtta 1080
gctttaggat ttttagcact taagagtgga cttcgtttta ctatttatgc agtacctgtt 1140
ttagcacttg gatttggttt tttaatgagt cttttgcaag aaagaaaaca aaaaaacaat 1200
aatacctatt ggtgggccaa tataggcgtt tttatttta ctttttaag tttaattcct 1260
atgttctatc atatcaacaa ttataaagca ccaactgttt tttctcaaaa tgaggctacg 1320
aaattagatg agcttaaaaa aattgcacaa agagaagatt atgtagtaac ttggtgggat 1380
tatggatatc ctattaggta ttacagcgat gttaaaactt tggctgatgg gggtaagcat 1440
ttaggcaagg ataatttttt cccatctttt gttctaagta aagatcaagt ggctgctgca 1500
aatatggcaa gacttagtgt agaatacaca gaaaaaagtt tttacgcccc tttaaatgat 1560
attttaaaaa atgatctttt acaagccatg atgaaagatt ataatcaaaa taatgtggat 1620
ttgtttttag cttcgctttc caagcctgat tttaaaatca atacgccaaa aacacgcgat 1680
gtgtatatct atatgccagc tagaatgtct ttgatttttt caactgtggc tagtttttct 1740
tttgtggatt tggagacagg tgagataaat aaacctttta cttttagtgc agcttatcca 1800
cttgatgtta aaaatggaga aatttatctt agcaatggta ttgcattaag tgatgatttt 1860
agaagtttta aaataaataa tagtactata tccgtaaata gtatcataga gattaattct 1920
atcaaacaag gtgaatataa aatcactcct attgatgata tggctcaatt ttatattttt 1980
tatcttaaag atagcaccat accttatgct cagtttattt taatggataa aactatgttt 2040
aatagtgctt atgtgcaaat gtttttcctt ggaaattatg ataaaaattt gtatgattta 2100
gtgattaatg ctagagatgc aaaagttttt aaactcaaaa tttaa                2145
```

Another *Campylobacter* OST that is suitable for use in this and all aspects of the present invention is PglB from *C. upsaliensis*. The amino acid sequence encoding PglB from *C. upsaliensis* (UniProtKB Accession No. E6LAJ2), which is 57% identical to that of *C. jejuni*, is provided below as SEQ ID NO: 8:

```
Met Lys Asn Glu Ala Val Lys Asn Ala Asn Leu Arg Leu Val Phe Phe
1               5                   10                  15

Ile Leu Leu Ala Phe Gly Phe Ser Val Leu Cys Arg Phe Tyr Trp Ile
            20                  25                  30

Tyr Trp Ala Ser Asp Phe Asn Glu Tyr Phe Phe Asn Asn Gln Leu Met
        35                  40                  45

Ile Ser Ser Asn Asp Gly Tyr Thr Phe Ala Glu Gly Ala Arg Asp Lys
    50                  55                  60

Ile Ala Gly Phe His Gln Glu Asn Asp Leu Ser Phe Ile Asn Ser Ser
65                  70                  75                  80

Leu Ser Ile Leu Thr Tyr Val Leu Tyr Lys Ile Thr Pro Phe Ser Phe
                85                  90                  95

Glu Ser Ile Ile Leu Tyr Met Ser Val Phe Phe Ser Ser Leu Ile Val
            100                 105                 110

Val Pro Leu Ile Leu Ile Ala Asn Glu Leu Lys Arg Pro Leu Met Gly
        115                 120                 125

Leu Phe Ala Ala Phe Leu Ala Ser Ile Ala Lys Ser Tyr Tyr Asn Arg
    130                 135                 140

Thr Met Ala Gly Tyr Tyr Asp Thr Asp Met Leu Ala Ile Val Leu Pro
145                 150                 155                 160

Met Phe Ile Leu Tyr Phe Phe Ile Arg Leu Ile Leu Arg Lys Asp Asp
                165                 170                 175

Phe Ser Leu Leu Ala Leu Pro Phe Phe Met Gly Leu Tyr Leu Trp Trp
            180                 185                 190

Tyr Pro Ser Ser Tyr Thr Leu Asn Val Ala Phe Ile Ala Leu Phe Thr
        195                 200                 205

Leu Tyr Val Leu Ile Tyr His Arg Lys Glu Arg Ser Phe Tyr Met Ala
    210                 215                 220

Ala Leu Leu Cys Ala Ile Thr Leu Ser Asn Ile Ala Trp Phe Tyr Gln
225                 230                 235                 240

Ser Ala Ile Ile Val Leu Leu Phe Ala Leu Phe Met Leu Lys Asn Ser
                245                 250                 255

Phe Phe Asn Phe Lys Phe Ile Ala Leu Leu Ala Leu Gly Val Leu Val
            260                 265                 270

Phe Leu Ala Leu Ser Gly Gly Ile Asp Pro Ile Leu Tyr Gln Leu Lys
        275                 280                 285

Phe Tyr Leu Leu Arg Ser Asp Glu Ser Ala Ser Leu Ala Arg Gly Phe
    290                 295                 300

Ala Tyr Phe Asn Val Asn Leu Thr Ile Gln Glu Val Glu Ser Ile Asp
305                 310                 315                 320

Leu Ser Thr Phe Met Gln Arg Ile Ser Gly Ser Glu Leu Val Phe Leu
                325                 330                 335

Leu Ser Leu Phe Gly Phe Leu Trp Leu Leu Lys Lys His Lys Val Met
            340                 345                 350

Leu Leu Thr Leu Pro Met Leu Leu Leu Gly Phe Leu Ala Leu Arg Gly
        355                 360                 365

Gly Leu Arg Phe Thr Ile Tyr Ala Val Pro Ile Met Ala Leu Gly Phe
    370                 375                 380

Gly Phe Leu Ser Val Gln Ile Leu Ser Leu Ile Gln Lys Met Arg Pro
385                 390                 395                 400
```

-continued

```
Leu Lys Glu Thr Arg Lys Leu Arg Ile Phe Phe Tyr Gly Ile Phe Pro
            405                 410                 415

Leu Phe Val Leu Val Leu Gly Ala Tyr Phe Tyr Phe Ser Gln Ser Ala
            420                 425                 430

Ile Tyr Glu Ser Met Gly Val Glu Phe Gln Lys Asn Phe Val Ser Phe
        435                 440                 445

Phe Val Glu Asp Thr Leu Leu Phe Ser Leu Leu Ile Leu Ala Ile Phe
    450                 455                 460

Thr Pro Leu Ile Phe Glu Leu Leu Trp Arg Lys Lys Asp Ile Arg Phe
465                 470                 475                 480

Val Cys Ser Phe Tyr Ile Val Gly Val Leu Leu Phe Ser Leu Trp Ala
                485                 490                 495

Asn Leu Ser His Ile Tyr Asn Tyr Arg Ala His Thr Val Phe Ser Tyr
            500                 505                 510

Asn Glu Ala Ser Ile Leu Asp Asn Leu Lys Ala Asn Val Ser Arg Glu
        515                 520                 525

Asp Tyr Ile Val Ala Trp Trp Asp Tyr Gly Tyr Pro Ile Arg Tyr Tyr
    530                 535                 540

Ser Asp Val Lys Thr Leu Ala Asp Gly Gly Lys His Leu Gly Lys Asp
545                 550                 555                 560

Asn Phe Phe Pro Ser Phe Val Leu Ser Gln Asn Pro Arg Ala Ala Ala
                565                 570                 575

Asn Met Ala Arg Leu Ser Val Glu Tyr Thr Glu Lys Gly Phe Lys Thr
            580                 585                 590

Pro Tyr Asn Asp Leu Leu Glu Ala Met Met Lys Asp Tyr Asn Tyr Ser
        595                 600                 605

Asn Val Asn Leu Phe Leu Ala Ala Leu Ser Lys Glu Asp Phe Thr Leu
    610                 615                 620

Gln Thr Pro Lys Thr Arg Asp Ile Tyr Ile Tyr Met Pro Ser Arg Met
625                 630                 635                 640

Ala Ala Ile Phe Gly Thr Val Ala Ser Phe Ser Tyr Met Ser Leu Glu
                645                 650                 655

Thr Gly Glu Leu Glu Asn Pro Phe Val Tyr Ser Val Ala Tyr Tyr Leu
            660                 665                 670

Gly Asn Glu Asp Gly Lys Leu Val Leu Ser Asn Asn Met Leu Leu His
        675                 680                 685

Ser Asp Phe Arg Ser Phe Asp Leu Asn Gly Lys Asn Tyr Ala Ile Asn
    690                 695                 700

Ser Leu Val Glu Phe Thr Ser Val Gln Gln Lys Tyr Tyr Ser Val Val
705                 710                 715                 720

Glu Ile Asp Lys Asn Ala Lys Tyr Tyr Leu Phe His Ile Lys Asp Ala
                725                 730                 735

Asn Ile Pro Asn Val Gln Phe Ile Leu Met Asp Lys Ala Met Tyr Glu
            740                 745                 750

Ser Ala Phe Val Gln Met Phe Phe Phe Gly Lys Tyr Asp Glu Ser Leu
        755                 760                 765

Tyr Glu Leu Ile Val Asp Ser Lys Glu Ala Lys Val Tyr Lys Leu Lys
    770                 775                 780

Leu
785
```

Amino acid sequences sharing at least about 70 percent, more preferably at least about 75 percent or 80 percent, most preferably at least about 85 percent or 90 percent or 95 percent as compared to the *C. upsaliensis* amino acid sequence of SEQ ID NO: 8 are also suitable for use in the present invention. The nucleic acid sequence encoding the amino acid sequence of SEQ ID NO: 8 is provided below as SEQ ID NO: 9 (EMBL Nucleotide Sequence Database No. EFU71695):

```
atgaaaaacg aggctgtgaa aaatgcgaat ttgaggctag tattttttat cttactagct   60
tttggtttta gtgttttatg tcgcttttat tggatttatt gggcgagtga ttttaacgaa  120
tattttttta ataatcagct tatgataagc tcaaatgacg gctacacttt tgcagagggt  180
gctagagata agatagcggg ctttcatcag gaaaatgatt taagctttat taattcctct  240
ctttctattt tgacttatgt gctttataaa atcacgcctt ttagttttga aagcattatt  300
ttatatatga gtgtattttt ttcttcactt atagttgtgc cgcttatttt aattgcaaat  360
gagcttaaac gccctttaat gggacttttt gcggcatttt tagcaagtat tgcaaaaagc  420
tattataacc gcactatggc aggatattat gatacagata tgttagccat tgtgcttcct  480
atgtttattt tatatttttt catcaggctt attttaagaa aagatgattt ttctttactt  540
gccttgccgt tttttatggg actttatctt tggtggtatc catcaagcta tactctaaat  600
gtcgctttta tcgcactttt taccctttat gttttgattt atcatagaaa agaaagatct  660
ttttatatgg cagcactttt gtgtgccatt accctttcaa atattgcttg gttttatcaa  720
agtgctatta ttgttttact ttttgctctt tttatgctta aaaattcgtt ttttaatttt  780
aaatttatcg cacttttagc cttaggagtt ttagtttttt tggctttaag tgggggggata  840
gaccccatac tttatcagct taaattttat cttttaagaa gtgatgaaag tgcaagttta  900
gcgcgtggtt ttgcgtattt taatgtaaat ttaaccatac aagaggttga aagtatcgat  960
ttaagcactt ttatgcaaag aattagcgga agtgagcttg tgtttttact ttctcttttt 1020
ggctttttat ggcttttaaa aaagcataag gtgatgcttt taaccctacc tatgcttttg 1080
ctcggttttt tagcacttag aggtgggctt agatttacta tttatgctgt gcctattatg 1140
gcgcttggct ttggcttttt aagcgttcaa attttaagct taatccaaaa aatgcgtccc 1200
ttaaaagaaa ctcgaaaatt aagaatattt ttttatggaa tctttccgct ttttgtgctt 1260
gttttggggg cttattttta ttttagtcaa agtgctattt atgagagtat gggagtggaa 1320
tttcaaaaga actttgtgag ctttttgta gaagatactt tgcttttttc tttgctgatt 1380
ttggctattt ttacgccttt aatttttgag cttttgtgga gaaaaaagga cattcgtttt 1440
gtgtgtagct tttatattgt gggggtttg ctttttcttt tatgggcaaa tttaagtcat 1500
atttataatt atagagcaca caccgttttt agctacaatg aagcgagtat tttggataat 1560
cttaaagcta atgtttctag ggaagattat attgtggctt ggtgggatta tggctatcct 1620
attcgttatt atagcgatgt gaaaacctta gctgatgggg gtaagcattt gggtaaggat 1680
aatttttttcc cttcttttgt tttaagtcaa aatccacgcg cagcggcaaa tatggcaaga 1740
cttagcgtag aatacacaga aaaaggcttt aaaacgcctt ataatgatct tttagaagcg 1800
atgatgaagg attataatta tagcaatgta aatttatttt tagcggcact ttctaaggag 1860
gattttactc ttcaaacgcc caaaactaga gatatttaca tctatatgcc ttctcgtatg 1920
gcggcgattt ttggcacggt ggcaagtttt tcttatatga gcttagaaac gggtgagctt 1980
gaaaatcctt ttgtttatag tgtggcgtat tatttgggaa atgaggacgg caaactcgtc 2040
ttaagtaata atatgctcct tcatagcgac tttagaagct ttgaccttaa tggcaagaat 2100
tatgctatta attctttggt tgaatttact tcggtgcagc aaaaatatta tagtgttgtg 2160
gagattgata aaaatgctaa atattatctc tttcacatca aagacgctaa tatccctaat 2220
```

-continued

```
gtgcaattta tcctaatgga taaggcgatg tatgagagtg ctttcgtgca aatgtttttc 2280

tttggtaagt atgatgagag tttgtatgaa ttaattgtag atagtaaaga agcaaaggtg 2340

tataaattaa aattatga                                               2358
```

An alignment of the *Campylobacter* PglB sequences is provided in FIGS. 6A-6C, and a PglB consensus sequence based on this alignment is presented as SEQ ID NO: 10 of FIG. 6. Residues that are not fully conserved between the four *Campylobacter* sequences are depicted as X, where X can be any amino acid residue. Alternatively, X is selected from one of the four depicted amino acid residue at the corresponding position in the depicted *Camplyobacter* sequences.

In another embodiment of the present invention, the OST is an archaea oligosaccharyltransferase. For example, the OST STT3 subunit from *Pyrococcus furiosus* which is capable of transferring a glycan to an asparagine residue of a target glycoprotein is suitable for use in this and all aspects of the present invention. The amino acid sequence of *P. furiosus* (UniProtKB Accession No. Q8U4D2) is provided below as SEQ ID NO: 11:

```
Met Val Lys Thr Gln Ile Lys Glu Lys Lys Lys Asp Glu Lys Val Thr
1               5                   10                  15

Ile Pro Leu Pro Gly Lys Ile Lys Thr Val Leu Ala Phe Leu Val Val
            20                  25                  30

Leu Ala Phe Ala Ala Tyr Gly Phe Tyr Ile Arg His Leu Thr Ala Gly
        35                  40                  45

Lys Tyr Phe Ser Asp Pro Asp Thr Phe Tyr His Phe Glu Ile Tyr Lys
    50                  55                  60

Leu Val Leu Lys Glu Gly Leu Pro Arg Tyr Tyr Pro Met Ala Asp Ala
65                  70                  75                  80

Pro Phe Gly Ser Leu Ile Gly Glu Pro Leu Gly Leu Tyr Ile Leu Pro
                85                  90                  95

Ala Ile Phe Tyr Lys Ile Ile Ser Ile Phe Gly Tyr Asn Glu Leu Glu
            100                 105                 110

Ala Phe Leu Leu Trp Pro Pro Phe Val Gly Phe Leu Ser Val Ile Gly
        115                 120                 125

Val Tyr Leu Leu Gly Arg Lys Val Leu Asn Glu Trp Ala Gly Met Trp
    130                 135                 140

Gly Ala Ile Ile Leu Ser Val Leu Thr Ala Asn Phe Ser Arg Thr Phe
145                 150                 155                 160

Ser Gly Asn Ala Arg Gly Asp Gly Pro Phe Met Met Leu Phe Thr Phe
                165                 170                 175

Ser Ala Val Leu Met Leu Tyr Tyr Leu Thr Glu Glu Asn Lys Asn Lys
            180                 185                 190

Lys Ile Ile Trp Gly Thr Leu Phe Val Leu Leu Ala Gly Ile Ser Thr
        195                 200                 205

Ala Ala Trp Asn Gly Ser Pro Phe Gly Leu Met Val Leu Leu Gly Phe
    210                 215                 220

Ala Ser Phe Gln Thr Ile Ile Leu Phe Ile Phe Gly Lys Ile Asn Glu
225                 230                 235                 240

Leu Arg Glu Phe Ile Lys Glu Tyr Tyr Pro Ala Tyr Leu Gly Ile Leu
                245                 250                 255

Ala Ile Ser Tyr Leu Leu Thr Ile Pro Gly Ile Gly Lys Ile Gly Gly
            260                 265                 270

Phe Val Arg Phe Ala Phe Glu Val Phe Leu Gly Leu Val Phe Leu Ala
        275                 280                 285

Ile Val Met Leu Tyr Gly Gly Lys Tyr Leu Asn Tyr Ser Asp Lys Lys
    290                 295                 300

His Arg Phe Ala Val Val Ala Val Ile Val Ile Ala Gly Phe Ala Gly
305                 310                 315                 320
```

-continued

```
Ala Tyr Ile Tyr Val Gly Pro Lys Leu Phe Thr Leu Met Gly Gly Ala
                325                 330                 335

Tyr Gln Ser Thr Gln Val Tyr Glu Thr Val Gln Glu Leu Ala Lys Thr
            340                 345                 350

Asp Trp Gly Asp Val Lys Val Tyr Tyr Gly Val Glu Lys Pro Asn Gly
        355                 360                 365

Ile Val Phe Phe Leu Gly Leu Val Gly Ala Met Ile Val Thr Ala Arg
    370                 375                 380

Tyr Leu Tyr Lys Leu Phe Lys Asp Gly Arg Arg Pro His Glu Glu Leu
385                 390                 395                 400

Phe Ala Ile Thr Phe Tyr Val Met Ser Ile Tyr Leu Leu Trp Thr Ala
                405                 410                 415

Ala Arg Phe Leu Phe Leu Ala Ser Tyr Ala Ile Ala Leu Met Ser Gly
            420                 425                 430

Val Phe Ala Gly Tyr Val Leu Glu Thr Val Glu Lys Met Lys Glu Ser
        435                 440                 445

Ile Pro Ile Lys Ala Ala Leu Gly Gly Val Ile Ala Ile Met Leu Leu
    450                 455                 460

Leu Ile Pro Leu Thr His Gly Pro Leu Leu Ala Gln Ser Ala Lys Ser
465                 470                 475                 480

Met Arg Thr Thr Glu Ile Glu Thr Ser Gly Trp Glu Asp Ala Leu Lys
                485                 490                 495

Trp Leu Arg Glu Asn Thr Pro Glu Tyr Ser Thr Ala Thr Ser Trp Trp
            500                 505                 510

Asp Tyr Gly Tyr Trp Ile Glu Ser Ser Leu Leu Gly Gln Arg Arg Ala
        515                 520                 525

Ser Ala Asp Gly Gly His Ala Arg Asp Arg Asp His Ile Leu Ala Leu
    530                 535                 540

Phe Leu Ala Arg Asp Gly Asn Ile Ser Glu Val Asp Phe Glu Ser Trp
545                 550                 555                 560

Glu Leu Asn Tyr Phe Leu Val Tyr Leu Asn Asp Trp Ala Lys Phe Asn
                565                 570                 575

Ala Ile Ser Tyr Leu Gly Gly Ala Ile Thr Arg Arg Glu Tyr Asn Gly
            580                 585                 590

Asp Glu Ser Gly Arg Gly Ala Val Thr Thr Leu Leu Pro Leu Pro Arg
        595                 600                 605

Tyr Gly Glu Lys Tyr Val Asn Leu Tyr Ala Lys Val Ile Val Asp Val
    610                 615                 620

Ser Asn Ser Ser Val Lys Val Thr Val Gly Asp Arg Glu Cys Asp Pro
625                 630                 635                 640

Leu Met Val Thr Phe Thr Pro Ser Gly Lys Thr Ile Lys Gly Thr Gly
                645                 650                 655

Thr Cys Ser Asp Gly Asn Ala Phe Pro Tyr Val Leu His Leu Thr Pro
            660                 665                 670

Thr Ile Gly Val Leu Ala Tyr Tyr Lys Val Ala Thr Ala Asn Phe Ile
        675                 680                 685

Lys Leu Ala Phe Gly Val Pro Ala Ser Thr Ile Pro Gly Phe Ser Asp
    690                 695                 700

Lys Leu Phe Ser Asn Phe Glu Pro Val Tyr Glu Ser Gly Asn Val Ile
705                 710                 715                 720

Val Tyr Arg Phe Thr Pro Phe Gly Ile Tyr Lys Ile Glu Glu Asn Ile
                725                 730                 735

Asn Gly Thr Trp Lys Gln Val Tyr Asn Leu Thr Pro Gly Lys His Glu
            740                 745                 750
```

-continued

```
Leu Lys Leu Tyr Ile Ser Ala Phe Gly Arg Asp Ile Glu Asn Ala Thr
        755                 760                 765

Leu Tyr Ile Tyr Ala Ile Asn Asn Glu Lys Ile Ile Glu Lys Ile Lys
    770                 775                 780

Ile Ala Glu Ile Ser His Met Asp Tyr Leu Asn Glu Tyr Pro Ile Ala
785                 790                 795                 800

Val Asn Val Thr Leu Pro Asn Ala Thr Ser Tyr Arg Phe Val Leu Val
                805                 810                 815

Gln Lys Gly Pro Ile Gly Val Leu Leu Asp Ala Pro Lys Val Asn Gly
            820                 825                 830

Glu Ile Arg Ser Pro Thr Asn Ile Leu Arg Glu Gly Glu Ser Gly Glu
        835                 840                 845

Ile Glu Leu Lys Val Gly Val Asp Lys Asp Tyr Thr Ala Asp Leu Tyr
    850                 855                 860

Leu Arg Ala Thr Phe Ile Tyr Leu Val Arg Lys Ser Gly Lys Asp Asn
865                 870                 875                 880

Glu Asp Tyr Asp Ala Ala Phe Glu Pro Gln Met Asp Val Phe Phe Ile
                885                 890                 895

Thr Lys Ile Gly Glu Asn Ile Gln Leu Lys Glu Gly Glu Asn Thr Val
            900                 905                 910

Lys Val Arg Ala Glu Leu Pro Glu Gly Val Ile Ser Ser Tyr Lys Asp
        915                 920                 925

Glu Leu Gln Arg Lys Tyr Gly Asp Lys Leu Ile Ile Arg Gly Ile Arg
    930                 935                 940

Val Glu Pro Val Phe Ile Ala Glu Lys Glu Tyr Leu Met Leu Glu Val
945                 950                 955                 960

Ser Ala Ser Ala Pro His His
                965
```

Amino acid sequences sharing at least about 70 percent, more preferably at least about 75 percent or 80 percent, most preferably at least about 85 percent or 90 percent or 95 percent as compared to the *P. furiosus* amino acid sequence of SEQ ID NO: 11 are also suitable for use in the present invention. The nucleic acid sequence encoding the amino acid sequence of SEQ ID NO: 11 is provided below as SEQ ID NO: 12 (EMBL Nucleotide Sequence Database No. AAL80280):

```
atggtgaaaa cccaaataaa ggagaaaaag aaagatgaaa aagttactat tccacttcct  60
gggaagataa aaactgtttt ggccttccta gtcgttttgg catttgccgc atatggattt 120
tacattagac atttaacagc cggaaagtat ttctcagatc cagatacctt ctaccatttc 180
gaaatttata agctagtcct caaagagggc cttcctaggt attacccaat ggcagatgct 240
ccatttggaa gtctcatagg agaacctctt ggactataca tccttccagc aatattctac 300
aaaataatct caatatttgg gtacaatgag ctagaggcat ttcttctttg gcccccattc 360
gtaggatttc tcagtgttat aggtgtttac ttactcggaa gaaaagttct gaacgaatgg 420
gcagggatgt ggggtgctat aattctctca gtcctcacgg caaacttttc aagaacattc 480
tcaggcaacg caagaggcga cggcccattc atgatgttgt ttacgttttc agcagtccta 540
atgctctatt atctaaccga ggaaaataaa aacaagaaaa taatctgggg aacactgttt 600
gtactcttgg caggaatatc aactgcagca tggaacggtt caccatttgg actaatggtt 660
ctccttggat tcgcatcgtt ccagacaata atcctcttta tttttggaaa gatcaatgag 720
cttagagaat tcataaagga atactaccca gcatacctgg gaattttagc tataagctac 780
cttctaacga tcccaggaat tggaaaaata ggaggatttg taagatttgc atttgaggtt 840
ttcttagggt tagttttctt agccatcgtc atgctctatg gaggaaaata cttgaactat 900
```

```
tctgacaaga agcacaggtt cgcagtggtt gcagttatag ttattgcggg gttcgcagga 960

gcttatattt acgttggtcc aaaactcttc actctaatgg gtggagctta tcagtcaacg 1020

caagtttatg aaacagtaca ggagctcgca aaaactgatt ggggagatgt aaaagtctat 1080

tatggagtag aaaagccaaa cggaatagtc ttcttccttg gattagttgg agcaatgatt 1140

gttacagcta ggtacctcta caaattattt aaagatggaa ggcgcccaca cgaagagtta 1200

tttgcaataa ctttctatgt aatgtcaatt tacctcctct ggacagctgc tagattccta 1260

ttcctagcga gttatgcgat agcattgatg tcaggtgtct ttgcaggata cgtcctagag 1320

actgtagaaa agatgaaaga gagtatacca ataaaagcag cactaggagg agtaattgct 1380

attatgcttc ttctaatacc cttaactcat ggcccactct tagctcaaag cgctaaaagt 1440

atgagaacaa ccgagatcga gactagtgga tgggaagatg cgctcaaatg gctcagagaa 1500

aacactccag aatattcgac cgcaacctct tggtgggact atggatattg gatagagtca 1560

agcctcctag gacagagaag ggccagtgct gatggtggac atgcaagaga tagagatcat 1620

atcttagccc tatttctagc cagagacggt aacattagtg aagtagactt tgagagttgg 1680

gagcttaact acttcctagt ttaccttaat gattgggcaa agttcaatgc aatcagctat 1740

ctaggcgggg ctataacgag gagagaatac aatggagatg aaagtggaag aggagccgta 1800

actacgctac ttcctctccc aaggtatgga gagaaatacg tcaacctcta tgccaaagtt 1860

atagttgatg tttcaaactc gagcgtaaag gttactgtag gagacagaga gtgtgatcca 1920

ctaatggtta cgtttactcc aagtggaaag acgataaaag gaactggaac ctgtagtgat 1980

ggcaacgcct tcccatatgt tttacactta actccaacaa ttggagtact tgcatactac 2040

aaagtagcaa ctgcaaactt cattaagtta gccttcggtg ttccagcttc aacaattcca 2100

ggattctctg ataagctatt ctcaaacttt gagccagtgt atgagtcagg aaacgtaata 2160

gtatatcgct tcacaccatt tggaatatac aaaattgagg aaaacattaa cggaacttgg 2220

aagcaagttt ataacctaac tcctggaaaa cacgagctca aactgtacat ttcagcattc 2280

ggaagagaca tcgaaaatgc aacgctgtac atttacgcca taaacaacga gaagatcata 2340

gagaaaatta agattgccga gatatcccac atggactatc taaatgaata cccgatagca 2400

gtgaacgtaa ccctaccaaa tgctacaagc tacaggtttg tactagttca aaaaggccca 2460

ataggtgttc ttctagatgc accaaaagtc aatggtgaga taagaagtcc aaccaacata 2520

ctaagggaag gagaaagtgg agaaatagag cttaaagttg gggttgataa agactacact 2580

gccgatctat acttaagggc tacgttcata tatttagtca gaaaaagtgg aaaggataac 2640

gaagattatg acgcagcgtt tgagccccaa atggatgttt tctttatcac aaagatcgga 2700

gaaaacattc aacttaaaga aggagagaat acagtaaagg ttagggcgga gcttccagaa 2760

ggagttatat ctagctacaa agatgaacta cagagaaaat acggagacaa gttgataatc 2820

agaggaataa gagtagagcc agtgttcata gcagaaaaag agtacctaat gctcgaggtc 2880

agtgcatcgg ctcctcatca ctaa                                       2904
```

OSTs from other *Pyrococcus* species or strains that share sequence identity to *P. furiosus* OST STT3 subunit related protein and/or are capable of transferring a glycan moiety to a target glycoprotein are also suitable for use in the present invention. For example, homologous OSTs derived from *Pyrococcus* sp. ST04 (SEQ ID NO: 13; UniProtKB No. I3RCF1), *Pyrococcus* sp. (strain NA2) (SEQ ID NO: 14; UniProtKB No. F4HM23), *P. horikoshii* (SEQ ID NO:15; UniProtKB No. O74088), *P. abyssi* (SEQ ID NO: 16; UniProtKB No. Q9V250), and *P. yayanosii* (SEQ ID NO: 17; UniProtKB No. F8AIG3) each share greater than 70% sequence identity with the amino acid sequence of *P. furiosus* OST (see alignment of FIG. 7), and are suitable for use in this and all aspects of the present invention. The nucleotide sequences encoding the aforementioned *Pyrococcus* OSTs are known and readily available in the art. A STT3 consensus sequence based on the alignment of *Pyrococcus* STT3 sequences is presented as SEQ ID NO: 18 in FIG. 7. Residues that are not fully conserved between the six *Pyrococcus* sequences are depicted as X, where X can be any amino acid residue. Alternatively, X is selected from an amino acid residue at the corresponding position in one of the six depicted *Pyrococcus* sequences.

In another embodiment of the present invention, the OST is a eukaryotic oligosaccharyltransferase. For example, the OST STT3 subunit from *Leishmania major*, which is capable of transferring a glycan to an asparagine residue of a target glycoprotein is suitable for use in this and all aspects of the present invention. The amino acid sequence of *L. major* (UniProtKB Accession No. Q9U5N8) is provided below as SEQ ID NO: 19.

```
Met Ala Ala Ala Ser Asn Val Asn Ala Pro Glu Ser Asn Val Met Thr
1               5                   10                  15

Thr Arg Ser Ala Val Ala Pro Pro Ser Thr Ala Ala Pro Lys Glu Ala
            20                  25                  30

Ser Ser Glu Thr Leu Leu Ile Gly Leu Tyr Lys Met Pro Ser Gln Thr
        35                  40                  45

Arg Ser Leu Ile Tyr Ser Ser Cys Phe Ala Val Ala Met Ala Ile Ala
    50                  55                  60

Leu Pro Ile Ala Tyr Asp Met Arg Val Arg Ser Ile Gly Val Tyr Gly
65                  70                  75                  80

Tyr Leu Phe His Ser Ser Asp Pro Trp Phe Asn Tyr Arg Ala Ala Glu
                85                  90                  95

Tyr Met Ser Thr His Gly Trp Ser Ala Phe Phe Ser Trp Phe Asp Tyr
            100                 105                 110

Met Ser Trp Tyr Pro Leu Gly Arg Pro Val Gly Ser Thr Thr Tyr Pro
        115                 120                 125

Gly Leu Gln Leu Thr Ala Val Ala Ile His Arg Ala Leu Ala Ala Ala
    130                 135                 140

Gly Met Pro Met Ser Leu Asn Asn Val Cys Val Leu Met Pro Ala Trp
145                 150                 155                 160

Phe Ser Leu Val Ser Ser Ala Met Ala Ala Leu Leu Ala His Glu Met
                165                 170                 175

Ser Gly Asn Met Ala Val Ala Ser Ile Ser Ser Ile Leu Phe Ser Val
            180                 185                 190

Val Pro Ala His Leu Met Arg Ser Met Ala Gly Glu Phe Asp Asn Glu
        195                 200                 205

Cys Ile Ala Val Ala Ala Met Leu Leu Thr Phe Tyr Cys Trp Val Arg
    210                 215                 220

Ser Leu Arg Thr Arg Ser Ser Trp Pro Ile Gly Val Leu Thr Gly Val
225                 230                 235                 240

Ala Tyr Gly Tyr Met Ala Ala Ala Trp Gly Gly Tyr Ile Phe Val Leu
                245                 250                 255

Asn Met Val Ala Met His Ala Gly Ile Ser Ser Met Val Asp Trp Ala
            260                 265                 270

Arg Asn Thr Tyr Asn Pro Ser Leu Leu Arg Ala Tyr Thr Leu Phe Tyr
        275                 280                 285

Val Val Gly Thr Ala Ile Ala Val Cys Val Pro Pro Val Gly Met Ser
    290                 295                 300

Pro Phe Lys Ser Leu Glu Gln Leu Gly Ala Leu Leu Val Leu Val Phe
305                 310                 315                 320

Ile Phe Gly Gln Ser Val Cys Glu Ala Gln Arg Arg Arg Leu Gly Ile
                325                 330                 335

Ala Arg Leu Ser Lys Glu Gly Val Ala Leu Leu Ile Arg Ile Asp Ala
            340                 345                 350

Ala Phe Phe Val Gly Ile Val Ala Val Ala Thr Ile Ala Pro Ala Gly
        355                 360                 365

Phe Phe Lys Pro Leu Ser Leu Gln Ala Asn Ala Ile Ile Thr Gly Val
    370                 375                 380
```

-continued

```
Ser Arg Thr Gly Asn Thr Leu Val Asp Ile Leu Leu Ala Gln Asp Ala
385                 390                 395                 400

Ser Asn Leu Leu Met Val Trp Gln Leu Phe Leu Phe Pro Phe Leu Gly
                405                 410                 415

Trp Val Ala Gly Met Ser Ala Phe Leu Arg Glu Leu Ile Arg Asn Tyr
            420                 425                 430

Thr Tyr Ala Lys Ser Phe Ile Leu Met Tyr Gly Val Val Gly Met Tyr
        435                 440                 445

Phe Ala Ser Gln Ser Val Arg Met Met Val Met Met Ala Pro Val Ala
    450                 455                 460

Cys Ile Phe Thr Ala Leu Leu Phe Arg Trp Ala Leu Asp Tyr Leu Leu
465                 470                 475                 480

Gly Ser Leu Phe Trp Ala Glu Met Pro Pro Ser Phe Asp Thr Asp Ala
                485                 490                 495

Gln Arg Gly Arg Gln Gln Gln Thr Ala Glu Glu Ser Glu Ala Glu Thr
            500                 505                 510

Lys Arg Lys Glu Glu Glu Tyr Asn Thr Met Gln Val Lys Lys Met Ser
        515                 520                 525

Val Arg Met Leu Pro Phe Met Leu Leu Leu Leu Leu Phe Arg Leu Ser
    530                 535                 540

Gly Phe Ile Glu Asp Val Ala Ala Ile Ser Arg Lys Met Glu Ala Pro
545                 550                 555                 560

Gly Ile Val Phe Pro Ser Glu Gln Val Gln Gly Val Ser Glu Lys Lys
                565                 570                 575

Val Asp Asp Tyr Tyr Ala Gly Tyr Leu Tyr Leu Arg Asp Ser Thr Pro
            580                 585                 590

Glu Asp Ala Arg Val Leu Ala Trp Trp Asp Tyr Gly Tyr Gln Ile Thr
        595                 600                 605

Gly Ile Gly Asn Arg Thr Ser Leu Ala Asp Gly Asn Thr Trp Asn His
    610                 615                 620

Glu His Ile Ala Thr Ile Gly Lys Met Leu Thr Ser Pro Val Ala Glu
625                 630                 635                 640

Ala His Ser Leu Val Arg His Met Ala Asp Tyr Val Leu Ile Ser Ala
                645                 650                 655

Gly Asp Thr Tyr Phe Ser Asp Leu Asn Arg Ser Pro Met Met Ala Arg
            660                 665                 670

Ile Gly Asn Ser Val Tyr His Asp Ile Cys Pro Asp Asp Pro Leu Cys
        675                 680                 685

Ser Gln Phe Val Leu Gln Lys Arg Pro Lys Ala Ala Ala Ala Lys Arg
    690                 695                 700

Ser Arg His Val Ser Val Asp Ala Leu Glu Glu Asp Asp Thr Ala Glu
705                 710                 715                 720

His Met Val Tyr Glu Pro Ser Ser Leu Ile Ala Lys Ser Leu Ile Tyr
                725                 730                 735

His Leu His Ser Thr Gly Val Val Thr Gly Val Thr Leu Asn Glu Thr
            740                 745                 750

Leu Phe Gln His Val Phe Thr Ser Pro Gln Gly Leu Met Arg Ile Phe
        755                 760                 765

Lys Val Met Asn Val Ser Thr Glu Ser Lys Lys Trp Val Ala Asp Ser
    770                 775                 780

Ala Asn Arg Val Cys His Pro Pro Gly Ser Trp Ile Cys Pro Gly Gln
785                 790                 795                 800

Tyr Pro Pro Ala Lys Glu Ile Gln Glu Met Leu Ala His Gln His Thr
                805                 810                 815
```

-continued

```
Asn Phe Lys Asp Leu Leu Asp Pro Arg Thr Thr Trp Ser Gly Ser Arg
            820                 825                 830

Arg
```

Amino acid sequences sharing at least about 70 percent, more preferably at least about 75 percent or 80 percent, most preferably at least about 85 percent or 90 percent or 95 percent as compared to the *L. major* amino acid sequence of SEQ ID NO: 19 are also suitable for use in the present invention. The nucleic acid sequence encoding the amino acid sequence of SEQ ID NO: 19 (*L. major* STT3) is provided below as SEQ ID NO: 20 (EMBL Nucleotide Sequence Database No. CAB61569):

```
atggcggcag cgtcaaacgt gaatgccccc gaaagcaacg tgatgacaac gagaagtgcc   60

gttgcaccac cgtcgacggc tgcacccaaa gaggcttcaa gtgaaacgct gctcattggc  120

ctatacaaga tgccctcgca aactcgtagc ctcatctact cctcctgctt tgcggtggcc  180

atggccattg ccctccctat cgcgtacgac atgcgtgtcc gctccatcgg cgtgtacggg  240

tacctcttcc acagcagtga cccgtggttc aactaccgcg ctgccgagta catgtccacg  300

cacggctggt ccgccttctt cagctggttc gactacatga gctggtaccc gctgggccgc  360

cccgtcggct ccaccacgta cccgggcctg cagctcactg ccgtcgccat tcaccgcgca  420

ctggcggctg ccggcatgcc gatgtctctc aacaacgtgt gcgtgctgat gccagcgtgg  480

ttttcacttg tctcttcagc gatggcggca ctgctggcgc atgagatgag cggcaatatg  540

gcggtagcca gcatctcgtc tatcttattc agtgtggttc cagcccacct gatgcggtcc  600

atggcgggtg agttcgacaa cgagtgtatc gccgtcgcag ccatgctcct caccttctac  660

tgctgggtgc gctcgctgcg cacgcggtcc tcgtggccca tcggtgtcct caccggtgtc  720

gcctacggct acatggcggc ggcgtggggc ggctacattt tcgtgctcaa catggttgcc  780

atgcatgccg gcatatcatc gatggtggac tgggcccgca acacgtacaa cccgtcgctg  840

ctgcgtgcat acacgctgtt ctacgtcgtg ggcaccgcca tcgccgtgtg cgtgccgcca  900

gtggggatgt cgcccttcaa gtcgctggag cagctgggtg cgctgctggt gcttgtcttc  960

attttcggtc agtctgtgtg tgaggcccag cgcagacgat tgggaatcgc gcgcctttca 1020

aaggagggcg tggcgctgct catccgcatc gacgcagcct tcttcgtcgg tatcgttgcc 1080

gtggccacca ttgccccggc tggattcttc aagccgctct ccctgcaagc gaacgcgata 1140

atcactggcg tatctcgtac cggaaacaca ctcgtagaca ttctgcttgc gcaagacgcg 1200

tccaacctac tcatggtgtg gcagcttttt ctctttccct tcttaggttg ggtggcgggc 1260

atgagcgcct tccttagaga gttgatccgg aactacacct acgcgaagag tttcatcctg 1320

atgtacggcg tggtcggtat gtacttcgcc agccagtctg tccgaatgat ggtgatgatg 1380

gcccccgtgg cgtgcatctt tactgccctc ttgttccgct gggcactgga ctacctcctc 1440

gggtctttgt tttgggctga gatgccacct tcctttgaca ccgacgcaca gcgtgggcgg 1500

cagcaacaga ccgccgagga gtcggaggca gagaccaagc gtaaggagga agagtacaac 1560

accatgcagg tcaagaagat gtcggtgcgc atgttgccct tcatgctgtt gctcttactg 1620

tttcgtcttt cggggttcat cgaagatgtg gcggcgatat cgcgcaagat ggaggcgccg 1680

ggtatagttt ttcccagtga acaggtgcaa ggcgtgtcgg agaaaaaggt cgacgactac 1740

tatgcggggt acctgtatct gcgcgacagc acgccagagg acgcgcgcgt tttggcctgg 1800

tgggactacg gctaccagat cacaggcatc ggcaaccgca cctcgctggc cgatggcaac 1860

acctggaacc acgagcacat cgccacgatc ggcaagatgc tgacgtcgcc cgtggcggag 1920

gcgcactcgc tggtgcgcca catggccgac tatgttctga tttctgctgg agacacatat 1980
```

-continued

```
ttttccgacc tgaatcgctc accgatgatg gcgcgcatcg gcaacagcgt gtaccacgac 2040

atctgccccg acgacccact ttgtagtcag ttcgtgttgc agaaaagacc gaaagctgct 2100

gcagcgaagc gcagtcggca cgtcagcgtt gacgcactag aggaggatga cactgcagag 2160

catatggtat acgagccgtc atcactcata gccaagtcgc tcatatatca cctgcactcc 2220

acaggggtgg tgacgggggt cacgctgaat gagacgctct tccagcacgt cttcacctca 2280

ccgcagggtc tcatgcgcat cttcaaggtc atgaacgtga gcacggagag caaaaagtgg 2340

gttgctgact cggcaaaccg cgtgtgccac ccgcctgggt cgtggatctg ccccgggcag 2400

tacccgccgg cgaaggagat ccaggagatg ctggcacacc aacacaccaa cttcaaggac 2460

cttcttgatc ccagaacgac ttggagcggg agcaggcgct ga                    2502
```

OSTs from other *Leishmania* species or strains that share sequence identity to *L. major* OST STT3 subunit related protein and/or are capable of transferring a glycan moiety to a target glycoprotein are also suitable for use in the present invention. For example, homologous OSTs derived from *L. donovani* (SEQ ID NO: 21; UniProtKB No. E9BRZ2), *L. infantum* (SEQ ID NO: 22; UniProtKB No. A4IB10), *L. mexicana* (SEQ ID NO: 23; UniProtKBKB No. E9B5Z4), and *L. braziliensis* (SEQ ID NO: 24; UniProtKB No. A4HMD6), which each share greater than 70% sequence identity with the amino acid sequence of *L. major* OST (see alignment of FIG. 8), are also suitable for use in the this and all aspects of the present invention. A STT3 consensus sequence based on the alignment of *Leishmania* STT3 sequences is presented as SEQ ID NO: 25 in FIG. 8. Residues that are not fully conserved between the five *Leishmania* sequences are depicted as X, where X can be any amino acid residue. Alternatively, X is selected from an amino acid residue at the corresponding position in one of the five depicted *Leishmania* sequences.

In another embodiment of the present invention, the eukaryotic oligosaccharyltransferase is STT3 from *Saccharomyces cerevisiae*. The amino acid sequence of *S. cerevisiae* (UniProtKB Accession No. P39007) is provided below as SEQ ID NO: 26.

```
Met Gly Ser Asp Arg Ser Cys Val Leu Ser Val Phe Gln Thr Ile Leu
1               5                   10                  15

Lys Leu Val Ile Phe Val Ala Ile Phe Gly Ala Ala Ile Ser Ser Arg
            20                  25                  30

Leu Phe Ala Val Ile Lys Phe Glu Ser Ile Ile His Glu Phe Asp Pro
        35                  40                  45

Trp Phe Asn Tyr Arg Ala Thr Lys Tyr Leu Val Asn Asn Ser Phe Tyr
    50                  55                  60

Lys Phe Leu Asn Trp Phe Asp Asp Arg Thr Trp Tyr Pro Leu Gly Arg
65                  70                  75                  80

Val Thr Gly Gly Thr Leu Tyr Pro Gly Leu Met Thr Thr Ser Ala Phe
                85                  90                  95

Ile Trp His Ala Leu Arg Asn Trp Leu Gly Leu Pro Ile Asp Ile Arg
            100                 105                 110

Asn Val Cys Val Leu Phe Ala Pro Leu Phe Ser Gly Val Thr Ala Trp
        115                 120                 125

Ala Thr Tyr Glu Phe Thr Lys Glu Ile Lys Asp Ala Ser Ala Gly Leu
    130                 135                 140

Leu Ala Ala Gly Phe Ile Ala Ile Val Pro Gly Tyr Ile Ser Arg Ser
145                 150                 155                 160

Val Ala Gly Ser Tyr Asp Asn Glu Ala Ile Ala Ile Thr Leu Leu Met
                165                 170                 175

Val Thr Phe Met Phe Trp Ile Lys Ala Gln Lys Thr Gly Ser Ile Met
            180                 185                 190

His Ala Thr Cys Ala Ala Leu Phe Tyr Phe Tyr Met Val Ser Ala Trp
        195                 200                 205

Gly Gly Tyr Val Phe Ile Thr Asn Leu Ile Pro Leu His Val Phe Leu
    210                 215                 220

Leu Ile Leu Met Gly Arg Tyr Ser Ser Lys Leu Tyr Ser Ala Tyr Thr
225                 230                 235                 240
```

-continued

Thr Trp Tyr Ala Ile Gly Thr Val Ala Ser Met Gln Ile Pro Phe Val
245 250 255

Gly Phe Leu Pro Ile Arg Ser Asn Asp His Met Ala Ala Leu Gly Val
260 265 270

Phe Gly Leu Ile Gln Ile Val Ala Phe Gly Asp Phe Val Lys Gly Gln
275 280 285

Ile Ser Thr Ala Lys Phe Lys Val Ile Met Met Val Ser Leu Phe Leu
290 295 300

Ile Leu Val Leu Gly Val Val Gly Leu Ser Ala Leu Thr Tyr Met Gly
305 310 315 320

Leu Ile Ala Pro Trp Thr Gly Arg Phe Tyr Ser Leu Trp Asp Thr Asn
325 330 335

Tyr Ala Lys Ile His Ile Pro Ile Ile Ala Ser Val Ser Glu His Gln
340 345 350

Pro Val Ser Trp Pro Ala Phe Phe Phe Asp Thr His Phe Leu Ile Trp
355 360 365

Leu Phe Pro Ala Gly Val Phe Leu Leu Phe Leu Asp Leu Lys Asp Glu
370 375 380

His Val Phe Val Ile Ala Tyr Ser Val Leu Cys Ser Tyr Phe Ala Gly
385 390 395 400

Val Met Val Arg Leu Met Leu Thr Leu Thr Pro Val Ile Cys Val Ser
405 410 415

Ala Ala Val Ala Leu Ser Lys Ile Phe Asp Ile Tyr Leu Asp Phe Lys
420 425 430

Thr Ser Asp Arg Lys Tyr Ala Ile Lys Pro Ala Ala Leu Leu Ala Lys
435 440 445

Leu Ile Val Ser Gly Ser Phe Ile Phe Tyr Leu Tyr Leu Phe Val Phe
450 455 460

His Ser Thr Trp Val Thr Arg Thr Ala Tyr Ser Ser Pro Ser Val Val
465 470 475 480

Leu Pro Ser Gln Thr Pro Asp Gly Lys Leu Ala Leu Ile Asp Asp Phe
485 490 495

Arg Glu Ala Tyr Tyr Trp Leu Arg Met Asn Ser Asp Glu Asp Ser Lys
500 505 510

Val Ala Ala Trp Trp Asp Tyr Gly Tyr Gln Ile Gly Gly Met Ala Asp
515 520 525

Arg Thr Thr Leu Val Asp Asn Asn Thr Trp Asn Asn Thr His Ile Ala
530 535 540

Ile Val Gly Lys Ala Met Ala Ser Pro Glu Glu Lys Ser Tyr Glu Ile
545 550 555 560

Leu Lys Glu His Asp Val Asp Tyr Val Leu Val Ile Phe Gly Gly Leu
565 570 575

Ile Gly Phe Gly Gly Asp Asp Ile Asn Lys Phe Leu Trp Met Ile Arg
580 585 590

Ile Ser Glu Gly Ile Trp Pro Glu Glu Ile Lys Glu Arg Tyr Phe Tyr
595 600 605

Thr Ala Glu Gly Glu Tyr Arg Val Asp Ala Arg Ala Ser Glu Thr Met
610 615 620

Arg Asn Ser Leu Leu Tyr Lys Met Ser Tyr Lys Asp Phe Pro Gln Leu
625 630 635 640

Phe Asn Gly Gly Gln Ala Thr Asp Arg Val Arg Gln Gln Met Ile Thr
645 650 655

Pro Leu Asp Val Pro Pro Leu Asp Tyr Phe Asp Glu Val Phe Thr Ser
660 665 670

-continued

```
Glu Asn Trp Met Val Arg Ile Tyr Gln Leu Lys Lys Asp Asp Ala Gln
        675                 680                 685

Gly Arg Thr Leu Arg Asp Val Gly Glu Leu Thr Arg Ser Ser Thr Lys
    690                 695                 700

Thr Arg Arg Ser Ile Lys Arg Pro Glu Leu Gly Leu Arg Val
705                 710                 715
```

Amino acid sequences sharing at least about 70 percent, more preferably at least about 75 percent or 80 percent, most preferably at least about 85 percent or 90 percent or 95 percent as compared to the *S. cerevisiae* amino acid sequence of SEQ ID NO: 26 are also suitable for use in the present invention. The nucleic acid sequence encoding the amino acid sequence of SEQ ID NO: 26 (*S. cerevisiae* STT3) is provided below as SEQ ID NO: 27 (EMBL Nucleotide Sequence Database No. BAA06079).

```
atgggatccg accggtcgtg tgttttgtct gtgtttcaga ccatcctcaa gctcgtcatc   60
ttcgtggcga tttttggggc tgccatatca tcacgtttgt ttgcagtcat caaatttgag  120
tctattatcc atgaattcga cccctggttc aattataggg ctaccaaata tctcgtcaac  180
aattcgtttt acaagttttt gaactggttt gacgaccgta cctggtaccc cctcggaagg  240
gttactggag ggactttata tcctggtttg atgacgacta gtgcgttcat ctggcacgcc  300
ctgcgcaact ggttgggctt gcccattgac atcagaaacg tttgtgtgct atttgcgcca  360
ctattttctg ggtcaccgc  ctgggcgact tacgaattta cgaaagagat taaagatgcc  420
agcgctgggc ttttggctgc tggttttata gccattgtcc ccggttatat atctagatca  480
gtggcggggt cctacgataa tgaggccatt gccattacac tattaatggt cactttcatg  540
ttttggatta aggcccaaaa gactggctct atcatgcacg caacgtgtgc agctttattc  600
tacttctaca tggtgtcggc ttggggtgga tacgtgttca tcaccaactt gatcccactc  660
catgtctttt tgctgatttt gatgggcaga tattcgtcca aactgtattc tgcctacacc  720
acttggtacg ctattggaac tgttgcatcc atgcagatcc catttgtcgg tttcctacct  780
atcaggtcta acgaccacat ggccgcattg ggtgttttcg gtttgattca gattgtcgcc  840
ttcggtgact tcgtgaaggg ccaaatcagc acagctaagt ttaaagtcat catgatggtt  900
tctctgtttt tgatcttggt ccttggtgtg gtcggacttt ctgccttgac ctatatgggg  960
ttgattgccc cttggactgg tagattttat tcgttatggg ataccaacta cgcaaagatc 1020
cacattccta tcattgcctc cgtttccgaa catcaacccg tttcgtggcc cgctttcttc 1080
tttgataccc actttttgat ctggctattc cccgccggtg tattcctact attcctcgac 1140
ttgaaagacg agcacgtttt tgtcatcgct tactccgttc tgtgttcgta ctttgccggt 1200
gttatggtta gattgatgtt gactttgaca ccagtcatct gtgtgtccgc cgccgtcgca 1260
ttgtccaaga tatttgacat ctacctggat ttcaagacaa gtgaccgcaa atacgccatc 1320
aaacctgcgg cactactggc caaattgatt gtttccggat cattcatctt ttatttgtat 1380
cttttcgtct tccattctac ttgggtaaca agaactgcat actcttctcc ttctgttgtt 1440
ttgccatcac aaaccccaga tggtaaattg gcgttgatcg acgacttcag ggaagcgtac 1500
tattggttaa gaatgaactc tgatgaggac agtaaggttg cagcgtggtg ggattacggt 1560
taccaaattg gtggcatggc agacagaacc actttagtcg ataacaacac gtggaacaat 1620
actcacatcg ccatcgttgg taaagccatg gcttcccctg aagagaaatc ttacgaaatt 1680
ctaaaagagc atgatgtcga ttatgtcttg gtcatctttg gtggtctaat tgggtttggt 1740
ggtgatgaca tcaacaaatt cttgtggatg atcagaatta gcgagggaat ctggccagaa 1800
gagataaaag agcgttattt ctataccgca gagggagaat acagagtaga tgcaagggct 1860
```

-continued

```
tctgagacca tgaggaactc gctactttac aagatgtcct acaaagattt cccacaatta 1920

ttcaatggtg gccaagccac tgacagagtg cgtcaacaaa tgatcacacc attagacgtc 1980

ccaccattag actacttcga cgaagttttt acttccgaaa actggatggt tagaatatat 2040

caattgaaga aggatgatgc ccaaggtaga actttgaggg acgttggtga gttaaccagg 2100

tcttctacga aaaccagaag gtccataaag agacctgaat taggcttgag agtctaa    2157
```

In another embodiment of the present invention, the eukaryotic oligosaccharyltransferase is STT3 from *Schizosaccharomyces pombe*. The amino acid sequence of *S. pombe* (UniProtKB Accession No. O94335) is provided below as SEQ ID NO: 28.

```
Met Ala Asn Ser Ala Thr Ile Thr Ser Lys Lys Gly Val Lys Ser His
1               5                   10                  15

Gln Lys Asp Trp Lys Ile Pro Leu Lys Val Leu Ile Leu Ile Cys Ile
            20                  25                  30

Ala Val Ala Ser Val Ser Ser Arg Leu Phe Ser Val Ile Arg Tyr Glu
        35                  40                  45

Ser Ile Ile His Glu Phe Asp Pro Trp Phe Asn Phe Arg Ala Ser Lys
    50                  55                  60

Ile Leu Val Glu Gln Gly Phe Tyr Asn Phe Leu Asn Trp Phe Asp Glu
65                  70                  75                  80

Arg Ser Trp Tyr Pro Leu Gly Arg Val Ala Gly Gly Thr Leu Tyr Pro
                85                  90                  95

Gly Leu Met Val Thr Ser Gly Ile Ile Phe Lys Val Leu His Leu Leu
            100                 105                 110

Arg Ile Asn Val Asn Ile Arg Asp Val Cys Val Leu Leu Ala Pro Ala
        115                 120                 125

Phe Ser Gly Ile Thr Ala Ile Ala Thr Tyr Tyr Leu Ala Arg Glu Leu
    130                 135                 140

Lys Ser Asp Ala Cys Gly Leu Leu Ala Ala Ala Phe Met Gly Ile Ala
145                 150                 155                 160

Pro Gly Tyr Thr Ser Arg Ser Val Ala Gly Ser Tyr Asp Asn Glu Ala
                165                 170                 175

Ile Ala Ile Thr Leu Leu Met Ser Thr Phe Ala Leu Trp Ile Lys Ala
            180                 185                 190

Val Lys Ser Gly Ser Ser Phe Trp Gly Ala Cys Thr Gly Leu Leu Tyr
        195                 200                 205

Phe Tyr Met Val Thr Ala Trp Gly Gly Tyr Val Phe Ile Thr Asn Met
    210                 215                 220

Ile Pro Leu His Val Phe Val Leu Leu Leu Met Gly Arg Tyr Thr Ser
225                 230                 235                 240

Lys Leu Tyr Ile Ala Tyr Thr Thr Tyr Tyr Val Ile Gly Thr Leu Ala
                245                 250                 255

Ser Met Gln Val Pro Phe Val Gly Phe Gln Pro Val Ser Thr Ser Glu
            260                 265                 270

His Met Ser Ala Leu Gly Val Phe Gly Leu Leu Gln Leu Phe Ala Phe
        275                 280                 285

Tyr Asn Tyr Val Lys Gly Leu Val Ser Ser Lys Gln Phe Gin Ile Leu
    290                 295                 300

Ile Arg Phe Ala Leu Val Cys Leu Val Gly Leu Ala Thr Val Val Leu
305                 310                 315                 320

Phe Ala Leu Ser Ser Thr Gly Val Ile Ala Pro Trp Thr Gly Arg Phe
                325                 330                 335
```

-continued

```
Tyr Ser Leu Trp Asp Thr Asn Tyr Ala Lys Ile His Ile Pro Ile Ile
            340                 345                 350

Ala Ser Val Ser Glu His Gln Pro Pro Thr Trp Ser Ser Leu Phe Phe
        355                 360                 365

Asp Leu Gln Phe Leu Ile Trp Leu Leu Pro Val Gly Val Tyr Leu Cys
    370                 375                 380

Phe Lys Glu Leu Arg Asn Glu His Val Phe Ile Ile Ile Tyr Pro Val
385                 390                 395                 400

Leu Gly Thr Tyr Phe Cys Gly Val Met Val Arg Leu Val Leu Thr Leu
                405                 410                 415

Thr Pro Cys Val Cys Ile Ala Ala Ala Val Ala Ile Ser Thr Leu Leu
            420                 425                 430

Asp Thr Tyr Met Gly Pro Glu Val Glu Glu Asp Lys Val Ser Glu Glu
        435                 440                 445

Ala Ala Ser Ala Lys Ser Lys Asn Lys Lys Gly Ile Ser Ser Ile Leu
    450                 455                 460

Ser Phe Phe Thr Ser Gly Ser Lys Asn Ile Gly Ile Tyr Ser Leu Leu
465                 470                 475                 480

Ser Arg Val Leu Val Ile Ser Ser Thr Ala Tyr Phe Leu Ile Met Phe
                485                 490                 495

Val Tyr His Ser Ser Trp Val Thr Ser Asn Ala Tyr Ser Ser Pro Thr
            500                 505                 510

Val Val Leu Ser Thr Val Leu Asn Asp Gly Ser Leu Met Tyr Ile Asp
        515                 520                 525

Asp Phe Arg Glu Ala Tyr Asp Trp Leu Arg Arg Asn Thr Pro Tyr Asp
    530                 535                 540

Thr Lys Val Met Ser Trp Trp Asp Tyr Gly Tyr Gln Ile Ala Gly Met
545                 550                 555                 560

Ala Asp Arg Ile Thr Leu Val Asp Asn Asn Thr Trp Asn Asn Thr His
                565                 570                 575

Ile Ala Thr Val Gly Lys Ala Met Ser Ser Pro Glu Glu Lys Ala Tyr
            580                 585                 590

Pro Ile Leu Arg Lys His Asp Val Asp Tyr Ile Leu Ile Ile Tyr Gly
        595                 600                 605

Gly Thr Leu Gly Tyr Ser Ser Asp Asp Met Asn Lys Phe Leu Trp Met
    610                 615                 620

Ile Arg Ile Ser Gln Gly Leu Trp Pro Asp Glu Ile Val Glu Arg Asn
625                 630                 635                 640

Phe Phe Thr Pro Asn Gly Glu Tyr Arg Thr Asp Asp Ala Ala Thr Pro
                645                 650                 655

Thr Met Arg Glu Ser Leu Leu Tyr Lys Met Ser Tyr His Gly Ala Trp
            660                 665                 670

Lys Leu Phe Pro Pro Asn Gln Gly Tyr Asp Arg Ala Arg Asn Gln Lys
        675                 680                 685

Leu Pro Ser Lys Asp Pro Gln Leu Phe Thr Ile Glu Glu Ala Phe Thr
    690                 695                 700

Thr Val His His Leu Val Arg Leu Tyr Lys Val Lys Lys Pro Asp Thr
705                 710                 715                 720

Leu Gly Arg Asp Leu Lys Gln Val Thr Leu Phe Glu Glu Gly Lys Arg
                725                 730                 735

Lys Lys Ser Ala Val Leu Gln Lys Leu Thr Lys Phe Leu
            740                 745
```

Amino acid sequences sharing at least about 70 percent, more preferably at least about 75 percent or 80 percent, most preferably at least about 85 percent or 90 percent or 95 percent as compared to the *S. pombe* amino acid sequence of SEQ ID NO: 28 are also suitable for use in the present invention. The nucleic acid sequence encoding the amino acid sequence of SEQ ID NO: 28 (*S. pombe* STT3) is provided below as SEQ ID NO: 29 (EMBL Nucleotide Sequence Database No. BAA76479).

atggctaatt ctgctacaat tacgagtaaa aaaggcgtga agtctcatca gaaggactgg 60
aaaattccac ttaaagtgct cattcttata tgtattgctg tggcttctgt ctcttcgagg 120 ctttttctg tcattcgtta cgagtccatt attcatgaat ttgatccttg gttcaatttc 180
cgagcttcca aaatattggt ggaacaaggt ttttataact tttaaattg gtttgatgaa 240 agaagttggt acccgttggg tcgtgtagcg ggtggtactt tgtacccagg acttatggtc 300
acgtctggta ttattttcaa agttttacat cttttaagaa ttaacgtgaa catccgtgat 360
gtatgtgttt tacttgcccc tgctttctct ggaatcactg cgattgctac ctattatctg 420
gctagagaat tgaaaagtga tgcatgtggc cttttagctg ccgcatttat gggtattgct 480
cctggataca cctcccgttc cgtcgctggt tcttacgata atgaagcaat tgctattacc 540
cttttgatgt caacgtttgc tttgtggatc aaggcagtga agtctggctc ctctttctgg 600
ggtgcctgca caggattgct ctacttctat atggtaactg cgtggggtgg ttatgtattc 660
atcacaaaca tgataccttt acacgtattt gttcttctac ttatgggtcg ctatactagc 720
aaattataca ttgcttacac aacatactat gttattggaa cgctggcttc tatgcaagtt 780
ccgtttgttg gtttccaacc cgtgtcgact agtgagcata tgtccgcttt aggagtgttt 840
ggcctgttac agctttttgc attctacaat tatgttaaag gtctagtttc atccaagcaa 900
ttccaaatac ttattcgttt tgccttggtt tgcttagtgg gtctagcaac agtcgtcctt 960
tttgctttat cttcaacagg tgttatcgct ccttggacag gacgtttcta ttctctttgg 1020
gatacaaact acgccaagat tcatattcct atcattgctt cggtatcaga acatcagcct 1080
cctacttgga gttcgttgtt ctttgatctt caatttttga tttggttatt gccagttggt 1140
gtttacttgt gtttcaagga acttcgtaat gaacatgtct ttattattat atatcctgtc 1200
ttaggaacat atttttgtgg tgtgatggtt cgtttggttt taaccttaac tccttgtgtt 1260
tgcatagctg ctgctgtagc aatttccact cttttagaca catatatggg tcctgaagtt 1320
gaagaggaca aagtgagcga agaagccgct tcagccaaat ctaagaacaa gaaaggtatt 1380
tcctctattc ttagtttctt cacttctggc tcaaaaaata ttggaattta cagtttgctt 1440
tccagagtat tagtcatttc ctctaccgca tatttcctaa taatgtttgt ttatcattcc 1500
agttgggtga cttctaatgc ttactcttcc cctaccgtgg ttttgtctac cgtgttaaac 1560
gatggtagtt taatgtatat tgatgacttc cgtgaagctt atgactggct tcgtagaaac 1620
actccttatg acacaaaggt tatgagttgg tgggattatg gttaccaaat tgctggtatg 1680
gctgatcgta ttactttagt cgacaacaat acgtggaaca acacacatat tgccacagtt 1740
ggaaaagcca tgtcttcacc tgaagaaaaa gcttacccta tcctccgtaa acacgatgtt 1800
gattatattc ttattatata tggtggtact cttggataca gcagcgacga catgaacaag 1860
ttcctttgga tgatccgaat ttctcaggga ttatggcccg atgaaatagt agagcgtaac 1920
ttttttactc ctaatggaga atatcgaact gacgatgcgg ctactcccac tatgcgtgag 1980
tctttattat ataagatgtc atatcacggt gcttggaaac ttttccctcc caatcaagga 2040
tatgaccgtg ctcgcaatca aaaactacca tcgaaagatc ctcaactatt tactatcgaa 2100
gaagcattca ctaccgttca tcatttagtt cgtttgtata aggttaagaa accggataca 2160

-continued

```
cttggacgcg atttgaaaca agtgacatta tttgaagaag gcaaaagaaa gaagtccgcc 2220

gtcctgcaaa aactaacgaa attcctttga                                  2250
```

In another embodiment of the present invention, the eukaryotic oligosaccharyltransferase is STT3 from *Dictyostelium discoideum*. The amino acid sequence of *D. discoideum* (UniProtKB Accession No. Q54NM9) is provided below as SEQ ID NO: 30.

```
Met Lys Arg Ser Glu Lys Ser Ser Thr Ser Val Val Ser Asn Asn Lys
1               5                   10                  15

Gln Gln Asp Val Asn Ile Ile Ser Ser Asn Glu Val Gly Val Lys Glu
            20                  25                  30

Glu Asn Lys Gly His Gln Glu Phe Leu Leu Lys Val Leu Ile Leu Ser
        35                  40                  45

Val Ile Tyr Val Leu Ala Phe Ser Thr Arg Leu Phe Ser Val Leu Arg
    50                  55                  60

Tyr Glu Ser Val Ile His Glu Phe Asp Pro Tyr Phe Asn Tyr Arg Ser
65                  70                  75                  80

Thr Ile Tyr Leu Val Gln Glu Gly Phe Tyr Asn Phe Leu Asn Trp Phe
                85                  90                  95

Asp Glu Arg Ala Trp Tyr Pro Leu Gly Arg Ile Val Gly Gly Thr Ile
            100                 105                 110

Tyr Pro Gly Leu Met Ala Thr Ala Ser Leu Val His Trp Ser Leu Asn
        115                 120                 125

Ser Leu Asn Ile Thr Val Asn Ile Arg Asn Val Cys Val Leu Leu Ser
    130                 135                 140

Pro Trp Phe Ala Ser Asn Thr Ala Met Val Thr Tyr Lys Phe Ala Lys
145                 150                 155                 160

Glu Val Lys Asp Thr Gln Thr Gly Leu Val Ala Ala Ala Met Ile Ala
                165                 170                 175

Ile Val Pro Gly Tyr Ile Ser Arg Ser Val Ala Gly Ser Phe Asp Asn
            180                 185                 190

Glu Gly Ile Ala Ile Phe Ala Leu Ile Phe Thr Tyr Tyr Cys Trp Ile
        195                 200                 205

Lys Ser Val Asn Thr Gly Ser Leu Met Trp Ala Ala Ile Cys Ser Leu
    210                 215                 220

Ala Tyr Phe Tyr Met Ala Ser Ala Trp Gly Gly Tyr Val Phe Ile Ile
225                 230                 235                 240

Asn Leu Ile Pro Leu His Ala Phe Phe Leu Leu Leu Thr Gly Arg Tyr
                245                 250                 255

Ser His Arg Leu Tyr Ile Ala Tyr Ser Thr Met Phe Val Ile Gly Thr
            260                 265                 270

Ile Leu Ser Met Gln Ile Thr Phe Ile Ser Phe Gln Pro Val Gin Ser
        275                 280                 285

Ser Glu His Leu Ala Ala Ile Gly Ile Phe Gly Leu Leu Gln Leu Tyr
    290                 295                 300

Ala Gly Leu Ser Trp Val Lys Ser His Leu Thr Asn Glu Ala Phe Lys
305                 310                 315                 320

Lys Leu Gln Arg Leu Thr Val Leu Phe Val Leu Ser Cys Ala Ala Ala
                325                 330                 335

Val Leu Val Val Gly Thr Leu Thr Gly Tyr Ile Ser Pro Phe Asn Gly
            340                 345                 350
```

-continued

```
Arg Phe Tyr Ser Leu Leu Asp Pro Thr Tyr Ala Arg Asp His Ile Pro
        355                 360                 365

Ile Ile Ala Ser Val Ser Glu His Gln Pro Thr Thr Trp Ala Ser Tyr
    370                 375                 380

Phe Phe Asp Leu His Ile Leu Val Phe Leu Phe Pro Ala Gly Leu Tyr
385                 390                 395                 400

Phe Cys Phe Gln Lys Leu Thr Asp Ala Asn Ile Phe Leu Ile Leu Tyr
                405                 410                 415

Gly Val Thr Ser Ile Tyr Phe Ser Gly Val Met Val Arg Leu Met Leu
            420                 425                 430

Val Leu Ala Pro Val Ala Cys Ile Leu Ala Ala Val Ala Val Ser Ala
        435                 440                 445

Thr Leu Thr Thr Tyr Met Lys Lys Leu Lys Ala Pro Ser Ser Pro Ser
    450                 455                 460

Asp Ala Asn Asn Ser Lys Glu Ser Gly Gly Val Met Val Ala Val Leu
465                 470                 475                 480

Thr Val Leu Leu Ile Leu Tyr Ala Phe His Cys Thr Trp Val Thr Ser
                485                 490                 495

Glu Ala Tyr Ser Ser Pro Ser Ile Val Leu Ser Ala Lys Gln Asn Asp
            500                 505                 510

Gly Ser Arg Val Ile Phe Asp Asp Phe Arg Glu Ala Tyr Arg Trp Ile
        515                 520                 525

Gly Gln Asn Thr Ala Asp Asp Ala Arg Ile Met Ser Trp Trp Asp Tyr
    530                 535                 540

Gly Tyr Gln Leu Ser Ala Met Ala Asn Arg Thr Val Leu Val Asp Asn
545                 550                 555                 560

Asn Thr Trp Asn Asn Ser His Ile Ala Gln Val Gly Lys Ala Phe Ala
                565                 570                 575

Ser Thr Glu Glu Asp Ala Tyr Ile Gln Met Lys Ala Leu Asp Val Asp
            580                 585                 590

Tyr Val Leu Val Ile Phe Gly Gly Leu Thr Gly Tyr Ser Ser Asp Asp
        595                 600                 605

Ile Asn Lys Phe Leu Trp Met Val Arg Ile Gly Gly Ser Cys Asp Pro
    610                 615                 620

Asn Ile Lys Glu Gln Asp Tyr Leu Thr Asn Gly Gln Tyr Arg Ile Asp
625                 630                 635                 640

Lys Gly Ala Ser Pro Thr Met Leu Asn Ser Leu Met Tyr Lys Leu Ser
                645                 650                 655

Tyr Tyr Arg Phe Ser Glu Val His Thr Asp Tyr Gln Arg Pro Thr Gly
            660                 665                 670

Phe Asp Arg Val Arg Asn Val Glu Ile Gly Asn Lys Asn Phe Asp Leu
        675                 680                 685

Thr Tyr Leu Glu Glu Ala Phe Thr Ser Val His Trp Leu Val Arg Val
    690                 695                 700

Tyr Lys Val Lys Asp Phe Asp Asn Arg Ala
705                 710
```

Amino acid sequences sharing at least about 70 percent, more preferably at least about 75 percent or 80 percent, most preferably at least about 85 percent or 90 percent or 95 percent as compared to the *D. discoideum* amino acid sequence of SEQ ID NO: 30 are also suitable for use in the present invention. The nucleic acid sequence encoding the amino acid sequence of SEQ ID NO: 30 (*D. discoideum* STT3) is provided below as SEQ ID NO: 31 (EMBL Nucleotide Sequence Database No. EAL64892).

```
atgaaaagat cagaaaaatc aagtacatct gttgttagta ataacaaaca acaagatgta   60
aatatcatca gttcaaatga agttggtgtt aaagaagaaa ataaaggaca tcaagaattc  120
ttattaaaag ttttaattct atcagtcatt tatgttttag cattttcaac tcgtttattc  180
tcagtattac gttatgaaag tgttattcat gaatttgatc catattttaa ttatagatca  240
acaatatatc ttgttcaaga aggtttttat aattttttaa attggtttga tgaaagagca  300
tggtatccat taggacgtat tgtaggtggt acaatttacc caggtttaat ggcaacagca  360
agtttagttc attggtcatt gaattcattg aatattacag ttaatattag aaatgtatgt  420
gtattgttat caccatggtt tgcatcaaat acagcaatgg taacctataa atttgccaaa  480
gaagttaagg atacacaaac tggtttggtt gcagcagcca tgattgcaat tgttccaggt  540
tatatttcac gttcagtagc aggttcattc gataatgaag gtattgcaat ctttgcattg  600
attttcacat attattgttg gattaagtca gtaaacacag gctcattgat gtgggctgcc  660
atctgttcat tggcctactt ttatatggca agtgcctggg gtggttatgt attcatcatt  720
aatttaatcc cattgcatgc ctttttcttg cttttgacag gccgttattc acatcgtctc  780
tacatagcct acagcacaat gtttgtcatt ggtacaatcc tctctatgca aattacattc  840
attagtttcc aaccagttca atcatctgaa catttggctg ccattggtat ctttggtctc  900
ctccaattgt acgctggttt gtcatgggta aagagtcacc tcaccaatga agccttcaag  960
aaacttcaac gtttgacagt gttattcgtt ttatcttgtg ctgctgccgt acttgtcgtt 1020
ggtacattaa ctggttacat ctcaccattc aatggtcgtt tctattcatt gttggatcca 1080
acctatgctc gtgaccacat tccaatcatt gcatcagtat cagagcatca accaaccact 1140
tgggcatcat actttttcga tctccatatc ttggtattcc ttttcccagc cggtttatac 1200
ttttgtttcc aaaaattaac cgatgctaat attttcctca ttctctacgg tgtcacctcc 1260
atttatttct ctggtgtaat ggtacgtctt atgttggttt tagcaccagt tgcatgtatt 1320
ttagccgccg ttgccgtcag tgcaaccctc accacctata tgaagaagtt aaaggctcca 1380
tcatcaccaa gtgatgctaa taattccaaa gagagtggtg gtgttatggt tgcagtctta 1440
actgttcttt taattctcta cgctttccat tgtacttggg tcactagtga agcctactca 1500
tctccatcca ttgtactctc tgccaaacaa aacgatggta gtcgtgtgat tttcgatgat 1560
ttccgtgaag cctaccgttg gattggtcaa aatactgccg acgacgctcg tattatgtct 1620
tggtgggatt atggttatca attatctgca atggccaatc gtaccgtatt ggttgataat 1680
aacacttgga acaatagtca tatcgctcaa gttggtaaag catttgcatc cactgaagaa 1740
gatgcttaca tacaaatgaa agcattggat gtcgattatg ttttagttat ttttggtggt 1800
ttaactggtt acagttctga tgatatcaat aaattccttt ggatggttag aattggtggt 1860
agttgtgatc caaatattaa agaacaagat tatctcacca atggtcaata tagaatagat 1920
aaaggtgcct caccaacaat gttaaattct ctcatgtaca aacttagtta ctatcgtttc 1980
tctgaagttc acactgacta tcaaagacca acaggtttcg atcgtgtaag aaatgttgaa 2040
attggtaata aaaatttcga tttaacttat ttagaagaag ctttcacatc tgttcattgg 2100
ttagttagag tttataaagt taaagatttt gataatagag cttaa                 2145
```

Other eukaryotic oligosaccharyltransferases that can be utilized in this and all aspects of the present invention are listed in the table of FIGS. 9A-9G. This table identifies each oligosaccharyltransferase by its UniProtKB entry number, which provides the amino acid sequence of the protein, and the EMBL database accession number, which provides the encoding nucleotide sequence. The UniProtKB and EMBL accession numbers, along with the corresponding amino acid and nucleotide sequence information for each oligosaccharyltransferase listed in FIG. 9 is hereby incorporated by reference in its entirety.

In another embodiment of the present invention, the oligosaccharyltransferase is an O-linked oligosaccharyltransferase. An exemplary O-linked OST is PilO from *Pseudomonas aeruginosa*. PilO is responsible for the en bloc transfer of an oligosaccharide from a lipid-linked donor to an oxygen atom of serine and threonine residues (Faridmoayer et al., "Functional Characterization of Bacterial Oligosaccharyltransferases Involved in O-Linked Protein Glycosylation," *J. Bacteriol.* 189(22): 8088-8098 (2007), which is hereby incorporated by reference in its entirety). The amino acid sequence of *P. aeruginosa* (UniProtKB Accession No. Q51353) is provided below as SEQ ID NO: 32

```
Met Ser Leu Ala Ser Ser Leu Glu Ser Leu Arg Lys Ile Asp Ile Asn
1               5                   10                  15

Asp Leu Asp Leu Asn Asn Ile Gly Ser Trp Pro Ala Ala Val Lys Val
            20                  25                  30

Ile Val Cys Val Leu Leu Thr Ala Ala Val Leu Ala Leu Gly Tyr Asn
        35                  40                  45

Phe His Leu Ser Asp Met Gln Ala Gln Leu Glu Gln Gln Ala Ala Glu
    50                  55                  60

Glu Glu Thr Leu Lys Gln Gln Phe Ser Thr Lys Ala Phe Gln Ala Ala
65                  70                  75                  80

Asn Leu Glu Ala Tyr Lys Ala Gln Met Lys Glu Met Glu Glu Ser Phe
                85                  90                  95

Gly Ala Leu Leu Arg Gln Leu Pro Ser Asp Thr Glu Val Pro Gly Leu
            100                 105                 110

Leu Glu Asp Ile Thr Arg Thr Gly Leu Gly Ser Gly Leu Glu Phe Glu
        115                 120                 125

Glu Ile Lys Leu Leu Pro Glu Val Ala Gln Gln Phe Tyr Ile Glu Leu
    130                 135                 140

Pro Ile Gln Ile Ser Val Val Gly Gly Tyr His Asp Leu Ala Thr Val
145                 150                 155                 160

Ser Gly Val Ser Ser Leu Pro Arg Ile Val Thr Leu His Asp Phe Glu
                165                 170                 175

Ile Lys Pro Val Ala Pro Gly Ser Thr Ser Lys Leu Arg Met Ser Ile
            180                 185                 190

Leu Ala Lys Thr Tyr Arg Tyr Asn Asp Lys Gly Leu Lys Lys
        195                 200                 205
```

Amino acid sequences sharing at least about 70 percent, more preferably at least about 75 percent or 80 percent, most preferably at least about 85 percent or 90 percent or 95 percent as compared to the *P. aeruginosa* amino acid sequence of SEQ ID NO: 32 are also suitable for use in the present invention. The nucleic acid sequence encoding the amino acid sequence of SEQ ID NO: 33 (*P. aeruginosa* PilO) is provided below as SEQ ID NO: 33 (EMBL Nucleotide Sequence Database No. AAA87404).

```
atgagtctgg ccagttccct ggaaagtctg cgcaagatcg atatcaacga tctcgacctg  60

aacaacatcg gttcctggcc ggcggcggtc aaggtcatcg tctgcgtgct gctgaccgcg 120

gcggtcctgg cgctgggcta caacttccat ctgagtgaca tgcaggctca gctcgaacag 180

caggccgcgg aagaggagac gctcaagcag cagttctcca ccaaggcctt ccaggccgcg 240

aacctggaag cctacaaggc acagatgaag gagatggaag agtcctttgg cgccttgctg 300

cggcagttgc ccagcgacac cgaggtaccc gggctgctcg aggacatcac tcgtaccggc 360
```

-continued

```
ctgggcagcg gcctggagtt cgaggaaatc aagctgcttc ccgaggttgc ccagcagttc 420

tacatcgagc tgccgatcca gatcagcgtg gtcggcggct accacgactt ggcgaccttc 480

gtcagcggcg tgtccagcct gccgcggatc gtcaccctgc atgacttcga gatcaagccg 540

gtcgcgcccg gcagcacgtc caagctgcgc atgagcatcc tggccaagac ctatcgctac 600

aacgacaagg ggctgaagaa atga                                       624
```

Another exemplary O-linked OST suitable for use in all aspects of the present invention is PglL from *Neisseria meningitidis* (Faridmoayer et al., "Functional Characterization of Bacterial Oligosaccharyltransferases Involved in O-Linked Protein Glycosylation," *J. Bacteriol.* 189(22): 8088-8098 (2007), which is hereby incorporated by reference in its entirety). The amino acid sequence of *N. meningitidis* (UniProtKB Accession No. GlFG65) is provided below as SEQ ID NO: 34:

```
Met Pro Ala Glu Thr Thr Val Ser Gly Ala His Pro Ala Ala Lys Leu
1               5                   10                  15

Pro Ile Tyr Ile Leu Pro Cys Phe Leu Trp Ile Gly Ile Val Pro Phe
            20                  25                  30

Thr Phe Ala Leu Lys Leu Lys Pro Ser Pro Asp Phe Tyr His Asp Ala
        35                  40                  45

Ala Ala Ala Ala Gly Leu Ile Val Leu Leu Phe Leu Thr Ala Gly Lys
    50                  55                  60

Lys Leu Phe Asp Val Lys Ile Pro Ala Ile Ser Phe Leu Leu Phe Ala
65                  70                  75                  80

Met Ala Ala Phe Trp Tyr Leu Gln Ala Arg Leu Met Asn Leu Ile Tyr
                85                  90                  95

Pro Gly Met Asn Asp Ile Val Ser Trp Ile Phe Ile Leu Leu Ala Val
            100                 105                 110

Ser Ala Trp Ala Cys Arg Ser Leu Val Ala His Phe Gly Gln Glu Arg
        115                 120                 125

Ile Val Thr Leu Phe Ala Trp Ser Leu Leu Ile Gly Ser Leu Leu Gln
    130                 135                 140

Ser Cys Ile Val Val Ile Gln Phe Ala Gly Trp Glu Asp Thr Pro Leu
145                 150                 155                 160

Phe Gln Asn Ile Ile Val Tyr Ser Gly Gln Gly Val Ile Gly His Ile
                165                 170                 175

Gly Gln Arg Asn Asn Leu Gly His Tyr Leu Met Trp Gly Ile Leu Ala
            180                 185                 190

Ala Ala Tyr Leu Asn Gly Gln Arg Lys Ile Pro Ala Ala Leu Gly Val
        195                 200                 205

Ile Cys Leu Ile Met Gln Thr Ala Val Leu Gly Leu Val Asn Ser Arg
    210                 215                 220

Thr Ile Leu Thr Tyr Ile Ala Ala Ile Ala Leu Ile Leu Pro Phe Trp
225                 230                 235                 240

Tyr Phe Arg Ser Asp Lys Ser Asn Arg Arg Thr Met Leu Gly Ile Ala
                245                 250                 255

Ala Ala Val Phe Leu Thr Ala Leu Phe Gln Phe Ser Met Asn Thr Ile
            260                 265                 270

Leu Glu Thr Phe Thr Gly Ile Arg Tyr Glu Thr Ala Val Glu Arg Val
        275                 280                 285

Ala Asn Gly Gly Phe Thr Asp Leu Pro Arg Gln Ile Glu Trp Asn Lys
    290                 295                 300

Ala Leu Ala Ala Phe Gln Ser Ala Pro Ile Phe Gly His Gly Trp Asn
305                 310                 315                 320

Ser Phe Ala Gln Gln Thr Phe Leu Ile Asn Ala Glu Gln His Asn Ile
                325                 330                 335
```

-continued

```
Tyr Asp Asn Leu Leu Ser Asn Leu Phe Thr His Ser His Asn Ile Val
            340                 345                 350

Leu Gln Leu Leu Ala Glu Met Gly Ile Ser Gly Thr Leu Leu Val Ala
        355                 360                 365

Ala Thr Leu Leu Thr Gly Ile Ala Gly Leu Leu Lys Arg Pro Leu Thr
    370                 375                 380

Pro Ala Ser Leu Phe Leu Ile Cys Thr Leu Ala Val Ser Met Cys His
385                 390                 395                 400

Ser Met Leu Glu Tyr Pro Leu Trp Tyr Val Tyr Phe Leu Ile Pro Phe
                405                 410                 415

Gly Leu Met Leu Phe Leu Ser Pro Ala Glu Ala Ser Asp Gly Ile Ala
            420                 425                 430

Phe Lys Lys Ala Ala Asn Leu Gly Ile Leu Thr Ala Ser Ala Ala Ile
        435                 440                 445

Phe Ala Gly Leu Leu His Leu Asp Trp Thr Tyr Thr Arg Leu Val Asn
    450                 455                 460

Ala Phe Ser Pro Ala Thr Asp Asp Ser Ala Lys Thr Leu Asn Arg Lys
465                 470                 475                 480

Ile Asn Glu Leu Arg Tyr Ile Ser Ala Asn Ser Pro Met Leu Ser Phe
                485                 490                 495

Tyr Ala Asp Phe Ser Leu Val Asn Phe Ala Leu Pro Glu Tyr Pro Glu
            500                 505                 510

Thr Gln Thr Trp Ala Glu Glu Ala Thr Leu Lys Ser Leu Lys Tyr Arg
        515                 520                 525

Pro His Ser Ala Thr Tyr Arg Ile Ala Leu Tyr Leu Met Arg Gln Gly
    530                 535                 540

Lys Val Ala Glu Ala Lys Gln Trp Met Arg Ala Thr Gln Ser Tyr Tyr
545                 550                 555                 560

Pro Tyr Leu Met Pro Arg Tyr Ala Asp Glu Ile Arg Lys Leu Pro Val
                565                 570                 575

Trp Ala Pro Leu Leu Pro Glu Leu Leu Lys Asp Cys Lys Ala Phe Ala
            580                 585                 590

Ala Ala Pro Gly His Pro Glu Ala Lys Pro Cys Lys
        595                 600
```

Amino acid sequences sharing at least about 70 percent, more preferably at least about 75 percent or 80 percent, most preferably at least about 85 percent or 90 percent or 95 percent as compared to the *N. menigitidis* amino acid sequence of SEQ ID NO: 34 are also suitable for use in the present invention. The nucleic acid sequence encoding the amino acid sequence of SEQ ID NO: 34 (*N. menigitidis* PglL) is provided below as SEQ ID NO: 35 (EMBL Nucleotide Sequence Database No. AEK98518).

```
atgcccgctg aaacgaccgt atccggcgcg caccccgccg ccaaactgcc gatttacatc  60

ctgccctgct tcctttggat aggcatcgtc ccctttacct tcgcgctcaa actgaaaccg 120

tcgcccgact tttaccacga tgccgccgcc gcagccggcc tgattgtcct gttgttcctc 180

acggcaggaa aaaaactgtt tgatgtcaaa atccccgcca tcagcttcct tctgtttgca 240

atggcggcgt tttggtatct tcaggcacgc ctgatgaacc tgatttaccc cggtatgaac 300

gacatcgtct cttggatttt catcttgctc gccgtcagcg cgtgggcctg ccggagcttg 360

gtcgcacact tcggacaaga acgcatcgtg accctgtttg cctggtcgct gcttatcggc 420

tccctgcttc aatcctgcat cgtcgtcatc cagtttgccg gctgggaaga cacccctctg 480

tttcaaaaca tcatcgttta cagcgggcaa ggcgtaatcg gacacatcgg gcagcgcaac 540

aacctcggac actacctcat gtggggcata ctcgccgccg cctacctcaa cggacaacga 600
```

-continued

```
aaaatccccg ccgccctcgg cgtaatctgc ctgattatgc agaccgccgt tttaggtttg  660

gtcaactcgc gcaccatctt gacctacata gccgccatcg ccctcatcct tcccttctgg  720

tatttccgtt cggacaaatc caacaggcgg acgatgctcg gcatagccgc agccgtattc  780

cttaccgcgc tgttccaatt ttccatgaac accattctgg aaacctttac tggcatccgc  840

tacgaaactg ccgtcgaacg cgtcgccaac ggcggtttca cagacttgcc gcgccaaatc  900

gaatggaata aagcccttgc cgccttccag tccgccccga tattcgggca cggctggaac  960

agttttgccc aacaaacctt cctcatcaat gccgaacagc acaacatata cgacaacctc 1020

ctcagcaact tgttcaccca ttcccacaac atcgtcctcc aactccttgc agagatggga 1080

atcagcggca cgcttctggt tgccgcaacc ctgctgacgg gcattgccgg gctgcttaaa 1140

cgccccctga cccccgcatc gcttttccta atctgcacgc ttgccgtcag tatgtgccac 1200

agtatgctcg aatatccttt gtggtatgtc tatttcctca tccctttcgg actgatgctc 1260

ttcctgtccc ccgcagaggc ttcagacggc atcgccttca aaaaagccgc caatctcggc 1320

atactgaccg cctccgccgc catattcgca ggattgctgc acttggactg gacatacacc 1380

cggctggtta acgccttttc ccccgccact gacgacagtg ccaaaaccct caaccggaaa 1440

atcaacgagt tgcgctatat ttccgcaaac agtccgatgc tgtcctttta tgccgacttc 1500

tccctcgtaa acttcgccct gccggaatac cccgaaaccc agacttgggc ggaagaagca 1560

accctcaaat cactaaaata ccgcccccac tccgccacct accgcatcgc cctctacctg 1620

atgcggcaag gcaaagttgc agaagcaaaa caatggatgc gggcgacaca gtcctattac 1680

ccctacctga tgccccgata cgccgacgaa atccgcaaac tgcccgtatg ggcgccgctg 1740

ctacccgaac tgctcaaaga ctgcaaagcc ttcgccgccg cgcccggtca tccggaagca 1800

aaaccctgca aatga                                                 1815
```

As used herein, an "isolated" oligosaccharyltransferase refers to an oligosaccharyltransferase that is substantially pure or substantially separated from other cellular components that naturally accompany the native protein in its natural host cell. Typically, the isolated oligosaccharyltransferase of the present invention is at about 80% pure, usually at least about 90% pure, and preferably at least about 95% pure. Purity can be assessed using any method known in the art, e.g., polyacrylamide gel electrophoresis, HPLC, etc. The isolated oligosaccharyltransferase can be obtained from the organism from which it is derived directly, or it can be recombinantly produced and purified from a host cell as described in the Examples herein or using techniques readily known in the art as described below.

Generally, the use of recombinant expression systems to produce and isolate a protein of interest involves inserting a nucleic acid molecule encoding the amino acid sequence of the desired protein into an expression system to which the molecule is heterologous (i.e., not normally present). One or more desired nucleic acid molecules encoding one or more proteins may be inserted into the vector. When multiple nucleic acid molecules are inserted, the multiple nucleic acid molecules may encode the same or different enzymes. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., Molecular Cloning: A Laboratory Manual (Cold Springs Harbor 1989) and U.S. Pat. No. 4,237,224 to Cohen and Boyer, which are hereby incorporated by reference in its entirety. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize enzyme production. For the purposes of expressing a cloned nucleic acid sequence encoding one or more desired enzymes, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize peptide production, e.g., the Shine-Dalgarno ribosome binding site. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression on a Plasmid Using Recombination In Vitro," *Methods in Enzymology* 68:473-82 (1979), which is hereby incorporated by reference in its entirety.

A nucleic acid molecule encoding an oligosaccharyltransferase or other protein component of the present invention (e.g., glycoprotein target, enzymes involved in glycan production), a promoter molecule of choice, including, without limitation, enhancers, and leader sequences, a suitable 3' regulatory region to allow transcription in the host, and any additional desired components, such as reporter or marker genes, are cloned into the vector of choice using standard cloning procedures in the art, such as described in Joseph Sambrook et al., Molecular Cloning: A Laboratory Manual (Cold Springs Harbor 1989); Frederick M. Ausubel, SHORT Protocols in Molecular Biology (Wiley 1999), and U.S. Pat. No. 4,237,224 to Cohen and Boyer, which are hereby incorporated by reference in their entirety.

Once the nucleic acid molecule encoding the protein or proteins has been cloned into an expression vector, it is ready to be incorporated into a host. Recombinant molecules can be introduced into cells, without limitation, via transfection (if the host is a eukaryote), transduction, conjugation, mobilization, electroporation, lipofection, protoplast fusion, calcium chloride transformation, mobilization, transfection using bacteriophage, or particle bombardment, using standard cloning procedures known in the art, as described by Joseph Sambrook et al., Molecular Cloning: A Laboratory Manual (Cold Springs Harbor 1989), which is hereby incorporated by reference in its entirety.

Suitable host cells for recombinant protein production include both prokaryotic and eukaryotic cells. Suitable prokaryotic host cells include, without limitation, *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix*, sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter sp, Stenotrophomonas* sp., *Micrococcus* sp., *Neisseria* sp., *Bdellovibrio* sp., *Hemophilus* sp., *Klebsiella* sp., *Proteus mirabilis, Enterobacter cloacae, Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobacteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive. In addition to bacteria cells, eukaryotic cells such as mammalian, insect, and yeast systems are also suitable host cells for transfection/transformation of the expression vector for recombinant protein production. Mammalian cell lines available in the art for expression of a heterologous protein or polypeptide include Chinese hamster ovary cells, HeLa cells, baby hamster kidney cells, COS cells and many others.

Purified proteins may be obtained from the host cell by several methods readily known in the art, including ion exchange chromatography, hydrophobic interaction chromatography, affinity chromatography, gel filtration, and reverse phase chromatography. The peptide is preferably produced in purified form (preferably at least about 70 to about 75% pure, or about 80% to 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein can be subjected to gel filtration in an appropriately sized dextran or polyacrylamide column to separate the protein from other cellular components and proteins. If necessary, the protein fraction may be further purified by HPLC.

The oligosaccharyltransferase catalyzes the transfer of a glycan from a lipid donor to an acceptor protein, peptide, or polypeptide. In one embodiment of the present invention, the lipid donor or carrier molecule is a prokaryotic lipid donor, i.e., it is made in a prokaryote or native to the prokaryote. Examples of prokaryotic lipid donors include an undecaprenyl-phosphate and an undecaprenyl phosphate-linked bacillosamine (Weerapana et al., "Investigating Bacterial N-Linked Glycosylation: Synthesis and Glycosyl Acceptor Activity of the Undecaprenyl Pyrophosphate-linked Bacillosamine," *J. Am. Chem. Soc.* 127: 13766-67 (2005), which is hereby incorporated by reference in its entirety). In another embodiment of the present invention, the lipid donor is a eukaryotic lipid donor, i.e., it is made in a eukaryotic cell or native to the eukaryotic cell. An exemplary eukaryotic lipid donor is dolichylpyrophosphate In accordance with this and all aspects of the present invention, the glycan comprises an oligosaccharide or polysaccharide that is linked to a lipid donor molecule. The composition of the glycan component varies in number and type of monosaccharide units that make up the oligosaccharide or polysaccharide chain. The monosaccharide components of a glycan include, but are not limited to, one or more of glucose (Glc), galactose (Gal), mannose (Man), fucose (Fuc), N-acetylgalactosamine (GalNAc), N-acetylglucosamine (GlcNAc), glucorionic acid, xylose, sialic acid (e.g., N-acetyl-neuraminic acid (NeuAc), 6-deoxy-talose, and rhamnose monosaccharides.

In accordance with this and all aspects of the present invention, the glycan can be a prokaryotic, archaea, or eukaryotic glycan. Alternatively, the glycan may comprise a completely unnatural glycan composition.

In one embodiment of the present invention, the glycan is a prokaryotic glycan that is produced by one or more prokaryotic glycosyltransferases. In another embodiment of the present invention, the prokaryotic glycan is produced using a combination of prokaryotic and eukaryotic glycosyltransferases, but has a monosaccharide composition that mimics a prokaryotic glycan structure. In another embodiment of the present invention, the prokaryotic glycan is synthetically produced (Seeberger et al., *Chemical and Enzymatic Synthesis of Glycans and Glycoconjugates*, in Essentials of Glycobiology (A. Varki et al. eds., 2009), which is hereby incorporated by reference in its entirety).

An exemplary prokaryotic glycan is a glycan produced by the glycosyltransferases of the *C. jejuni, C. Coli, C. lari*, or *C. upsaliensis* Pgl gene clusters or a modified *C. jejuni, C. Coli, C. lari*, or *C. upsaliensis* Pgl gene cluster. Genes of the Pgl cluster include wlaA, galE, wlaB, pglH, pglI, pglJ, pglB, pglA, pglC, pglD, wlaJ, pglE, pglF, and pglG (Szymanski and Wren, "Protein Glycosylation in Bacterial Mucosal Pathogens," *Nature Microbiol.* 3:225-237 (2005), which is hereby incorporated by reference in its entirety). A prokaryotic glycan typically comprises the diacetamido-trideoxysugar, bacillosamine (Bac; 2,4-diacetamido-2,4,6-trideoxyglucose). A suitable prokaryotic glycan of this and all aspects of the present invention is a heptasaccharide comprising glucose, N-acetylgalactosamine, and bacillosamine, i.e., $GlcGalNAc_5Bac$.

As described in the Examples herein, the glycan of this and all aspects of the present invention can be recombinantly produced. For example, a modified or unmodified *C. jejuni* pgl gene cluster encoding the enzymes that carry out the biosynthesis of the $GlcGalNac_5Bac$ heptasaccharide and other glycan structures can be isolated and transferred to a suitable host cell for production of a lipid-linked glycan (see also Wacker et al., "N-Linked Glycosylation in *Campylobacter jejuni* and its Functional Transfer into *E. coli," Science* 298(5599): 1790-93 (2002), which is hereby incorporated by reference in its entirety). Pgl gene clusters from other *Campylobacter* species, e.g., *C. coli, C. lari*, and *C. upsaliensis*, are also suitable for recombinant production of glycans for use in all aspects of the present invention (Szymanski and Wren, "Protein Glycosylation in Bacterial Mucosal Pathogens," *Nature Microbiol.* 3:225-237 (2005), which is hereby incorporated by reference in its entirety). Additionally, similar Pgl-like glycosylation gene loci have been identified in *Wolinella succinogens, Desulfovibrio desulfuricans*, and *D. vulgaris* that are also suitable for recombinant production of glycans for the present invention (Baar et al., "Complete Genome Sequence and Analysis of *Wolinella succinogenes," Proc. Natl. Acad. Sci. USA* 100: 11690-11695 (2003) and Szymanski and Wren, "Protein Glycosylation in Bacterial Mucosal Pathogens," *Nature Microbiol.* 3:225-237 (2005), which are hereby incorporated by reference in their entirety).

The Pgl gene cluster may be modified to enhance lipid-linked glycan production, accumulation, and isolation in the host cell. For example, inactivation of the oligosaccharyltransferase component of the gene cluster (e.g., the pglB gene in the pgl gene cluster) is desirable to prevent transfer of the lipid-linked glycan to a glycoprotein target of the host cell. Additionally, in some embodiments of the present invention, it may be desirable to attenuate, disrupt, or delete competing glycan biosynthesis reactions of the host cell. In particular, inactivation of host cell glycosyltransferase enzymes (N-linked or O-linked reaction enzymes) or other enzymes involved in the transfer or ligation of a glycan to acceptor moieties of the host cell may also be desirable. For instance, when *E. coli* is utilized as the host cell, deletion of the WaaL enzyme which transfers glycans from the undecaprenyl lipid carrier onto lipid A, which in turn shuttles the oligosaccharides to the outer leaflet of the outer membrane, will ensure that the recombinantly produced lipid-linked glycans accumulate in the inner membrane. Other *E. coli* host cell glycosylation related enzymes that may be deleted, disrupted, or modified include, without limitation, wecA, wbbL, glcT, glf, gafT, wzx, wzy, and enzymes of the O16 antigen biosynthesis pathway.

In another embodiment of the present invention, the glycan is a eukaryotic glycan, i.e., a glycan produced by one or more eukaryotic glycosyltransferases. In one embodiment, of the present invention, a eukaryotic glycan is produced by only eukaryotic glycosyltransferases. In another embodiment of the present invention, the eukaryotic glycan is produced using a combination of both eukaryotic and prokaryotic glycosyltransferase enzymes, but mimics eukaryotic glycan structure. In another embodiment of the present invention, the eukaryotic glycan is synthetically produced (Seeberger et al., *Chemical and Enzymatic Synthesis of Glycans and Glycoconjugates*, in Essentials of Glycobiology (A. Varki et al. eds., 2009), which is hereby incorporated by reference in its entirety).

In one embodiment, the eukaryotic glycan comprises a $GlcNAc_2$ core. The $GlcNac_2$ core may further comprise at least one mannose residue. Suitable eukaryotic glycan structures may comprise, but are not limited to, $Man_1GlcNAc_2$, $Man_2GlcNAc_2$, and $Man_3GlcNAc_2$.

As described above, the eukaryotic lipid-linked glycan can be recombinantly produced by introducing one or more eukaryotic glycosyltransferase enzymes in a suitable host cell. A eukaryotic glycosyltransferase as used herein refers to an enzyme that catalyzes the transfer of a sugar reside from a donor substrate, e.g. from an activated nucleotide sugar, to an acceptor substrate, e.g., a growing lipid-linked oligosaccharide chain. Suitable glycosyltransferase enzyme that can be utilized in host cells to facilitate the recombinant production of a eukaryotic lipid-linked glycan of the system include, without limitation, galactosyltransferases (e.g., β1,4-galactosyltransferase, β1,3-galactosyltransferase), fucosyltransferases, glucosyltransferases, N-acetylgalactosaminyltransferases (e.g., GalNAcT, GalNAc-T1, GalNAc-T2, GalNAc-T3), N-acetylglucosaminyltransferases (e.g., β-1,2-N-acetylglucosaminyltransferase I (GnTI-), GnT-II, GnT-III, GnT-IV, GnT-V, GnT-Vl, and GvT-IVH), glucuronyltransferases, sialytransferases (e.g., α(2,3)sialyltransferase, α-N-acetylgalactosaminide α-2,6-sialytransferase I, Galβ1,3GalNAc α2,3-sialyltransferase, β galactoside-α-2,6-sialyltransferaase, and α2,8-sialyltransferase), mannosyltransferases (e.g., α-1,6-mannosyltransferase, α-1,3-mannosyltransferase, β-1,4-mannosyltransferase), glucuronic acid transferases, galacturonic acid transferases, and the like. The aforementioned glycosyltransferase enzymes have been extensively studied in a variety of eukaryotic systems. Accordingly, the nucleic acid and amino acid sequences of these enzymes are known and readily available to one of skill in the art. Additionally, many of these enzymes are commercially available (e.g., Sigma-Aldrich, St. Louis, Mo.).

Suitable host cells for the production of a prokaryotic or eukaryotic lipid-linked glycan include both prokaryotic host cells and eukaryotic cells. An exemplary list of suitable host cells is provided supra. When utilizing eukaryotic glycosyltransferases in prokaryotic host cells, the nucleotide sequences of the eukaryotic glycosyltransferases can be codon optimized to overcome limitations associated with the codon usage bias between *E. coli* (and other bacteria) and higher organisms, such as yeast and mammalian cells. Codon usage bias refers to differences among organisms in the frequency of occurrence of codons in protein-coding DNA sequences (genes). A codon is a series of three nucleotides (triplets) that encodes a specific amino acid residue in a polypeptide chain. Codon optimization can be achieved by making specific transversion nucleotide changes, i.e. a purine to pyrimidine or pyrimidine to purine nucleotide change, or transition nucleotide change, i.e. a purine to purine or pyrimidine to pyrimidine nucleotide change.

In accordance with this and all aspects of the present invention, a "glycoprotein target" includes any peptide, polypeptide, or protein that comprise one or more glycan acceptor amino acid residues. Typically glycan acceptor residues comprise an asparagine (N or Asn) to form an N-linked glycoprotein, or hydroxyl oxygen on the side chain of hydroxylysine, hydroxyproline, serine, threonine, or tyrosine to form an O-linked glycoprotein. A wide variety of glycoprotein targets exist including, without limitation, structural molecules (e.g., collagens), lubricant and protective agents (e.g., mucins), transport proteins (e.g., transferrin), immunological proteins (immunoglobulins, histocompatibility antigens), hormones, enzymes, cell attachment recognition sites, receptors, protein folding chaperones, developmentally regulated proteins, and proteins involved in hemostasis and thrombosis. Therapeutic proteins, such as antibodies are important glycoprotein targets of the system of the present invention.

According to this and all aspect of the present invention, the one or more oligosaccharide acceptor residues of the glycoprotein target may be an asparagine (N or Asn) residue. The asparagine residue is positioned within a glycosylation consensus sequence comprising N-$X_1$-S/T (eukaryotic consensus sequence) or D/E-$X_1$-N-$X_2$-S/T (SEQ ID NO: 1) (prokaryotic consensus sequence) where D is aspartic acid, $X_1$ and $X_2$ are any amino acid other than proline, N is asparagine, and T is threonine.

The glycoprotein target according to this and all aspects of the present invention can be a purified protein, peptide, or polypeptide comprising the requisite glycan acceptor residues. Alternatively, the glycoprotein target can be in the form of an isolated nucleic acid molecule encoding the glycoprotein target. In accordance with this embodiment of the present invention, the system further includes reagents suitable for synthesizing the glycoprotein target from said nucleic acid molecule, i.e., translation reagents.

Reagents for synthesizing proteins from nucleic acid molecules in vitro (i.e., in a cell-free environment) are well known in the art. These reagents or systems typically consist of extracts from rabbit reticulocytes, wheat germ, and *E. coli*. The extracts contain all the macromolecule components necessary for translation of an exogenous RNA molecule, including, for example, ribosomes, tRNAs, aminoacyl-tRNA synthetases, initiation, elongation, and termination factors. The other required components of the system include amino acids, energy sources (e.g., ATP, GTP), energy regenerating systems (creatine phosphate and creatine phosphokinase for eukaryote systems, and phosphoenol pyruvate and pyruvate kinase for prokaryote systems), and other cofactors (e.g., $Mg^{2+}$, $K^+$, etc.). If the nucleic acid molecule encoding the glycoprotein target is a DNA molecule, the cell-free translation reaction is coupled or linked to an initial transcription reaction that utilizes a RNA polymerase.

Another aspect of the present invention is directed to a kit comprising an isolated oligosaccharyltransferase capable of transferring a glycan from a lipid carrier molecule to a glycoprotein target, and one or more isolated glycans, wherein each glycan is linked to a lipid carrier molecule.

In accordance with this aspect of the present invention, the isolated oligosaccharyltransferase of the kit may be a purified protein or may be in the form of a nucleic acid encoding the oligosaccharyltransferase. The nucleic acid molecule can be a DNA or RNA molecule, and it can be linearized (naked) or circularized (housed in an expression vector). Exemplary prokaryotic, archaea, and eukaryotic oligosaccharyltransferases are described supra.

As described supra, the one or more glycans are linked to a lipid carrier molecule (e.g., an undecaprenol-pyrophosphate, an undecaprenyl pyrophosphate-linked bacillosamine, or a dolichylpyrophosphate). The glycan may comprise a prokaryotic, archaea, eukaryotic, or completely unnatural synthetic glycan as also described supra. Suitable prokaryotic core glycan structures comprise a heptasaccharide containing glucose, N-acetylgalactosamine, and optionally bacillosamine (e.g., $GlcGalNAc_5Bac$). Suitable eukaryotic glycan core structures comprises N-acetylglucosamine and mannose (e.g., $Man_1GlcNAc_2$, $Man_2GlcNAc_2$, and $Man_3GlcNAc_2$).

In one embodiment of this aspect of the present invention, the one or more isolated glycans linked to a lipid carrier molecule of the kit are in an assembled and purified form. Alternatively, the kit of the present invention comprises one or more nucleic acid molecules encoding one or more eukaryotic and/or prokaryotic glycosyltransferase enzymes, and host cells (eukaryotic or prokaryotic) that contain a polyisoprenyl pyrophosphate glycan carrier and are capable of expressing the one or more nucleic acid molecules. In accordance with this embodiment, the kit may further contain instructions for recombinantly producing and isolating the lipid-linked glycan in the host cells prior to use with the other kit components.

The kit of the present invention may further include in vitro or cell-free transcription and/or translation reagents for synthesizing the oligosaccharyltransferase and/or a glycoprotein, peptide or polypeptide of choice.

Another aspect of the present invention relates to a method for producing a glycosylated protein in a cell-free system. This method involves providing an isolated oligosaccharyltransferase capable of transferring a glycan from a lipid carrier molecule to a glycoprotein target, providing one or more isolated glycans, wherein each glycan is linked to a lipid carrier molecule, and providing a glycoprotein target comprising one or more glycan acceptor amino acid residues. This method further involves combining the oligosaccharyltransferase, one or more isolated glycans, and glycoprotein target to form a cell-free glycosylation reaction mixture, and subjecting the cell-free glycosylation reaction mixture to conditions effective for the oligosaccharyltransferase to transfer the glycan from the lipid carrier molecule to the one or more glycan acceptor residues of the glycoprotein target to produce a glycosylated protein.

The components of the method of the present invention, i.e., the oligosaccharyltransferase, isolated glycans linked to a lipid carrier molecule, and glycoprotein target are described in detail supra.

The method of the present invention may comprise one or more additional steps. For example, glycoprotein target translation may be coupled with glycosylation by providing reagents suitable for synthesizing a glycoprotein target from a nucleic acid molecule. In this embodiment of the present invention, the nucleic acid molecule encoding the glycoprotein target, the translation reagents, oligosaccharyltransferase, isolated glycans are all combined to form a translation-glycosylation reaction mixture. The glycoprotein target is then synthesized from the target nucleic acid molecule prior to or concurrent with the glycosylation reaction.

EXAMPLES

Materials and Methods for Examples 1-4

Protein Purification.

For the purification of CjPglB, E. strain C43(DE3) (Lucigen, Middleton, Wis.) was freshly transformed with plasmid pSN18 (Kowarik et al., "N-Linked Glycosylation of Folded Proteins by the Bacterial Oligosaccharyltransferase," Science 314:1148-1150 (2006), which is hereby incorporated by reference in its entirety), a modified pBAD expression plasmid encoding *C. jejuni* pglB with a C-terminal decahistidine affinity tag. Cells were grown in 1.5 L of terrific Broth supplemented with 100 μg/mL of ampicillin at 37° C. When the optical density (A600) of the culture reached 1.0, cells were induced by the addition of 0.02% arabinose (w/v) for 4.5 h at 30° C. All following steps were performed at 4° C. unless specified differently. Cells were harvested by centrifugation, resuspended in 25 mM Tris, pH 8.0, and 250 mM NaCl and lysed by three passages through a French press (SLM-Aminco; 10,000 PSI, SLM Instruments, Inc., Urbana, Ill.). Following the removal of cell debris by centrifugation, the membrane fraction was isolated by ultracentrifugation at 100,000×g for 1 h. Membranes containing PglB were resuspended in 25 mM Tris-HCl, pH 8.0, 250 mM NaCl, 10% glycerol (v/v) and 1% DDM (w/v) (DDM, Anatrace, Affymetrix, Inc., Santa Clara, Calif.) and incubated for 2 h. The insoluble fraction was removed by ultracentrifugation at 100,000×g for 1 h. All subsequent buffers contained DDM as the detergent. The solubilized membranes were supplemented with 10 mM imidazole, loaded onto a Ni-NTA superflow affinity column (Qiagen, Valencia, Calif.) and washed with 60 mM imidazole before PglB was eluted with 200 mM imidazole. The purified protein was then injected onto a SUPERDEX® 200 gel filtration column using AKTA-FPLC (GE Healthcare, Waukesha, Wis.). Eluate fractions were subjected to sodium dodecyl sulfate-polyacrylamide gel electrophoresis (SDS-PAGE) and stained with Coomassie blue to identify the fractions containing PglB (FIG. 2). The protein was desalted with a PD10 desalting column (GE Healthcare) into 20 mM Tris, pH 7.5, 100 mM NaCl, 5% glycerol (w/v) and 0.05% DDM (w/v) and concentrated to 5-10 mg/mL in an Amicon centricon with a molecular mass cutoff of 100 kDa. Expression and purification of the inactive CjPglB mutant was performed identically except C43(DE3) cells carrying plasmid pSN18.1, which encodes an inactive copy of pglB subcloned from pACYCpglmut (see below) were used. ClPglB was purified from BL2-Gold(DE3) cells (Stratagene, La Jolla, Calif.) carrying plasmid pSF2 as described elsewhere (Lizak et al., "X-ray Structure of a Bacterial Oligosaccharyltransferase," *Nature* 474:350-355 (2011), which is hereby incorporated by reference in its entirety). For long-term storage at −20° C., the glycerol content in PglB samples was increased to 10% (w/v). Purification of AcrA and scFv13-R4-GT was from periplasmic fractions isolated from BL21(DE3) cells carrying plasmid pET24(AcrA-per) (Nita-Lazar et al., "The N-X-S/T Consensus Sequence is Required but not Sufficient for Bacterial N-Linked Protein Glycosylation," *Glycobiology* 15:361-367 (2005), which is hereby incorporated by reference in its entirety) or pET24-ssDsbAscFv13-R4-GT (see below). Periplasmic extracts were prepared as described previously (Schwarz et al., "Relaxed Acceptor Site Specificity of Bacterial Oligosaccharyltransferase in Vivo," *Glycobiology* 21:45-54 (2011), which is hereby incorporated by reference in its entirety), supplemented with imidazole to reach a final concentration of 10 mM, sterile filtered (0.22 μm), and purified by nickel affinity chromatography using Ni-NTA superflow affinity column (Qiagen, Valencia, Calif.).

Isolation of Lipid-Linked Glycans.

*Escherichia coli* SCM6 cells transformed with pACYCpglmut (Wacker et al., "N-Linked Glycosylation in *Campylobacter jejuni* and its Functional Transfer Into *E. coli,*" *Science* 298:1790-1793 (2002), which is hereby incorporated by reference in its entirety), which codes for the biosynthesis of the *C. jejuni* LLO and an inactivated *C. jejuni* pglB gene (W458A and D459A), were grown in 1 L of Luria-Burtani supplemented with 25 μg/mL of chloramphenicol at 37° C. When the A600 reached ~1.0, cells were harvested by centrifugation and the pellet was lyophilized to dryness for 20 h at −80° C. and 0.04 mbar. All subsequent steps were performed using glass tubes and glass pipettes. Homogenized pellets were extracted in 25 mL of 10:20:3 $CHCl_3$:MeOH:$H_2O$ followed by centrifugation at 3000×g for 30 min. The supernatants were evaporated using a rotary evaporator (Büchi, Flawil, Sankt Gallen, Switzerland), after which the resulting pellet was resuspended in 1 mL of 10:20:3 $CHCl_3$:MeOH:$H_2O$ and sonicated until homogenous. The sample was dried under nitrogen gas at 37° C., dissolved in 10 mM HEPES (4-(2-hydroxyethyl)-1-piperazineethanesulfonic acid), pH 7.5, 1 mM MnCl2 and 0.1% DDM (w/v) and stored at −20° C. An identical procedure was followed to extract lipids from SCM6 cells carrying empty pACYC.

Cell-Free Translation and Glycosylation.

For in vitro glycosylation of purified acceptor proteins, a 50 μL solution containing 3 μg of purified PglB, 5-10 μL of extracted LLOs and 5 μg of purified AcrA or scFv13-R4-GT in 10 mM HEPES, pH 7.5, 1 mM $MnCl_2$ and 0.1% DDM (w/v) was incubated for 12 h at 30° C. For in vitro translation of AcrA and scFv13-R4-GT in the absence of glycosylation, a 50 μL reaction was prepared using the S30 T7 High-Yield Expression System (Promega, Fitchburg, Wis.) or PUREXPRESS® (New England Biolabs, Ipswich, Mass.) according to the manufacturer's instructions. A total of 1 μg of the following plasmids were added to each reaction: pET24b (Novagen, Madison, Wis.); pET24-AcrA encoding full-length *C. jejuni* AcrA with a C-terminal hexahistidine tag (Nita-Lazar et al., "The N-X-S/T Consensus Sequence is Required but not Sufficient for Bacterial N-Linked Protein Glycosylation," *Glycobiology* 15:361-367 (2005), which is hereby incorporated by reference in its entirety); pET24 (AcrA-per) encoding a version of AcrA with an N-terminal PelB signal peptide in place of its native export signal (Nita-Lazar et al., "The N-X-S/T Consensus Sequence is Required but not Sufficient for Bacterial N-Linked Protein Glycosylation," *Glycobiology* 15:361-367 (2005), which is hereby incorporated by reference in its entirety); pET24 (AcrA-cyt) encoding a version of AcrA without an N-terminal export signal (ΔssAcrA) (Nita-Lazar et al., "The N-X-S/T Consensus Sequence is Required but not Sufficient for Bacterial N-Linked Protein Glycosylation," *Glycobiology* 15:361-367 (2005), which is hereby incorporated by reference in its entirety), and pET24-ssDsbA-scFv13-R4-GT encoding the expression-optimized scFv13-R4 intrabody gene (Martineau et al., "Expression of an Antibody Fragment at High Levels in the Bacterial Cytoplasm," *J. Mol. Biol.* 280:117-127 (1998), which is hereby incorporated by reference in its entirety) with an N-terminal signal peptide from *E. coli* DsbA for secretion and a C-terminal GT (Fisher et al., "Production of Secretory and Extracellular N-Linked Glycoproteins in *Escherichia coli*," *Appl. Environ. Microbiol.* 77:871-881 (2011), which is hereby incorporated by reference in its entirety) followed by a FLAG and a hexahistidine epitope tag. For in vitro translation/glycosylation reactions, 50 μL of translation reactions was supplemented with 3 μg purified PglB, 5 μL extracted LLOs, 1 μg purified plasmid DNA, 1 mM $MnCl_2$ and 0.1% DDM (w/v) and incubated for 12 h at 30° C. DDM was chosen for in vitro translation/glycosylation because it was previously observed to be well tolerated in an *E. coli*-derived CFE system (Klammt et al., "Evaluation of Detergents for the Soluble Expression of Alpha-Helical and Beta-Barrel-Type Integral Membrane Proteins by a Preparative Scale Individual Cell-Free Expression System," *Febs J.* 272:6024-6038 (2005), which is hereby incorporated by reference in its entirety).

Western Blot Analysis.

Expression and glycosylation of AcrA and scFv13-R4-GT was analyzed by immunoblot following SDS-PAGE. Immunodetection was performed with monoclonal anti-His antibody (Qiagen, Valencia, Calif.), monoclonal anti-FLAG antibody (Abcam, Cambridge, Mass.), polyclonal anti-AcrA serum (Wacker et al., "N-Linked Glycosylation in *Campylobacter jejuni* and its Functional Transfer Into *E. coli*," *Science* 298:1790-1793 (2002), which is hereby incorporated by reference in its entirety) and polyclonal anti-glycan serum hR6. All in vitro translation samples were treated with RNase A (Roche Diagnostics GmbH, Mannheim, Germany) prior to SDS-PAGE to reduce the irregularity of gel electrophoresis due to excess RNA. All experiments were performed at least in triplicate, and representative samples are shown.

Example 1

Preparation of N-Linked Glycosylation Components

Figures 2A, 2B:
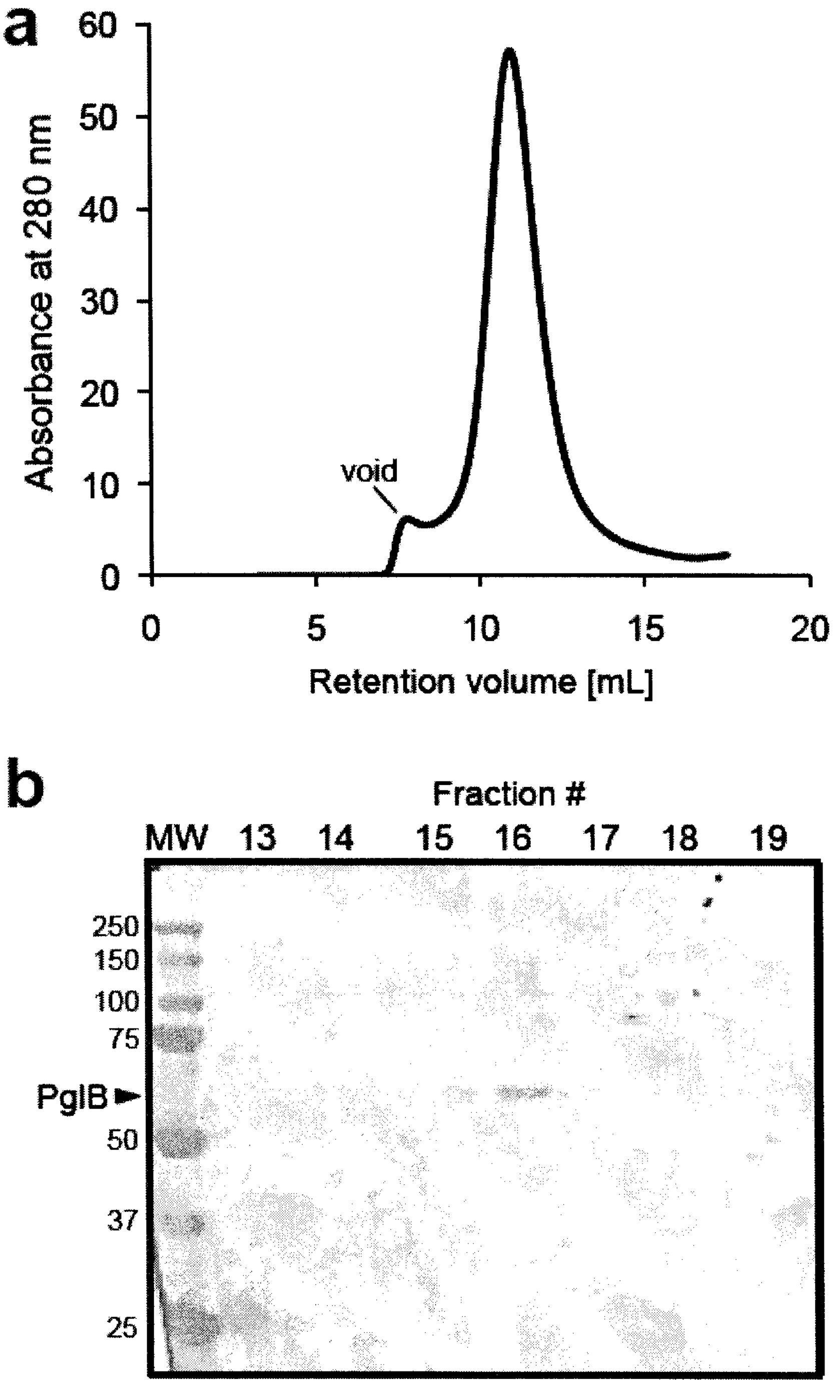
FIGS. 2A-2B show the purification of bacterial OST. CjPglB was expressed in *E. coli* C43(DE3) cells and purified to near homogeneity. Elution fractions (as indicated) from gel filtration columns were examined by SDS-PAGE, and the Coomassie Blue-stained gel images (FIG. 2B) are shown together with the elution profiles (FIG. 2A). MW, molecular weight standard.

To begin, functional reconstitution of bacterial N-linked glycosylation in vitro was attempted. Minimally, this required three components: an OST, a lipid-linked oligosaccharide (LLO) (i.e., a lipid-linked glycan) and an acceptor protein carrying the D/E-$X_1$-N-$X_2$-S/T motif. For the OST, CjPglB was expressed in the membrane fraction of *E. coli* cells, solubilized with 1% N-dodecyl-β-D-maltopyranoside (DDM) and purified to near homogeneity by nickel affinity chromatography followed by gel filtration (FIG. 2B). Separately, *E. coli* cells carrying the *C. jejuni* pgl locus were used for producing the oligosaccharide donor. This gene cluster encodes enzymes that carry out the biosynthesis of a GlcGalNAc5Bac heptasaccharide (where Bac is bacillosamine) and its transfer from membrane-anchored undecaprenylpyrophosphate (UndPP) to asparagine residues. Here, a modified version of this cluster that carried an inactivated PglB gene (Wacker et al., "N-Linked Glycosylation in *Campylobacter jejuni* and its Functional Transfer Into *E. coli*," *Science* 298:1790-1793 (2002), which is hereby incorporated by reference in its entirety) was transferred to *E. coli* SCM6 cells and used to prepare LLOs. SCM6 cells were chosen for several reasons. First, these cells lack the WaaL enzyme that naturally transfers oligosaccharides (e.g. O-antigens, glycans) from the lipid carrier undecaprenyl onto lipid A, which in turn shuttles the oligosaccharides to the outer leaflet of the outer membrane (Feldman et al., "Engineering N-Linked Protein Glycosylation With Diverse 0 Antigen Lipopolysaccharide Structures in *Escherichia coli*," *Proc. Nat'l. Acad. Sci. U.S.A.* 102:3016-3021 (2005), which is hereby incorporated by reference in its entirety). Thus, in the absence of WaaL, the desired lipid-linked glycans accumulate in the inner membrane. Second, the lipopolysaccharide and enterobacterial common antigen initiating GlcNAc transferase, WecA, is removed. Thus, this strain should only produce LLOs with GlcGalNAc5Bac at the reducing end. In support of this notion, previous mass spectrometry analysis of LLOs extracted from an *E. coli* strain similar to the one used here (i.e. ΔwaaL ΔwecA) revealed that only LLOs containing GlcGalNAc5Bac heptasaccharide were detected (Reid et al., "Affinity-Capture Tandem Mass Spectrometric Characterization of Polyprenyl-Linked Oligosaccharides: Tool to Study Protein N-Glycosylation Pathways," *Anal. Chem.* 80:5468-5475 (2008), which is hereby incorporated by reference in its entirety). For the oligosaccharide acceptor, the model glycoprotein AcrA from *C. jejuni* (Nita-Lazar et al., "The N-X-S/T Consensus Sequence is Required but not Sufficient for Bacterial N-Linked Protein Glycosylation," *Glycobiology* 15:361-367 (2005), which is hereby incorporated by reference in its entirety) was purified from the periplasm. AcrA presents two consensus D/E-$X_1$-N-$X_2$-S/T sites that are glycosylated by CjPglB (Kowarik et al., "Definition of the Bacterial N-Glycosylation Site Consensus Sequence," *EMBO J.* 25:1957-1966 (2006), which is hereby incorporated by reference in its entirety). Alternatively, a glycoengineered single-chain variable fragment (scFv) called scFv13-R4-GT, which carried a C-terminal glycosylation tag (GT) consisting of four consecutive DQNAT motifs separated from one another by consecutive glycine residues (Fisher et al., "Production of Secretory and Extracellular N-Linked Glycoproteins in *Escherichia coli*," *Appl. Environ. Microbiol.* 77:871-881 (2011), which is hereby incorporated by reference in its entirety), was similarly purified.

Example 2

Figures 3A, 3B, 3C:
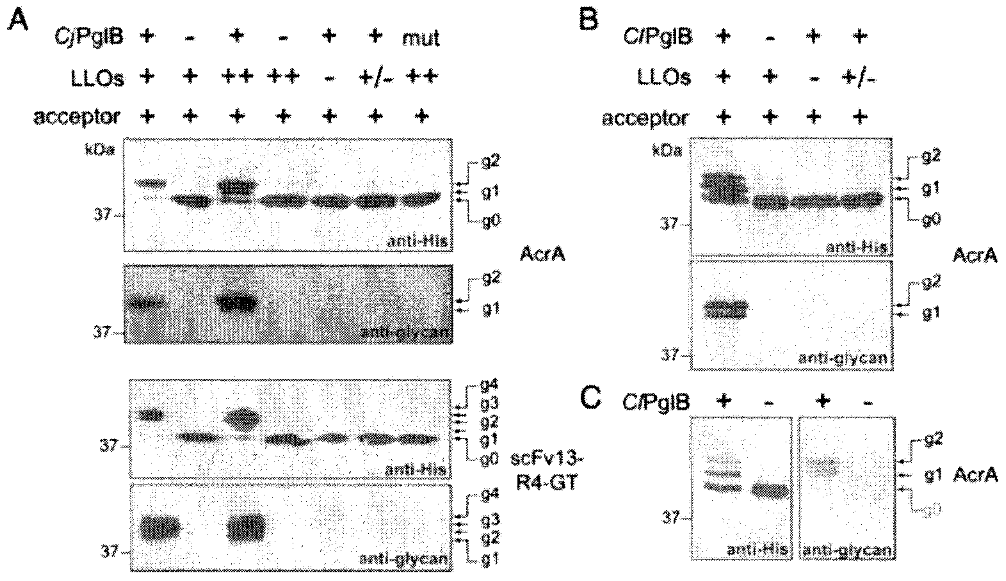
FIGS. 3A-3C show reconstituted glycosylation with defined components.

Functional Reconstitution In Vitro of the *C. jejuni* Protein Glycosylation Pathway To evaluate the reconstituted glycosylation pathway, CjPglB OST was combined with LLOs extracted from *E. coli* cells and purified AcrA. This reaction resulted in efficient glycosylation of both AcrA sites as evidenced by the mobility shift of nearly all of the AcrA from the unmodified (g0) to the fully glycosylated (g2) form (FIG. 3A). This activity was dependent on PglB and LLOs. Doubling the LLO concentration resulted in the appearance of the g0 and g1 forms of AcrA, in addition to g2, suggesting slightly less efficient glycosylation. Importantly, glycosylation activity was lost when lipid extracts from cells lacking the pgl cluster or an inactive CjPglB mutant was used (FIG. 3A). These results were corroborated by detecting glycosylated AcrA with serum specific for the *C. jejuni* N-glycan (FIG. 3A). Nearly identical results were observed when the glycoengineered scFv13-R4-GT protein was used as the oligosaccharide acceptor (FIG. 3A). It should be noted that g2, g3 and g4 were the predominant glycoforms detected here, with barely detectable levels of g1. To demonstrate that other OSTs could be used in this system, in vitro glycosylation of AcrA was also performed using *Campylobacter lari* PglB (ClPglB), which is 56% identical to that of *C. jejuni* (Schwarz et al., "Relaxed Acceptor Site Specificity of Bacterial Oligosaccharyltransferase in Vivo," *Glycobiology* 21:45-54 (2011), which is hereby incorporated by reference in its entirety). This resulted in nearly equal amounts of the g0, g1 and g2 forms of AcrA under the conditions tested (FIG. 3B). To be useful for translation/glycosylation reactions, the purified glycosylation components must tolerate long-term storage and freeze-thaw cycles. To test this, the components were stored separately at −20° C. for 3 months. No changes were made to the storage buffers except that the final concentration of glycerol in the PglB samples was increased to 10%. Each of the components was thawed and refrozen 5-10 times during this period, after which an in vitro reaction with ClPglB was performed. This reaction yielded the glycosylation of AcrA that appeared to be only slightly less efficient than the glycosylation observed with freshly purified components (compare FIGS. 3B and 3C).

Example 3

Cell-Free Translation of Protein Targets

Figures 4A, 4B:
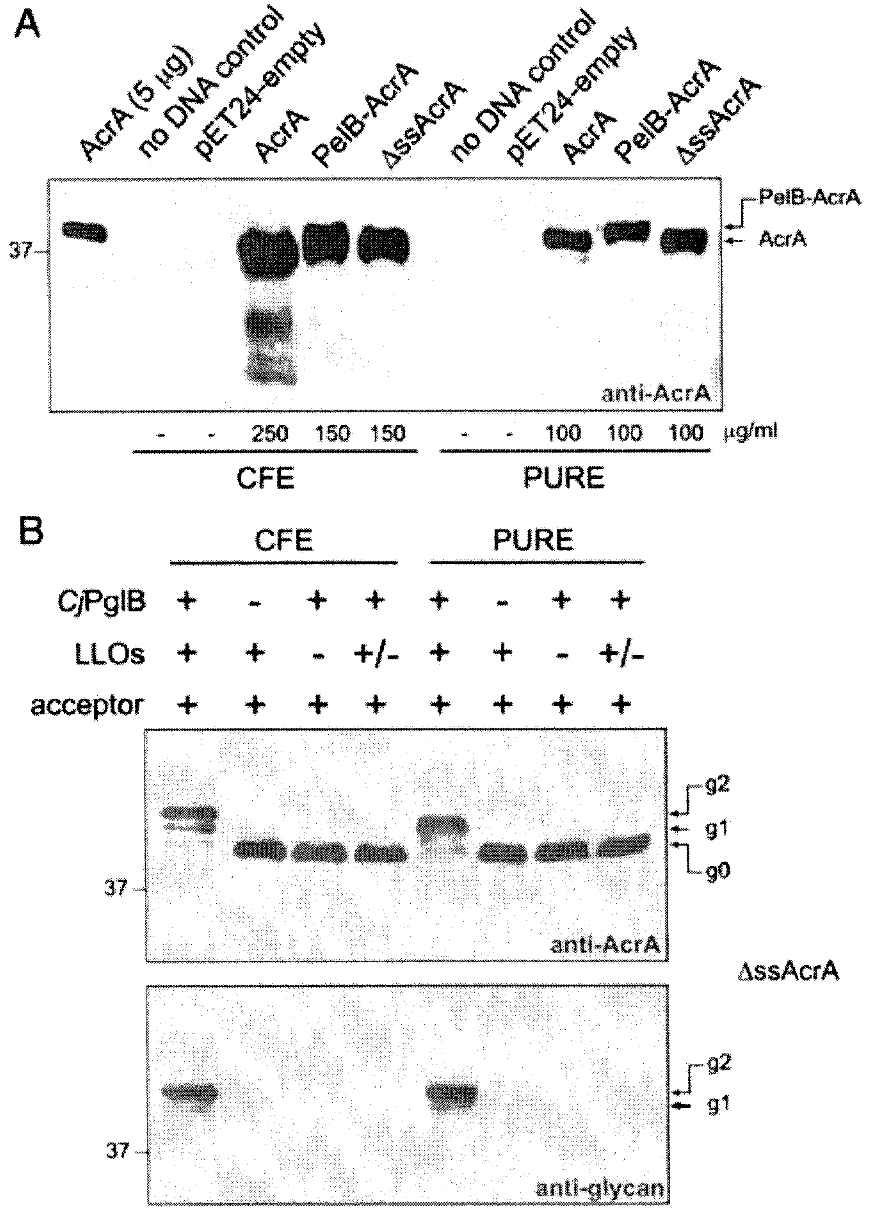
FIGS. 4A-4B demonstrate the cell-free translation/glycosylation of AcrA.
Figures 5A, 5B:
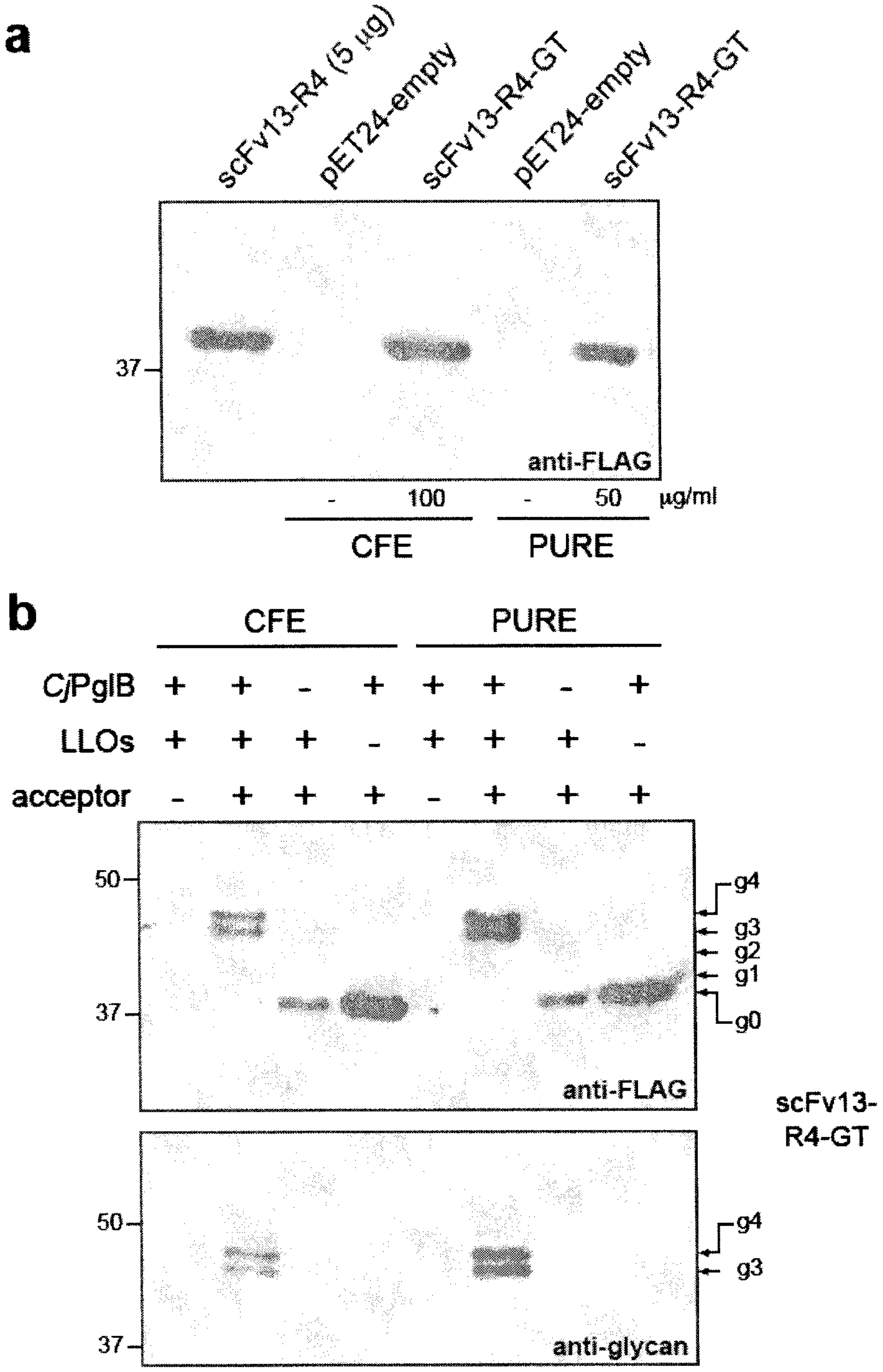
FIGS. 5A-5B depict the cell-free translation/glycosylation of scFv13-R4-GT.

To determine whether existing cell-free translation systems could synthesize protein targets of interest, both an *E. coli* CFE-based protein synthesis system and the PURE (protein synthesis using recombinant elements) system that uses purified translation components and T7 RNA polymerase (Shimizu et al., "Cell-Free Translation Reconstituted With Purified Components," *Nat. Biotechnol.* 19:751-755 (2001), which is hereby incorporated by reference in its entirety) were evaluated. This involved priming the CFE and PURE systems with three different AcrA DNA sequences cloned in a T7 promoter-driven pET vector. Using the CFE system, ~150-250 ng/mL of each AcrA variant was produced as a full-length polypeptide in 1 h (FIG. 4A). AcrA carrying its native signal peptide accumulated to the highest level but also experienced the greatest amount of degradation. In contrast, AcrA carrying a PelB signal peptide in place of the native signal and AcrA lacking a signal peptide each accumulated to a slightly lower concentration but experienced no visible degradation. The PURE system similarly produced all three AcrA variants as full-length polypeptides albeit at a slightly lower level (~100 μg/mL/h of each) than the CFE-based system (FIG. 4A). Both systems were also able to generate appreciable amounts of scFv13-R4-GT (FIG. 5A). It should be noted that this scFv was previously optimized for expression under nonoxidizing conditions (i.e., in the absence of disulfide bonds) (Martineau et al., "Expression of an Antibody Fragment at High Levels in the Bacterial Cytoplasm," *J. Mol. Biol.* 280:117-127 (1998), which is hereby incorporated by reference in its entirety) and thus did not require special transcription/translation conditions.

Example 4

Cell-Free Translation and Glycosylation of Target Glycoproteins

Encouraged by these results, the glycoCFE, and glycoPURE translation/glycosylation systems were constructed by combining the purified glycosylation components (minus the acceptor protein) with one of the cell-free translation systems. The plasmid pET24(AcrA-cyt) that encodes AcrA without an N-terminal signal peptide was chosen to evaluate these systems because it gave rise to significant amounts of target protein in both translation systems with no detectable degradation. When either the CFE or the PURE system were primed with this plasmid along with CjPglB and LLOs, AcrA was produced primarily as the doubly glycosylated g2 glycoform with lesser amounts of g1 and virtually no detectable unmodified AcrA (FIG. 4B). It was estimated that ~100-150 μg of glycosylated AcrA was produced in a 1 mL reaction volume after 12 h. Likewise, scFv13-R4-GT was efficiently produced by both the glycoCFE and glycoPURE systems, with ~50% of the protein in the fully glycosylated g4 form and 50% in the g3 form (FIG. 5B). Both systems produced ~50-100 μg/mL of glycosylated scFv13-R4-GT in 12 h. Thus, the glycoCFE and glycoPURE systems contain all the components essential for efficiently translating N-linked glycoproteins.

Discussion of Examples 1-4

A major advantage of the open prokaryote-based translation/glycosylation systems developed here is that the supply of purified glycosylation components as well as their substrates and cofactors (Lizak et al., "X-ray Structure of a Bacterial Oligosaccharyltransferase," *Nature* 474:350-355 (2011), which is hereby incorporated by reference in its entirety) can be provided at precise ratios. Likewise, the concentration of inhibitory substances such as proteases and glycosidases that catalyze the hydrolysis of glycosidic linkages can be reduced or eliminated entirely. Additionally, the in vitro systems permit the introduction of components that may be incompatible with in vivo systems such as certain LLOs that cannot be produced or flipped in vivo. This level of controllability is unavailable in any previous translation/glycosylation system and is significant for several reasons. First, it helps to avoid glycoprotein heterogeneity, which is particularly bothersome in fundamental studies to assess the contribution of specific glycan structures or in pharmaceutical glycoprotein production. Along these lines, the glycoCFE and glycoPURE systems should allow the examination of factors that interact with or stimulate the glycosylation machinery and promote increased acceptor site occupancy. While the glycosylation efficiency observed here with CjPglB exceeded the level typically observed in vivo (Kowarik et al., "N-Linked Glycosylation of Folded Proteins by the Bacterial Oligosaccharyltransferase," *Science* 314:1148-1150 (2006); Kowarik et al., "Definition of the Bacterial N-Glycosylation Site Consensus Sequence," *EMBO J.* 25:1957-1966 (2006); Fisher et al., "Production of Secretory and Extracellular N-Linked Glycoproteins in *Escherichia coli,*" *Appl. Environ. Microbiol.* 77:871-881 (2011), which are hereby incorporated by reference in their entirety), it should be pointed out that further study of the reaction conditions should lead to increases in productivity and glycosylation efficiency. Second, it facilitates the integration/co-activation of multiple complex metabolic systems and pathways in vitro including transcription, translation, protein folding and glycosylation. Therefore, the glycoCFE and glycoPURE systems should provide a unique opportunity for studying the interplay of these important mechanisms under conditions where system complexity is reduced and structural barriers are removed. For instance, since the bacterial OST can glycosylate locally flexible structures in folded proteins (Kowarik et al., "N-Linked Glycosylation of Folded Proteins by the Bacterial Oligosaccharyltransferase," Science 314:1148-1150 (2006), which is hereby incorporated by reference in its entirety) and also structured domains of some proteins, these systems should help to decipher the influence of protein structure on glycosylation efficiency. Also, since bacterial and eukaryotic glycosylation mechanisms display significant similarities, these bacterial systems could provide a simplified model framework for understanding the more complex eukaryotic process. Third, it allows for further customization of the system by reconstituting additional or alternative steps (both natural and unnatural) in the glycosylation pathway. For instance, the sequential activities of the glycosyltransferases in the pgl pathway have been reconstituted in vitro (Glover et al., "In Vitro Assembly of the Undecaprenylpyrophosphate-Linked Heptasaccharide for Prokaryotic N-Linked Glycosylation," *Proc. Nat'l. Acad. Sci. U.S.A.* 102:14255-14259 (2005), which is hereby incorporated by reference in its entirety) and could easily be integrated with the translation/glycosylation reactions into a single integrated platform. While glycoengineered *E. coli* have the potential to provide a wide array of UndPP-linked glycans (Feldman et al., "Engineering N-Linked Protein Glycosylation With Diverse O Antigen Lipopolysaccharide Structures in *Escherichia coli," Proc. Nat'l. Acad. Sci. U.S.A.* 102:3016-3021 (2005); Yavuz et al., "Glycomimicry: Display of Fucosylation on the Lipo-Oligosaccharide of Recombinant *Escherichia coli* K12," *Glycoconj. J.* 28:39-47 (2011), which are hereby incorporated by reference in their entirety), the ability to extend beyond bacterial glycans can be achieved by supplementation with specific glycosyltransferases and the requisite activated sugars. This approach can be used for making eukaryotic glycan mimetics (Schwarz et al., "A Combined Method for Producing Homogeneous Glycoproteins With Eukaryotic N-Glycosylation," *Nat. Chem. Biol.* 6:264-266 (2010), which is hereby incorporated by reference in its entirety) and will allow finer control over the diversity of glycoforms that can be used for modifying target proteins in vitro. Since CjPglB has relaxed specificity toward the glycan structure (Feldman et al., "Engineering N-Linked Protein Glycosylation With Diverse 0 Antigen Lipopolysaccharide Structures in *Escherichia coli," Proc. Nat'l. Acad. Sci. U.S.A.* 102:3016-3021 (2005), which is hereby incorporated by reference in its entirety), all of these UndPP-linked glycans are likely to be suitable substrates. Even if CjPglB should prove insufficient, the demonstration here that two different OSTs could be used interchangeably suggests that virtually any single-subunit OST including those from other bacteria, archaea and even some eukaryotes (Nasab et al., "All in One: *Leishmania Major* STT3 Proteins Substitute for the Whole Oligosaccharyltransferase Complex in *Saccharomyces cerevisiae," Mol. Biol. Cell* 19:3758-3768 (2008), which is hereby incorporated by reference in its entirety) could be used in these systems. In support of this notion, the *Leishmania major* and *Pyrococcus furiosus* single-subunit OSTs can be functionally expressed in *E. coli* membranes (Igura & Kohda, "Selective Control of Oligosaccharide Transfer Efficiency for the N-Glycosylation Sequon by a Point Mutation in Oligosaccharyltransferase," *J. Biol. Chem.* 286:13255-13260 (2011), which is hereby incorporated by reference in its entirety). Finally, because one is not limited to natural glycans, the glycoCFE and glycoPURE systems should permit synthesis of hybrid natural/unnatural or even completely artificial glycans. For example, the addition of synthetic sugar-nucleotide donor substrates and/or mutant glycosyltransferases and OSTs having new specificities will enable the construction of a glycosylation system founded on a noncanonical glycan code. For all of these reasons, the glycoCFE and glycoPURE systems are useful additions to the cell-free translation and glycobiology tookits alike.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A recombinant system for producing a glycosylated protein comprising:

an isolated prokaryotic oligosaccharyltransferase which transfers, in the recombinant system, a eukaryotic glycan from a prokaryotic lipid carrier molecule to a glycoprotein target;

one or more isolated eukaryotic glycans, wherein each eukaryotic glycan comprises a GlcNAc2 core and is linked to a prokaryotic lipid carrier molecule; and either (i) a glycoprotein target comprising one or more glycan acceptor amino acid residues or (ii) a nucleic acid molecule encoding said glycoprotein target and reagents suitable for synthesizing the glycoprotein target from said nucleic acid molecule, wherein the isolated prokaryotic oligosaccharyltransferase, the one or more isolated eukaryotic glycans, and the glycoprotein target or the nucleic acid molecule together with the reagents of the recombinant system are cell-free.

2. The system of claim 1, wherein the prokaryotic oligosaccharyltransferase is derived from *Campylobacter*.

3. The system of claim 1, wherein the lipid carrier molecule comprises undecaprenyl-phosphate.

4. The system of claim 1, wherein the eukaryotic glycan further comprises at least one mannose residue.

5. The system of claim 1, wherein the eukaryotic glycan comprises a composition selected from $Man_1GlcNAc_2$, $Man_2GlcNAc_2$, and $Man_3GlcNAc_2$.

6. The system of claim 1, wherein the one or more glycan acceptor amino acid residues of the glycoprotein target is an asparagine residue.

7. The system of claim 6, wherein the glycoprotein target further comprises an N-$X_1$-S/T or a D/E-$X_1$-N-$X_2$-S/T glycan acceptor amino acid sequence motif wherein D is aspartic acid, E is glutamic acid, $X_1$ and $X_2$ are any amino acid other than proline, N is asparagine, S is serine, and T is threonine.

8. The system of claim 1, wherein the glycoprotein target comprises an antibody.

9. A kit comprising a recombinant system, said recombinant system comprising:

reagents suitable for synthesizing a glycoprotein target;

an isolated prokaryotic oligosaccharyltransferase which transfers, in the recombinant system, a eukaryotic glycan from a prokaryotic lipid carrier molecule to said glycoprotein target; and one or more isolated eukaryotic glycans, wherein each eukaryotic glycan comprises a $GlcNAc_2$ core and is linked to a prokaryotic lipid carrier molecule, wherein the reagents, the isolated prokaryotic oligosaccharyltransferase, and the one or more isolated eukaryotic glycans of the recombinant system are cell-free.

10. A method for producing a glycosylated protein in a recombinant system, said method comprising:

providing an isolated prokaryotic oligosaccharyltransferase which transfers, in the recombinant system, a eukaryotic glycan from a prokaryotic lipid carrier molecule to a glycoprotein target;

providing one or more isolated eukaryotic glycans, wherein each eukaryotic glycan comprises a $GlcNAc_2$ core and is linked to a prokaryotic lipid carrier molecule;

providing the glycoprotein target with one or more glycan acceptor residues, wherein the isolated prokaryotic oligosaccharyltransferase, the one or more isolated eukaryotic glycans, and the glycoprotein target of the recombinant system are cell-free;

combining the prokaryotic oligosaccharyltransferase, the one or more isolated eukaryotic glycans, and the glycoprotein target to form a cell-free glycosylation reaction mixture; and subjecting the glycoprotein target to conditions effective for the prokaryotic oligosaccharyltransferase to transfer the eukaryotic glycan from the prokaryotic lipid carrier molecule to the one or more glycan acceptor residues of the glycoprotein target to produce a glycosylated protein.

11. The method of claim 10, wherein the prokaryotic oligosaccharyltransferase is derived from *Campylobacter.*

12. The method of claim 10, wherein the lipid carrier molecule comprises undecaprenyl phosphate.

13. The method of claim 10, wherein the one or more eukaryotic glycans further comprise at least one mannose residue.

14. The method of claim 10, wherein the one or more eukaryotic glycans comprise a composition selected from $Man_1GlcNAc_2$, $Man_2GlcNAc_2$, and $Man_3GlcNAc_2$.

15. The method of claim 10, wherein said providing the glycoprotein target with one or more glycan acceptor residues comprises:

providing a nucleic acid molecule encoding the glycoprotein target;

providing reagents suitable for synthesizing the glycoprotein target from said nucleic acid molecule; and blending the nucleic acid molecule and the reagents with the glycosylation reaction mixture under conditions effective to synthesize the glycoprotein target from the nucleic acid molecule prior to, or concurrent with, said subjecting.

16. The method of claim 10, wherein the one or more glycan acceptor amino acid residues of the glycoprotein target is an asparagine residue.

17. The method of claim 16, wherein the glycoprotein target further comprises an N-$X_1$-S/T or a D/E-$X_1$-N-$X_2$-S/T glycan acceptor amino acid sequence motif wherein D is aspartic acid, E is glutamic acid, $X_1$ and $X_2$ are any amino acid other than proline, N is asparagine, S is serine, and T is threonine.

18. The method of claim 10, wherein the protein comprises an antibody.

* * * * *

UNITED STATES PATENT AND TRADEMARK OFFICE

CERTIFICATE OF CORRECTION

PATENT NO. : 11,193,154 B2
APPLICATION NO. : 14/356258
DATED : December 7, 2021
INVENTOR(S) : Matthew Delisa It is certified that error appears in the above-identified patent and that said Letters Patent is hereby corrected as shown below:

In the Specification

Column 1, Line 8, delete "November 5, 2011" and insert --November 4, 2011--

Column 75, Line 9, delete "E. strain" and insert --*E. coli* strain--

In the Claims

Claim 1 at Column 239, Line 57, delete "GlcNAc2" and insert --$GlcNAc_2$--

Signed and Sealed this
Tenth Day of May, 2022

Katherine Kelly Vidal

Katherine Kelly Vidal
*Director of the United States Patent and Trademark Office*